(12) United States Patent
Venkatramesh et al.

(10) Patent No.: US 7,709,666 B2
(45) Date of Patent: May 4, 2010

(54) TRANSGENIC PLANTS CONTAINING ALTERED LEVELS OF STEROL COMPOUNDS AND TOCOPHEROLS

(75) Inventors: Mylavarapu Venkatramesh, Ballwin, MO (US); David R. Corbin, Chesterfield, MO (US); B. Ganesh Bhat, St. Louis, MO (US); Sekhar S. Boddupalli, San Jose, CA (US); Robert J. Grebenok, East Amherst, NY (US); Ganesh M. Kishore, Creve Coeur, MO (US); Kathryn D. Lardizabal, Woodland, CA (US); Michael W. Lassner, Foster City, CA (US); Shaukat H. Rangwala, Chesterfield, MO (US); Balasulojini Karunanandaa, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1467 days.

(21) Appl. No.: 10/647,517

(22) Filed: Jan. 16, 2004

(65) Prior Publication Data

US 2005/0102716 A1 May 12, 2005

Related U.S. Application Data

(63) Continuation of application No. 09/548,256, filed on Apr. 12, 2000, now abandoned.

(60) Provisional application No. 60/128,995, filed on Apr. 12, 1999.

(51) Int. Cl.
*C07C 59/147* (2006.01)

(52) U.S. Cl. ....................... 554/117; 435/468

(58) Field of Classification Search ................. 554/117; 436/468
See application file for complete search history.

(56) References Cited

U.S. PATENT DOCUMENTS 4,588,717 A 5/1986 Mitchell (Continued)

FOREIGN PATENT DOCUMENTS

EP 0 255 378 A3 2/1988

(Continued)

OTHER PUBLICATIONS

E. Fernholz et al., "Brassicasterol. I. Empirical formula and hydrogenation", Journal of the American Chemical Society (1939), vol. 61, pp. 142-143.*
Venkatramesh, Mylavarapu, et al., "Expression of a *Streptomyces* 3-Hydroxysterioid Oxidase Gene in Oilseeds for Converting Phytosterols to Phytostanols", *Phytochemistry*, 62 (2003) 39-46.
Database EST Id.: 1036015, GenBank Accession No. AA394495.
Database EST Id.: 1456547, GenBank Accession No. AA739734.

(Continued)

*Primary Examiner*—Deborah D Carr
(74) *Attorney, Agent, or Firm*—Chunping Li; Arnold & Porter LLP

(57) ABSTRACT

Provided are recombinant constructs comprising DNA sequences encoding enzymes effective in altering the biosynthesis and accumulation of sterol compounds and tocopherols in transgenic plants. Also provided are methods of using such constructs to produce transgenic plants, seeds of which contain elevated levels of sitostanol and/or sitostanol esters, and α-tocopherol, as well as reduced levels of campesterol and campestanol and their corresponding esters. These seeds also contain the novel sterol brassicastanol. Oil obtained from seeds of such transgenic plants is also provided. This oil can be used to prepare food and pharmaceutical compositions effective in lowering the level of low density lipoprotein cholesterol in blood serum. In addition, novel DNA sequences encoding plant steroid 5α-reductases are also disclosed.

6 Claims, 10 Drawing Sheets

U.S. PATENT DOCUMENTS

| | | |
|---|---|---|
| 5,244,887 A | 9/1993 | Straub |
| 5,270,041 A | 12/1993 | Eugster et al. |
| 5,306,862 A | 4/1994 | Chappell et al. |
| 5,365,017 A | 11/1994 | Chappell et al. |
| 5,420,034 A | 5/1995 | Kridl et al. |
| 5,432,069 A | 7/1995 | Grüninger et al. |
| 5,451,513 A | 9/1995 | Maliga et al. |
| 5,518,908 A | 5/1996 | Corbin et al. |
| 5,530,185 A | 6/1996 | Martineau et al. |
| 5,530,191 A | 6/1996 | Maliga |
| 5,554,369 A | 9/1996 | Corbin et al. |
| 5,558,862 A | 9/1996 | Corbin et al. |
| 5,576,198 A | 11/1996 | McBride et al. |
| 5,589,619 A | 12/1996 | Chappell et al. |
| 5,608,152 A | 3/1997 | Kridl et al. |
| 5,693,507 A | 12/1997 | Daniell et al. |
| 5,753,475 A | 5/1998 | Houck |
| 5,763,245 A | 6/1998 | Greenplate et al. |
| 5,811,636 A | 9/1998 | Hanna et al. |

FOREIGN PATENT DOCUMENTS

| | | |
|---|---|---|
| EP | 0 706 320 B1 | 4/1996 |
| EP | 0 839 458 | 5/1998 |
| EP | 1 033 405 | 9/2000 |
| WO | 90/05788 | 5/1990 |
| WO | 92/19640 | 11/1992 |
| WO | 93/16187 | 8/1993 |
| WO | 95/01098 | 1/1995 |
| WO | 95/16783 | 6/1995 |
| WO | 95/24492 | 9/1995 |
| WO | 95/24493 | 9/1995 |
| WO | 96/38047 | 12/1996 |
| WO | 97/27285 | 7/1997 |
| WO | 97/39112 | 10/1997 |
| WO | 97/42830 | 11/1997 |
| WO | 97/48793 | 12/1997 |
| WO | 98/06405 | 2/1998 |
| WO | 98/06714 | 2/1998 |
| WO | 98/06862 | 2/1998 |
| WO | 98/17789 | 4/1998 |
| WO | 98/45457 | 10/1998 |
| WO | 99/04622 | 2/1999 |
| WO | 99/07867 | 2/1999 |
| WO | 99/63096 | 12/1999 |
| WO | 00/08190 | 2/2000 |
| WO | 00/10380 | 3/2000 |
| WO | 00/32757 | 6/2000 |
| WO | 00/32791 | 6/2000 |
| WO | 01/04330 | 1/2001 |

OTHER PUBLICATIONS

Database EST Id.: 2304763, GenBank Accession No. AI491090.
Database EST Id.: 2949724, GenBank Accession No. AI861123.
Database LOCUS ATT22E16, Accession No. AL132975.
Database EST Id.: 4171593, GenBank Accession No. AV442303.
Database EST Id.: 3548916, GenBank Accession No. AW203676.
Database EST Id.: 3592347, GenBank Accession No. AW234714.
Database EST Id.: 3799016, GenBank Accession No. AW396663.
Database EST Id.: 3925593, GenBank Accession No. AW506800.
Database EST Id.: 4003115, GenBank Accession No. AW570599.
Database EST Id.: 37082, GenBank Accession No. D23767.
Database EST Id.: 1446792, GenBank Accession No. T44209.
Database EST Id.: 1448982, GenBank Accession No. T45440.
Bouvier-Nave et al., "Identification of cDNAs Encoding Sterol Methyl-Transferases Involved in the Second Methylation Step of Plant Sterol Biosynthesis", *Europ. J. Biochem.*, 246(2):518-519 (1997).
Broun and Somerville, "Progress in Plant Metabolic Engineering", *PNAS*, 98(16):8925-8927 (2001).
Caelles et al., "Isolation and Structural Characterization of a cDNA Encoding *Aradidopsis thaliana* 3-hydroxy-3-Methylglytaryl Coenzyme A Reductase", *Plant Mol. Biol.*, 13(6):627-638 (1989).
Chappell et al., "Is the Reaction Catalyzed by 3-Hydroxy-3-methylglutaryl Coenzyme A Reductase a Rate-Limiting Step for Isoprenoid Biosynthesis in Plants?", *Plant Physiology, US*, American Society of Plant Physiologists, Rockville, MD, 109(4):1337-1343 (1995).
Cho et al., "Introduction and Expression of the *Streptomyces* Cholesterol Oxidase Gene (ChoA), a Potential Insecticidal Protein Active Against Boll Weevil Larvae, Into Tobacco Cells", *Appl. Micro. Biotech.*, 44(1-2):133-138(1995).
Chye et al., "Characterization of cDNA and Genomic Clones Encoding 3-Hydroxy-3-Methylglutaryl-Coenzyme A Reductase from *Hevea brasiliensis*", *Plant Mol. Biol.*, 16(4):567-577 (1991).
Corbin et al., "Cloning of an Insecticidal Cholesterol Oxidase Gene and Its Expression in Bacteria and in Plant Protoplasts", *Appl. and Environ. Micro.*, 60(12):4239-4244 (1994).
Corbin et al., "New Proteins for the Control of Insects in Transgenic Crops", *HortScience*, 34(4):699, No. 786 (1996).
Corbin et al., "The Identification and Development of Proteins for control of Insects in Genetically Modified Crops", *HortScience*, 33(4):614-617 (1998).
d'Harlingue et al., "Plastid Enzymes of Terpenoid Biosynthesis", *J. Biol. Chem.*, 260(28):15200-15203 (1985).
Dyas et al., "Steryl Fatty Acyl Esters in Plants", *Phytochemistry*, 34(1):17-29 (1993).
Estruch et al., "Transgenic Plants: An Emerging Approach to Pest Control", *Nature Biotechnology*, 15(2):137-141 (1997).
Falco et al., "Transgenic canola and soybean seeds with increased lysine", *Bio-Technology*, 13(6):577-582 (1995) (Abstract).
Fujioka et al., "The *Arabidopsis deetiolated2* Mutant in Blocked Early in Brassinosteroid Biosynthesis", *The Plant Cell*, 9(11):1951-1962 (1997).
Fujishiro et al., "Isolation and Identification of the Gene of Cholesterol Oxidase from *Brevibacterium sterollicum* ATCC 21387, a Widely Used Enzyme in Clinical Analysis", *Biochem. and Biophy. Res. Comm.*, 172(2):721-727 (1990).
Fuqua et al., "Characterization of melA: A Gene Encoding Melanin Biosynthesis from the Marine Bacterium *Shewanella colwelliana*", *Gene 109*, 109(1):131-136 (1991).
Godoy-Hernandez et al., "Antisense Expression of *hmgl* from *Arabidopsis thaliana* Enclding 3-hydroxy-3-methylglutaryl Coenzyme A Reductase, Reduces Isoprenoid Production in Transgenic Tobacco Plants", *Journal of Plant Physiology*, 153(3-4):415-424 (1998).
Gonzalez et al., "Overexpression of HMG-COA Reductase in *Arabidoppsis thaliana*", Third Terpnet Meeting of the European Network on Plant Isoprenoids Abstracts, Abstract No. 33, p. 33 (1997).
Guo et al., "Developmental Regulation of Sterol Biosynthesis in Zea Mays", *Lipids*, 30(3):203-219 (1995).
Halliwell, "Antioxidants and Human Disease: A General Introduction", *Nutrition Reviews*, 55(1)(Part II):S44-52 (1997).
Husselstein et al., "Transformation of *Saccharomyces cerevisiae* with a cDNA encoding a Sterol C-methyltransferase from *Aradidopsis thaliana* Results in the Synthesis of 24-ethyl Sterols", *FEBS Letters*, 381(1,2,26):87-92 (1996).
International Search Report from International Application No. PCT/US00/09696.
Jouanin et al., "Transgenic Plants for Insect Resistance", *Plant Science*, 131(1):1-11 (1998).
Klahre et al., "The *Arabidopsis* DIMINUTO/DWARF1 Gene Encodes a Protein Involed in Steroid Synthesis", *The Plant Cell*, 10(10):1677-1690 (1998).
Kochhar, "Influence of Processing of Sterols of Edible Vegetable Oils", *Progress in Lipid Research*, 22:161-188 (1983).
Li et al., "Conservation of Function Between Mammalian and Plant Steroid 5 α-Reductases", *Proc. Natl. Acad. Sci. USA*, 94:3554-3559 (1997).
Ling et al., "Minireview Dietary Phytosterols: A Review of Metabolism, Benefits and Side Effects", *Life Sciences*, 57(3):195-206 (1995).

Long et al., "Fatty Acid Compositions of Lipid Fractions from Vegetable Cells and Mature Sorocarps of the Cellular Slime Mold *Dictyostelim discoideum*", *Chem. Abs.*, 87(5):213 (1977) (Abstract).

Maimann et al., "Enhanced Cystathionine beta-lyase Activity in Transgenic Potato Plants does not Force Metabolite Flow Towards Methionine", *Planta*, 214(2):163-170 (2001) (Abstract).

Murooka et al., "Cloning and Expression of a *Streptomyces* Cholesterol Oxidase Gene in *Streptomyces lividans* with Plasmid pIJ702", *Appl. Environ. Microbiol.*, 52(6):1382-1385.

Nawrath et al., "Targeting of the Polyhydroxybutyrate Biosynthetic Pathway to the Plastids of *Arabidoppsis thaliana* Results in High Levels of Polymer Accumulation", *Proc. Natl. Acad. Sci.*, 91(27):12760-12764 (1994).

Padgette et al., "Development, Identification, and Characterization of a Glyphosate-Tolerant Soybean Line", *Crop Science*, 35(5):1451-1461 (1995).

Ruzafa et al., "The Protein Encoded by the *Shewanella colwelliana* melA Gene is a p-Hydroxyphenylpyruvate Dioxygenase", *FEMS Micro Letters*, 142/2:179-184 (1994).

Schaller et al., "Expression of the *Hevea brasiliensis* (H.B.K.) Müll. Arg. 3-Hydroxy-3-Methylglutaryl-Coenzyme A Reductase 1 in Tobacco Results in Sterol Overproduction", *Plant Physiol.*, 109:761-770 (1995).

Schaller et al., "Sterol Composition of Tobacco Expressing an *Arabidopsis* cDNA Encoding a Sam-Sterol-C24-Methyl-Transferase", *Third Terpnet Meeting of the European Network on Plant Isoprenoids Abstracts*, Abstract No. 44, p. 44 (1997).

Schaller et al., "Overexpression of an *Arabidopsis* cDNA Encoding a Sterol-C24[1]-Methyltransferase in Tobacco Modifies the Ratio of 24-Methyl Cholesterol to Sitosterol and is Associated with Growth Reduction", *Plant Physiol.*, 118:461-469 (1998).

Seitz, "Stanol and Sterol Esters of Ferulic and p-Coumaric Acids in Wheat, Corn, Rye, and Triticale", *J. Agri. and Food Chem.*, pp. 662-667 (1989).

Shigeoka et al., "Isolation and Properties of γ-Tocopherol Methyltransferase in *Euglena gracilis*", *Biochem. Biophys. Acta.*, 1128(2/3):220-226 (1992).

Shintani et al., "Elevating the Vitamine E Content of Plants Through Metabolic Engineering", *Science*, 282(5396):2098-2100 (1998).

Smith et al., "Cholesterol Oxidases: Properties and Applications", *J. Steroid Biochem.*, 7(9):705-713 (1976).

Sucrow et al., "Die Synthesis von α-Stigmasta-22,25-dien-3b-ol, 5a-Stigmast-22-en-3β-ol and 5α-Stigmastan-3b-ol-und ihren 24-Epimeren", *Chem. Ber.*, 108:1101-1110 (1975).

Vu et al., "Effects of Inhibitors on the Biosynthesis of Sterols Reducing Sugars and Chlorophyll and the Development of Iso Citrate Lyase in Germinating Seeds of Longleaf Pine Pinus-Palustris", *Plant Sci. Let.*, 16:255-266 (1979) (Abstract).

Withers et al., "Sterol Patterns of Cultured Zooxanthellae Isolated from Marine Invertebrates Synthesis of Gorgosterol and 23-Demthylgorgosterol by Aposymbiotic Algae", *Proceedings of the National Academy of Sciences of the United States*, 79(12):3764-3768 (1982).

* cited by examiner

SEQUENCE LISTING

```
<160> NUMBER OF SEQ ID NOS: 31

<210> SEQ ID NO 1
<211> LENGTH: 43
<212> TYPE: PRT
<213> ORGANISM: jojoba

<400> SEQUENCE: 1

Met Lys Val Thr Val Gln Thr Arg Ser Gly Arg Glu Leu Ile Lys Gly
 1               5                  10                  15

Gly Ile Glu Leu His Asp Ser Ala Thr Val Thr Asp Leu Gln Glu Ala
            20                  25                  30

Ile Tyr Ile Lys Thr Lys Lys Tyr Tyr Arg Ala
        35                  40

<210> SEQ ID NO 2
<211> LENGTH: 1258
<212> TYPE: DNA
<213> ORGANISM: Arabidopsis thaliana

<400> SEQUENCE: 2
acccacgcgt ccgctctatc tctctcaatt tcctcatctg ggtcttcctc gtttgctccg      60
cttaagcacc atgaaggtca ccgtcgtctc ccgcagcggc agagaagtcc tcaaagctcc     120
ccttgacctc cccgattcgg cgactgttgc tgatctgcaa gaagcgtttc ataagagagc     180
taagaagttt tacccgtcga ggcaaagact gactcttccc gtgactcctg gatcgaagga     240
caaacctgtt gtcctcaata gcaagaaatc actgaaggag tactgtgatg gaaacaacaa     300
```

-continued

```
ctccttaact gtagtcttca aagacctggg ggcacaagtt tcctaccgca cactcttctt      360
cttcgagtat cttggccctc tccttatcta ccctgtcttt tactacttcc ctgtttacaa      420
gtttcttggt tatggagagg actgtgtgat ccatccggtc cagacgtacg ctatgtacta      480
ctggtgcttt cactacttca aacggatctt agaaacgttt ttcgtacatc ggttcagcca      540
cgcaacctcc ccaatcggga atgtgttcag gaactgtgct tattactgga gctttggtgc      600
ttacattgct tattacgtca accatccctt gtacactcca gttagtgacc ttcagatgaa      660
gattggtttc gggtttggtt tggttttgcca agtcgcaaac ttttactgtc acatattgct      720
gaagaatctg agggacccca gtggggctgg aggctaccag attccacgcg gtttcctctt      780
caacattgtt acatgtgcca attacactac cgagatttac caatggctag gattcaacat      840
cgctactcag accattgcag gatatgtttt cctcgctgtt gctgctctaa tcatgactaa      900
ttgggctctt ggaaagcaca gccgtytgag aaagatattt gatggaaaag atggaaagcc      960
aaagtatcca agaagatggg tgatacttcc tccattcctt tagaagccat tgttgcttat      1020
cagtaaaagc tcttaataaa gctgaaaatg agactttctt tgggttctct gtatcgtttc      1080
cttttttgtt cggtctatgt attggttata acatgtttat tccttttgtt tcaatatgtt      1140
ttgattttg aagttagaga gatttagaaa tgtacttgtg tagttgtttc tcacgcaaac      1200
caattcctct ttatgtatcg catacatgag tcaataataa atatgattac tagtaaaa      1258
```

<210> SEQ ID NO 3
<211> LENGTH: 309
<212> TYPE: PRT
<213> ORGANISM: Arabidopsis thaliana

<400> SEQUENCE: 3

```
Met Lys Val Thr Val Ser Arg Ser Gly Arg Glu Val Leu Lys Ala
  1               5                  10                  15

Pro Leu Asp Leu Pro Asp Ser Ala Thr Val Ala Asp Leu Gln Glu Ala
             20                  25                  30

Phe His Lys Arg Ala Lys Lys Phe Tyr Pro Ser Arg Gln Arg Leu Thr
         35                  40                  45

Leu Pro Val Thr Pro Gly Ser Lys Asp Lys Pro Val Val Leu Asn Ser
     50                  55                  60

Lys Lys Ser Leu Lys Glu Tyr Cys Asp Gly Asn Asn Asn Ser Leu Thr
 65                  70                  75                  80

Val Val Phe Lys Asp Leu Gly Ala Gln Val Ser Tyr Arg Thr Leu Phe
                 85                  90                  95

Phe Phe Glu Tyr Leu Gly Pro Leu Leu Ile Tyr Pro Val Phe Tyr Tyr
            100                 105                 110

Phe Pro Val Tyr Lys Phe Leu Gly Tyr Gly Glu Asp Cys Val Ile His
        115                 120                 125

Pro Val Gln Thr Tyr Ala Met Tyr Tyr Trp Cys Phe His Tyr Phe Lys
    130                 135                 140

Arg Ile Leu Glu Thr Phe Phe Val His Arg Phe Ser His Thr Ser Pro
145                 150                 155                 160

Ile Gly Asn Val Phe Arg Asn Cys Ala Tyr Tyr Trp Ser Phe Gly Ala
                165                 170                 175

Tyr Ile Ala Tyr Tyr Val Asn His Pro Leu Tyr Thr Pro Val Ser Asp
            180                 185                 190

Leu Gln Met Lys Ile Gly Phe Gly Phe Gly Leu Val Cys Gln Val Ala
        195                 200                 205
```

Asn Phe Tyr Cys His Ile Leu Leu Lys Asn Leu Arg Asp Pro Ser Gly
            210                 215                 220

Ala Gly Gly Tyr Gln Ile Pro Arg Gly Phe Leu Phe Asn Ile Val Thr
225                 230                 235                 240

Cys Ala Asn Tyr Thr Thr Glu Ile Tyr Gln Trp Leu Gly Phe Asn Ile
                245                 250                 255

Ala Thr Gln Thr Ile Ala Gly Tyr Val Phe Leu Ala Val Ala Ala Leu
            260                 265                 270

Ile Met Thr Asn Trp Ala Leu Gly Lys His Ser Arg Leu Arg Lys Ile
        275                 280                 285

Phe Asp Gly Lys Asp Gly Lys Pro Lys Tyr Pro Arg Arg Trp Val Ile
290                 295                 300

Leu Pro Pro Phe Leu
305

<210> SEQ ID NO 4
<211> LENGTH: 1361
<212> TYPE: DNA
<213> ORGANISM: Zea mays

<400> SEQUENCE: 4
gaattcggct cgagctctcc tctcctctcc tctccccgc atccacggcc gcaggcagca      60
ggcagccact cgacgatcta gtcgtctctc tccccgctct gccgcctcgc tgccgcggct    120
tcccgtcggc gggaggatga aggtcacggt cgtgtcccgg agcggccggg aggtcgtcaa    180
gggcggcatc gacctcaagg actcggccaa ggtcgcggac ctgcaggagg ccatccatgc    240
caggactaag aagtattatc cttctaggca gcggctcacc ctccccttc aacctggaaa     300
aggcgggaag ccagttgtcc tcagtccgaa ggccagcctg ctagaatact gcgagaaggg    360
ttctgggtca ctgacagtgg tcttcaaaga tttaggccca caggtctact acagcacact    420
gttcttcttc gagtacctgg gtcctctcat catctacccc atgttctact atctgcccgt    480
ctacaagtac ttcgggcacg agggggagcg ggccatgcac cctgtccaga cctacgcaat    540
gtactactgg tgcttccact acttcaagcg gatcatggag acgttcttcg tgcaccgctt    600
cagccacgcg acgtcgccgc tctcgaacgt cttcaggaac tgtgcctact actggacctt    660
cggcgcttac attgcttact actgcaacca cccgctgtac accccagtga gtgatctgca    720
gatgaagatt gggtttggtt ttggggtcgt ctgccaggtc gcgaacttct actgccacat    780
cctgctgcgg aacctcagga gcccaagcgg cagcggcggg taccagatcc cccgcggttt    840
cttgttcaac atcgtgacct gcgccaatta caccaccgag atctaccagt gggtcggctt    900
caacatcgcc acacagaccg tggcaggtta cgtcttcctt gtcgtggcgg cgggcatcat    960
gaccaactgg gcgctcggca agcacagccg tctgaagaag ctgtttgacg gcaaggatgg   1020
gaggcccaag taccctcgcc ggtgggtgat tctccctccg ttcctgtgaa gaggcggtgg   1080
tggtggctca ctgttggtgg tcggcccatt gtgattcgat gtctacagac agttgtactg   1140
tactaatcgt gcctgtttag cggttgaact tggattccgt tgtccgaagt ttctaatccg   1200
aaagatggat ttcatttct tcttcttctt cttagcatta tgtcactgtc tcacgtcgtc   1260
ctgtctcaat acagtctaag gttcatgtga tgttatcccc atttgtccac gcagaagtga   1320
agtgaatgca gtcactattt cgattcgaca aaaaaaaaa a                        1361

<210> SEQ ID NO 5
<211> LENGTH: 309

```
<212> TYPE: PRT
<213> ORGANISM: Zea mays

<400> SEQUENCE: 5

Met Lys Val Thr Val Val Ser Arg Ser Gly Arg Glu Val Val Lys Gly
  1               5                  10                  15

Gly Ile Asp Leu Lys Asp Ser Ala Lys Val Ala Asp Leu Gln Glu Ala
             20                  25                  30

Ile His Ala Arg Thr Lys Lys Tyr Tyr Pro Ser Arg Gln Arg Leu Thr
         35                  40                  45

Leu Pro Leu Gln Pro Gly Lys Gly Gly Lys Pro Val Val Leu Ser Pro
     50                  55                  60

Lys Ala Ser Leu Leu Glu Tyr Cys Glu Lys Gly Ser Gly Ser Leu Thr
 65                  70                  75                  80

Val Val Phe Lys Asp Leu Gly Pro Gln Val Tyr Ser Thr Leu Phe
                 85                  90                  95

Phe Phe Glu Tyr Leu Gly Pro Leu Ile Ile Tyr Pro Met Phe Tyr Tyr
                100                 105                 110

Leu Pro Val Tyr Lys Tyr Phe Gly His Glu Gly Glu Arg Ala Met His
                115                 120                 125

Pro Val Gln Thr Tyr Ala Met Tyr Tyr Trp Cys Phe His Tyr Phe Lys
                130                 135                 140

Arg Ile Met Glu Thr Phe Phe Val His Arg Phe Ser Ala Thr Ser Pro
145                 150                 155                 160

Leu Ser Asn Val Phe Arg Asn Cys Ala Tyr Tyr Trp Thr Phe Gly Ala
                165                 170                 175

Tyr Ile Ala Tyr Tyr Cys Asn His Pro Leu Tyr Thr Pro Val Ser Asp
                180                 185                 190

Leu Gln Met Lys Ile Gly Phe Gly Phe Gly Val Val Cys Gln Val Ala
                195                 200                 205

Asn Phe Tyr Cys His Ile Leu Leu Arg Asn Leu Arg Ser Pro Ser Gly
                210                 215                 220

Ser Gly Gly Tyr Gln Ile Pro Arg Gly Phe Leu Phe Asn Ile Val Thr
225                 230                 235                 240

Cys Ala Asn Tyr Thr Thr Glu Ile Tyr Gln Trp Val Gly Phe Asn Ile
                245                 250                 255

Ala Thr Gln Thr Val Ala Gly Tyr Val Phe Leu Val Val Ala Ala Gly
                260                 265                 270

Ile Met Thr Asn Trp Ala Leu Gly Lys His Ser Arg Leu Lys Lys Leu
                275                 280                 285

Phe Asp Gly Lys Asp Gly Arg Pro Lys Tyr Pro Arg Arg Trp Val Ile
                290                 295                 300

Leu Pro Pro Phe Leu
305

<210> SEQ ID NO 6
<211> LENGTH: 926
<212> TYPE: DNA
<213> ORGANISM: Glycine max

<400> SEQUENCE: 6
gaattcggct cgagcgggga tgtcagtgat aagccttgtg tcactggcta atgctggctt    60
ctcagagatt agagggaagc atttgaacta ttcaaagttt tggaatgcta atccctctgc   120
agaaaagcag gtcaagttgt ctagcaaagc tggcatgctt tgctgtaca ctcctgcttt   180
```

```
tcttgctggc cttgcatcct tctggatctt tcctcatcaa ggcctcagat ccaccctcct    240
tcagtctgca gttaccctgc atttcttcaa gagggtcttt gaggttgtgt ttattcacaa    300
atatagtggt gccatgcttc ttgattctgc aatccccatc actctgagtt atttcctatc    360
aactgcaact atgatctatg ctcaacactt aacacaaggg cttccagaac caccaatcga    420
tctgttgtat cctggcattg ttttgtttgt ggtgggcatc attggcaact tctaccacca    480
ctaccttcta tccaacttaa ggggaaaggg tgaaaaggag tacaagattc caaagggtgg    540
catgtttgag cttgtcatat gtccccacta cctgtttgag attattgagt tttatgggtt    600
ctccttcatt tcgcagacgc tatatgcatt ctctttcacc gtaggcacta ctttatactt    660
gctaggtagg agttattcaa ctaggaaatg gtatctttct aagtttgaag atttccctga    720
gcatgttaag gctatcatcc catttgtctt ctagaaatgt tggaaggaat aactaatttt    780
actttcattt ctcagacgct atatgcatta tctttcactg taggcgctac tttgtacttg    840
ctatgtagga gtgattcgac taggaaatgg tatctttcta ggtttgaaga tttccctaaa    900
aaaaaaaaaa aagggcgggc cgccg                                         926
```

```
<210> SEQ ID NO 7
<211> LENGTH: 244
<212> TYPE: PRT
<213> ORGANISM: Glycine max

<400> SEQUENCE: 7
```

Met Ser Val Ile Ser Leu Val Ser Leu Ala Asn Ala Gly Phe Ser Glu
1               5                   10                  15

Ile Arg Gly Lys His Leu Asn Tyr Ser Lys Phe Trp Asn Ala Asn Pro
            20                  25                  30

Ser Ala Glu Lys Gln Val Lys Leu Ser Ser Lys Ala Gly Met Leu Leu
        35                  40                  45

Leu Tyr Thr Pro Ala Phe Leu Ala Gly Leu Ala Ser Phe Trp Ile Phe
    50                  55                  60

Pro His Gln Gly Leu Arg Ser Thr Leu Leu Gln Ser Ala Val Thr Leu
65                  70                  75                  80

His Phe Phe Lys Arg Val Phe Glu Val Val Phe Ile His Lys Tyr Ser
                85                  90                  95

Gly Ala Met Leu Leu Asp Ser Ala Ile Pro Ile Thr Leu Ser Tyr Phe
            100                 105                 110

Leu Ser Thr Ala Thr Met Ile Tyr Ala Gln His Leu Thr Gln Gly Leu
        115                 120                 125

Pro Glu Pro Pro Ile Asp Leu Leu Tyr Pro Gly Ile Val Leu Phe Val
    130                 135                 140

Val Gly Ile Ile Gly Asn Phe Tyr His His Tyr Leu Leu Ser Asn Leu
145                 150                 155                 160

Arg Gly Lys Gly Glu Lys Glu Tyr Lys Ile Pro Lys Gly Gly Met Phe
                165                 170                 175

Glu Leu Val Ile Cys Pro His Tyr Leu Phe Glu Ile Ile Glu Phe Tyr
            180                 185                 190

Gly Phe Ser Phe Ile Ser Gln Thr Leu Tyr Ala Phe Ser Phe Thr Val
        195                 200                 205

Gly Thr Thr Leu Tyr Leu Gly Arg Ser Tyr Ser Thr Arg Lys Trp
    210                 215                 220

Tyr Leu Ser Lys Phe Glu Asp Phe Pro Glu His Val Lys Ala Ile Ile
225                 230                 235                 240

Pro Phe Val Phe

<210> SEQ ID NO 8
<211> LENGTH: 917
<212> TYPE: DNA
<213> ORGANISM: Glycine max

<400> SEQUENCE: 8

```
gaattcggct cgagaacaag caaacaccat ggtgattaag tctgtgttgt tcagcttcat      60
tttccccccg ccaccttctc tggtggtttg ggggttgact gtgacaagct tcctgatact     120
ggctaatgct tcttgtcag aaattagagg gaagcatttg aactattcaa agttttggaa      180
tgctaatccc tctgcagaaa agcaggtcaa gttgtctagc aaagctggca tgcttttgct     240
gtacactcct gcttttcttg ctggccttgc atccttctgg gtctttcctc atcaagggct     300
cagattcacc atccttcaat ctgctgttac tctgcactac ttcaagaggg tctttgaggg     360
tctgtttatt cacaaatata gtggaggcat gacacttgaa tctgcaatcc ccatcactct     420
gagttatttc ctctcagctg taactatggt ctattctcaa cacctaacaa aagggtttcc     480
agaaccacca atcaatctgt tctaccctgg cattgtgttg tttctagttg gcatcattgg     540
caacttctac caccattacc ttctgtccaa attgagggga agggtgaaaa ggagtacaa      600
gattccaaag ggtggctttt tgagcttgt gatttgcccc cactacttct ttgagattac      660
tgtgttttat gggatcttct tcatttctca gacattatat tcattcgctt tcgctgtagg     720
cactactatg tacttggtgg gtaggagtta ctcaactagg aaatggtatc tttctaagtt     780
tgaagatttc cctaagcatg ttaaggctgt catcccattt gtcttctaaa tgttgtaatg     840
aacatctaat tctacttgag ttgtaagtgt gctgctagat tgtgtttaaa aaaaaaaaa      900
aaaagggcgg ccgccgg                                                    917
```

<210> SEQ ID NO 9
<211> LENGTH: 266
<212> TYPE: PRT
<213> ORGANISM: Glycine max

<400> SEQUENCE: 9

```
Met Val Ile Lys Ser Val Leu Phe Ser Phe Ile Phe Pro Pro Pro Pro
 1               5                  10                  15

Ser Leu Val Val Trp Gly Leu Thr Val Thr Ser Phe Leu Ile Leu Ala
            20                  25                  30

Asn Ala Phe Leu Ser Glu Ile Arg Gly Lys His Leu Asn Tyr Ser Lys
        35                  40                  45

Phe Trp Asn Ala Asn Pro Ser Ala Glu Lys Gln Val Lys Leu Ser Ser
    50                  55                  60

Lys Ala Gly Met Leu Leu Leu Tyr Thr Pro Ala Phe Leu Ala Gly Leu
65                  70                  75                  80

Ala Ser Phe Trp Val Phe Pro His Gln Gly Leu Arg Phe Thr Ile Leu
                85                  90                  95

Gln Ser Ala Val Thr Leu His Tyr Phe Lys Arg Val Phe Glu Gly Leu
            100                 105                 110

Phe Ile His Lys Tyr Ser Gly Gly Met Thr Leu Glu Ser Ala Ile Pro
        115                 120                 125

Ile Thr Leu Ser Tyr Phe Leu Ser Ala Val Thr Met Val Tyr Ser Gln
    130                 135                 140

His Leu Thr Lys Gly Phe Pro Glu Pro Pro Ile Asn Leu Phe Tyr Pro
145                 150                 155                 160
```

```
Gly Ile Val Leu Phe Leu Val Gly Ile Ile Gly Asn Phe Tyr His His
                165                 170                 175

Tyr Leu Leu Ser Lys Leu Arg Gly Lys Gly Glu Lys Glu Tyr Lys Ile
            180                 185                 190

Pro Lys Gly Gly Phe Phe Glu Leu Val Ile Cys Pro His Tyr Phe Phe
        195                 200                 205

Glu Ile Thr Val Phe Tyr Gly Ile Phe Phe Ile Ser Gln Thr Leu Tyr
    210                 215                 220

Ser Phe Ala Phe Ala Val Gly Thr Thr Met Tyr Leu Val Gly Arg Ser
225                 230                 235                 240

Tyr Ser Thr Arg Lys Trp Tyr Leu Ser Lys Phe Glu Asp Phe Pro Lys
                245                 250                 255

His Val Lys Ala Val Ile Pro Phe Val Phe
            260                 265

<210> SEQ ID NO 10
<211> LENGTH: 1942
<212> TYPE: DNA
<213> ORGANISM: Arabidopsis thaliana

<400> SEQUENCE: 10
```

| | | | | | |
|---|---|---|---|---|---|
| ctctcgtgaa | tcctttttcc | tttcttcttc | ttcttctctt | cagagaaaac | tttgcttctc | 60 |
| tttctataag | gaaccagaca | cgaatcccat | tcccaccgat | ttcttagctt | cttccttcaa | 120 |
| tccgctcttt | ccctctccat | tagattctgt | ttcctctttc | aatttcttct | gcatgcttct | 180 |
| cgattctctc | tgacgcctct | tttctcccga | cgctgtttcg | tcaaacgctt | ttcgaaatgg | 240 |
| cgattttgga | ttctgctggc | gttactacgg | tgacggagaa | cggtggcgga | gagttcgtcg | 300 |
| atcttgatag | gcttcgtcga | cggaaatcga | gatcggattc | ttctaacgga | cttcttctct | 360 |
| ctggttccga | taataattct | ccttcggatg | atgttggagc | tcccgccgac | gttagggatc | 420 |
| ggattgattc | cgttgttaac | gatgacgctc | agggaacagc | caatttggcc | ggagataata | 480 |
| acggtggtgg | cgataataac | ggtggtggaa | gaggcggcgg | agaaggaaga | ggaaacgccg | 540 |
| atgctacgtt | tacgtatcga | ccgtcggttc | cagctcatcg | gagggcgaga | gagagtccac | 600 |
| ttagctccga | cgcaatcttc | aaacagagcc | atgccggatt | attcaacctc | tgtgtagtag | 660 |
| ttcttattgc | tgtaaacagt | agactcatca | tcgaaaatct | tatgaagtat | ggttggttga | 720 |
| tcagaacgga | tttctggttt | agttcaagat | cgctgcgaga | ttggccgctt | ttcatgtgtt | 780 |
| gtatatccct | ttcgatcttt | cctttggctg | cctttacggt | tgagaaattg | gtacttcaga | 840 |
| aatacatatc | agaacctgtt | gtcatctttc | ttcatattat | tatcaccatg | acagaggttt | 900 |
| tgtatccagt | ttacgtcacc | ctaaggtgtg | attctgcttt | tttatcaggt | gtcactttga | 960 |
| tgctcctcac | ttgcattgtg | tggctaaagt | tggtttctta | tgctcatact | agctatgaca | 1020 |
| taagatccct | agccaatgca | gctgataagg | ccaatcctga | agtctcctac | tacgttagct | 1080 |
| tgaagagctt | ggcatatttc | atggtcgctc | ccacattgtg | ttatcagcca | agttatccac | 1140 |
| gttctgcatg | tatacggaag | ggttgggtgg | ctcgtcaatt | tgcaaaactg | gtcatattca | 1200 |
| ccggattcat | gggatttata | atagaacaat | atataaatcc | tattgtcagg | aactcaaagc | 1260 |
| atcctttgaa | aggcgatctt | ctatatgcta | ttgaaagagt | gttgaagctt | tcagttccaa | 1320 |
| atttatatgt | gtggctctgc | atgttctact | gcttcttcca | cctttggtta | aacatattgg | 1380 |
| cagagcttct | ctgcttcggg | gatcgtgaat | tctacaaaga | ttggtggaat | gcaaaaagtg | 1440 |
| tgggagatta | ctgagaatg | tggaatatgc | ctgttcataa | atggatggtt | cgacatatat | 1500 |

-continued

```
acttcccgtg cttgcgcagc aagataccaa agacactcgc cattatcatt gctttcctag    1560
tctctgcagt ctttcatgag ctatgcatcg cagttccttg tcgtctcttc aagctatggg    1620
cttttcttgg gattatgttt caggtgcctt tggtcttcat cacaaactat ctacaggaaa    1680
ggtttggctc aacggtgggg aacatgatct tctggttcat cttctgcatt tcggacaac    1740 cgatgtgtgt gcttctttat taccacgacc tgatgaaccg aaaaggatcg atgtcatgaa    1800
acaactgttc aaaaaatgac tttcttcaaa catctatggc ctcgttggat ctccgttgat    1860
gttgtggtgg ttctgatgct aaaacgacaa atagtgttat aaccattgaa gaagaaaga    1920 caattagagt tgttgtatcg ca                                              1942
```

<210> SEQ ID NO 11
<211> LENGTH: 520
<212> TYPE: PRT
<213> ORGANISM: Arabidopsis thaliana

<400> SEQUENCE: 11

```
Met Ala Ile Leu Asp Ser Ala Gly Val Thr Thr Val Thr Glu Asn Gly
  1               5                  10                  15

Gly Gly Glu Phe Val Asp Leu Asp Arg Leu Arg Arg Lys Ser Arg
             20                  25                  30

Ser Asp Ser Ser Asn Gly Leu Leu Leu Ser Gly Ser Asp Asn Asn Ser
         35                  40                  45

Pro Ser Asp Asp Val Gly Ala Pro Ala Asp Val Arg Asp Arg Ile Asp
     50                  55                  60

Ser Val Val Asn Asp Asp Ala Gln Gly Thr Ala Asn Leu Ala Gly Asp
 65                  70                  75                  80

Asn Asn Gly Gly Gly Asp Asn Asn Gly Gly Arg Gly Gly Gly Glu
                 85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285
```

```
Met Val Ala Pro Thr Leu Cys Tyr Gln Pro Ser Tyr Pro Arg Ser Ala
    290                 295                 300
Cys Ile Arg Lys Gly Trp Val Ala Arg Gln Phe Ala Lys Leu Val Ile
305                 310                 315                 320
Phe Thr Gly Phe Met Gly Phe Ile Ile Glu Gln Tyr Ile Asn Pro Ile
                    325                 330                 335
Val Arg Asn Ser Lys His Pro Leu Lys Gly Asp Leu Leu Tyr Ala Ile
                340                 345                 350
Glu Arg Val Leu Lys Leu Ser Val Pro Asn Leu Tyr Val Trp Leu Cys
            355                 360                 365
Met Phe Tyr Cys Phe Phe His Leu Trp Leu Asn Ile Leu Ala Glu Leu
        370                 375                 380
Leu Cys Phe Gly Asp Arg Glu Phe Tyr Lys Asp Trp Trp Asn Ala Lys
385                 390                 395                 400
Ser Val Gly Asp Tyr Trp Arg Met Trp Asn Met Pro Val His Lys Trp
                    405                 410                 415
Met Val Arg His Ile Tyr Phe Pro Cys Leu Arg Ser Lys Ile Pro Lys
                420                 425                 430
Thr Leu Ala Ile Ile Ile Ala Phe Leu Val Ser Ala Val Phe His Glu
            435                 440                 445
Leu Cys Ile Ala Val Pro Cys Arg Leu Phe Lys Leu Trp Ala Phe Leu
        450                 455                 460
Gly Ile Met Phe Gln Val Pro Leu Val Phe Ile Thr Asn Tyr Leu Gln
465                 470                 475                 480
Glu Arg Phe Gly Ser Thr Val Gly Asn Met Ile Phe Trp Phe Ile Phe
                    485                 490                 495
Cys Ile Phe Gly Gln Pro Met Cys Val Leu Leu Tyr Tyr His Asp Leu
                500                 505                 510
Met Asn Arg Lys Gly Ser Met Ser
            515                 520

<210> SEQ ID NO 12
<211> LENGTH: 381
<212> TYPE: DNA
<213> ORGANISM: Caenorhabditis elegans
<220> FEATURE:
<221> NAME/KEY: unsure
<222> LOCATION: (46)
<223> OTHER INFORMATION: n=a,t,c or g

<400> SEQUENCE: 12
tgcaaatgcg tcaacaaacg ggacgacggc ggcgtcagcc ttcggnaaac atctaatggt      60
tctttggctt ccagtagacg ctcctcattt gcacaaaatg gtaattcgtc aagggaaaag     120
ttcagaaatg agaggacctt gcgagaaagt ggtacatact gctcaagatt cattgttttc     180
gacgagttct ggatggacaa atttccgtgg attcttcaat tgtctatttt tacttttggt     240
actttcaaat ggacgcgtgg cacttgaaaa tgtgatcaaa tatggtattt tgataacacc     300
ccttcagtgg atctcaacgt tgttgagca tcactactca atttggagct ggccaaatct     360
tgctctcatc ctatgctcaa a                                               381

<210> SEQ ID NO 13
<211> LENGTH: 300
<212> TYPE: DNA
<213> ORGANISM: Caenorhabditis elegans

<400> SEQUENCE: 13
```

-continued

```
tttgatatgt acggtaaatg gaaaaaaggt attcatgtat ggcaaggtgg taataaatgg      60
cactaaatat gtttcaaaag tgtgagcaaa cgtatgtgag agacgagaaa aataagaaaa     120
cgacctgtaa tacatgaaaa atatcaatag gaattttgag ataatttggc aacatgcaat     180
ataatgatta taataaaaaa cttgtcttaa gactagagaa ctgctaattc aaaaaaaaca     240
aattgagata aatcaaatac caacggtttg gttttgaact gctgaaacac caaagttcaa     300
```

```
<210> SEQ ID NO 14
<211> LENGTH: 496
<212> TYPE: PRT
<213> ORGANISM: Caenorhabditis elegans

<400> SEQUENCE: 14
```

| | | | | | | | | | | | | | | |
|---|---|---|---|---|---|---|---|---|---|---|---|---|---|---|
|Met|Arg|Gln|Gln|Thr|Gly|Arg|Arg|Arg|Gln|Pro|Ser|Glu|Thr|Ser|
|1| | | |5| | | | |10| | | | |15|

| | | | | | | | | | | | | | | |
|---|---|---|---|---|---|---|---|---|---|---|---|---|---|---|
|Asn|Gly|Ser|Leu|Ala|Ser|Ser|Arg|Arg|Ser|Ser|Phe|Ala|Gln|Asn|Gly|
| | | | |20| | | | |25| | | | |30|

Asn Ser Ser Arg Lys Ser Ser Glu Met Arg Gly Pro Cys Glu Lys Val
             35                  40                  45

Val His Thr Ala Gln Asp Ser Leu Phe Ser Thr Ser Ser Gly Trp Thr
 50                  55                  60

Asn Phe Arg Gly Phe Phe Asn Leu Ser Ile Leu Leu Val Leu Ser
 65                  70                  75                  80

Asn Gly Arg Val Ala Leu Glu Asn Val Ile Lys Tyr Gly Ile Leu Ile
                 85                  90                  95

Thr Pro Leu Gln Trp Ile Ser Thr Phe Val Glu His His Tyr Ser Ile
            100                 105                 110

Trp Ser Trp Pro Asn Leu Ala Leu Ile Leu Cys Ser Asn Ile Gln Ile
            115                 120                 125

Leu Ser Val Phe Gly Met Glu Lys Ile Leu Glu Arg Gly Trp Leu Gly
        130                 135                 140

Asn Gly Phe Ala Ala Val Phe Tyr Thr Ser Leu Val Ile Ala His Leu
145                 150                 155                 160

Thr Ile Pro Val Val Thr Leu Thr His Lys Trp Lys Asn Pro Leu
                165                 170                 175

Trp Ser Val Val Met Met Gly Val Tyr Val Ile Glu Ala Leu Lys Phe
            180                 185                 190

Ile Ser Tyr Gly His Val Asn Tyr Trp Ala Arg Asp Ala Arg Arg Lys
            195                 200                 205

Ile Thr Glu Leu Lys Thr Gln Val Thr Asp Leu Ala Lys Lys Thr Cys
        210                 215                 220

Asp Pro Lys Gln Phe Trp Asp Leu Lys Asp Glu Leu Ser Met His Gln
225                 230                 235                 240

Met Ala Ala Gln Tyr Pro Ala Asn Leu Thr Leu Ser Asn Ile Tyr Tyr
                245                 250                 255

Phe Met Ala Ala Pro Thr Leu Cys Tyr Glu Phe Lys Phe Pro Arg Leu
            260                 265                 270

Leu Arg Ile Arg Lys His Phe Leu Ile Lys Arg Thr Val Glu Leu Ile
            275                 280                 285

Phe Leu Ser Phe Leu Ile Ala Ala Leu Val Gln Gln Trp Val Val Pro
        290                 295                 300

Thr Val Arg Asn Ser Met Lys Pro Leu Ser Glu Met Glu Tyr Ser Arg
305                 310                 315                 320

Cys Leu Glu Arg Leu Leu Lys Leu Ala Ile Pro Asn His Leu Ile Trp

```
                    325                 330                 335
Leu Leu Phe Phe Tyr Thr Phe Phe His Ser Phe Leu Asn Leu Ile Ala
            340                 345                 350

Glu Leu Leu Arg Phe Ala Asp Arg Glu Phe Tyr Arg Asp Phe Trp Asn
            355                 360                 365

Ala Glu Thr Ile Gly Tyr Phe Trp Lys Ser Trp Asn Ile Pro Val His
            370                 375                 380

Arg Phe Ala Val Arg His Ile Tyr Ser Pro Met Met Arg Asn Asn Phe
385                 390                 395                 400

Ser Lys Met Ser Ala Phe Phe Val Val Phe Val Ser Ala Phe Phe
            405                 410                 415

His Glu Tyr Leu Val Ser Val Pro Leu Lys Ile Phe Arg Leu Trp Ser
            420                 425                 430

Tyr Tyr Gly Met Met Gly Gln Ile Pro Leu Ser Ile Ile Thr Asp Lys
            435                 440                 445

Val Val Arg Gly Gly Arg Thr Gly Asn Ile Ile Val Trp Leu Ser Leu
            450                 455                 460

Ile Val Gly Gln Pro Leu Ala Ile Leu Met Tyr Gly His Asp Trp Tyr
465                 470                 475                 480

Ile Leu Asn Phe Gly Val Ser Ala Val Gln Asn Gln Thr Val Gly Ile
            485                 490                 495

<210> SEQ ID NO 15
<211> LENGTH: 257
<212> TYPE: DNA
<213> ORGANISM: Glycine max

<400> SEQUENCE: 15
aacggaattg agactccaga gaatatgcca aatgtattaa taattgtca caacttggaa      60 ggcttttgga aaactggca tgcttccttc aacaagtggc ttgtgaggta tatatacatt    120
cctcttgggg gatctaagaa aaagctacta aatgtgtggg ttgttttcac atttgttgca    180
atctggcatg atttagagtg gaagcttctt tcatgggcat ggttgacgtg tttattcttc    240
atccctgagt tggtttt                                                    257

<210> SEQ ID NO 16
<211> LENGTH: 234
<212> TYPE: DNA
<213> ORGANISM: Glycine max
<220> FEATURE:
<221> NAME/KEY: unsure
<222> LOCATION: (24)
<223> OTHER INFORMATION: n=a, t, c or g
<220> FEATURE:
<221> NAME/KEY: unsure
<222> LOCATION: (41)
<223> OTHER INFORMATION: n=a, t, c or g
<220> FEATURE:
<221> NAME/KEY: unsure
<222> LOCATION: (60)
<223> OTHER INFORMATION: n=a, t, c or g

<400> SEQUENCE: 16
gtaagcttca agagcttagc atanttcctg gttgcccta ncattatgtt accagccaan     60
ctatcctcgc acaccttata ttcgaaaggg ttggctgttt cgccaacttg tcaactgata   120
atatttacag gagttatggg atttataata gaacaataca ttaatcccat tgtacaaaat   180
tcacagcatc ctctcaaggg aaaccttctt tacgccatcg agagagttct gaag          234
```

```
<210> SEQ ID NO 17
<211> LENGTH: 275
<212> TYPE: DNA
<213> ORGANISM: Glycine max
<220> FEATURE:
<221> NAME/KEY: unsure
<222> LOCATION: (192)
<223> OTHER INFORMATION: n=a, t, c or g
<220> FEATURE:
<221> NAME/KEY: unsure
<222> LOCATION: (202)
<223> OTHER INFORMATION: n=a, t, c or g
<220> FEATURE:
<221> NAME/KEY: unsure
<222> LOCATION: (204)
<223> OTHER INFORMATION: n=a, t, c or g
<220> FEATURE:
<221> NAME/KEY: unsure
<222> LOCATION: (211)
<223> OTHER INFORMATION: n=a, t, c or g
<220> FEATURE:
<221> NAME/KEY: unsure
<222> LOCATION: (222)
<223> OTHER INFORMATION: n=a, t, c or g
<220> FEATURE:
<221> NAME/KEY: unsure
<222> LOCATION: (234)
<223> OTHER INFORMATION: n=a, t, c or g
<220> FEATURE:
<221> NAME/KEY: unsure
<222> LOCATION: (238)..(239)
<223> OTHER INFORMATION: n=a, t, c or g
<220> FEATURE:
<221> NAME/KEY: unsure
<222> LOCATION: (244)..(245)
<223> OTHER INFORMATION: n=a, t, c or g
<220> FEATURE:
<221> NAME/KEY: unsure
<222> LOCATION: (251)
<223> OTHER INFORMATION: n=a, t, c or g
<220> FEATURE:
<221> NAME/KEY: unsure
<222> LOCATION: (262)..(263)
<223> OTHER INFORMATION: n=a, t, c or g

<400> SEQUENCE: 17
gtggaatgcc aaaactgttg aagattattg gaggatgtgg aatatgcctg ttcacaaatg      60
gatgatccgc cacctatatt ttccatgttt aaggcacggt ataccaaagg ccgttgctct     120
tttaattgcc ttcctggttc tgctttattc catgagctgt gcatcgctgt tccttgccca     180
catattcaag tngtgggttt cngnggaatt nagtttcagg tnccttgggt ttcnaccnna     240
attnntnggc naaaaaattc cnngaaccccc ggggg                               275

<210> SEQ ID NO 18
<211> LENGTH: 267
<212> TYPE: DNA
<213> ORGANISM: Glycine max

<400> SEQUENCE: 18
ctgcttttgt atctggtgtc acgttgatgc tattaacttg cattgtgtgg ttaaaattgg      60
tgtcatatgc acatacaaac tatgatatga gagcacttac tgtttcgaat gaaaagggag     120
aaacattacc caatactttg atatggagta tccgtacact gtgaccttca ggagtttggc     180
atacttcatg gttgctccta cattatgcta tcagacaagc tatcctcgca caccttcagt     240
tcgaaagggt tgggtgtttc gtcaact                                         267

<210> SEQ ID NO 19
<211> LENGTH: 1895
<212> TYPE: DNA
```

<213> ORGANISM: Human
<220> FEATURE:
<221> NAME/KEY: unsure
<222> LOCATION: (209)
<223> OTHER INFORMATION: n=a, t, c or g

<400> SEQUENCE: 19

```
gtctggtgtg atggggacag ggagggactt ccccttaccc agcactggtg ttggctgagg      60
tgggtgctga gtctcagagc ttggcatgga gaccagacag ggctgggtct gcaagcctga     120
ggctgccgcc ctgagctcgg gctgggacgt gcccagaggt gttgggagga tctggggtga     180
gtaccctgtg gccaggacta aggggctnc accctcctgt ccatccctcg cagatcttga     240
gcaatgcccg gttatttctg gagaacctca tcaagtatgg catcctggtg gaccccatcc     300
aggtggtttc tctgttcctg aaggatccct atagctggcc cgcccatgc ctggttattg      360
cggccaatgt ctttgctgtg gctgcattcc aggttgagaa gcgcctggcg gtgggtgccc     420
tgacggagca ggcgggactg ctgctgcacg tggccaacct ggccaccatt ctgtgtttcc     480
cagcggctgt ggtcttactg gttgagtcta tcactccagt gggctccctg ctggcgctga     540
tggcgcacac catcctcttc ctcaagctct tctcctaccg cgacgtcaac tcatggtgcc     600
gcagggccag ggccaaggct gcctctgcag ggaagaaggc cagcagtgct gctgccccgc     660
acaccgtgag ctacccggac aatctgacct accgcgatct ctactacttc ctcttcgccc     720
ccaccttgtg ctacgagctc aactttcccc gctctccccg catccggaag cgctttctgc     780
tgcgacggat ccttgagatg ctgttcttca cccagctcca ggtggggctg atccagcagt     840
ggatggtccc caccatccag aactccatga agcccttcaa ggacatggac tactcacgca     900
tcatcgagcg cctcctgaag ctggcggtcc ccaatcacct catctggctc atcttcttct     960
actggctctt ccactcctgc ctgaatgccg tggctgagct catgcagttt ggagaccggg    1020
agttctaccg ggactggtgg aactccgagt ctgtcaccta cttctggcag aactggaaca    1080
tccctgtgca caagtggtgc atcagacact tctacaagcc catgcttcga cggggcagca    1140
gcaagtggat ggccaggaca ggggtgttcc tggcctcggc cttcttccac gagtacctgg    1200
tgagcgtccc tctgcgaatg ttccgcctct gggcgttcac gggcatgatg gctcagatcc    1260
cactggcctg gttcgtgggc cgcttttttcc agggcaacta tggcaacgca gctgtgtggc    1320
tgtcgctcat catcggacag ccaatagccg tcctcatgta cgtccacgac tactacgtgc    1380
tcaactatga ggccccagcg gcagaggcct gagctgcacc tgagggcctg gcttctcact    1440
gccacctcac acccgctgcc agagcccacc tctcctccta ggcctcgagt gctggggatg    1500
ggcctggctg cacagcatcc tcctctggtc ccagggaggc ctctctgccc ctatggggct    1560
ctgtcctgca cccctcaggg atggcgacag caggccagac acagtctgat gccagctggg    1620
agtcttgctg accctgcccc gggtccgagg gtgtcaataa agtgctgtcc agtgacctct    1680
tcagcctgcc aggggcctgg ggcctggtgg ggggtatggc cacacccaca agggcgagtg    1740
ccagagctgt gtggacagct gtcccaggac ctgccgggga gcagcagctc cactgcagca    1800
gggcgggcat ggccggtagg gggagtgcaa ggccaggcag acgcccccat tccccacact    1860
cccctaccta gaaaagctca gctcaggcgt cctct                              1895
```

<210> SEQ ID NO 20
<211> LENGTH: 519
<212> TYPE: DNA
<213> ORGANISM: Montierella alphina
<220> FEATURE:
<221> NAME/KEY: unsure

```
<222> LOCATION: (4)..(7)
<223> OTHER INFORMATION: n=a, t, c or g
<220> FEATURE:
<221> NAME/KEY: unsure
<222> LOCATION: (22)
<223> OTHER INFORMATION: n=a, t, c or g
<220> FEATURE:
<221> NAME/KEY: unsure
<222> LOCATION: (46)
<223> OTHER INFORMATION: n=a, t, c or g
<220> FEATURE:
<221> NAME/KEY: unsure
<222> LOCATION: (48)
<223> OTHER INFORMATION: n=a, t, c or g
<220> FEATURE:
<221> NAME/KEY: unsure
<222> LOCATION: (52)
<223> OTHER INFORMATION: n=a, t, c or g
<220> FEATURE:
<221> NAME/KEY: unsure
<222> LOCATION: (58)
<223> OTHER INFORMATION: n=a, t, c or g
<220> FEATURE:
<221> NAME/KEY: unsure
<222> LOCATION: (64)
<223> OTHER INFORMATION: n=a, t, c or g
<220> FEATURE:
<221> NAME/KEY: unsure
<222> LOCATION: (68)
<223> OTHER INFORMATION: n=a, t, c or g
<220> FEATURE:
<221> NAME/KEY: unsure
<222> LOCATION: (73)
<223> OTHER INFORMATION: n=a, t, c or g
<220> FEATURE:
<221> NAME/KEY: unsure
<222> LOCATION: (80)
<223> OTHER INFORMATION: n=a, t, c or g
<220> FEATURE:
<221> NAME/KEY: unsure
<222> LOCATION: (82)..(84)
<223> OTHER INFORMATION: n=a, t, c or g
<220> FEATURE:
<221> NAME/KEY: unsure
<222> LOCATION: (93)
<223> OTHER INFORMATION: n=a, t, c or g
<220> FEATURE:
<221> NAME/KEY: unsure
<222> LOCATION: (102)..(103)
<223> OTHER INFORMATION: n=a, t, c or g
<220> FEATURE:
<221> NAME/KEY: unsure
<222> LOCATION: (113)
<223> OTHER INFORMATION: n=a, t, c or g
<220> FEATURE:
<221> NAME/KEY: unsure
<222> LOCATION: (148)
<223> OTHER INFORMATION: n=a, t, c or g
<220> FEATURE:
<221> NAME/KEY: unsure
<222> LOCATION: (430)
<223> OTHER INFORMATION: n=a, t, c or g

<400> SEQUENCE: 20
gagnnnngna acgtttagcc tnccgtagcc gccaaaatcc aagggncnac cnaccctncg      60
ttanactnaa ttngaaaatn cnnncccaac ttnaggnact tnnagncccc ccnacttgac     120
aacggagcac tatatttacc ccgtggtngt tcaacccagc catctcaccc ttgcgagcat     180
tggtgctgct cttgataccc ttcatgctta actatctcat gatcttttac atcattttcg     240
agtgcatctg caacgccttt gcggaactaa gttgctttgc ggatcgcaac ttttacgagg     300
attggtggaa ctgcgtcagc tttgatgagt gggcacgcaa atggaacaag cctgtgcaac     360
acttcttgct ccgccacgtg tacgactcga gcatccgagt ccttccactt gtccgaaatc     420
```

| | |
|---|---|
| caatgccgcn aattgcaaac gttccttccc ggtcgtcaat gcgttcaacg aacctgggtg | 480 |
| aagaatgggt ggtgacaacg ttaaagtgcg cccggtatc | 519 |

```
<210> SEQ ID NO 21
<211> LENGTH: 518
<212> TYPE: DNA
<213> ORGANISM: mouse

<400> SEQUENCE: 21
```

| | |
|---|---|
| tggaggacaa cgcggggtct gatacgactc actataggga atttggccct cgagcagtag | 60 |
| attcggcacg atgggcacga ggactccatc atgttcctca agctttattc ctaccgggat | 120 |
| gtcaacctgt ggtgccgcca gcgaagggtc aaggccaaag ctgtctctac agggaagaag | 180 |
| gtcagtgggg ctgctgcgag caagctgtga gctatccaga caacctgacc taccgagatc | 240 |
| tcgattactt catctttgct cctactttgt gttatgaact caactttcct cggtcccccc | 300 |
| gaatacgaga gcgcttctg ctacgacgag ttcttgagat gctcttttt acccagcttc | 360 |
| aagtggggct gatccaacag tggatggtcc ctactatcca gaactccatg gaagcccttt | 420 |
| caagagcttc tgcagttttg gagaccgcga gttctacaga gattggtgga atgctgagtc | 480 |
| tgtcaccgac ttttggcaga actggaatat ccccgtgg | 518 |

```
<210> SEQ ID NO 22
<211> LENGTH: 299
<212> TYPE: DNA
<213> ORGANISM: mouse

<400> SEQUENCE: 22
```

| | |
|---|---|
| ccatgatggc tcaggtccca ctggcctgga ttgtgggccg attcttccaa gggaactatg | 60 |
| gcaatgcagc tgtgtgggtg acactcatca ttgggcaacc ggtggctgtc tcatgtatgt | 120 |
| ccacgactac tacgtgctca actacgatgc cccagtgggt catgagctac tgccaaaggc | 180 |
| agccctccct aacctgggcc tggagttctg gaggggttcc tggctgcctg cacactcctc | 240 |
| ctagtctggg aggcctctct gccccctatgc gctactcctg ctcttgggga tggcatttg | 299 |

```
<210> SEQ ID NO 23
<211> LENGTH: 1766
<212> TYPE: DNA
<213> ORGANISM: Rat

<400> SEQUENCE: 23
```

| | |
|---|---|
| cacgactggg ccgcgacgtg gtgcgggccg aagccatggg cgaccgcgga ggcgcgggaa | 60 |
| gctctcggcg tcggaggacc ggctcgcggg tttccatcca gggtggtagt gggcccatgg | 120 |
| tagacgaaga ggaggtgcga gacgccgctg tgggccccga cttgggcgcc gggggtgacg | 180 |
| ctccggctcc ggctccggtt ccggctccag cccacacccg ggacaaagac cggcagacca | 240 |
| gcgtgggcga cggccactgg gagctgaggt gccatcgtct gcaagactct tgttcagct | 300 |
| cagacagcgg tttcagcaat taccgtggta tcctgaattg gtgcgtggtg atgctgatcc | 360 |
| tgagtaatgc aaggttattt ttagagaatc ttatcaagta tggcatcctg gtggatccca | 420 |
| tccaggtggt gtctctgttt ctgaaggacc cctacagctg gcctgcccca tgcttgatca | 480 |
| ttgcatccaa tatctttatt gtggctacat ttcagattga gaagcgcctg tcagtgggtg | 540 |
| ccctgacaga gcagatgggg ctgctgctac atgtggttaa cctggccaca attatctgct | 600 |
| tcccagcagc tgtggcctta ctggttgagt ctatcactcc agtgggttcc ctgtttgctc | 660 |
| tggcatcata ctccatcatc ttcctcaagc ttttctccta ccgggatgtc aatctgtggt | 720 |

```
gccgccagcg aagggtcaag gccaaagctg tgtctgcagg gaagaaggtc agtggggctg      780
ctgcccagaa cactgtaagc tatccggaca acctgaccta ccgagatctc tattacttca      840
tctttgctcc tactttgtgt tatgaactca actttcctcg atccccccga atacgaaagc      900
gctttctgct acggcgggtt cttgagatgc tcttttttcac ccagcttcaa gtggggctga     960
tccagcagtg gatggtccct actatccaga actccatgaa gcccttcaag gacatggact     1020
attcacgaat cattgagcgt ctcttaaagc tggcggtccc caaccatctg atatggctca     1080
tcttcttcta ttggctttc cactcatgtc tcaatgctgt ggcagagctc ctgcagtttg      1140
gagaccgcga gttctacagg gactggtgga atgctgagtc tgtcacctac ttttggcaga     1200
actggaatat ccccgtgcac aagtggtgca tcagacactt ctacaagcct atgctcagac     1260
tgggcagcaa caaatggatg ccaggactg gggtcttttt ggcgtcagcc ttcttccatg     1320
agtacctagt gagcattccc ctgaggatgt tccgcctctg gcattcaca gccatgatgg      1380 ctcaggtccc actggcctgg attgtgaacc gcttcttcca agggaactat ggcaatgcag     1440
ctgtgtgggt gacactcatc attgggcaac cggtggctgt gctcatgtat gtccacgact     1500
actacgtgct caactatgat gccccagtgg gggcctgagc tactgccaaa ggccagccct     1560
ccctaacctg ggcctggagt tctggagggc ttcctggctg cctgcacact cctcctagtc     1620
tgggaggcct ctctgcccct atgggcccta ctcctgctct tggggatggc acctgagtcc     1680
agctggtatg agccagtgct gggagtctgt gctgaccagg ggctgaggat atcaataaag     1740
agctatctaa aaaaaaaaaa aaaaaa                                          1766

<210> SEQ ID NO 24
<211> LENGTH: 500
<212> TYPE: PRT
<213> ORGANISM: rat

<400> SEQUENCE: 24

Met Gly Asp Arg Gly Gly Ala Gly Ser Ser Arg Arg Arg Thr Gly
 1               5                  10                  15

Ser Arg Val Ser Ile Gln Gly Gly Ser Gly Pro Met Val Asp Glu Glu
            20                  25                  30

Glu Val Arg Asp Ala Ala Val Gly Pro Asp Leu Gly Ala Gly Gly Asp
        35                  40                  45

Ala Pro Ala Pro Ala Pro Val Pro Ala Pro Ala His Thr Arg Asp Lys
    50                  55                  60

Asp Arg Gln Thr Ser Val Gly Asp Gly His Trp Glu Leu Arg Cys His
65                  70                  75                  80

Arg Leu Gln Asp Ser Leu Phe Ser Asp Ser Gly Phe Ser Asn Tyr
                85                  90                  95

Arg Gly Ile Leu Asn Trp Cys Val Val Met Leu Ile Leu Ser Asn Ala
            100                 105                 110

Arg Leu Phe Leu Glu Asn Leu Ile Lys Tyr Gly Ile Leu Val Asp Pro
        115                 120                 125

Ile Gln Val Val Ser Leu Phe Leu Lys Asp Pro Tyr Ser Trp Pro Ala
    130                 135                 140

Pro Cys Leu Ile Ile Ala Ser Asn Ile Phe Ile Val Ala Thr Phe Gln
145                 150                 155                 160

Ile Glu Lys Arg Leu Ser Val Gly Ala Leu Thr Glu Gln Met Gly Leu
                165                 170                 175

Leu Leu His Val Val Asn Leu Ala Thr Ile Ile Cys Phe Pro Ala Ala
```

```
            180                 185                 190
Val Ala Leu Leu Val Glu Ser Ile Thr Pro Val Gly Ser Leu Phe Ala
        195                 200                 205

Leu Ala Ser Tyr Ser Ile Ile Phe Leu Lys Leu Phe Ser Tyr Arg Asp
    210                 215                 220

Val Asn Leu Trp Cys Arg Gln Arg Val Lys Ala Lys Ala Val Ser
225                 230                 235                 240

Ala Gly Lys Lys Val Ser Gly Ala Ala Gln Asn Thr Val Ser Tyr
                245                 250                 255

Pro Asp Asn Leu Thr Tyr Arg Asp Leu Tyr Tyr Phe Ile Phe Ala Pro
            260                 265                 270

Thr Leu Cys Tyr Glu Leu Asn Phe Pro Arg Ser Pro Arg Ile Arg Lys
        275                 280                 285

Arg Phe Leu Leu Arg Arg Val Leu Glu Met Leu Phe Phe Thr Gln Leu
    290                 295                 300

Gln Val Gly Leu Ile Gln Gln Trp Met Val Pro Thr Ile Gln Asn Ser
305                 310                 315                 320

Met Lys Pro Phe Lys Asp Met Asp Tyr Ser Arg Ile Ile Glu Arg Leu
                325                 330                 335

Leu Lys Leu Ala Val Pro Asn His Leu Ile Trp Leu Ile Phe Phe Tyr
            340                 345                 350

Trp Leu Phe His Ser Cys Leu Asn Ala Val Ala Glu Leu Leu Gln Phe
        355                 360                 365

Gly Asp Arg Glu Phe Tyr Arg Asp Trp Trp Asn Ala Glu Ser Val Thr
    370                 375                 380

Tyr Phe Trp Gln Asn Trp Asn Ile Pro Val His Lys Trp Cys Ile Arg
385                 390                 395                 400

His Phe Tyr Lys Pro Met Leu Arg Leu Gly Ser Asn Lys Trp Met Ala
                405                 410                 415

Arg Thr Gly Val Phe Leu Ala Ser Ala Phe Phe His Glu Tyr Leu Val
            420                 425                 430

Ser Ile Pro Leu Arg Met Phe Arg Leu Trp Ala Phe Thr Ala Met Met
        435                 440                 445

Ala Gln Val Pro Leu Ala Trp Ile Val Asn Arg Phe Phe Gln Gly Asn
    450                 455                 460

Tyr Gly Asn Ala Ala Val Trp Val Thr Leu Ile Ile Gly Gln Pro Val
465                 470                 475                 480

Ala Val Leu Met Tyr Val His Asp Tyr Tyr Val Leu Asn Tyr Asp Ala
                485                 490                 495

Pro Val Gly Ala
        500

<210> SEQ ID NO 25
<211> LENGTH: 325
<212> TYPE: DNA
<213> ORGANISM: Zea mays
<220> FEATURE:
<221> NAME/KEY: unsure
<222> LOCATION: (6)
<223> OTHER INFORMATION: n=a, t, c or g
<220> FEATURE:
<221> NAME/KEY: unsure
<222> LOCATION: (14)
<223> OTHER INFORMATION: n=a, t, c or g
<220> FEATURE:
<221> NAME/KEY: unsure
<222> LOCATION: (16)
<223> OTHER INFORMATION: n=a, t, c or g
```

-continued

```
<220> FEATURE:
<221> NAME/KEY: unsure
<222> LOCATION: (18)
<223> OTHER INFORMATION: n=a, t, c or g
<220> FEATURE:
<221> NAME/KEY: unsure
<222> LOCATION: (32)
<223> OTHER INFORMATION: n=a, t, c or g
<220> FEATURE:
<221> NAME/KEY: unsure
<222> LOCATION: (67)
<223> OTHER INFORMATION: n=a, t, c or g
<220> FEATURE:
<221> NAME/KEY: unsure
<222> LOCATION: (71)
<223> OTHER INFORMATION: n=a, t, c or g
<220> FEATURE:
<221> NAME/KEY: unsure
<222> LOCATION: (76)
<223> OTHER INFORMATION: n=a, t, c or g
<220> FEATURE:
<221> NAME/KEY: unsure
<222> LOCATION: (82)..(83)
<223> OTHER INFORMATION: n=a, t, c or g
<220> FEATURE:
<221> NAME/KEY: unsure
<222> LOCATION: (85)
<223> OTHER INFORMATION: n=a, t, c or g
<220> FEATURE:
<221> NAME/KEY: unsure
<222> LOCATION: (94)
<223> OTHER INFORMATION: n=a, t, c or g
<220> FEATURE:
<221> NAME/KEY: unsure
<222> LOCATION: (107)
<223> OTHER INFORMATION: n=a, t, c or g
<220> FEATURE:
<221> NAME/KEY: unsure
<222> LOCATION: (111)
<223> OTHER INFORMATION: n=a, t, c or g
<220> FEATURE:
<221> NAME/KEY: unsure
<222> LOCATION: (170)
<223> OTHER INFORMATION: n=a, t, c or g
<220> FEATURE:
<221> NAME/KEY: unsure
<222> LOCATION: (176)
<223> OTHER INFORMATION: n=a, t, c or g
<220> FEATURE:
<221> NAME/KEY: unsure
<222> LOCATION: (180)
<223> OTHER INFORMATION: n=a, t, c or g
<220> FEATURE:
<221> NAME/KEY: unsure
<222> LOCATION: (204)..(209)
<223> OTHER INFORMATION: n=a, t, c or g
<220> FEATURE:
<221> NAME/KEY: unsure
<222> LOCATION: (261)
<223> OTHER INFORMATION: n=a, t, c or g
<220> FEATURE:
<221> NAME/KEY: unsure
<222> LOCATION: (289)
<223> OTHER INFORMATION: n=a, t, c or g
<220> FEATURE:
<221> NAME/KEY: unsure
<222> LOCATION: (296)
<223> OTHER INFORMATION: n=a, t, c or g
<220> FEATURE:
<221> NAME/KEY: unsure
<222> LOCATION: (301)
<223> OTHER INFORMATION: n=a, t, c or g
<220> FEATURE:
<221> NAME/KEY: unsure
<222> LOCATION: (304)
<223> OTHER INFORMATION: n=a, t, c or g
<220> FEATURE:
<221> NAME/KEY: unsure
<222> LOCATION: (317)
```

<223> OTHER INFORMATION: n=a, t, c or g
<220> FEATURE:
<221> NAME/KEY: unsure
<222> LOCATION: (321)
<223> OTHER INFORMATION: n=a, t, c or g

<400> SEQUENCE: 25

```
taatcnaacc tcgntncngg ttcagctgta tnccatgaga tatgtaatgc ggtgccgtgc      60
cacatantca natctnggca tnncngggat catngttcag ataccgntgg nattcttgac     120
aagatatctc catgctacgt tcaagcatgt aatggtgggc aacatgatan tttggntctn     180
cagtatagtc ggacagccga tgtnnnnnna tctatactac catgacgtca tgaacaggca     240
ggcccaggca agtagatagt ncggcagaga catgtacttc aacatcganc atcagnagca     300
nacngagcga gcggcangaa ncagc                                           325
```

<210> SEQ ID NO 26
<211> LENGTH: 262
<212> TYPE: DNA
<213> ORGANISM: Zea mays

<400> SEQUENCE: 26

```
gaagtatggc ttattaataa gatctggctt ttggtttaat gctacatcat tgcgagactg      60
gccactgcta atgtgttgcc ttagtctacc catatttccc cttggtgcat ttgcagtcga     120
aaagttggca ttcaacaatc tcattagtga tcctgctact acctgttttc acatcctttt     180
tacaacattt gaaattgtat atccagtgct cgtgattctt aagtgtgatt ctgcagtttt     240
acaggctttg tgttgatgtt ta                                              262
```

<210> SEQ ID NO 27
<211> LENGTH: 253
<212> TYPE: DNA
<213> ORGANISM: Zea mays

<400> SEQUENCE: 27

```
agaaaatgga acatgcctgt gcataaatgg attgttcgtc atatatattt tccttgcatg      60
cgaaatggta tatcaaagga agttgctgtt tttatatcgt tcttgtttct gctgtacttc     120
atgagttatg tgttgctgtt ccctgccaca tactcaagtt ctgggctttt tttaggaatc     180
atgcttcaga ttcccctcat catattgaca tcatacctca aaataaaatt cagtgacaca     240
atggttggca ata                                                        253
```

<210> SEQ ID NO 28
<211> LENGTH: 254
<212> TYPE: DNA
<213> ORGANISM: Zea mays

<400> SEQUENCE: 28

```
tgaagtatgg cttattaata agatctggct tttggtttaa tgctacatca ttgcgagact      60
ggccactgct aatgtgttgc cttagtctac ccatatttcc ccttggtgca tttgcagtcg     120
aaaagttggc attcaacaat ctcattagtg atcctgctac tacctgtttt cacatccttt     180
ttacaacatt tgaaattgta tatccagtgc tcgtgattct taagtgtgat tctgcagttt     240
tatcaggctt tgtg                                                       254
```

<210> SEQ ID NO 29
<211> LENGTH: 1645
<212> TYPE: DNA
<213> ORGANISM: Maize

<400> SEQUENCE: 29

```
gaattcggct cgagggcggc ggctgcgggt ggcggtggtg ggaggcggcc ccgccggtgg    60
cgccgcggcg gaggcgctgg ccaagggcgg cgtggagacg gtgctgatcg agcggaagat   120
ggacaactgc aagccctgcg gcggcgctat cccgctgtgc atggtgtcgg agttcgacct   180
gccgctcgac ctcgtggacc gcaaggtgag gaagatgaag atgatttcgc cgtccaacgt   240
cgccgtcgac atcggccgca cgctcgcgcc ccacgagtac atcgggatgg tcaggcgcga   300
ggtgctcgac gcctacctcc gctcacgggc acagtccgtc ggcgcggagg tcgtcaacgg   360
cctcttccta aggtacgagg cgcccaaaga gccgaacggc tcgtacgtgg tgcactacaa   420
ccactacgac ggcagcaacg gcaaggtcgg cggcgagaag cggtcgttcg aggtggacgc   480
gatcgtgggc gcggacggcg ccaactctcg cgtggccaac gacatgggcg cgggcgacta   540
cgagtacgcc atcgcgttcc aggagcgcgt caagatcccc gacgacaaga tggtgtacta   600
cgaggagcgc gcggagatgt acgtcggcga cgacgtctct cccgacttct acggctgggt   660
gttccccaag tgcgaccacg tcgccgtcgg caccggcacc gtcacgcaca aggccgacat   720
caagaagttt caggccgcca cgcgcctccg cgccaaggac aagattgagg cggcaagat   780
catccgcgtc gaggcgcacc ccatcccga gcacccagg cctaagaggg tgtccgggcg   840
ggtgacgctt gtgggcgatg ccgcggggta cgtgaccaag tgctctggcg agggcatcta   900
cttcgcggcg aagagcgggc ggatgtgcgc cgaggccatc gtggcgggct ccgccaacgg   960
gacgcggatg gtggaggaga cgacctgcg caagtacctg ccgagttcg accgcctcta  1020
ctggcccact acaaggtgc tggacatcct gcagaaggtg ttctaccgct ccaacgcggc  1080
gcgcgaggcc ttcgtggaga tgtgcgccga cgactacgtg cagaagatga ccttcgacag  1140
ctacctctac aagcgcgtcg tgccgggcaa cccgctcgac gacatcaagc tcgccgtcaa  1200
caccatcggc agcctcgtca gggccaccgc actgcgccgg gagatggaga aggtcacctt  1260
gtgagccgcc gcccgccacc tcattgccgt cgaaatggtg tcgcagctga tcggccggtg  1320
tattagtaga gatttgcggc tgatcgggtt aatttaggcc aacatgcgtg ggcagtgggc  1380
gcggagagga agagaaacaa gttgtgcaag tgcagcaagt agatcaaaag tgctgcctgt  1440
ttgtatcgat ggatcctgca acatatagca tctggtgatg ttgagaattc ggagcagttc  1500
atcgactgga ttctgacgcc ggcaagcatc gacgtcaatg aatgtctaat acttagtaca  1560
tcaagacatg taataaaact gaaactcccc cgttctggtt caaaaaaaaa aaaaaaaaa   1620
aaaaaaaaaa aaaagggcg gccgc                                         1645
```

<210> SEQ ID NO 30
<211> LENGTH: 541
<212> TYPE: PRT
<213> ORGANISM: Maize
<220> FEATURE:
<221> NAME/KEY: UNSURE
<222> LOCATION: (414)
<223> OTHER INFORMATION: Xaa=any amino acid
<220> FEATURE:
<221> NAME/KEY: UNSURE
<222> LOCATION: (445)
<223> OTHER INFORMATION: Xaa=any amino acid
<220> FEATURE:
<221> NAME/KEY: UNSURE
<222> LOCATION: (482)

```
<223> OTHER INFORMATION: Xaa=any amino acid
<220> FEATURE:
<221> NAME/KEY: UNSURE
<222> LOCATION: (498)
<223> OTHER INFORMATION: Xaa=any amino acid
<220> FEATURE:
<221> NAME/KEY: UNSURE
<222> LOCATION: (509)
<223> OTHER INFORMATION: Xaa=any amino acid
<220> FEATURE:
<221> NAME/KEY: UNSURE
<222> LOCATION: (517)..(518)
<223> OTHER INFORMATION: Xaa=any amino acid
<220> FEATURE:
<221> NAME/KEY: UNSURE
<222> LOCATION: (520)
<223> OTHER INFORMATION: Xaa=any amino acid

<400> SEQUENCE: 30

Leu Arg Val Ala Val Gly Gly Gly Pro Ala Gly Gly Ala Ala Ala
  1               5                  10                  15

Glu Ala Leu Ala Lys Gly Gly Val Glu Thr Val Leu Ile Glu Arg Lys
             20                  25                  30

Met Asp Asn Cys Lys Pro Cys Gly Gly Ala Ile Pro Leu Cys Met Val
             35                  40                  45

Ser Glu Phe Asp Leu Pro Leu Asp Leu Val Asp Arg Lys Val Arg Lys
         50                  55                  60

Met Lys Met Ile Ser Pro Ser Asn Val Ala Val Asp Ile Gly Arg Thr
 65                  70                  75                  80

Leu Ala Pro His Glu Tyr Ile Gly Met Val Arg Arg Glu Val Leu Asp
                 85                  90                  95

Ala Tyr Leu Arg Ser Arg Ala Gln Ser Val Gly Ala Glu Val Val Asn
                100                 105                 110

Gly Leu Phe Leu Arg Tyr Glu Ala Pro Lys Glu Pro Asn Gly Ser Tyr
            115                 120                 125

Val Val His Tyr Asn His Tyr Asp Gly Ser Asn Gly Lys Val Gly Gly
        130                 135                 140

Glu Lys Arg Ser Phe Glu Val Asp Ala Ile Val Gly Ala Asp Gly Ala
145                 150                 155                 160

Asn Ser Arg Val Ala Asn Asp Met Gly Ala Gly Asp Tyr Glu Tyr Ala
                165                 170                 175

Ile Ala Phe Gln Glu Arg Val Lys Ile Pro Asp Asp Lys Met Val Tyr
            180                 185                 190

Tyr Glu Glu Arg Ala Glu Met Tyr Val Gly Asp Asp Val Ser Pro Asp
        195                 200                 205

Phe Tyr Gly Trp Val Phe Pro Lys Cys Asp His Val Ala Val Gly Thr
    210                 215                 220

Gly Thr Val Thr His Lys Ala Asp Ile Lys Lys Phe Gln Ala Ala Thr
225                 230                 235                 240

Arg Leu Arg Ala Lys Asp Lys Ile Glu Gly Lys Ile Ile Arg Val
                245                 250                 255

Glu Ala His Pro Ile Pro Glu His Pro Arg Pro Lys Arg Val Ser Gly
            260                 265                 270

Arg Val Thr Leu Val Gly Asp Ala Ala Gly Tyr Val Thr Lys Cys Ser
        275                 280                 285
```

-continued

```
Gly Glu Gly Ile Tyr Phe Ala Ala Lys Ser Gly Arg Met Cys Ala Glu
            290                 295                 300

Ala Ile Val Ala Gly Ser Ala Asn Gly Thr Arg Met Val Glu Glu Ser
305                 310                 315                 320

Asp Leu Arg Lys Tyr Leu Ala Glu Phe Asp Arg Leu Tyr Trp Pro Thr
                325                 330                 335

Tyr Lys Val Leu Asp Ile Leu Gln Lys Val Phe Tyr Arg Ser Asn Ala
            340                 345                 350

Ala Arg Glu Ala Phe Val Glu Met Cys Ala Asp Asp Tyr Val Gln Lys
        355                 360                 365

Met Thr Phe Asp Ser Tyr Leu Tyr Lys Arg Val Val Pro Gly Asn Pro
    370                 375                 380

Leu Asp Asp Ile Lys Leu Ala Val Asn Thr Ile Gly Ser Leu Val Arg
385                 390                 395                 400

Ala Thr Ala Leu Arg Arg Glu Met Glu Lys Val Thr Leu Xaa Ala Ala
                405                 410                 415

Ala Arg Asp Val Ile Ala Val Glu Met Val Ser Gln Leu Ile Gly Arg
            420                 425                 430

Cys Ile Ser Arg Asp Leu Arg Leu Ile Gly Leu Ile Xaa Ala Asn Met
        435                 440                 445

Arg Gly Gln Trp Ala Arg Arg Gly Arg Glu Thr Ser Cys Ala Ser Ala
    450                 455                 460

Ala Ser Arg Ser Lys Val Leu Pro Val Cys Ile Asp Gly Ser Cys Asn
465                 470                 475                 480

Ile Xaa His Leu Val Met Leu Arg Ile Arg Ser Ser Ser Thr Gly
                485                 490                 495

Phe Xaa Arg Arg Gln Ala Ser Thr Ser Met Asn Val Xaa Tyr Leu Val
            500                 505                 510

His Gln Asp Met Xaa Xaa Asn Xaa Asn Ser Pro Val Leu Val Gln Lys
        515                 520                 525

Lys Lys Lys Lys Lys Lys Lys Lys Lys Gly Gly Arg
    530                 535                 540

<210> SEQ ID NO 31
<211> LENGTH: 80
<212> TYPE: PRT
<213> ORGANISM: Artificial Sequence
<220> FEATURE:
<223> OTHER INFORMATION: Description of Artificial Sequence: transit
      peptide

<400> SEQUENCE: 31

Met Ala Ser Ser Met Ile Ser Ser Pro Ala Val Thr Thr Val Asn Arg
1               5                   10                  15

Ala Gly Ala Gly Met Val Ala Pro Phe Thr Gly Leu Lys Ser Met Ala
            20                  25                  30

Gly Phe Pro Phe Thr Gly Leu Lys Ser Met Ala Gly Phe Pro Thr Arg
        35                  40                  45

Lys Thr Asn Asn Asp Ile Thr Ser Ile Ala Ser Asn Gly Gly Arg Val
    50                  55                  60

Gln Cys Met Gln Val Trp Pro Pro Ile Gly Lys Lys Lys Phe Glu Thr
65                  70                  75                  80
```

TRANSGENIC PLANTS CONTAINING ALTERED LEVELS OF STEROL COMPOUNDS AND TOCOPHEROLS

CROSS REFERENCE TO RELATED APPLICATIONS

This application is a continuation of Ser. No. 09/548,256, filed Apr. 12, 2000 now abandoned and claims priority from provisional application 60/128,995, filed Apr. 12, 1999, which is hereby incorporated by reference in its entirety for all purposes.

BACKGROUND OF THE INVENTION

1. Field of the Invention

The present invention relates to transgenic plants having improved nutritional characteristics. More particularly, the present invention relates to transgenic plants, fruit and vegetable parts of which contain modified levels of sterol compounds, such as elevated levels of beneficial phytosterols, e.g., sitosterol, phytostanols, e.g., sitostanol, and esters thereof. Such transgenic plants can also contain elevated levels of tocopherols, such as α-tocopherol. In addition, these transgenic plants can contain reduced levels of campesterol and campestanol, and their respective esters, in their fruit and vegetable parts. Nucleic acid sequences encoding a variety of different enzymes that affect the biosynthesis and accumulation of sterol compounds and tocopherols in plants, and methods for using these sequences to produce such transgenic plants, are also provided. These methods comprise, for example, introducing a 3-hydroxysteroid oxidase such as a cholesterol oxidase, optionally in combination with a steroid 5α-reductase, and further optionally in combination with at least one tocopherol biosynthetic enzyme, into plants to elevate the levels of sitostanol and tocopherols, respectively, especially in seeds.

2. Description of Related Art

Phytosterols and Phytostanols

Phytosterols and phytostanols are well known to be beneficial for lowering serum cholesterol (Ling et al. (1995) *Life Sciences* 57: 195-206) and reducing the risk of cardiac disease. These compounds are poorly absorbed in the liver, and block the absorption of dietary cholesterol. Phytosterols and phytostanols, however, are present only in low amounts in seeds of dicotyledonous plants such as soybean, cotton, etc. Recently, strong evidence has been obtained demonstrating the role of phytostanols (hydrogenated forms of phytosterols, for example sitostanol) in reducing serum cholesterol in humans (Ling et al., supra). Ferulate and fatty acyl esters of sitostanol are naturally present in cereal grains in low levels (Seitz (1989) *J. Agric. Food Chem.* 37: 662-667; Dyas et al. (1993) *Phytochem.* 34: 17-29). In addition to phytosterols and phytostanols, grains and seeds also contain tocopherols and tocotrienols. Tocopherols act as antioxidants, and play a major role in protecting cells from damage caused by free radicals (Halliwell (1997) *Nutrition Review* 55: 44-60).

Insect-Resistant Transgenic Plants Expressing 3-Hydroxysteroid Oxidases

U.S. Pat. No. 5,518,908 discloses a method of controlling insect infestation in plants, comprising expressing a structural coding sequence encoding a 3-hydroxysteroid oxidase in cells of such plants, or in plant-colonizing microorganisms that can be applied to the plants, to impart insect resistance to the latter. In the case of transgenic plants, the goal was to provide monocotyledonous and dicotyledonous plants constitutively expressing an insecticidally effective amount of a 3-hydroxysteroid oxidase in plant parts such as leaves, flowers, and, in the case of cotton, bolls. The inventors expressed a preference for the use of constitutive promoters such as the nos, ocs, CaMV 19S and 35S, ssRUBISCO, and FMV 35S promoters to achieve this goal. Expression of the 3-hydroxysteroid oxidase in the cell cytoplasm, in extracellular spaces via the use of a secretory signal sequence, and in vacuoles and chloroplasts via the use of appropriate targeting sequences, is disclosed. However, no transgenic plants expressing a 3-hydroxysteroid oxidase transgene were produced. The invention disclosed in U.S. Pat. No. 5,518,908 is therefore distinctly different from that provided herein, as will become apparent from the description below.

U.S. Pat. No. 5,554,369, a divisional of the '908 patent, claims a method of controlling lepidopteran or boll weevil insect infestation of plants, comprising providing a 3-hydroxysteroid oxidase for ingestion by the insect.

U.S. Pat. No. 5,558,862, to the same inventors, claims a method of controlling insect infestation in plants by applying to the plant environment or plant seed a plant-colonizing microorganism that expresses heterologous DNA encoding a 3-hydroxysteroid oxidase.

U.S. Pat. No. 5,763,245, also to the same inventors, claims a method of controlling insect infestation in plants, comprising providing both a 3-hydroxysteroid oxidase and an insectidical *Bacillus thuringiensis* (Bt) protein for ingestion by lepidopteran insects. A method of producing a genetically transformed plant producing an insecticidally effective amount of a Bt protein and a 3-hydroxysteroid oxidase, comprising inserting into the genome of a plant cell a recombinant vector comprising nucleic acid sequences encoding the two proteins, as well as a promoter heterologous to the protein coding sequences which is effective to result in expression of the protein coding sequences in an insecticidally effective amount in a genetically transformed plant, is also claimed. As in their '908, '369, and '862 patents, supra, the inventors emphasize the use of constitutive promoters to provide uniform expression in the flowering portions of plants. Transgenic corn expressing either a Bt protein alone, or in combination with a 3-hydroxysteroid oxidase, i.e., cholesterol oxidase, is disclosed. Two populations of F1 generation plants expressing both proteins were produced by crossing plants subjected to a cholesterol oxidase transformation event with a plant subjected to a Bt transformation event.

Finally, European Pat. EP 0 706 320 B1 (corresponding to PCT International Publication WO 95/01098), also to the same inventors, and claiming priority from the same U.S. patent application from which the '908 patent issued, discloses transgenic tobacco expressing a 3-hydroxysteroid oxidase gene under the control of the constitutive FMV 35 promoter. As in the other patents discussed supra, the inventors again emphasized the use of plant constitutive promoters for expressing the 3-hydroxysteroid oxidase transgene to produce insect resistant plants.

Thus, a common feature of the disclosure of each of these patents is an emphasis on the use of a constitutive plant promoter to achieve expression of an insecticidally effective amount of a 3-hydroxysteroid oxidase in the flowering parts of plants to control insect infestation. Seed-specific, embryo-specific, and plastid-specific expression are neither disclosed nor suggested. Furthermore, no reason is given why such expression would be desirable, nor is any motivation provided therefor.

In addition to the foregoing patents, several reports relating to the expression of a 3-hydroxysteroid oxidase gene in transgenic plants have appeared in the technical literature. Corbin et al. (1994) *Appl. Environ. Microbiol.* 60: 4239-4244 discloses the cloning and expression of the insecticidal choM cholesterol oxidase gene from *Streptomyces* in *E. coli*, and transient expression thereof in tobacco protoplasts using the constitutive FMV 35S promoter. Cho et al. (1995) *Appl. Microbiol. Biotechnol.* 44: 133-138 discloses the expression of the *Streptomyces* cholesterol oxidase gene choA in transformed tobacco callus under the control of the constitutive CaMV 35S promoter. Corbin et al. (1996) *HortScience* 31: 699, Abstract No. 786, discloses the cloning and expression of a cholesterol oxidase gene in transgenic tobacco plants to yield plant tissue that exerted potent activity against boll weevils. Estruch et al. (1997) *Nature Biotechnology* 15: 137-141 is a review of approaches to pest control in transgenic plants, focusing primarily on *Bacillus thuringiensis* endotoxins. The use of cholesterol oxidases as insecticidal proteins is also discussed. The authors note that enzymatically active cholesterol oxidase was detected in extracts of tobacco protoplasts transformed with native cholesterol oxidase genes, citing the 1994 Corbin et al. and 1995 Cho et al. papers, supra. Discussing future directions in the area of insect resistant transgenic plants, the authors speculate on the use of "tighter tissue-specific promoters," without giving any specific examples or suggestions. Jouanin et al. (1998) *Plant Science* 131: 1-11, another review article, focuses on the use of *Bacillus thuringiensis* δ-endotoxins and plant-derived genes such as those encoding enzyme inhibitors and lectins, to create insect resistant transgenic plants. The authors note the insecticidal activity of *Streptomyces* cholesterol oxidase genes, as well as the fact that most of the existing insect-resistant plants express a single resistance gene placed under the control of a constitutive promoter. In discussing strategies to retain insect susceptibility to *B. thuringiensis* genes expressed in transgenic plants, the authors note the use of constitutive, tissue-specific, and inducible promoters. They suggest that a means of avoiding the development of resistance by insects due to high selection pressure when constitutive toxin expression is employed in transgenic plants is via the use of tissue-specific promoters to limit insect exposure to the toxin in certain parts of the plant attacked by the insect. However, no specific examples or suggestions as to any particular tissues or tissue-specific promoters are disclosed. Interestingly, the authors note that targeted expression of insecticidal genes in transgenic plants could ensure public acceptance thereof, giving as an example the expression of an insect toxin in leaves of potato plants rather than in the tubers to control the Colorado potato beetle. This suggests toxin expression in plants only where it is needed to control insect pests, e.g., in non-food plant parts, when possible. Finally, Corbin et al. (1998) *HortScience* 33: 614-617 reviews strategies for identifying and developing new insecticidal proteins for insect control in transgenic crop plants. In addition to discussing *Bacillus thuringiensis* δ-endotoxins, the authors also review research on cholesterol oxidase. Without providing any experimental details, they note that they expressed the cholesterol oxidase gene from *Streptomyces* A19249 in transgenic tobacco, and demonstrated insecticidal activity of this tissue against boll weevil larvae. They also note that they are currently characterizing the expression and biological activity of cholesterol oxidase produced in transgenic cotton plants, again providing no experimental details.

Taken together, the foregoing patents and journal articles reveal that the approach generally employed up to this time to confer insect resistance on plants by recombinant methods has been to express an insecticidal protein constitutively in a transgenic plant. While suggesting that tissue-specific expression may have certain advantages, these publications provide no specific examples or strategies. Targeting of enzymes involved in insect resistance to plastids via the use of appropriate signal peptides in conjunction with constitutive promoters has been suggested. Note, for example, U.S. Pat. No. 5,518,908. The use of tissue-specific promoters, such as seed-specific promoters, for this purpose, and direct transformation of plastids, especially those in seed tissues, has not been disclosed or suggested. This literature does suggest, however, that limiting expression to plant parts attacked by insects, for example leaves, and avoiding expression in plant parts used as food or sources of food products or ingredients, for example potato tubers, is desirable. Thus, these references teach away from the concept of expressing an insecticidal protein such as a cholesterol oxidase in a plant part such as a seed, which can be a food, and a source of food products or ingredients such as oil and meal. Nor do any of these references teach or suggest the modification of endogenous phytostanol levels in plants transformed with such genes, or that such modification is even possible using such genes. Thus, these references provide no motivation to employ a cholesterol oxidase to alter phytosterol/phytostanol levels in plants, nor do they suggest that overexpression thereof in planta to modify phytosterol/phytostanol profiles carries with it a reasonable expectation of success.

Nutritional Value of Plant Oils

Vegetable and bran oils are the best natural sources of phytosterols and phytostanols. However, the amount of phytostanols in these oils is low relative to that of other sterol compounds. Increasing the content of phytostanols such as sitostanol in plant oils is thus desired in the art. Currently, most sitostanol is produced by processing soy oil, and converting β-sitosterol to sitostanol by hydrogenation. Such modifications are known to improve the anti-atherogenic activity of these phytosterols. However, besides adding cost, such chemical interventions can result in the formation of undesirable isomers. Therefore, modification of phytosterols by transesterification and/or reduction of double bonds in planta is an economical, efficient means of producing desired phytosterol derivatives, including phytosterol esters, phytostanols, and phytostanol esters. The ability to convert phytosterols to phytostanol esters naturally would add significant nutritional value to grains and seeds. Furthermore, naturally enhancing the levels of sitostanol, sitostanol esters, and tocopherols would not only improve the nutritional value of cereal grains and seeds, but also facilitates "stacking" of a combination of nutritionally important bioactive molecules in a single, convenient source. In this way, foods and food products containing bioactive molecules having superior bioavailability and efficacy can be designed to improve human nutrition and cardiovascular health.

SUMMARY OF THE INVENTION

Accordingly, the present invention provides a number of different methods to enhance the levels of desirable phytosterol and phytostanol compounds, such as sitostanol and sitostanol esters, as well as tocopherol compounds, in plants. This is achieved by expressing in plants genes or other DNA or RNA coding sequences that elevate the levels of these important nutrients. In a preferred embodiment, elevation of the levels of sitostanol and tocopherol compounds is achieved by seed- or grain-specific enhancement by the use of seed-specific or plastid-specific promoters. This includes improvement of seed oil quality, for example in cotton and *Brassica* species.

In general, the methods disclosed herein for enhancing the levels of phytostanols, such as sitostanol, and tocopherol compounds in plants employ the introduction and expression in plant cells of a 3-hydroxysteroid oxidase, such as cholesterol oxidase, optionally in combination with a steroid 5α-reductase, such as the enzyme encoded by the *Arabidopsis* DET2 gene. Concomitantly, tocopherol levels can be elevated by the introduction and expression of one or more genes in the tocopherol biosynthetic pathway. The use of other polynucleotide sequences encoding enzymes that enhance the biosynthesis and accumulation of desirable phytosterols, phytostanols, esters thereof, and tocopherol compounds, is also disclosed. For example, sterol acyltransferases can be employed to elevate the level of sitostanol and other phytostanol esters; sterol methyltransferases can be employed to decrease the levels of campesterol, campestanol, and their respective esters.

Thus, in a first aspect, the present invention provides recombinant DNA constructs, comprising as operably linked components in the 5' to 3' direction, a member selected from:

a seed-specific promoter or a promoter functional in a plant plastid, a DNA sequence encoding a 3-hydroxysteroid oxidase enzyme, and a transcription termination signal sequence;

a seed-specific promoter or a promoter functional in a plant plastid, a DNA sequence encoding a steroid 5α-reductase enzyme, and a transcription termination signal sequence;

a seed-specific promoter or a promoter functional in a plant plastid, a DNA sequence encoding a 3-hydroxy-3-methylglutaryl-CoA reductase enzyme, and a transcription termination signal sequence;

a seed-specific promoter or a promoter functional in a plant plastid, a DNA sequence encoding a sterol methyl transferase enzyme, and a transcription termination signal sequence;

a seed-specific promoter or a promoter functional in plant plastid, a DNA sequence encoding a sterol acyltransferase enzyme, and a transcription termination signal sequence; and a seed-specific promoter or a promoter functional in a plant plastid, a DNA sequence encoding an S-adenosylmethionine-dependent γ-tocopherol methyltransferase enzyme, and a transcription termination signal sequence.

When the promoter is a seed-specific promoter, the recombinant construct can further comprise a transit peptide coding region capable of directing transport of the enzyme into a plastid, operatively linked to said DNA sequence. When the promoter is one that is functional in a plant plastid, the recombinant construct can further comprise a gene encoding a selectable marker for selection of plant cells comprising a plastid expressing the marker, and DNA regions of homology to the genome of the plastid, wherein the regions of homology flank the plastid-function promoter, the DNA sequence, the transcription termination signal sequence, and the gene encoding a selectable marker. In addition, the recombinant construct can further comprise a ribosome binding site joined to said plastid promoter.

In a second aspect, the present invention provides recombinant vectors, including plant expression vectors, comprising any of the foregoing recombinant constructs.

In another aspect, the present invention provides transformed host cells, including plant cells, comprising any of the foregoing recombinant constructs or vectors.

In another aspect, the present invention provides plants and seeds comprising at least one of the foregoing transformed host cells.

In another aspect, the present invention provides a plant, the genome of which comprises introduced DNA selected from:

DNA encoding a 3-hydroxysteroid oxidase enzyme, wherein said introduced DNA is operatively linked to regulatory signals that cause seed-specific or plastid-specific expression of said introduced DNA, and wherein seeds of said plant contain an elevated level of sitostanol, at least one sitostanol ester, or a mixture thereof, compared to seeds of an otherwise identical plant, the genome of which does not comprise said introduced DNA;

DNA encoding a steroid 5α-reductase enzyme, wherein said introduced DNA is operatively linked to regulatory signals that cause seed-specific or plastid-specific expression of said introduced DNA, and wherein seeds of said plant contain an elevated level of sitostanol, at least one sitostanol ester, or a mixture thereof, compared to seeds of an otherwise identical plant, the genome of which does not comprise said introduced DNA;

DNAs encoding a 3-hydroxysteroid oxidase enzyme and a steroid 5α-reductase enzyme, wherein said introduced DNAs are operatively linked to regulatory signals that cause seed-specific or plastid-specific expression of said introduced DNAs, and wherein seeds of said plant contain an elevated level of sitostanol, at least one sitostanol ester, or a mixture thereof, compared to seeds of an otherwise identical plant, the genome of which does not comprise said introduced DNAs;

DNAs encoding a 3-hydroxysteroid oxidase enzyme and a tocopherol biosynthetic enzyme, wherein said introduced DNAs are operatively linked to regulatory signals that cause seed-specific or plastid-specific expression of said introduced DNAs, and wherein seeds of said plant contain an elevated level of sitostanol, at least one sitostanol ester, or a mixture thereof, and at least one tocopherol compound, compared to seeds of an otherwise identical plant, the genome of which does not comprise said introduced DNAs;

DNAs encoding a steroid 5α-reductase enzyme and a tocopherol biosynthetic enzyme, wherein said introduced DNAs are operatively linked to regulatory signals that cause seed-specific or plastid-specific expression of said introduced DNAs, and wherein seeds of said plant contain an elevated level of sitostanol, at least one sitostanol ester, or a mixture thereof, and at least one tocopherol compound, compared to seeds of an otherwise identical plant, the genome of which does not comprise said introduced DNAs;

DNAs encoding a 3-hydroxysteroid oxidase enzyme, a steroid 5α-reductase enzyme, and a tocopherol biosynthetic enzyme, wherein said introduced DNAs are operatively linked to regulatory signals that cause seed-specific or plastid-specific expression of said introduced DNAs, and wherein seeds of said plant contain an elevated level of sitostanol, at least one sitostanol ester, or a mixture thereof, and at least one tocopherol compound, compared to seeds of an otherwise identical plant, the genome of which does not comprise said introduced DNAs;

DNA encoding a 3-hydroxy-3-methylglutaryl-CoA reductase enzyme, wherein said introduced DNA is operatively linked to regulatory signals that cause seed-specific or plastid-specific expression of said introduced DNA, and wherein seeds of said plant contain an elevated level of at least one sterol, at least one phytosterol, at least one phytosterol ester, at least one phytostanol, at least one phytostanol ester, or mixtures thereof, compared to seeds of an otherwise identical plant, the genome of which does not comprise said introduced DNA;

DNAs encoding a 3-hydroxysteroid oxidase enzyme and a 3-hydroxy-3-methylglutaryl-CoA reductase enzyme, wherein said introduced DNAs are operatively linked to regulatory signals that cause seed-specific or plastid-specific expression of said introduced DNAs, and wherein seeds of said plant contain an elevated level of at least one sterol, at least one phytosterol, at least one phytosterol ester, at least one phytostanol, at least one phytostanol ester, or mixtures thereof, compared to seeds of an otherwise identical plant, the genome of which does not comprise said introduced DNAs;

DNAs encoding a steroid 5α-reductase enzyme and a 3-hydroxy-3-methylglutaryl-CoA reductase enzyme, wherein said introduced DNAs are operatively linked to regulatory signals that cause seed-specific or plastid-specific expression of said introduced DNAs, and wherein seeds of said plant contain an elevated level of at least one sterol, at least one phytosterol, at least one phytosterol ester, at least one phytostanol, at least one phytostanol ester, or mixtures thereof, compared to seeds of an otherwise identical plant, the genome of which does not comprise said introduced DNAs;

DNAs encoding a 3-hydroxysteroid oxidase enzyme, a steroid 5α-reductase enzyme, and a 3-hydroxy-3-methylglutaryl-CoA reductase enzyme, wherein said introduced DNAs are operatively linked to regulatory signals that cause seed-specific or plastid-specific expression of said introduced DNAs, and wherein seeds of said plant contain an elevated level of at least one sterol, at least one phytosterol, at least one phytosterol ester, at least one phytostanol, at least one phytostanol ester, or mixtures thereof, compared to seeds of an otherwise identical plant, the genome of which does not comprise said introduced DNAs;

DNAs encoding a 3-hydroxysteroid oxidase enzyme, a 3-hydroxy-3-methylglutaryl-CoA reductase enzyme, and a sterol methyltransferase enzyme, wherein said introduced DNAs are operatively linked to regulatory signals that cause seed-specific or plastid-specific expression of said introduced DNAs, and wherein seeds of said plant contain an elevated level of at least one sterol, at least one phytosterol, at least one phytosterol ester, at least one phytostanol, at least one phytostanol ester, or mixtures thereof, as well as a reduced level of campesterol, campestanol, or both campesterol and campestanol, compared to seeds of an otherwise identical plant, the genome of which does not comprise said introduced DNAs;

DNAs encoding a steroid 5α-reductase enzyme, a 3-hydroxy-3-methylglutaryl-CoA reductase enzyme, and a sterol methyltransferase enzyme, wherein said introduced DNAs are operatively linked to regulatory signals that cause seed-specific or plastid-specific expression of said introduced DNAs, and wherein seeds of said plant contain an elevated level of at least one sterol, at least one phytosterol, at least one phytosterol ester, at least one phytostanol, at least one phytostanol ester, or mixtures thereof, as well as a reduced level of campesterol, campestanol, or both campesterol and campestanol, compared to seeds of an otherwise identical plant, the genome of which does not comprise said introduced DNAs; and DNAs encoding a 3-hydroxysteroid oxidase enzyme, a steroid 5α-reductase enzyme, a 3-hydroxy-3-methylglutaryl-CoA reductase enzyme, and a sterol methyltransferase enzyme, wherein said introduced DNAs are operatively linked to regulatory signals that cause seed-specific or plastid-specific expression of said introduced DNAs, and wherein seeds of said plant contain an elevated level of at least one sterol, at least one phytosterol, at least one phytosterol ester, at least one phytostanol, at least one phytostanol ester, or mixtures thereof, as well as a reduced level of campesterol, campestanol, or both campesterol and campestanol, compared to seeds of an otherwise identical plant, the genome of which does not comprise said introduced DNAs.

In another aspect, the present invention provides any of the foregoing plants wherein said genome further comprises introduced DNA encoding a sterol acyltransferase enzyme, wherein said introduced DNAs are operatively linked to regulatory signals that cause seed-specific or plastid-specific expression of said introduced DNAs, and wherein seeds of said plant contain an elevated level of at least one sterol (when DNA encoding a 3-hydroxy-3-methylglutaryl-CoA reductase enzyme is introduced), at least one phytosterol, at least one phytosterol ester, at least one phytostanol, at least one phytostanol ester, and mixtures thereof, compared to seeds of an otherwise identical plant, the genome of which does not comprise said introduced DNAs.

In a further aspect, the present invention provides any of the foregoing plants, wherein said genome further comprises introduced DNA encoding an S-adenosylmethionine-dependent γ-tocopherol methyltransferase enzyme, wherein said introduced DNAs are operatively linked to regulatory signals that cause seed-specific or plastid-specific expression of said introduced DNAs, and wherein seeds of said plant contain an elevated level of at least one sterol (when DNA encoding a 3-hydroxy-3-methylglutaryl-CoA reductase enzyme is introduced), at least one phytosterol, at least one phytosterol ester, at least one phytostanol, at least one phytostanol ester, or mixtures thereof, as well as an elevated level of α-tocopherol compared to seeds of an otherwise identical plant, the genome of which does not comprise said introduced DNAs.

In another aspect, the present invention provides any of the foregoing plants, seed of which contains brassicastanol, a brassicastanol ester, stigmastanol or a stigmastanol ester.

In another aspect, the present invention provides a plant, the genome of which contains at least one introduced DNA sequence encoding a peptide, polypeptide, or protein that affects the biosynthesis and accumulation of at least one sterol, at least one phytosterol, at least one phytosterol ester, at least one phytostanol, at least one phytostanol ester, or combinations thereof, wherein said introduced DNA is operably linked to regulatory signals that cause seed-specific or plastid-specific expression of said introduced DNA, and wherein said plant produces seed having an elevated level of at least one sterol, at least one phytosterol, at least one phytosterol ester, at least one phytostanol, at least one phytostanol ester, or combinations thereof, compared to a corresponding transgenic or non-transgenic plant that does not contain said introduced DNA. The phytostanol or phytostanol ester can be sitostanol or at least one sitostanol ester. Alternatively, a mixture thereof can be present.

In a further aspect, the present invention provides a plant that produces seed having an elevated level of a compound selected from sitosterol, at least one sitosterol ester, sitostanol, at least one sitostanol ester, or mixtures thereof, as well as a reduced level of a compound selected from the group consisting of campesterol, a campesterol ester, brassicasterol, a brassicasterol ester, campestanol, a campestanol ester, brassicastanol, a brassicastanol ester, or mixtures thereof, compared to a corresponding transgenic or non-transgenic plant that does not contain introduced DNA encoding a peptide, polypeptide, or protein that affects phytosterol or phytostanol biosynthesis and accumulation in said corresponding plant. The present invention also provides a plant that produces seed having a reduced level of a compound selected from the group consisting of campesterol, a campesterol ester, brassicasterol, a brassicasterol ester, campestanol, a campestanol ester, brassicastanol, a brassicastanol ester, or mixtures thereof, compared to a corresponding transgenic or non-transgenic plant that does not contain introduced DNA encoding a peptide, polypeptide, or protein that affects phytosterol or phytostanol biosynthesis and accumulation in said corresponding plant.

In another aspect, the present invention provides the foregoing plants, wherein said seed contains an elevated level of α-tocopherol. Such seed can also contain a compound selected from brassicastanol, at least one brassicastanol ester, stigmastanol, at least one stigmastanol ester, or a mixture thereof.

In another aspect, the present invention provides the foregoing plants, wherein said regulatory signals cause seed-specific expression of said introduced DNAs, and wherein each of said introduced DNAs is further operatively linked to a transit peptide coding region capable of directing transport of said enzyme encoded thereby into a plastid. Alternatively, the regulatory signals in the foregoing plants can cause plastid-specific expression of said introduced DNAs, and said genome can then be a plastid genome.

In further aspects, the present invention provides seed of any of the foregoing plants, and progeny of any of these plants as well.

In yet a further aspect, the present invention provides a cell of any of the foregoing plants, as well as a cell culture comprising such cells.

In another aspect, the present invention provides a method of producing oil containing sitostanol or a sitostanol ester, comprising culturing the foregoing cells for a time and under conditions conducive to the production of oil containing sitostanol or a sitostanol ester, and recovering said oil containing sitostanol or sitostanol ester produced thereby.

In another aspect, the present invention provides a method of producing sitostanol or a sitostanol ester, comprising culturing the foregoing cells for a time and under conditions conducive to the production of sitostanol or a sitostanol ester, and recovering said sitostanol or sitostanol ester produced thereby.

In another aspect, the present invention provides a plant produced from any of the foregoing seed.

In another aspect, the present invention provides a method of producing a plant that accumulates an elevated level of a compound selected from sitosterol, at least one sitosterol ester, sitostanol, at least one sitostanol ester, or mixtures thereof, in seed of said plant compared to seed of a corresponding plant comprising no introduced DNA encoding a peptide, polypeptide, or protein that affects the biosynthesis and accumulation of a phytosterol or a phytosterol ester, or a phytostanol or a phytostanol ester, comprising sexually crossing any of the foregoing plants with said corresponding plant. The invention also encompasses plants produced by this method, seed produced by these plants, and uniform populations of these and any of the other foregoing plants.

In another aspect, the present invention provides a method of producing a plant that accumulates an elevated level of a compound selected from sitosterol, at least one sitosterol ester, sitostanol, at least one sitostanol ester, or mixtures thereof, which are apomictic as well as a seed resulting from a cross of an apomitic plant of the present invention with a nurse cultivar.

In another aspect, the present invention encompasses a method of producing a compound selected from at least one phytosterol, at least one phytosterol ester, at least one phytostanol, at least one phytostanol ester, or mixtures thereof, in a seed, comprising obtaining a transformed plant that produces said seed, wherein said plant has and expresses in its genome DNA selected from the group consisting of:

DNA encoding a 3-hydroxysteroid oxidase enzyme, wherein said DNA is operatively linked to regulatory signals that cause seed-specific or plastid-specific expression of said DNA;

DNA encoding a steroid 5α-reductase enzyme, wherein DNA is operatively linked to regulatory signals that cause seed-specific or plastid-specific expression of said DNA;

DNAs encoding a 3-hydroxysteroid oxidase enzyme and a steroid 5α-reductase enzyme, wherein said DNAs are operatively linked to regulatory signals that cause seed-specific or plastid-specific expression of said DNAs;

DNAs encoding a 3-hydroxysteroid oxidase enzyme and a tocopherol biosynthetic enzyme, wherein said DNAs are operatively linked to regulatory signals that cause seed-specific or plastid-specific expression of said DNAs;

DNAs encoding a steroid 5α-reductase enzyme and a tocopherol biosynthetic enzyme, wherein said DNAs are operatively linked to regulatory signals that cause seed-specific or plastid-specific expression of said DNAs;

DNAs encoding a 3-hydroxysteroid oxidase enzyme, a steroid 5α-reductase enzyme, and a tocopherol biosynthetic enzyme, wherein said DNAs are operatively linked to regulatory signals that cause seed-specific or plastid-specific expression of said DNAs;

DNA encoding a 3-hydroxy-3-methylglutaryl-CoA reductase enzyme, wherein said DNA is operatively linked to regulatory signals that cause seed-specific or plastid-specific expression of said DNA;

DNAs encoding a 3-hydroxysteroid oxidase enzyme and a 3-hydroxy-3-methylglutaryl-CoA reductase enzyme, wherein said DNAs are operatively linked to regulatory signals that cause seed-specific or plastid-specific expression of said DNAs;

DNAs encoding a steroid 5α-reductase enzyme and a 3-hydroxy-3-methylglutaryl-CoA reductase enzyme, wherein said DNAs are operatively linked to regulatory signals that cause seed-specific or plastid-specific expression of said DNAs;

DNAs encoding a 3-hydroxysteroid oxidase enzyme, a steroid 5α-reductase enzyme, and a 3-hydroxy-3-methylglutaryl-CoA reductase enzyme, wherein said DNAs are operatively linked to regulatory signals that cause seed-specific or plastid-specific expression of said DNAs;

DNAs encoding a 3-hydroxysteroid oxidase enzyme, a 3-hydroxy-3-methylglutaryl-CoA reductase enzyme, and a sterol methyltransferase enzyme, wherein said DNAs are operatively linked to regulatory signals that cause seed-specific or plastid-specific expression of said DNAs;

DNAs encoding a steroid 5α-reductase enzyme, a 3-hydroxy-3-methylglutaryl-CoA reductase enzyme, and a sterol methyltransferase enzyme, wherein said DNAs are operatively linked to regulatory signals that cause seed-specific or plastid-specific expression of said DNAs; and DNAs encoding a 3-hydroxysteroid oxidase enzyme, a steroid 5α-reductase enzyme, a 3-hydroxy-3-methylglutaryl-CoA reductase enzyme, and a sterol methyltransferase enzyme, wherein said DNAs are operatively linked to regulatory signals that cause seed-specific or plastid-specific expression of said DNAs; and recovering said at least one phytosterol, at least one phytosterol ester, at least one phytostanol, at least one phytostanol ester, or mixtures thereof. In a preferred embodiment, sitostanol, a sitostanol ester, or a mixture thereof is recovered.

Such plants can further contain and express in their genome DNA encoding a sterol acyltransferase enzyme operatively linked to regulatory signals that cause seed-specific or plastid-specific expression of said acyltransferase enzyme-encoding DNA. Furthermore, these and the foregoing plants can also contain and express in their genome DNA encoding an S-adenosylmethionine-dependent γ-tocopherol methyltransferase enzyme operatively linked to regulatory signals that cause seed-specific or plastid-specific expression of said DNA methyltransferase enzyme-encoding DNA.

In the foregoing method, when said regulatory signals cause seed-specific expression of said enzyme-encoding DNAs, each of said enzyme-encoding DNAs can be further operatively linked to a transit peptide coding region capable of directing transport of said enzyme encoded thereby into a plastid, and said genome is the nuclear genome. When said regulatory signals cause plastid-specific expression of said enzyme-encoding DNAs, said genome is a plastid genome.

In another aspect, the present invention provides a method of producing sitostanol or at least one sitostanol fatty acid ester, comprising growing any of the foregoing plants, and recovering said sitostanol or sitostanol fatty acid ester produced thereby.

In a further aspect, the present invention provides a method of producing brassicastanol, at least one brassicastanol ester, stigmastanol, or at least one stigmastanol ester, comprising growing any of the foregoing plants, and recovering said brassicastanol, at least one brassicastanol ester, stigmastanol, or at least one stigmastanol ester produced thereby.

In another aspect, the present invention provides a part, other than a seed, of any of the foregoing transgenic plants. Such parts include fruit and vegetable parts of these plants.

In yet another aspect, the present invention provides oil containing a compound selected from at least one sterol, at least one phytosterol, at least one phytosterol ester, at least one phytostanol, at least one phytostanol ester, or mixtures thereof, extracted from seed of any of the foregoing plants, or produced by any of the foregoing methods.

In another aspect, the present invention provides a sitostanol ester composition extracted from seed of any of the foregoing plants, or produced by any of the foregoing methods.

In yet another aspect, the present invention provides cholesterol-lowering compositions, comprising any of the foregoing oils or sitostanol ester compositions. These compositions can take the form of a food, a food ingredient, a food composition, a food additive composition, a dietary supplement, or a pharmaceutical composition.

In a further aspect, the present invention provides methods of lowering the plasma concentration of low density lipoprotein cholesterol, or treating or preventing an elevated plasma concentration of low density lipoprotein cholesterol, comprising orally administering to a human or animal subject an effective amount of any of the foregoing oils, sitostanol ester compositions, foods, food ingredients, food compositions, food additive compositions, dietary supplements, or pharmaceutical compositions.

In another aspect, the present invention provides a method of achieving effective absorption of sitostanol into host, comprising producing at least one sitostanol ester by any of the methods described herein, and administering said at least one sitostanol ester to said host.

In a further aspect, the present invention provides a method of making a food additive composition, comprising obtaining oil containing a phytostanol compound selected from sitostanol, at least one sitostanol ester, or mixtures thereof from seed of a transgenic plant according the present invention, and mixing said oil with an edible solubilizing agent, an effective amount of an antioxidant, and an effective amount of a dispersant. Alternatively, the food additive composition can be made by a method comprising obtaining oil containing at least one tocopherol, and a phytostanol compound selected from sitostanol, at least one sitostanol ester, or mixtures thereof, from seed of a transgenic plant according to the present invention, and mixing said oil with an edible solubilizing agent and an effective amount of a dispersant. Food additive compositions prepared according to these methods are also provided, as are compositions, such as food compositions, comprising said food additive compositions.

In another aspect, the present invention provides the novel sterol brassicastanol, as well as novel brassicastanol esters.

In another aspect, the present invention provides the novel sterol stigmastanol, as well as novel stigmastanol esters.

In yet another aspect, the present invention provides an isolated DNA molecule, having a nucleotide sequence selected from:

(a) SEQ ID NO: 2, SEQ ID NO: 4, or the complement of either of these nucleotide sequences, respectively;

(b) a nucleotide sequence that hybridizes to said nucleotide sequence of (a) under a wash stringency equivalent to 0.5× SSC to 2×SSC, 0.1% SDS, at 55-65° C., and which encodes a polypeptide having steroid 5α-reductase enzymatic activity substantially similar to that of *Arabidopsis thaliana* or *Zea mays* steroid 5α-reductase, respectively;

(c) a nucleotide sequence encoding the same genetic information as said nucleotide sequence of (a), but which is degenerate in accordance with the degeneracy of the genetic code; or (d) a nucleotide sequence encoding the same genetic information as said nucleotide sequence of (b), but which is degenerate in accordance with the degeneracy of the genetic code.

In another aspect, the present invention provides an isolated DNA molecule that encodes a steroid 5α-reductase enzyme or fragment thereof, comprising a nucleic acid sequence selected from:

(a) the nucleotide sequences shown in SEQ ID:6, SEQ ID NO: 8, or the complement of any of these nucleotide sequences, respectively;

(b) a nucleotide sequence that hybridizes to said nucleotide sequence of (a) under a wash stringency equivalent to 0.5× SSC to 2×SSC, 0.1% SDS, at 55-65° C., and which encodes a polypeptide having steroid 5α-reductase enzymatic activity substantially similar to that of *Glycine max* steroid 5α-reductase;

(c) a nucleotide sequence encoding the same genetic information as said nucleotide sequence of (a), but which is degenerate in accordance with the degeneracy of the genetic code; and (d) a nucleotide sequence encoding the same genetic information as said nucleotide sequence of (b), but which is degenerate in accordance with the degeneracy of the genetic code.

In yet a further aspect, the present invention provides a recombinant construct, comprising as operably linked components in the 5' to 3' direction, a seed-specific promoter or a promoter functional in a plant plastid, any of said isolated DNA molecules described immediately above encoding a polypeptide having steroid 5α-reductase enzymatic activity, or fragment thereof, and a transcription termination signal sequence.

In another aspect, the present invention provides an isolated DNA molecule that encodes geranylgeranylpyrophosphate hydrogenase or a fragment thereof, comprising a nucleic acid sequence selected from:

(a) the nucleotide sequences shown in SEQ ID NO:29, or the complement thereof;

(b) a nucleotide sequence that hybridizes to said nucleotide sequence of (a) under a wash stringency equivalent to 0.5× SSC to 2×SSC, 0.1% SDS, at 55-65° C., and which encodes a polypeptide having enzymatic activity substantially similar to that of geranylgeranylpyrophosphate hydrogenase in maize;

(c) a nucleotide sequence encoding the same genetic information as said nucleotide sequence of (a), but which is degenerate in accordance with the degeneracy of the genetic code; and (d) a nucleotide sequence encoding the same genetic information as said nucleotide sequence of (b), but which is degenerate in accordance with the degeneracy of the genetic code.

In yet a further aspect, the present invention provides a recombinant construct, comprising as operably linked components in the 5' to 3' direction, a seed-specific promoter or a promoter functional in a plant plastid, any of said isolated DNA molecule described immediately above encoding a polypeptide having geranylgeranylpyrophosphate hydrogenase enzymatic activity, or a fragment thereof, and a transcription termination signal sequence.

In another aspect, the present invention provides recombinant vectors comprising said recombinant constructs comprising said isolated DNA molecules encoding polypeptides, or fragments thereof, having steroid 5α-reductase or geranylgeranylpyrophosphate hydrogenase enzymatic activity.

In another aspect, the present invention provides transformed host cells comprising any of the foregoing recombinant constructs or vectors comprising said isolated DNA molecules encoding polypeptides, or fragments thereof, having steroid 5α-reductase or geranylgeranylpyrophosphate hydrogenase enzymatic activity.

In yet another aspect, the present invention provides a method of producing a steroid 5α-reductase, comprising culturing any of said transformed host cells immediately above for a time and under conditions conducive to the production of said steroid 5α-reductase, or enzymatically active fragment thereof, and recovering said steroid 5α-reductase or enzymatically active fragment thereof produced thereby.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which.

Descriptions of these plasmids and explanations of the abbreviations used in the plasmid maps are as follows:

FIG. 1: pMON30423

Recombinant shuttle vector carrying the *Streptomyces* A19249 3-hydroxysteroid oxidase gene ("cholesterol oxidase gene") disclosed in U.S. Pat. No. 5,518,908 driven by the enhanced 35S promoter. Ori-M13: M13 bacteriophage origin of replication; P-e35S: enhanced promoter for 35S RNA from cauliflower mosaic virus; HSP70 intron: intron from heat shock protein 70; P-MaizeSSU: maize RUBISCO small subunit chloroplast target peptide; chox: cholesterol oxidase gene from *Streptomyces hygroscopicus* A19249; NOS 3': 3' termination end of nopaline synthase coding region; ori-pUC: plasmid origin of replication in *E. coli*; AMP: promoter and coding sequence for beta-lactamase protein to confer resistance to ampicillin, penicillin, and carbenicillin.

FIG. 2: pMON29141

Recombinant shuttle vector carrying *Synechocystis* chlp gene driven by the napinB promoter. Ori-M13: M13 bacteriophage origin of replication; p-napB: promoter region of napin B gene of *Brassica campestris*; PEA SSU CTP, SOY SSU: RUBISCO small subunit chloroplast transit peptide from pea fused with the N-terminus of mature soy small subunit; chlp: *Synechocystis* sp. PCC6803 chlp gene (X97972); NOS 3': 3' termination end of nopaline synthase coding region; ori-pUC: plasmid origin of replication in *E. coli*; AMP: promoter and coding sequence for beta-lactamase protein to confer resistance to ampicillin, penicillin, and carbenicillin.

FIG. 3: pMON43007

Recombinant shuttle vector carrying the *Streptomyces hygroscopicus* A19249 cholesterol oxidase gene driven by the napinB promoter. Ori-M13: M13 bacteriophage origin of replication; p-napB: promoter region of napin B gene of *Brassica campestris*; PEA SSU CTP, SOY SSU: RUBISCO small subunit chloroplast transit peptide from pea fused with the N-terminus of mature soy small subunit; chox: cholesterol oxidase gene from *Streptomyces hygroscopicus* A19249; NOS 3': 3' termination end of nopaline synthase coding region; ori-pUC: plasmid origin of replication in *E. coli*; AMP: promoter and coding sequence for beta-lactamase protein to confer resistance to ampicillin, penicillin, and carbenicillin.

FIG. 4: pCGN5139

Binary vector for *Agrobacterium*-mediated canola transformation containing the kanamycin resistance gene from the prokaryotic transposon Tn5 driven by 35S promoter from cauliflower mosaic virus. Tn5: transposon Tn5; 35S: promoter for 35S RNA from cauliflower mosaic virus; Tn5 kan: kanamycin resistance gene from transposon Tn5; Tml 3': 3' termination end of the T-DNA locus "tumor morphology large"; LB fragment: *Agrobacterium* T-DNA left border sequence; ori pRi: *Agrobacterium* origin of replication.

FIG. 5: pMON43011

Figure 4:
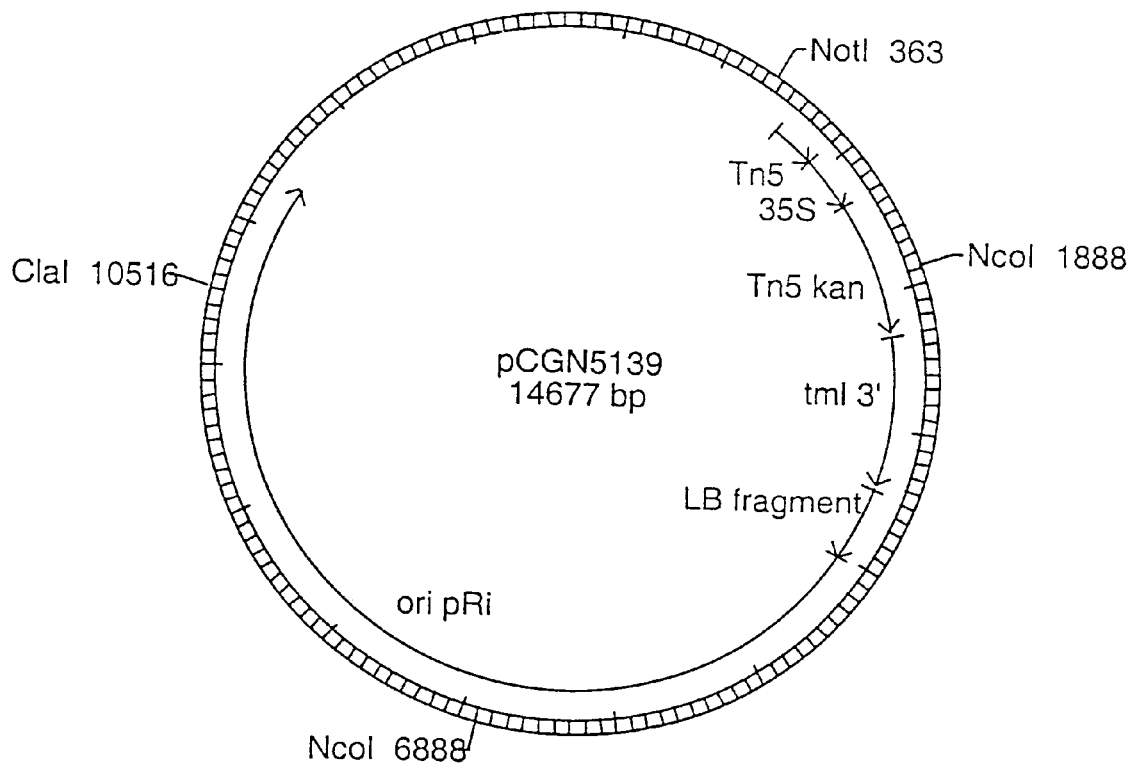
Figure 5:
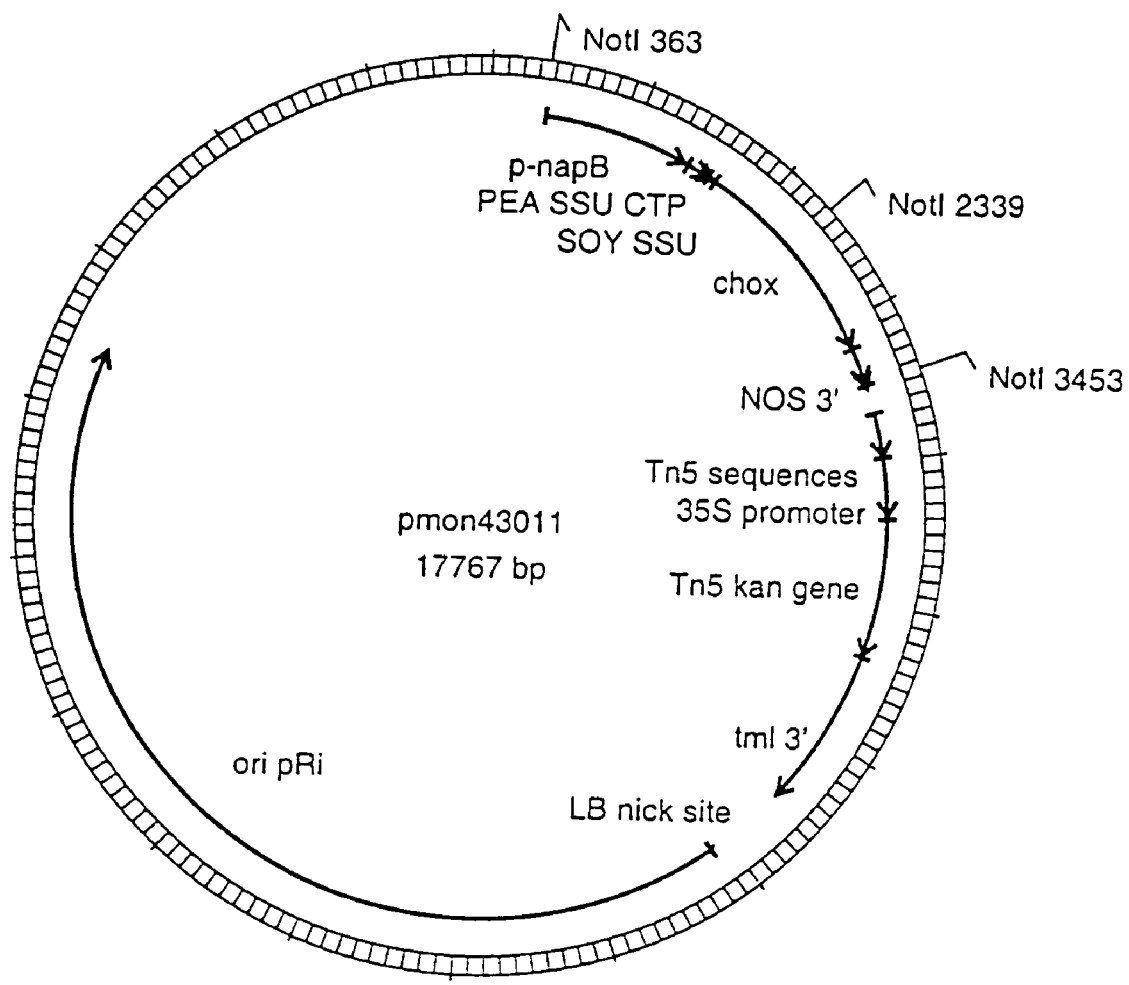

Recombinant binary vector for *Agrobacterium*-mediated canola transformation, carrying the *Streptomyces hygroscopicus* A19249 cholesterol oxidase gene cassette. The cholesterol oxidase gene is driven by napin B promoter, and the protein is targeted to the chloroplast using the pea SSU CTP, SOY SSU. p-napB: promoter region of napin B gene of *Brassica campestris*; PEA SSU CTP, SOY SSU: RUBISCO small subunit chloroplast transit peptide from pea fused with the N-terminus of the mature soy small subunit; chox: cholesterol oxidase gene from *Streptomyces hygroscopicus* A19249; NOS 3': 3' termination end of nopaline synthase coding region; LB nick site: site at which the *Agrobacterium* left border sequence is cut in planta for insertion of T-DNA into the plant genome; remaining abbreviations as for pCGN5139 (FIG. 4).

FIG. 6: pMON29920

P-7S/E9 3' cassette and the KAN gene flanked by two borders in a binary transformation vector where P-7S is the promoter of alpha' beta conglycinin protein from soybean, E9 3' is the 3' end of pea rbc E9 gene and KAN is the coding sequence for NPTII that confers resistance to kanamycin. The NPTII gene is driven by the 35S promoter from cauliflower mosaic virus. Spc.Str is the coding region for Tn7 adenylyl-transferase conferring resistance to spectinomycin and streptomycin; ori-V: the vegetative origin of replication; rop: coding region for repressor of primer; ori-322: minimum known sequence required for a functional origin of replication; NOS 3': the 3' termination end of nopaline synthase coding region.

FIG. 7: pMON43800

Recombinant binary vector for *Agrobacterium*-mediated transformation, carrying the rubber HMGR1 gene cassette. The HMGR1 gene is driven by the 7S alpha' beta conglycinin promoter from soybean. P-7S: 7S promoter; rubber HMGR1 gene: coding sequence for 3-hydroxy-3-methylglutaryl reductase from *Hevea brasiliensis*; E9 3': 3' end of pea rbcS E9 gene; P-35S: 35S promoter from cauliflower mosaic virus; KAN: coding region for NPTII gene conferring resistance kanamycin; NOS 3': 3' termination end of nopaline synthase coding region; Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycin and streptomycin.

FIG. 8: pMON23616

Plant expression plasmid containing P-NOS/ORF-7/KAN/NOS3'. P-NOS: NOS promoter from *Agrobacterium tumefaciens* pTiT37; ORF-7: a short open reading frame that attenuates expression of KAN in plants; KAN: coding sequence of NPTII gene that confers resistance to kanamycin and neomycin; ble: confers resistance to bleomycin; NOS 3': 3' termination end of nopaline synthase coding region; Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycin and streptomycin.

FIG. 9: pMON43818

Recombinant binary vector for *Agrobacterium*-mediated transformation, carrying the rubber HMGR1 gene cassette. The HMGR1 gene is driven by the 7S alpha' beta conglycinin promoter from soybean. P-7S: 7S promoter; rubber HMGR1 gene: coding sequence for 3-hydroxy-3-methylglutaryl reductase from *Hevea brasiliensis*; E9 3': 3' end of pea rbcS E9 gene; P-NOS: NOS promoter from *Agrobacterium tumefaciens* pTiT37; KAN: coding region for NPTII gene conferring resistance kanamycin; NOS 3': 3' termination end of nopaline synthase coding region; Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycin and streptomycin.

FIG. 10: pMON43039

Recombinant binary vector for *Agrobacterium*-mediated transformation, carrying the rubber HMGR1 and *Arabidopsis* SMT 2 genes cassette. The HMGR1 and SMT2 genes are driven by the 7S alpha' beta conglycinin promoter from soybean. *Arabidopsis* SMT2: cDNA coding for the C-24 sterol methyltransferase 2 enzyme from *Arabidopsis thaliana*; P-7S: 7S promoter; rubber HMGR1 gene: coding sequence for 3-hydroxy-3-methylglutaryl reductase from *Hevea brasiliensis*; E9 3': 3' end of pea rbcS E9 gene; P-NOS: NOS promoter from *Agrobacterium tumefaciens* pTiT37; KAN: coding region for NPTII gene conferring resistance kanamycin; NOS 3': 3' termination end of nopaline synthase coding region; Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycin and streptomycin.

FIG. 11: pMON43008

Recombinant binary vector for *Agrobacterium*-mediated transformation, carrying the *Streptomyces hygroscopicus* A19249 cholesterol oxidase gene cassette. The cholesterol oxidase gene is driven by the 7S alpha' beta conglycinin promoter from soybean. P-7S: 7S promoter; chox: cholesterol oxidase gene from *Streptomyces hygroscopicus* A19249; E9 3': 3' end of pea rbcS E9 gene; P-35S: 35S promoter from cauliflower mosaic virus; KAN: coding region for NPTII gene conferring resistance kanamycin; NOS 3': 3' termination end of nopaline synthase coding region; Left Border: Octapine left border from Octapine Ti plasmid pTiA6; ori-V: the vegetative origin of replication; rop: coding region for repressor of primer; Spc/Str: coding region for Tn7 adenylyltransferase conferring resistance to spectinomycin and streptomycin.

Conventional methods of gene isolation, molecular cloning, vector construction, etc., are well known in the art and are summarized, for example, in Sambrook et al. (1989) *Molecular Cloning, A Laboratory Manual*, Second Edition, Cold Spring Harbor Laboratory Press, and Ausubel et al. (1989) *Current Protocols in Molecular Biology*, John Wiley & Sons, Inc. One skilled in the art can readily reproduce the plasmid vectors described above, or similar plasmids, without undue experimentation employing these methods in conjunction with the cloning information provided by the figures attached hereto. The various DNA sequences, fragments, linkers, etc., necessary for this purpose can be readily obtained as components of commercially available plasmids, or are otherwise well known in the art and publicly available.

Figure 12:
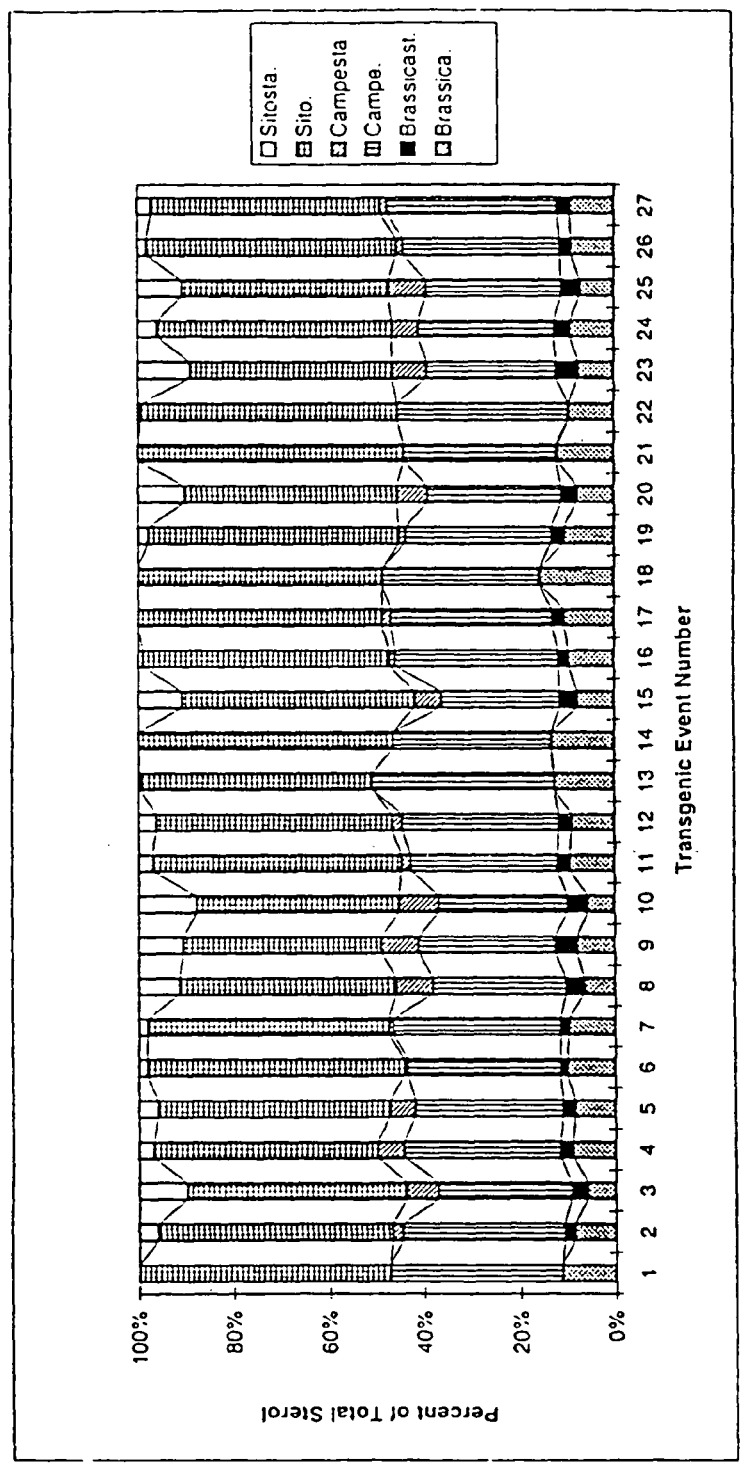

FIG. 12 shows the phytosterol and phytostanol composition of seeds of transgenic *Brassica napus* (rapeseed; canola), produced as described in Example 10, expressing the *Streptomyces* A19249 3-hydroxysteroid oxidase gene disclosed in U.S. Pat. No. 5,518,908, including the presence of the novel phytostanol brassicastanol. 1 is the non-transgenic control; 2-27 are independent transgenic events (plants) from which 10 R1 seeds per plant were analyzed for sterol composition. Sitosta.: sitostanol; Sito.: sitosterol; Campesta.: campestanol; Campe.: campesterol; Brassicast.: brassicastanol; *Brassica*.: brassicasterol.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein are herein incorporated by reference in their entirety.

As used herein, the term "structural coding sequence" means a DNA sequence which encodes for a peptide, polypeptide, or protein which may be made by a cell following transcription of the DNA to mRNA, followed by translation to the desired peptide, polypeptide, or protein.

The term "sterol" as applied to plants refers to any chiral tetracyclic isopentenoid which may be formed by cyclization of squalene oxide through the transition state possessing stereochemistry similar to the trans-syn-trans-anti-trans-anti configuration, i.e., protosteroid cation, and which retains a polar group at C-3 (hydroxyl or keto), an all-trans-anti stereochemistry in the ring system, and a side-chain 20R-configuration (Parker et al. (1992) In Nes et al., Eds., *Regulation of Isopentenoid Metabolism*, ACS Symposium Series No. 497, p. 110; American Chemical Society, Washington, D.C.). The numbering of the carbon atoms of a representative sterol (cholesterol) is shown in the following structure:

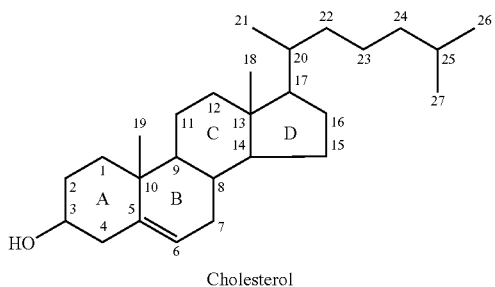
Cholesterol

Sterols may or may not contain a C-5-C-6 double bond, as this is a feature introduced late in the biosynthetic pathway (note Scheme 1, below). Sterols contain a $C_5$-$C_{10}$ side chain at the C-17 position, as shown above.

The term "phytosterol," which applies to sterols found uniquely in plants, refers to a sterol containing a C-5, and in some cases a C-22, double bond. Phytosterols are further characterized by alkylation of the C-17 side-chain with a methyl or ethyl substituent at the C-24 position. Major phytosterols include, but are not limited to, sitosterol, stigmasterol, campesterol, brassicasterol, etc. Cholesterol, which lacks a C-24 methyl or ethyl side chain, is found in plants but is not unique thereto, and is not a "phytosterol."

"Phytostanols" are saturated forms of phytosterols wherein the C-5 and, when present, C-22 double bond(s) is(are) reduced, and include, but are not limited to, sitostanol, campestanol, and 22-dihydrobrassicastanol.

"Phytosterol esters" and "phytostanol esters" are further characterized by the presence of a fatty acid or phenolic acid moiety rather than a hydroxyl group at the C-3 position.

The term "sterol compounds" includes sterols, phytosterols, phytosterol esters, phytostanols, and phytostanol esters.

The term "phytosterol compound" refers to at least one phytosterol, at least one phytosterol ester, or a mixture thereof.

The term "phytostanol compound" refers to at least one phytostanol, at least one phytostanol ester, or a mixture thereof.

The foregoing definitions are commonly found in the literature, and those of ordinary skill in the art understand that biosynthetic precursors and intermediates can have other unique structural features associated with them.

The term "constitutive promoter" refers to a promoter that operates continuously in a cell, and which is not subject to quantitative regulation. The gene with which such a promoter is associated is always "turned on."

The terms "seed-specific," "fruit-specific," "plastid-specific," etc., as they apply to promoters refer to preferential or exclusive activity of these promoters in these organs or organelles, respectively. "Preferential expression" refers to promoter activity substantially greater in the indicated organs or organelles than elsewhere in the plant. "Substantially greater" comprehends expression that occurs exclusively in the indicated organ or organelle, or that occurs in other tissues, organs, or organelles, but that is significantly greater in the specifically recited organ or organelle. "Seed-specific" comprehends expression in the aleurone layer, endosperm, and/or embryo of the seed.

For the production of seed having an increase in sitostanol biosynthesis, transformation of a plant with a 3-hydroxysteroid oxidase gene is sufficient. Levels of sitostanol and sitostanol esters can be elevated further by introducing a steroid 5α-reductase gene. Transgenic plants in which both sitostanol and tocopherol biosynthesis are enhanced can be produced by transforming a plant with a 3-hydroxysteroid oxidase gene and, optionally, a steroid 5α-reductase gene, along with at least one tocopherol biosynthesis gene. Other enzyme-encoding DNAs can be introduced into plants to elevate even further the levels of desirable phytostanols, phytostanol esters, and tocopherols.

Thus, the DNA sequences contemplated for use in the present invention, which can be used alone or in various combinations as discussed below, include, but are not limited to, those encoding the following enzymes: 3-hydroxysteroid oxidases; steroid 5α-reductases; 3-hydroxy-3-methylglutaryl-CoA reductases (HMG Co-A reductases); sterol methyltransferases; sterol acyltransferases; and S-adenosylmethionine-dependent γ-tocopherol methyltransferases. In each case, the sequences encoding these enzymes can comprise an expression cassette comprising, operably linked in the 5' to 3' direction, a seed-specific promoter or a promoter functional in a plant plastid, the enzyme coding sequence, and a transcriptional termination signal sequence functional in a plant cell such that the enzyme is successfully expressed. When the promoter is a seed-specific promoter, the expression cassette or recombinant construct can further comprise an operably linked transit peptide coding region capable of directing transport of the enzyme into a plastid. When the promoter is one that is functional in a plant plastid, the expression cassette or recombinant construct can further comprise a gene encoding a selectable marker for selection of plant cells comprising a plastid expressing the marker, and DNA regions of homology to the genome of the plastid, wherein the regions of homology flank the promoter, the enzyme coding sequence, the transcription termination signal sequence, and the gene encoding the selectable marker. In addition, the recombinant construct or expression cassette can further comprise a ribosome binding site joined to the plastid promoter. The ribosome binding site can be obtained from a leader sequence derived from a plastid, bacterial, or bacteriophage leader sequence, for example the binding site of the gene 10 leader or the rbcLRBS site.

For use in the methods disclosed herein, the recombinant constructs or expression cassettes can be incorporated in a vector, for example a plant expression vector. Such vectors can be transformed into host cells such as bacterial cells, for example during the preparation or modification of the recombinant constructs, and plant cells. Thus, the invention encompasses plants and seeds comprising such transformed plant cells.

In order to obtain seed producing oil containing elevated levels of phytostanols and phytostanol esters such as sitostanol and sitostanol esters, and tocopherols such as α-tocopherol, these recombinant constructs or expression cassettes can be introduced into plant cells by any number of conventional means known in the art and regenerated into fertile transgenic plants. The genome of such plants can then comprise introduced DNA encoding various enzymes, alone or in combination, that achieves the desirable effect of enhancing the levels of phytostanols, phytostanol esters, mixtures thereof, and tocopherols in the oil of seed thereof. Preferably, the genome can comprise introduced DNA encoding an enzyme selected from the following:

1. a 3-hydroxysteroid oxidase enzyme;
2. a steroid 5α-reductase enzyme;
3. a 3-hydroxysteroid oxidase enzyme and a steroid 5α-reductase enzyme;
4. a 3-hydroxysteroid oxidase enzyme and a tocopherol biosynthetic enzyme;

5. a steroid 5α-reductase enzyme and a tocopherol biosynthetic enzyme;

6. a 3-hydroxysteroid oxidase enzyme, a steroid 5α-reductase enzyme, and a tocopherol biosynthetic enzyme;

7. a 3-hydroxy-3-methylglutaryl-CoA reductase enzyme;

8. a 3-hydroxysteroid oxidase enzyme and a 3-hydroxy-3-methylglutaryl-CoA reductase enzyme;

9. a steroid 5α-reductase enzyme and a 3-hydroxy-3-methylglutaryl-CoA reductase enzyme;

10. a 3-hydroxysteroid oxidase enzyme, a steroid 5α-reductase enzyme, and a 3-hydroxy-3-methylglutaryl-CoA reductase enzyme;

11. a 3-hydroxysteroid oxidase enzyme, a 3-hydroxy-3-methylglutaryl-CoA reductase enzyme, and a sterol methyltransferase enzyme;

12. a steroid 5α-reductase enzyme, a 3-hydroxy-3-methylglutaryl-CoA reductase enzyme, and a sterol methyltransferase enzyme; and 13. a 3-hydroxysteroid oxidase enzyme, a steroid 5α-reductase enzyme, a 3-hydroxy-3-methylglutaryl-CoA reductase enzyme, and a sterol methyltransferase enzyme.

By further introducing into the genome of such plants DNA encoding a sterol acyltransferase, the level(s) of phytosterol and/or phytostanol esters can be increased. Further introducing into the genome of such plants DNA encoding an S-adenosylmethionine-dependent γ-tocopherol methyltransferase will elevate the level of α-tocopherol in oil of seed thereof.

In each case, the foregoing introduced DNAs can be operatively linked to regulatory signals that cause seed-specific or plastid-specific expression thereof. When the regulatory signals cause seed-specific expression, each of the introduced DNAs can be operatively linked to a transit peptide coding region capable of directing transport of the enzyme encoded thereby into a plastid.

The present invention encompasses not only such transgenic plants, but also transformed plant cells, including cells and seed of such plants, as well as progeny of such plants, for example produced from the seed.

Transformed plant cells and cells of the transgenic plants encompassed herein can be grown in culture for a time and under appropriate conditions to produce oil containing elevated levels of phytosterols and/or phytostanols, their corresponding esters, and tocopherols. Alternatively, the phytosterols, phytostanols, their corresponding esters, and/or tocopherols can be isolated directly from the cultures.

In addition, of course, seed obtained from the transgenic, progeny, hybrid, etc., plants disclosed herein can be used in methods for obtaining oil containing phytosterols, phytosterol esters, phytostanols, phytostanol esters, or mixtures thereof employing extraction and processing procedures known in the art. Note, in this regard, Kochhar (1983) *Prog. Lipid Res.* 22: 161-188.

The present invention also encompasses a method of producing a plant that accumulates an elevated level of sitosterol, at least one sitosterol ester, sitostanol, at least one sitostanol ester, or mixtures thereof, in seeds thereof compared to seeds of a corresponding plant comprising no introduced DNA encoding a polypeptide or protein that affects the biosynthesis of sterols, phytosterols, phytosterol esters, phytostanols, phytostanol esters, or combinations thereof, comprising sexually crossing a transgenic plant of the present invention with such a corresponding plant. The latter can be a non-transgenic plant, or a transgenic plant containing introduced DNA encoding a trait other than one affecting sterol, phytosterol, etc., biosynthesis. For example, such trait may be insect or herbicide resistance. Plants produced by this method also form part of the present invention.

Also included are plants that accumulate an elevated level of sitosterol, at least one sitosterol ester, sitostanol, at least one sitostanol ester, or mixtures thereof, in seeds thereof compared to seeds of a corresponding plant comprising no introduced DNA encoding a polypeptide or protein that affects the biosynthesis of sterols, phytosterols, phytosterol esters, phytostanols, phytostanol esters, or combinations thereof, which are apomictic. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucellus, 2) diplospory where the embryo develops from an unreduced egg in an embryo sac derived from the megaspore mother cell, and 3) adventitious embryony where the embryo develops directly from a somatic cell. In most forms of apomixis, psuedogamy or fertilization of the polar nuclei to produce endosperm is necessary for seed viability. In apospory, a "nurse" cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636 and references cited therein which are herein incorporated by reference.

The present invention also encompasses uniform populations of any of the plants discussed herein.

Besides seed, elevated levels of sterols, phytosterols, such as sitosterol, phytostanols, such as sitostanol, esters thereof, and tocopherols, such as α-tocopherol, can be found in other parts of the plants encompassed herein. While the seed-specific promoters contemplated in the present invention function preferentially in seed tissues, expression in other plant parts can be expected, depending upon the specificity of the particular promoter. Furthermore, promoters functional in plant plastids can be expected to drive expression of the recombinant constructs or expression cassettes disclosed herein in plastids present in tissues and organs other than seeds. For example, elevated levels of sterols, phytosterols, etc., can be expected in fruits, as well as vegetable parts of plants other than seeds. Vegetable parts of plants include, for example, pollen, inflorescences, terminal buds, lateral buds, stems, leaves, tubers, and roots. Thus, the present invention also encompasses these and other parts of the plants disclosed herein that contain elevated levels of desirable phytosterol, phytostanol, etc., and tocopherol compounds.

Of course, a significant effect of introducing into plants the coding sequences disclosed herein will be on the content of phytosterols/phytostanols and their esters of seed oil. Therefore, additional aspects of the present invention include oil obtainable from the seed of the plants described herein, and methods for producing such plants and oil. Methods for extracting and processing seed oils are well known in the art.

Oils produced by the cells, plants, and methods disclosed herein are superior in phytosterol/phytostanol composition to conventional oils in a variety of ways. Oil of the present invention can contain an elevated level of at least one sterol, at least one phytosterol, at least one phytosterol ester, at least one phytostanol, at least one phytostanol ester, or mixtures thereof. Preferred compounds include sitosterol, sitostanol, and their esters. Surprisingly, oils of the present invention have also been found to contain the novel compound brassicastanol. Prior to the present invention, no method was known for producing this phytostanol. Oil of appropriately engineered plants, i.e., those transformed with one or more DNAs encoding tocopherol biosynthetic enzymes, also contains elevated levels of at least one tocopherol compound, for example α-tocopherol.

Oils of the present invention comprise sitostanol, at least one sitostanol ester, or mixtures thereof in an amount of at least about 57% by weight of the total sterol compounds in the oils, preferably about 57% to about 90% by weight of the total sterol compounds, more preferably about 57% to about 65% by weight of the total sterol compounds. Expressed on a percent dry weight basis of the seed, oils of the present invention comprise sitostanol, at least one sitostanol ester, or mixtures thereof in an amount of at least about 0.08% of the dry weight of the seed, preferably about 0.08% to about 0.8% of the dry weight of the seed, and more preferably about 0.08% to about 0.4% of the dry weight of the seed. Such oils can further comprise a tocopherol compound, for example α-tocopherol, in an amount of at least about 0.02% of the dry weight of the seed, preferably about 0.02% to about 0.2% of the dry weight of the seed, and more preferably about 0.02% to about 0.025% of the dry weight of the seed. Oils of the present invention can further comprise the novel phytostanol brassicastanol, or at least one brassicastanol ester.

Oil from seed of plants containing and expressing introduced DNA encoding a sterol methyltransferase advantageously contains a reduced level of campesterol, at least one campesterol ester, campestanol, at least one campestanol ester, or mixtures thereof. The sterol methyltransferase-encoding DNA can be introduced alone, or in combination with other introduced DNA sequences encoding enzymes affecting the biosynthesis of sterol compounds as discussed herein. Campesterol/campestanol and their esters are considered to be undesirable because they are readily absorbed in the intestine, while their safety in the blood is unknown. Employing the plants and methods disclosed herein, one can obtain seed oil comprising about 0% to about 19%, preferably about 0% to about 12%, more preferably about 5% to about 9% campesterol, at least one campesterol ester, campestanol, at least one campestanol ester, or mixtures thereof by weight of the total sterol compounds of the oil. (The levels of these compounds are difficult to express on a percent seed dry weight basis because different seeds contain different percentages of these compounds expressed on this basis) These values represent a reduction of about 10% to about 100% in the amount of these compounds compared to those in conventional oils.

Introduction into plant cells of the enzyme-encoding DNA sequences discussed above modifies the biosynthesis of sterol compounds carried out by the methods, and in the cells, plants, and seeds, disclosed herein. In particular, the expression of a sterol acyltransferase in conjunction with these DNA sequences is expected to result in alteration of the phytosterol ester and phytostanol ester profiles in oil as fatty acids having two to 22 carbon atoms in the main chain can be substrates for the enhanced sterol acyltransferase enzymatic activity. The novel phytostanol ester compositions, e.g., sitostanol ester compositions, thus produced constitute another aspect of the present invention.

As discussed in the "Description of Related Art," phytostanols such as sitostanol are beneficial for lowering serum cholesterol (Ling et al. (1995) *Life Sciences* 57: 195-206) and preventing cardiac disease. Tocopherols act as antioxidants, and play a major role in protecting cells from damage caused by free radicals (Halliwell (1997) *Nutrition Review* 55: 44-60). As the amount of sitostanol in conventional vegetable and bran oils is low relative to that of other sterol compounds, the oils of the present invention are particularly useful for reducing the concentration of low density lipoprotein cholesterol in plasma. Furthermore, oils of the present invention, containing enhanced levels of tocopherols such as α-tocopherol, in addition to phytostanols and phytostanol esters, provide a single, convenient source of a combination of bioactive compounds having superior bioavailability and efficacy in improving human nutrition and cardiovascular health.

Thus, further aspects of the present invention include the following:

Cholesterol-lowering compositions comprising the oils and sitostanol ester compositions disclosed herein. Such cholesterol-lowering compositions can take the form of, or be used in, foods, food products, processed foods, food ingredients, food additive compositions, or dietary supplements that contain oils and/or fats. Non-limiting examples include margarines; butters; shortenings; cooking oils; frying oils; dressings, such as salad dressings; spreads; mayonnaises; and vitamin/mineral supplements. Patent documents relating to such compositions include U.S. Pat. Nos. 4,588,717 and 5,244,887, and PCT International Publication Nos. WO 96/38047, WO 97/42830, WO 98/06405, and WO 98/06714. Additional non-limiting examples include toppings; dairy products such as cheese and processed cheese; processed meat; pastas; sauces; cereals; desserts, including frozen and shelf-stable desserts; dips; chips; baked goods; pastries; cookies; snack bars; confections; chocolates; beverages; unextracted seed; and unextracted seed that has been ground, cracked, milled, rolled, extruded, pelleted, defatted, dehydrated, or otherwise processed, but which still contains the oils, etc., disclosed herein.

Food additive compositions of the present invention can be made by a method comprising obtaining oil containing a phytostanol or phytostanol ester selected from sitostanol, at least one sitostanol ester, or mixtures thereof, from cultured cells, or seed of a plant, of the present invention, and evenly distributing the oil or desired phytostanol compound in finely divided form throughout the food product or food additive composition to which it is added by dissolution or by suspension in an emulsion. For example, the oil or phytostanol compound can be dissolved in an edible solubilizing agent, or can be mixed with an edible solubilizing agent, an effective amount of a dispersant, and optionally, an effective amount of an antioxidant. Examples of useful edible solubilizing agents include, but are not limited to, monoglycerides, diglycerides, triglycerides, vegetable oils, tocopherols, alcohols, polyols, or mixtures thereof. Examples of useful antioxidants include, but are not limited to, tocopherols, such as α-tocopherol, ascorbic acid, inexpensive synthetic antioxidants, and mixtures thereof. Effective carriers for preparing emulsions or suspensions include water, alcohols, polyols, other edible compounds in which the oil or phytostanol compound is soluble or insoluble, and mixtures thereof. Examples of useful dispersants include, but are not limited to, lecithin, other phospholipids, sodium lauryl sulfate, fatty acids, salts of fatty acids, fatty acid esters, other detergent-like molecules, and mixtures thereof. Alternatively, the food additive composition can be made by a method comprising obtaining oil containing at least one tocopherol, and a phytostanol or phytostanol ester selected from sitostanol, at least one sitostanol ester, and mixtures thereof, from cultured cells, or seed of a plant, of the present invention, and mixing the oil with an edible solubilizing agent and an effective amount of a dispersant. Again, the edible solubilizing agent can include, but is not limited to, monoglycerides, diglycerides, triglycerides, vegetable oils, tocopherols, alcohols, polyols, or mixtures thereof, and the dispersant can include, but is not limited to, lecithin, other phospholipids, sodium lauryl sulfate, fatty acids, salts of fatty acids, fatty acid esters, other detergent-like molecules, and mixtures thereof.

The cholesterol-lowering compositions can also take the form of pharmaceutical compositions comprising a cholesterol-lowering effective amount of the oils or sitostanol ester compositions disclosed herein, along with a pharmaceutically acceptable carrier, excipient, or diluent. These pharmaceutical compositions can be in the form of a liquid or a solid. Liquids can be solutions or suspensions; solids can be in the form of a powder, a granule, a pill, a tablet, a gel, or an extrudate. U.S. Pat. No. 5,270,041 relates to sterol-containing pharmaceutical compositions.

Any of the foregoing cholesterol-lowering compositions can be used alone or in combination in methods to lower the risk of developing an elevated plasma concentration of low density lipoprotein cholesterol, to lower the plasma concentration of low density lipoprotein cholesterol, or to treat or prevent an elevated plasma concentration of low density lipoprotein cholesterol. Such methods comprise orally administering to a human or animal subject an effective amount of cholesterol-lowering composition. What constitutes an effective amount of cholesterol-lowering composition can be determined empirically, and depends in part on a variety of factors, including the age, weight, sex, diet, general medical condition of the subject, and the severity of hypercholesterolemia. Subjects undergoing treatment with the cholesterol-lowering combinations disclosed herein can be monitored by routine measurement of serum cholesterol levels to determine the effectiveness of therapy. Continuous analysis of the data obtained in this way permits modification of the treatment regimen during therapy so that optimal effective amounts of the cholesterol-lowering compositions of this invention are administered, and so that the duration of treatment can be determined as well. In this way, the treatment regimen/dosing schedule can be rationally modified over the course of treatment so as to achieve the lowest cholesterol-lowering effective amount of the present compositions which results in satisfactory anti-cholesterolemic effectiveness, and so that administration of these compositions is continued only so long as is necessary to successfully treat this condition. In general, an effective amount of a cholesterol-lowering composition of the present invention in the form of a phytostanol- or phytostanol ester-containing composition is in the range of from about 0.1 gm/day to about 4.5 gm/day. By way of example, a phytostanol ester composition, for example a sitostanol ester composition, can be administered in an amount in the range of from about 0.1 gm/day to about 4.5 gm/day, preferably from about 1 gm/day to about 4.5 gm/day, more preferably from about 2 gm/day to about 4.5 gm/day. A phytostanol composition, for example a sitostanol composition, can be administered in an amount in the range of from about 0.1 gm/day to about 3 gm/day, preferably from about 1 gm/day to about 3 gm/day, more preferably from about 2 gm/day to about 3 gm/day.

The cholesterol-lowering compositions of the present invention can be administered daily to patients in accordance with a number of different regimens. Fundamentally, these compositions should be administered in a cholesterol-lowering effective amount for a period of time effective to exert their anti-hypercholesterolemic preventing, reducing, or reversing action. Administration of the present cholesterol-lowering compositions should be continued until the hypercholesterolemic condition has been controlled or eliminated.

Another method encompassed by the present invention is that of achieving or improving effective absorption of sitostanol into a host, comprising producing at least one sitostanol ester by any of the methods disclosed herein, and administering this sitostanol ester to a host, which can be a human or animal. The sitostanol ester can be administered by a route selected from oral route, parenteral route, or topical route. The dose, which can be administered daily, can be up to about 10 milligrams of the sitostanol ester per kilogram of body weight. U.S. Pat. No. 5,202,045 relates to the use of stanol fatty acid esters to reduce serum cholesterol.

Yet another aspect of the present invention is the surprising discovery of the novel compound brassicastanol, having the structure shown below, in oils obtained by the methods disclosed herein.

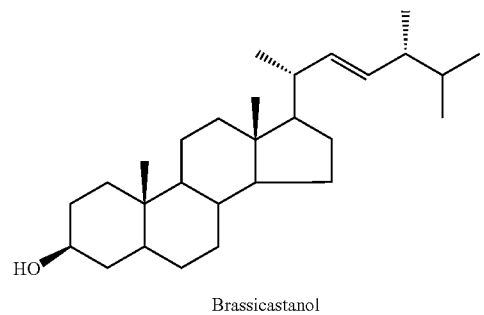

Brassicastanol

Also included in the present invention are esters of brassicastanol wherein the hydrogen of the hydroxyl group at C-3 of brassicastanol is replaced with a straight or branched chain fatty acid having two to 22 carbon atoms in the main chain.

Still another aspect of the invention is the surprising discovery of the novel compound stigmastanol, having the structure shown below, in oils obtained by the method disclosed herein.

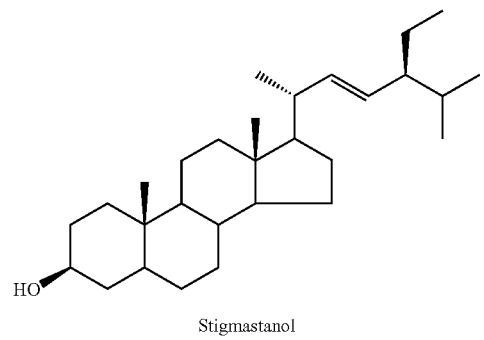

Stigmastanol

Also included in the present invention are esters of stigmastanol wherein the hydrogen of the hydroxyl group at C-3 of stigmastanol is replaced with a straight or branched chain fatty acid having two to 22 carbon atoms in the main chain.

In order to facilitate the modifications to sterol biosynthesis and accumulation described herein, the present invention also provides an isolated DNA molecule, having a nucleotide sequence selected from:

(a) SEQ ID NO: 2, SEQ ID NO: 4, or the complement of either of these nucleotide sequences, respectively;

(b) a nucleotide sequence that hybridizes to said nucleotide sequence of (a) under a wash stringency equivalent to 0.5× SSC to 2×SSC, 0.1% SDS, at 55-65° C., and which encodes a polypeptide having steroid 5α-reductase enzymatic activity substantially similar to that of *Arabidopsis thaliana* or *Zea mays* steroid 5α-reductase, respectively;

(c) a nucleotide sequence encoding the same genetic information as said nucleotide sequence of (a), but which is degenerate in accordance with the degeneracy of the genetic code; or (d) a nucleotide sequence encoding the same genetic information as said nucleotide sequence of (b), but which is degenerate in accordance with the degeneracy of the genetic code.

The present invention also provides an isolated DNA molecule that encodes a steroid 5α-reductase enzyme or fragment thereof, comprising a nucleic acid sequence selected from:

(a) SEQ ID NO:6, SEQ ID NO:8, or the complement of any of these nucleotide sequences, respectively;

(b) a nucleotide sequence that hybridizes to said nucleotide sequence of (a) under a wash stringency equivalent to 0.5× SSC to 2×SSC, 0.1% SDS, at 55-65° C., and which encodes a polypeptide having steroid 5α-reductase enzymatic activity substantially similar to that of *Glycine max* steroid 5α-reductase;

(c) a nucleotide sequence encoding the same genetic information as said nucleotide sequence of (a), but which is degenerate in accordance with the degeneracy of the genetic code; and (d) a nucleotide sequence encoding the same genetic information as said nucleotide sequence of (b), but which is degenerate in accordance with the degeneracy of the genetic code.

These isolated DNA molecules encoding steroid 5α-reductase enzymes or fragments thereof can be incorporated into recombinant constructs comprising, as operably linked components in the 5' to 3' direction, a seed-specific promoter or a promoter functional in a plant plastid, the isolated DNA molecule, and a transcription termination signal sequence. When the promoter is a seed-specific promoter, the recombinant construct can further comprise a transit peptide coding region capable of directing transport of the steroid 5α-reductase or fragment thereof into a plastid, operatively linked to the isolated DNA molecule. When the promoter is one that is functional in a plant plastid, the recombinant construct can further comprise a gene encoding a selectable marker for selection of plant cells comprising a plastid expressing the marker, and DNA regions of homology to the genome of the plastid, wherein the regions of homology flank the promoter functional in a plant plastid, the DNA sequence, the transcription termination signal sequence, and the gene encoding a selectable marker. Furthermore, when the promoter is one functional in a plant plastid, the recombinant construct can further comprise a ribosome binding site joined to the plastid promoter. The ribosome binding site can be obtained from a leader sequence selected from a site derived from a plastid, bacterial, or bacteriophage leader sequence, for example the binding site of the gene 10 leader, or the rbcLRBS site.

Any of the foregoing recombinant constructs can be incorporated into recombinant vectors comprising the recombinant constructs comprising the isolated DNA molecules encoding polypeptides having steroid 5α-reductase enzymatic activity. Such vectors can be bacterial or plant expression vectors.

In another aspect, the present invention encompasses transformed host cells comprising any of the foregoing recombinant constructs or vectors comprising the isolated DNA molecules encoding polypeptides having steroid 5α-reductase enzymatic activity. The host cells can be bacterial cells or plant cells. The steroid 5α-reductases, or fragments thereof possessing steroid 5α-reductase enzymatic activity, can be produced by culturing any of these transformed bacterial or plant host cells for a time and under conditions conducive to the production of the steroid 5α-reductase or enzymatically active fragment thereof, and recovering the peptide, polypeptide, or protein possessing steroid 5α-reductase enzymatic activity produced thereby.

To aid the reader in understanding the present invention, descriptions of the sterol compound and tocopherol biosynthetic pathways are presented below. These descriptions identify enzymes useful in achieving the modifications to the biosynthesis and accumulation of sterol compounds and tocopherols described herein, and identify sources of nucleic acid sequences encoding these enzymes.

The Sterol Compound Biosynthetic Pathway in Plants

Various steps in the sterol compound biosynthetic pathway in plants are shown in Scheme 1, below. The numbers over the arrows refer to plant sterol compound biosynthetic pathway enzymes and genes as indicated in Table 1.

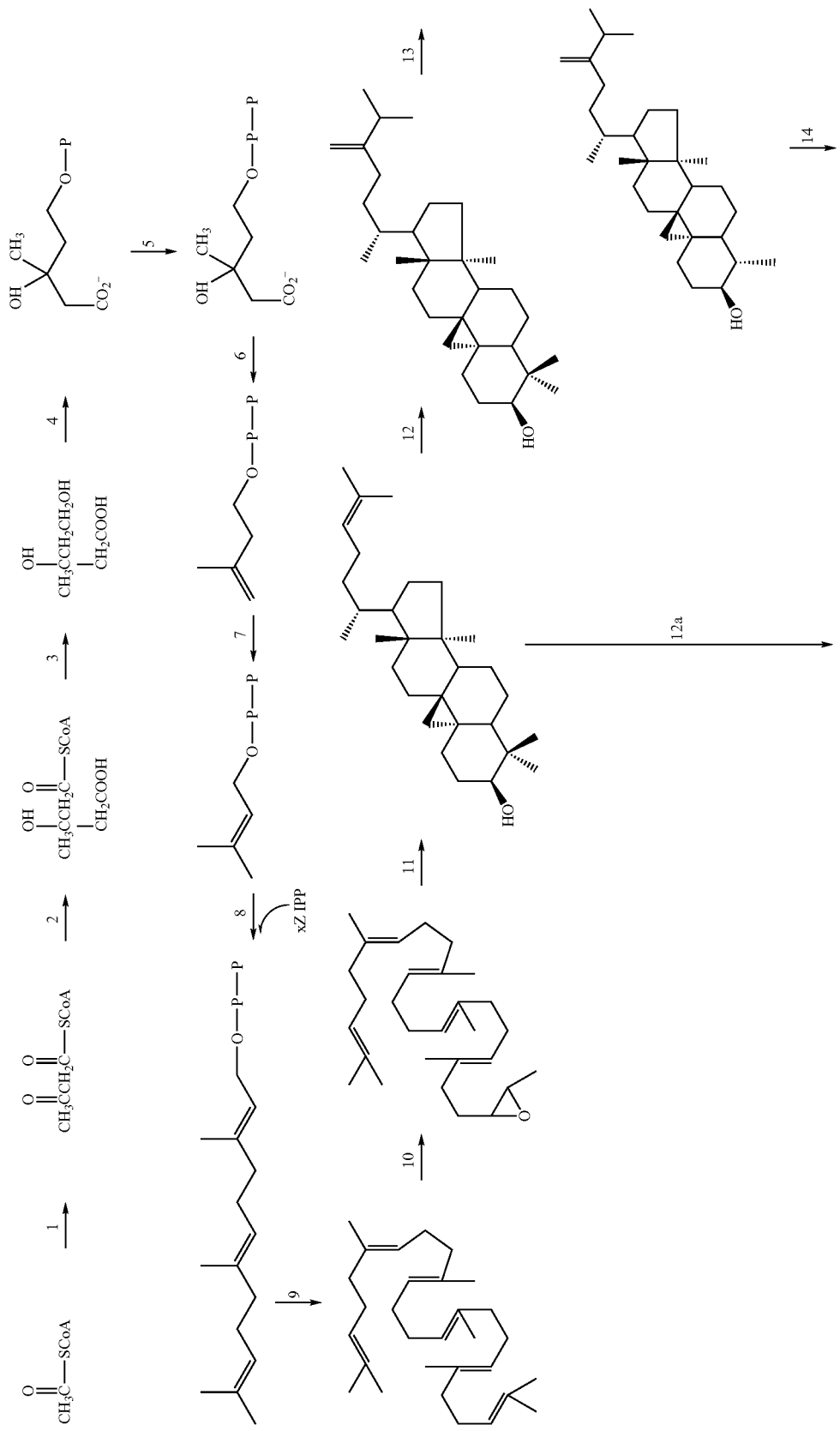

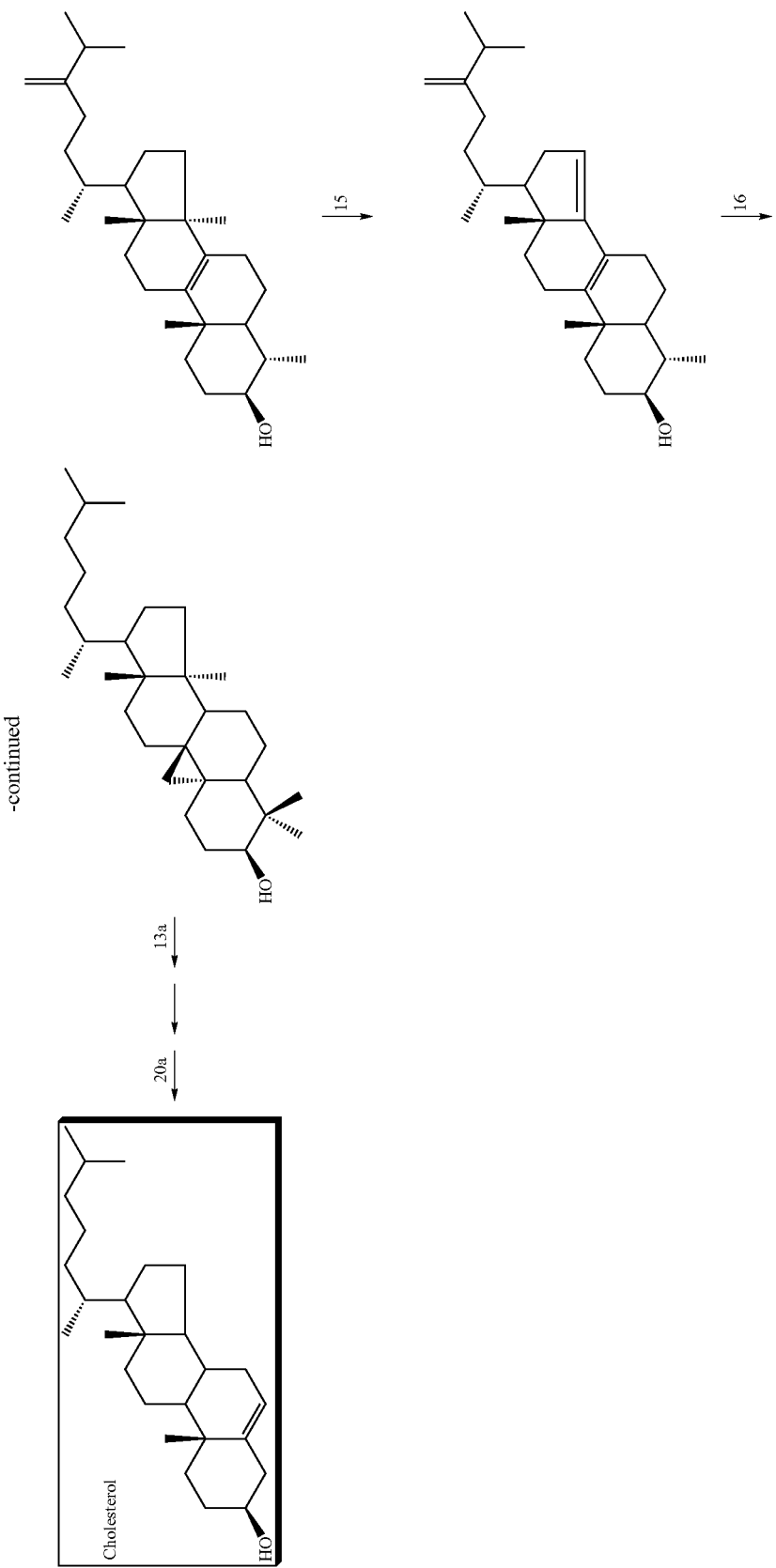

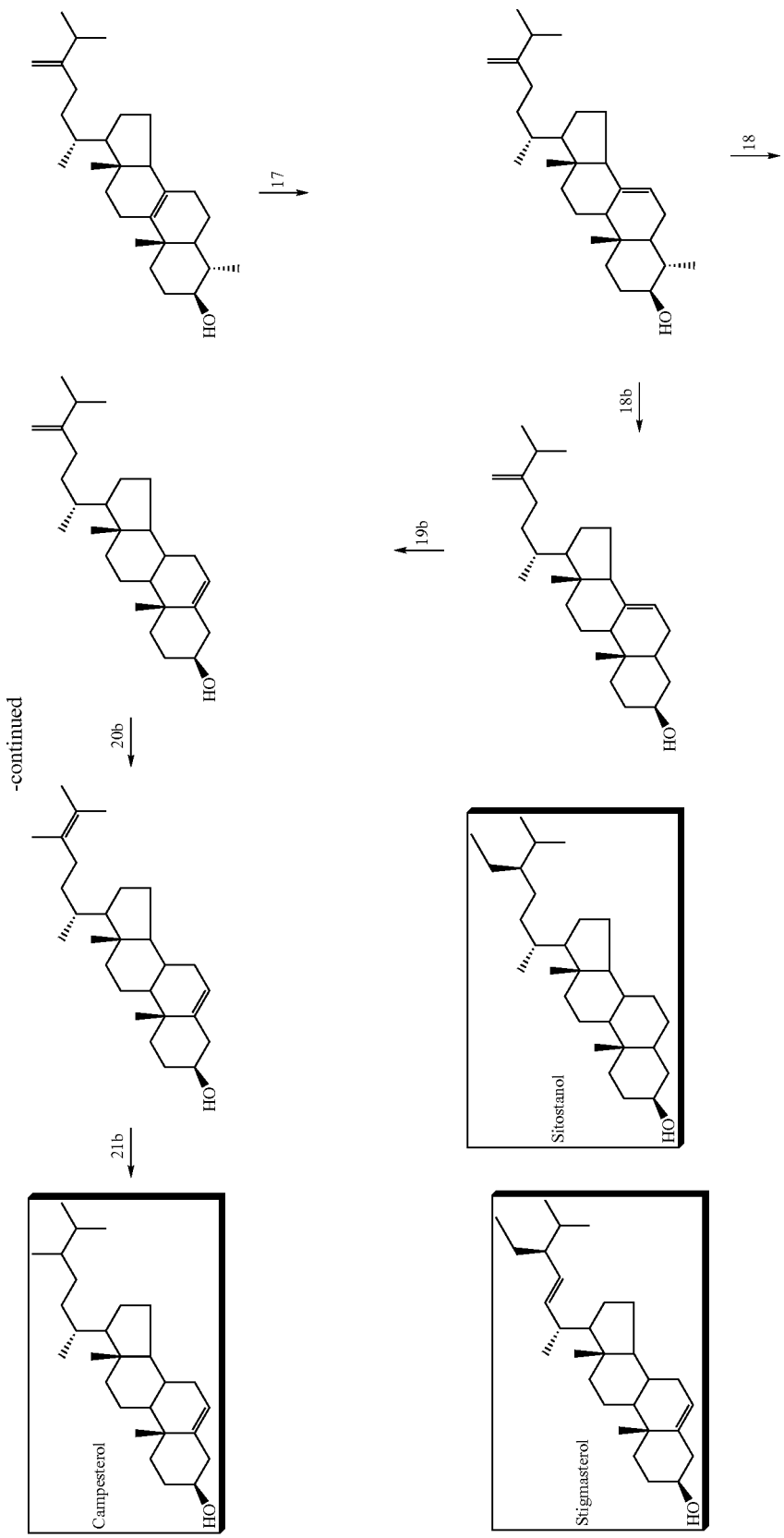

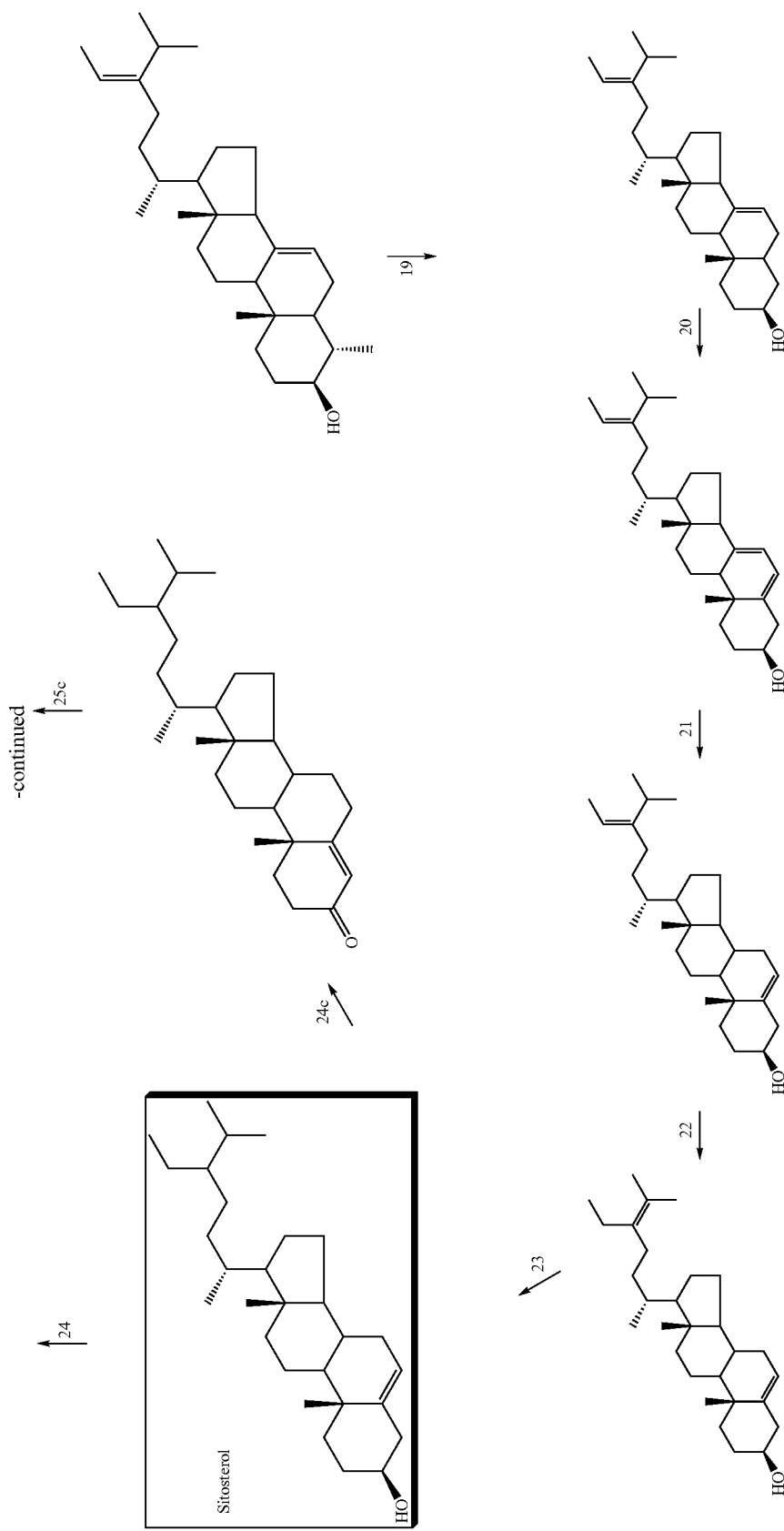

TABLE 1

Plant Sterol Compound Pathway Enzymes and Genes

| Enzyme | Step in Pathway | GenBank Gene ID |
|---|---|---|
| Acetoacetyl-CoA thiolase | 1 | X78116 |
| HMG-CoA synthase | 2 | X83882 |
| HMG-CoA reductase | 3 | X15032 |
|  |  | L19262 |
| Mevalonate kinase | 4 | X77793 |
| Phosphomevalonate kinase | 5 | Not available |
| Mevalonate pyrophosphate decarboxylase | 6 | Y14325 |
| Isopentenyl diphosphate isomerase | 7 | U49259 |
|  |  | U47324 |
| Farnesyl pyrophosphate synthase | 8 | X75789 |
| Squalene synthase | 9 | AF004560 |
| Squalene epoxidase | 10 | Not available |
| Squalene cyclase | 11 | U87266 |
| Sterol C-24 methyltransferase | 12,18 | U71400 |
| Sterol C-4 demethylase | 13,19 | Not available |
| Cycloeucalenol-obtusifoliol isomerase | 14 | Not available |
| Sterol C-14 demethylase | 15 | U74319 |
| Sterol C-14 reductase | 16 | PCT WO 97/48793 |
| Sterol C-8 isomerase | 17 | AF030357 |
| Sterol C-5 desaturase | 20 | X90454 |
| Sterol C-7 reductase | 21 | U49398 |
| Sterol C-24 isomerase | 22 | Klahre et al. (1998) Plant Cell 10: 1677-1690 |
| Sterol C-24 reductase | 23 | Same as 22 |
| Sterol C-22 desaturase | 24 | Not available |
| Sterol C-5 reductase | 25 | This patent |

The plant sterol compound biosynthesis pathway has two distinct components. The early pathway reactions, leading from acetyl-CoA to squalene via mevalonic acid, are common to other isoprenoids. The later pathway reactions, leading from squalene to the major plant sterol compounds such as sitosterol, campesterol and stigmasterol, are committed biosynthetic reactions.

The early pathway reactions have been studied in fungi and plants (Lees et al., *Biochemistry and Function of Sterols*, Nes and Parish, Eds., CRC Press, 85-99 (1997); Newman and Chappell, *Biochemistry and Function of Sterols*, Nes and Parish, Eds., CRC Press, 123-134 (1997); Bach et al., *Biochemistry and Function of Sterols*, Nes and Parish, Eds., CRC Press, 135-150 (1997)).

Acetoacetyl CoA thiolase (EC 2.3.1.9) catalyzes the first reported reaction, which consists of the formation of acetoacetyl CoA from two molecules of acetyl CoA (Dixon et al., *J. Steroid Biochem. Mol. Biol.* 62: 165-171 (1997)). This enzyme has been purified from radish. A radish cDNA has been isolated by functional complementation in *Saccharomyces cerevisiae* (GeneBank Accession #X78116). A radish cDNA has also been screened against a cDNA library of *Arabidopsis thaliana* (Vollack and Bach, *Plant Physiology* 111: 1097-1107 (1996)).

HMGCoA synthase (EC 4.1.3.5) catalyzes the production of HMGCoA. This reaction condenses acetyl CoA with acetoacetyl CoA to yield HMGCoA. HMGCoA synthase has been purified from yeast. A plant HMGCoA synthase cDNA has been isolated from *Arabidopsis thaliana* (Montamat et al., *Gene* 167: 197-201 (1995)).

HMGCoA reductase, also referred to as 3-hydroxy-3-methyglutaryl-coenzyme A (EC 1.1.1.34), catalyzes the reductive conversion of HMGCoA to mevalonic acid (MVA). This reaction is reported to play a role in controlling plant isoprenoid biosynthesis (Gray, *Adv. Bot. Res.* 14: 25-91 (1987); Bach et al., *Lipids* 26: 637-648 (1991); Stermer et al., *J. Lipid Res.* 35: 1133-1140 (1994). Plant HMGCoA reductase genes are often encoded by multigene families. The number of genes comprising each multigene family varies, depending on the species, ranging from two in *Arabidopsis thaliana* to at least seven in potato. Overexpression of plant HMGCoA reductase genes in transgenic tobacco plants has been reported to result in the overproduction of phytosterols (Schaller et al., *Plant Physiol.* 109: 761-770 (1995)).

Mevalonate kinase (EC 2.7.1.36) catalyzes the phosphorylation of mevalonate to produce mevalonate 5-phosphate. It has been reported that mevalonate kinase plays a role in the control of isoprenoid biosynthesis (Lalitha et al., *Indian. J. Biochem. Biophys.* 23: 249-253 (1986)). A mevalonate kinase gene from *Arabidopsis thaliana* has been cloned (GeneBank accession number X77793; Riou et al., *Gene* 148: 293-297 (1994)).

Phosphomevalonate kinase (EC 2.7.4.2) (MVAP kinase) is an enzyme associated with isoprene and ergosterol biosynthesis that converts mevalonate-5-phosphate to mevalonate-5-pyrophosphate utilizing ATP (Tsay et al., *Mol. Cell. Biol.* 11: 620-631 (1991)).

Mevalonate pyrophosphate decarboxylase ("MVAPP decarboxylase") (EC 4.1.1.33) catalyzes the conversion of mevalonate pyrophosphate to isopentenyl diphosphate ("IPP"). The reaction is reported to be a decarboxylation/dehydration reaction which hydrolyzes ATP and requires $Mg^{2+}$. A cDNA encoding *Arabidopsis thaliana* MVAPP decarboxylase has been isolated (Toth et al., *J. Biol. Chem.* 271: 7895-7898 (1996)). An isolated *Arabidopsis thaliana* MVAPP decarboxylase gene was reported to be able to complement the yeast MVAPP decarboxylase.

Isopentenyl diphosphate isomerase ("IPP:DMAPP") (EC 5.3.3.2) catalyzes the formation of dimethylallyl pyrophosphate (DMAPP) from isopentenyl pyrophosphate (IPP). Plant IPP:DMAPP isomerase gene sequences have been reported for this enzyme. It has also been reported that IPP:DMAPP isomerase is involved in rubber biosynthesis in a latex extract from *Hevea* (Tangpakdee et al., *Phytochemistry* 45: 261-267 (1997).

Farnesyl pyrophosphate synthase (EC 2.5.1.1) is a prenyltransferase which has been reported to play a role in providing polyisoprenoids for sterol compound biosynthesis as well as a number of other pathways (Li et al., *Gene* 17: 193-196 (1996)). Farnesyl pyrophosphate synthase combines DMAPP with IPP to yield geranyl pyrophosphate ("GPP"). The same enzyme condenses GPP with a second molecule of IPP to produce farnesyl pyrophosphate ("FPP"). FPP is a molecule that can proceed down the pathway to sterol compound synthesis, or that can be shuttled through other pathways leading to the synthesis of quinones or sesquiterpenes.

Squalene synthase (EC 2.5.1.21) reductively condenses two molecules of FPP in the presence of $Mg^{2+}$ and NADPH to form squalene. The reaction involves a head-to-head condensation, and forms a stable intermediate, presqualene diphosphate. The enzyme is subject to sterol demand regulation similar to that of HMGCoA reductase. The activity of squalene synthase has been reported to have a regulatory effect on the incorporation of FPP into sterol and other compounds for which it serves as a precursor (Devarenne et al., *Arch. Biochem. Biophys.* 349: 205-215 (1998)).

Squalene epoxidase (EC 1.14.99.7) (also called squalene monooxygenase) catalyzes the conversion of squalene to squalene epoxide (2,3-oxidosqualene), a precursor to the initial sterol molecule in the sterol compound biosynthetic pathway, cycloartenol. This is the first reported step in the pathway where oxygen is required for activity. The formation of squalene epoxide is also the last common reported step in sterol biosynthesis of animals, fungi, and plants.

The later pathway of sterol compound biosynthetic steps starts with the cyclization of squalene epoxide and ends with the formation of Δ5-24-alkyl sterols in plants.

2,3-oxidosqualene cycloartenol cyclase (EC 5.4.99.8) (also called cycloartenol synthase) is the first step in the sterol compound pathway that is plant-specific. The cyclization of 2,3-oxidosqualene leads to lanosterol in animals and fungi, while in plants the product is cycloartenol. Cycloartenol contains a 9,19-cyclopropyl ring. The cyclization is reported to proceed from the epoxy end in a chair-boat-chair-boat sequence that is mediated by a transient C-20 carbocationic intermediate.

S-adenosyl-L-methionine:sterol C-24 methyl transferase ("SMT1") (EC 2.1.1.41) catalyzes the transfer of a methyl group from S-adenosyl-L-methionine to the C-24 center of the sterol side chain (Nes et al. (1991) *J. Biol. Chem.* 266(23): 15202-15212). This is the first of two methyl transfer reactions that have been reported to be an obligatory and rate-limiting step of the sterol compound-producing pathway in plants. The second methyl transfer reaction occurs later in the pathway after the $\Delta^{8-7}$ isomerase. The enzyme responsible for the second methyl transfer reaction is named SMT2 (Bouvier-Nave, P. et al., (1997) *Eur. J. Biochem.*, 246: 518-529). An isoform, SMTII, catalyzes the conversion of cycloartenol to a $\Delta^{23(24)}$-24-alkyl sterol, cyclosadol (Guo et al. (1996) *Tetrahed. Lett.* 37(38):6823-6826).

Sterol C-4 demethylase catalyzes the first of several demethylation reactions, which results in the removal of the two methyl groups at C-4. While in animals and fungi the removal of the two C-4 methyl groups occurs consecutively, in plants it has been reported that there are other steps between the first and second C-4 demethylations. The C-4 demethylation is catalyzed by a complex of microsomal enzymes consisting of a monooxygenase, an NAD$^+$-dependent sterol 4-decarboxylase, and an NADPH-dependent 3-ketosteroid reductase.

Cycloeucalenol-obtusifoliol isomerase ("COI") catalyzes the opening of the cyclopropyl ring at C-9. The opening of the cyclopropyl ring at C-9 creates a double bond at C-8.

Sterol C-14 demethylase catalyzes demethylation at C-14, which removes the methyl group at C-14 and creates a double bond at that position. In both fungi and animals, this is the first step in the sterol synthesis pathway. Sterol 14-demethylation is mediated by a cytochrome P-450 complex.

Sterol C-14 reductase catalyzes a C-14 demethylation that results in the formation of a double bond at C-14 (Ellis et al., *Gen. Microbiol.* 137: 2627-2630 (1991)). This double bond is removed by a $\Delta^{14}$ reductase. The normal substrate is 4α-methyl-8,14,24 (24$^1$)-trien-3β-ol. NADPH is the normal reductant.

Sterol C-8 isomerase catalyzes a reaction that involves further modification of the tetracyclic rings or the side chain (Duratti et al., *Biochem. Pharmacol.* 34: 2765-2777 (1985)). The kinetics of the sterol isomerase-catalyzed reaction favor a $\Delta^8 \rightarrow \Delta^7$ isomerase reaction that produces a $\Delta^7$ group.

Sterol C-5 desaturase catalyzes the insertion of the $\Delta^5$-double bond that normally occurs at the $\Delta^7$-sterol level, thereby forming a $\Delta^{5,7}$-sterol (Parks et al., *Lipids* 30: 227-230 (1995)). The reaction has been reported to involve the stereospecific removal of the 5α and 6α hydrogen atoms, biosynthetically derived from the 4 pro-R and 5 pro-S hydrogens of the (+) and (−)R-mevalonic acid, respectively. The reaction is obligatorily aerobic, and requires NADPH or NADH. The desaturase has been reported to be a multienzyme complex present in microsomes. It consists of the desaturase itself, cytochrome $b_5$, and a pyridine nucleotide-dependent flavoprotein. The $\Delta^5$-desaturase is reported to be a mono-oxygenase that utilizes electrons derived from a reduced pyridine nucleotide via cytochrome $b_5$.

Sterol C-7 reductase catalyzes the reduction of a $\Delta^7$-double bond in $\Delta^{5,7}$-sterols to generate the corresponding $\Delta^5$-sterol. It has been reported that the mechanism involves, like many other sterol enzymes, the formation of a carbocationic intermediate via electrophilic "attack" by a proton.

Sterol C-24(28) isomerase catalyzes the reduction of a $\Delta^{24(28)}$-$\Delta^{24}$, a conversion that modifies the side chain. The product is a $\Delta^{24(25)}$-24-alkyl sterol. Sterol C-24 reductase catalyzes the reduction of the $\Delta^{24(25)}$ double bond at C-24, which produces sitosterol. Recently, Klahre et al. ((1998) *Plant Cell* 10:1677-1690) discovered that both the isomerization and reduction steps are catalyzed by an enzyme coded by the same gene, i.e., DIM/DWF1.

Sterol C-22 desaturase (EC 2.7.3.9) catalyzes the formation of a double bond at C-22 on the side chain. This formation of a double bond at C-22 on the side chain marks the end of the sterol compound biosynthetic pathway, and results in the formation of stigmasterol (Benveniste (1986) *Annu. Rev. Plant Physiol.* 37:275-308). The C-22 desaturase in yeast, which is the reported final step in the biosynthesis of ergosterol in that organism, requires NADPH and molecular oxygen. In addition, the reaction is also reported to involve a cytochrome P450 that is distinct from a cytochrome P450 participating in demethylation reactions (Lees et al. (1995) *Lipids* 30: 221-226).

Phytosterols are biogenetic precursors of brassinosteroids, steroid alkaloids, steroid sapogenins, ecdysteroids, and steroid hormones. This precursor role of phytosterols is often described as a "metabolic" function. A common transformation of free sterols in tissues of vascular plants is the conjugation at the 3-hydroxy group of sterols with long-chain fatty acids to form steryl esters, or with a sugar, usually with a single molecule of β-D-glucose, to form steryl glycosides. Some of the steryl glycosides are additionally esterified, at the 6-hydroxy group of the sugar moiety, with long-chain fatty acids to form acylated steryl glycosides.

The existence of several enzymes that are specifically associated with the synthesis and breakdown of conjugated sterols has been reported (Wojciechowski, *Physiology and Biochemistry of Sterols*, eds. Patterson, Nes, AOCS Press, 361 (1991)). Enzymes involved in this process include: UDPGlc:Sterol glucosyltransferase, phospho(galacto)glyceride steryl glucoside acyltransferase, and sterylglycoside and sterylester hydrolases.

UDPGlc:sterol glucosyltransferase (EC 2.4.1.173) catalyzes glucosylation of phytosterols by glucose transfer from UDP-glucose ("UDPG1"). The formation of steryl glycosides can be measured using UDP-[$^{14}$C]glucose as the substrate. Despite certain differences in their specificity patterns, all reported UDPGlc:sterol glucosyltransferases preferentially glucosylate only sterols or sterol-like molecules that contain a C-3 hydroxy group, a β-configuration, and which exhibit a planar ring. It has been reported that UDPGlc:sterol glucosyltransferases are localized in the microsomes.

Phospho(galacto)glyceride steryl glucoside acyltransferase catalyzes the formation of acylated steryl glycosides from the substrate steryl glycoside by transfer of acyl groups from some membranous polar acyllipids to steryl glycoside molecules.

Acylglycerol:sterol acyltransferase (EC 2.3.1.26) catalyzes the reaction wherein certain acylglycerols act as acyl donors in a phytosterol esterification. In plants, the activity of acylglycerol:sterol acyltransferase is reported to be associated with membranous fractions. A pronounced specificity for shorter chain unsaturated fatty acids was reported for all acyltransferase preparations studied in plants. For example, acylglycerol:sterol acyltransferases from spinach leaves and mustard roots can esterify a number of phytosterols.

Sterylglycoside and sterylester hydrolases ("SG-hydrolases") catalyze the enzymatic hydrolysis of sterylglycosides to form free sterols. The SG-hydrolase activity is not found in mature, ungerminated seeds, is reported to emerge only after the third day of germination, and is found mainly in the cotyledons. It has been reported that phospho(galacto)glyceride:SG acyltranaferase may catalyze a reversible reaction. Enzymatic hydrolysis of sterylesters in germinating seeds of mustard, barley and corn is reported to be low in dormant seeds, but increases during the first ten days of germination. This activity is consistent with a decrease in sterylesters and an increase in free sterols over the same temporal period.

Brassinosteroids

Brassinosteroids are steroidal compounds with plant growth regulatory properties, including modulation of cell expansion and photomorphogenesis (Artecal, *Plant Hormones, Physiology, Biochemistry and Molecular Biology*, Davies and Kluwer, Eds., Academic Publishers, 66 (1995); Yakota, *Trends in Plant Science* 2: 137-143 (1997)). Brassinolide (2α, 3α, 22α, 23αa -tetrahydroxy-24-methyl-B-homo-7-oxa-5α-cholestan-6-one) is a biologically active brassinosteroid. More than 40 natural analogs of brassinolide have been reported, and these analogues differ primarily in substitutions of the A/B ring system and side chain at position C-17 (Fujioka and Sakurai, *Natural Products Report* 14: 1-10 (1997)).

The pathway leading to brassinolide branches from the synthesis and catabolism of other sterols at campesterol. A synthetic pathway has been reported to campesterol, (24R)-24-methylcholest-4-en-3-one, (24R)-24-5α-methyl-cholestan-3-one, campestanol, cathasterone, teasterone, 3-dehydroteasterone, typhasterol, castasterone, brassinolide (Fujioka et al., *Plant Cell* 9: 1951-1962 (1997)). An alternative pathway branching from campestanol has also been reported where the 6-oxo group is lacking and is not introduced until later in the sequential conversion process. 6-deoxy brassinosteroids have low biological activity, and may be catabolic products. However, enzymatic activity converting 6-deoxocastasterone to castasterone has been reported, and thus links the alternative pathway to production of bioactive brassinolide.

Two genes encoding BR biosynthetic enzymes have been cloned from *Arabidopsis*. The earliest acting gene is DET2, which encodes a steroid 5α-reductase with homology to mammalian steroid 5α-reductases (Li et al., *Science* 272: 398-401 (1996)). The only reductive step in the brassinolide pathway occurs between campesterol and campestanol. A det2 mutation is reported to block the second step in the BR (24R)-24-methylcholest-4-en-3-one to (24R)-24-5-methyl-cholestan-3-one conversion (Fujioka et al., *Plant Cell* 9: 1951-1962 (1997)).

A second gene, CPD, encodes a cytochrome P450 that has domains homologous to mammalian steroid hydroxylases (Szekeres et al., *Cell* 85: 171-182 (1996)). CPD has been reported to be a teasterone-23-hydroxylase. Mutation of this gene blocks the cathasterone to teasterone conversion. Additional cytochrome P450 enzymes may participate in brassinolide biosynthesis, including the tomato DWARF gene that encodes a P450 cytochrome with 38% identity to CPD (Bishop, *Plant Cell* 8: 959-969 (1996)).

Sources of Nucleic Acid Sequences Encoding Enzymes Useful in Modifying Sterol Compound Biosynthesis and Accumulation in Plants 3-Hydroxysteroid Oxidases 3-hydroxysteroid oxidases catalyze the oxidation of the 3-hydroxy group of 3-hydroxysteroids to produce ketosteroids and hydrogen peroxide. They are capable of catalyzing the oxidation of various 3-hydroxysteroids, such as, for example, cholesterol. Most of the previously known 3-hydroxysteroid oxidases are called "cholesterol oxidases" (enzymatically catalogued as E.C.1.1.3.6), but cholesterol is only one of a number of 3-hydroxysteroid substrates for these enzymes. The use of all 3-hydroxysteroid oxidases and the nucleic acids encoding such proteins for the purpose of elevating phytostanol, for example sitostanol, levels within plants is within the scope of the present invention.

3-hydroxysteroid oxidases useful in the present invention include those naturally produced by microorganisms such as *Streptomyces* spp., *Brevibacterium* spp., *Pseudomonas* spp., *Mycobacterium* spp., *Schizophyllum commune*, *Nocardia* spp., and *Rhodococcus* spp. (Smith et al. (1976) *J. Steroid Biochem.* 7: 705-713; Long et al., PCT International Publication WO 90/05788; Corbin et al. (1994) *Appl. Environ. Microbiol.* 60: 4239). Genes encoding 3-hydroxysteroid oxidases have been cloned from *Streptomyces* sp. strain SA-COO (Murooka et al. (1986) *Appl. Environ. Microbiol.* 52: 1382) and *Brevibacterium sterolicum* ATCC 21387 (Fujishiro et al. (1990) *Biochem. Biophys. Res. Commun.* 172: 721).

Other organisms producing 3-hydroxysteroid oxidases useful in the present invention can be identified by assaying culture filtrates or individual proteins for 3-hydroxysteroid oxidase activity via the spectrophotometric assay disclosed in U.S. Pat. No. 5,518,908.

New *Streptomyces* genes that control the expression of 3-hydroxysteroid oxidase have been isolated and sequenced. U.S. Pat. No. 5,518,908 discloses the sequence of a 3-hydroxysteroid oxidase gene obtained from *Streptomyces* A19249, isolated in Madagascar. Any 3-hydroxysteroid oxidase gene, cDNA, synthetic DNA, plasmid-derived DNA, etc., can be inserted into a transformation vector cassette which is used to transform a plant. Such nucleic acids can be incorporated into the genome of the plant, which then produces an elevated level of phytostanols or phytostanol esters, such as sitostanol or sitostanol esters.

Steroid 5α-Reductases

Steroid 5α-reductases useful in the present invention include those obtainable from any source, including, for example, algae, bacteria, fungi, plants, or mammalian cells. A non-limiting example is the enzyme encoded by the *Arabidopsis* DET2 gene (Fujioka et al. (1997) *The Plant Cell* 9: 1951-1962). Other plant-derived sequences include full length cDNAs from *Arabidopsis*, corn, and soybean, presented below. The standard IUPAC code for nucleotides used herein is:

| | |
|---|---|
| B = C, G, or T | Y = C or T |
| D = A, G, or T | K = G or T |
| H = A, C, or T | M = A or C |
| V = A, C, or G | S = G or C |
| R = A or G | W = A or T |
| | N = any base |

The sequences below are putative steroid 5α-reductases, or fragments thereof, based on homology to mammalian sequences. These sequences were originally identified by homology to a jojoba microsomal membrane protein having the N-terminal amino acid sequence (SEQ ID NO: 1)
MKVTVQTRSGRELIKGGIELHDSATVTDLQEAIYIKTKKYYRA.

This sequence was used to search EST databanks from *Arabidopsis*, corn, and soybean for cDNAs encoding peptides similar to the jojoba N-terminal sequence. The *Arabidopsis* and corn cDNA sequences were determined, and the protein sequences of the ORFs encoded thereby were used to search GenPept. This revealed that the protein sequences share similarity with mammalian steroid 5α-reductases involved in sterol biosynthesis. By analogy, the plant proteins should catalyze similar reactions. The sequence of a human steroid 5α-reductase is available as GenBank accession No. 338476.

The full length cDNA sequence of *Arabidopsis thaliana* steroid 5α-reductase is:

(SEQ ID NO: 2)
ACCCACGCGTCCGCTCTATCTCTCTCAATTTCCTCATCTGGGTCTTCCTC

GTTTGCTCCGCTTAAGCACCATGAAGGTCACCGTCGTCTCCCGCAGCGGC

AGAGAAGTCCTCAAAGCTCCCCTTGACCTCCCCGATTCGGCGACTGTTGC

TGATCTGCAAGAAGCGTTTCATAAGAGAGCTAAGAAGTTTTACCCGTCGA

GGCAAAGACTGACTCTTCCCGTGACTCCTGGATCGAAGGACAAACCTGTT

GTCCTCAATAGCAAGAAATCACTGAAGGAGTACTGTGATGGAAACAACAA

CTCCTTAACTGTAGTCTTCAAAGACCTGGGGGCACAAGTTTCCTACCGCA

CACTCTTCTTCTTCGAGTATCTTGGCCCTCTCCTTATCTACCCTGTCTTT

TACTACTTCCCTGTTTACAAGTTTCTTGGTTATGGAGAGGACTGTGTGAT

CCATCCGGTCCAGACGTACGCTATGTACTACTGGTGCTTTCACTACTTCA

AACGGATCTTAGAAACGTTTTTCGTAGATCGGTTCAGCCACGCAACCTCC

CCAATCGGGAATGTGTTCAGGAACTGTGCTTATTACTGGAGCTTTGGTGC

TTACATTGCTTATTACGTCAACCATCCCTTGTACACTCCAGTTAGTGACC

TTCAGATGAAGATTGGTTTCGGGTTTGGTTTGGTTTGCCAAGTCGCAAAC

TTTTACTGTCACATATTGCTGAAGAATCTGAGGGACCCCAGTGGGCTGG

AGGCTACCAGATTCCACGCGGTTTCCTCTTCAACATTGTTACATGTGCCA

ATTACACTACCGAGATTTACCAATGGCTAGGATTCAACATCGCTACTCAG

ACCATTGCAGGATATGTTTTCCTCGCTGTTGCTGCTCTAATCATGACTAA

TTGGGCTCTTGGAAAGCACAGCCGTYTGAGAAAGATATTTGATGGAAAAG

ATGGAAAGCCAAAGTATCCAAGAAGATGGGTGATACTTCCTCCATTCCTT

TAGAAGCCATTGTTGCTTATCAGTAAAAGCTCTTAATAAAGCTGAAAATG

AGACTTTCTTTGGGTTCTCTGTATCGTTTCCTTTTTTGTTCGGTCTATGT

ATTGGTTATAACATGTTTATTCCTTTTGTTTCAATATGTTTTGATTTTTG

AAGTTAGAGAGATTTAGAAATGTACTTGTGTAGTTGTTTCTCACGCAAAC

CAATTCCTCTTTATGTATCGCATACATGAGTCAATAATAAATATGATTAC

TAGTAAAA.

The deduced amino acid sequence of the *Arabidopsis* steroid 5α-reductase is:

(SEQ ID NO: 3)
MKVTVVSRSGREVLKAPLDLPDSATVADLQEAFHKRAKKFYPSRQRLTLP

VTPGSKDKPVVLNSKKSLKEYCDGNNNSLTVVFKDLGAQVSYRTLFFFEY

LGPLLIYPVFYYFPVYKFLGYGEDCVIHPVQTYAMYYWCFHYFKRILETF

FVHRFSHTSPIGNVFRNCAYYWSFGAYIAYYVNHPLYTPVSDLQMKIGFG

FGLVCQVANFYCHILLKNLRDPSGAGGYQIPRGFLFNIVTCANYTTEIYQ

WLGFNIATQTIAGYV FLAVAALIMTNWALGKHSRLRKIFDGKDGKPKYP

RRWVILPPFL.

The full length cDNA sequence of *Zea mays* steroid 5α-reductase is:

(SEQ ID NO: 4)
GAATTCGGCTCGAGCTCTCCTCTCCTCTCCTCTCCCCCGCATCCACGGCC

GCAGGCAGCAGGCAGCCACTCGACGATCTAGTCGTCTCTCTCCCCGCTCT

GCCGCCTCGCTGCCGCGGCTTCCCGTCGGCGGGAGGATGAAGGTCACGGT

CGTGTCCCGGAGCGGCCGGGAGGTCGTCAAGGGCGGCATCGACCTCAAGG

ACTCGGCCAAGGTCGCGGACCTGCAGGAGGCCATCCATGCCAGGACTAAG

AAGTATTATCCTTCTAGGCAGCGGCTCACCCTCCCCCTTCAACCTGGAAA

AGGCGGGAAGCCAGTTGTCCTCAGTCCGAAGGCCAGCCTGCTAGAATACT

GCGAGAAGGGTTCTGGGTCACTGACAGTGGTCTTCAAAGATTTAGGGCCA

CAGGTCTACTACAGCACACTGTTCTTCTTCGAGTACCTGGGTCCTCTCAT

CATCTACCCCATGTTCTACTATCTGCCCGTCTACAAGTACTTCGGGCACG

AGGGGGAGCGGGCCATGCACCCTGTCCAGACCTACGCAATGTACTACTGG

TGCTTCCACTACTTCAAGCGGATCATGGAGACGTTCTTCGTGCACCGCTT

CAGCCACGCGACGTCGCCGCTCTCGAACGTCTTCAGGAACTGTGCCTACT

ACTGGACCTTCGGCGCTTACATTGCTTACTACTGCAACCACCCGCTGTAC

ACCCCAGTGAGTGATCTGCAGATGAAGATTGGGTTTGGTTTTGGGGTCGT

CTGCCAGGTCGCGAACTTCTACTGCCACATCCTGCTGCGGAACCTCAGGA

GCCCAAGCGGCAGCGGCGGGTACCAGATCCCCCGCGGTTTCTTGTTCAAC

ATCGTGACCTGCGCCAATTACACCACCGAGATCTACCAGTGGGTCGGCTT

CAACATCGCCACACAGACCGTGGCAGGTTACGTCTTCCTTGTCGTGGCGG

CGGGCATCATGACCAACTGGGCGCTCGGCAAGCACAGCCGTCTGAAGAAG

CTGTTTGACGGCAAGGATGGGAGGCCCAAGTACCCTCGCCGGTGGGTGAT

TCTCCCTCCGTTCCTGTGAAGAGGCGGTGGTGGTGGCTCACTGTTGGTGG

TCGGCCCATTGTGATTCGATGTCTACAGACAGTTGTACTGTACTAATCGT

GCCTGTTTAGCGGTTGAACTTGGATTCCGTTGTCCGAAGTTTCTAATCCG

AAAGATGGATTTCATTTTCTTCTTCTTCTTAGCATTATGTCACTGTC

TCACGTCGTCCTGTCTCAATACAGTCTAAGGTTCATGTGATGTTATCCCC

ATTTGTCCACGCAGAAGTGAAGTGAATGCAGTCACTATTTCGATTCGACA

AAAAAAAAAA.

The deduced amino acid sequence of the *Zea mays* steroid 5α-reductase is:

(SEQ ID NO: 5)
MKVTVVSRSGREVVKGGIDLKDSAKVADLQEAIHARTKKYYPSRQRLTLP

LQPGKGGKPVVLSPKASLLEYCEKGSGSLTVVFKDLGPQVYYSTLFFFEY

LGPLIIYPMFYYLPVYKYFGHEGERAMHPVQTYAMYYWCFHYFKRIMETF

FVHRFSATSPLSNVFRNCAYYWTFGAYIAYYCNHPLYTPVSDLQMKIGFG

FGVVCQVANFYCHILLRNLRSPSGSGGYQIPRGFLFNIVTCANYTTEIYQ

WVGFNIATQTVAGYVFLVVAAGIMTNWALGKHSRLKKLFDGKDGRPKYPR

RWVILPPFL.

The cDNA Sequence of a first *Glycine max* Steroid 5α-Reductase is:

(SEQ ID NO: 6)
GAATTCGGCTCGAGCGGGGATGTCAGTGATAAGCCTTGTGTCACTGGCTA

ATGCTGGCTTCTCAGAGATTAGAGGGAAGCATTTGAACTATTCAAAGTTT

TGGAATGCTAATCCCTCTGCAGAAAAGCAGGTCAAGTTGTCTAGCAAAGC

TGGCATGCTTTTGCTGTACACTCCTGCTTTTCTTGCTGGCCTTGCATCCT

TCTGGATCTTTCCTCATCAAGGCCTCAGATCCACCCTCCTTCAGTCTGCA

GTTACCCTGCATTTCTTCAAGAGGGTCTTTGAGGTTGTGTTTATTCACAA

ATATAGTGGTGCCATGCTTCTTGATTCTGCAATCCCCATCACTCTGAGTT

ATTTCCTATCAACTGCAACTATGATCTATGCTCAACACTTAACACAAGGG

CTTCCAGAACCACCAATCGATCTGTTGTATCCTGGCATTGTTTTGTTTGT

GGTGGGCATCATTGGCAACTTCTACCACCACTACCTTCTATCCAACTTAA

GGGGAAAGGGTGAAAAGGAGTACAAGATTCCAAAGGGTGGCATGTTTGAG

CTTGTCATATGTCCCCACTACCTGTTTGAGATTATTGAGTTTTATGGGTT

CTCCTTCATTTCGCAGACGCTATATGCATTCTCTTTCACCGTAGGCACTA

CTTTATACTTGCTAGGTAGGAGTTATTCAACTAGGAAATGGTATCTTTCT

AAGTTTGAAGATTTCCCTGAGCATGTTAAGGCTATCATCCCATTTGTCTT

CTAGAAATGTTGGAAGGAATAACTAATTTTACTTTCATTTCTCAGACGCT

ATATGCATTATCTTTCACTGTAGGCGCTACTTTGTACTTGCTATGTAGGA

GTGATTCGACTAGGAAATGGTATCTTTCTAGGTTTGAAGATTTCCCTAAA

AAAAAAAAAAAAGGGCGGGCCGCCG

The deduced amino acid sequence of SEQ ID NO: 6 is:

(SEQ ID NO: 7)
MSVISLVSLANAGFSEIRGKHLNYSKFWNANPSAEKQVKLSSKAGMLLLY

TPAFLAGLASFWIFPHQGLRSTLLQSAVTLHFFKRVFEVVFIHKYSGAML

LDSAIPITLSYFLSTATMIYAQHLTQGLPEPPIDLLYPGIVLFVVGIIGN

FYHHYLLSNLRGKGEKEYKIPKGGMFELVICPHYLFEIIEFYGFSFISQT

LYAFSFTVGTTLYLLGRSYSTRKWYLSKFEDFPEHVKAIIPFVF*.

The cDNA Sequence of a second *Glycine max* Steroid 5α-Reductase is:

(SEQ ID NO: 8)
GAATCGGCTCGAGAACAAGCAAACACCATGGTGATTAAGTCTGTGTTGTT

CAGCTTCATTTTCCCCCCGCCACCTTCTCTGGTGGTTGGGGGTTGACTGT

GACAAGCTTCCTGATACTGGCTAATGCTTTCTTGTCAGAAATTAGAGGGA

AGCATTTGAACTATTCAAAGTTTTGGAATGCTAATCCCTCTGCAGAAAAG

CAGGTCAAGTTGTCTAGCAAAGCTGGCATGCTTTTGCTGTACACTCCTGC

TTTTCTTGCTGGCCTTGCATCCTTCTGGGTCTTTCCTCATCAAGGGCTCA

GATTCACCATCCTTCAATCTGCTGTTACTCTGCACTACTTCAAGAGGGTC

TTTGAGGGTCTGTTTATTCACAAATATAGTGGAGGCATGACACTTGAATC

TGCAATCCCCATCACTCTGAGTTATTTCCTCTCAGCTGTAACTATGGTCT

ATTCTCAACACCTAACAAAAGGGTTTCCAGAACCACCAATCAATCTGTTC

TACCCTGGCATTGTGTTGTTTCTAGTTGGCATCATTGGCAACTTCTACCA

CCATTACCTTCTGTCCAAATTGAGGGGAAAGGGTGAAAAGGAGTACAAGA

TTCCAAAGGGTGGCTTTTTTGAGCTTGTGATTTGCCCCCACTACTTCTTT

GAGATTACTGTGTTTTATGGGATCTTCTTCATTTCTCAGACATTATATTC

ATTCGCTTTCGCTGTAGGCACTACTATGTACTTGGTGGGTAGGAGTTACT

CAACTAGGAAATGGTATCTTTCTAAGTTTGAAGATTTCCCTAAGCATGTT

AAGGCTGTCATCCCATTTGTCTTCTAAATGTTGTAATGAACATCTAATTC

TACTTGAGTTGTAAGTGTGCTGCTAGATTGTGTTTAAAAAAAAAAAAAAA

AAGGGCGGCCGCCGG

The deduced amino acid sequence of SEQ ID NO:8 is:

(SEQ ID NO: 9)
MVIKSVLFSFIFPPPPSLVVWGLTVTSFLILANAFLSEIRGKHLNYSKFW

NANPSAEKQVKLSSKAGMLLLYTPAFLAGLASFWVFPHQGLRFTILQSAV

TLHYFKRVFEGLFIHKYSGGMTLESAIPITLSYFLSAVTMVYSQHLTKGF

PEPPINLFYPGIVLFLVGIIGNFYHHYLLSKLRGKGEKEYKIPKGGFFEL

VICPHYFFEITVFYGIFFISQTLYSFAFAVGTTMYLVGRSYSTRKWYLSK

FEDFPKHVKAVIPFVF

HMG-CoA Reductase

A nucleic acid sequence encoding HMG-CoA reductase from *Hevea brasiliensis* has been disclosed by Chye et al. (1991) *Plant Mol. Biol.* 16: 567-577. A nucleic acid sequence encoding an *Arabidopsis thaliana* HMG-CoA reductase has been published by Caelles et al. (1989) *Plant Mol. Biol.* 13: 627-638, and is also available as GenBank accession number L19261. U.S. Pat. Nos. 5,306,862 and 5,365,017 disclose additional DNA sequences encoding HMG-CoA reductases.

Sterol Acyltransferases

Sterol O-acyltransferase enzymes such as acyl CoA:cholesterol acyltransferase (EC 2.3.1.26; ACAT) catalyze the formation of cholesterol esters from cholesterol and long chain fatty acids. Such enzymes can be used in the present invention to produce elevated levels of phytosterol and/or phytostanol esters.

Examples of nucleic acid sequences encoding full length ACAT or ACAT-like enzymes, or ESTs, include those from Arabidopsis thaliana, Caenorhabditis elegans, Glycine max (soybean), humans, Mortierella alpina, mouse, rat, and Zea mays (corn) are shown below.

The full length Arabidopsis thaliana ACAT DNA sequence is:

(SEQ ID NO: 10)
CTCTCGTGAATCCTTTTTCCTTTCTTCTTCTTCTTCTTCAGAGAAAAC
TTTGCTTCTCTTTCTATAAGGAACCAGACACGAATCCCATTCCCACCGAT
TTCTTAGCTTCTTCCTTCAATCCGCTCTTTCCCTCTCCATTAGATTCTGT
TTCCTCTTTCAATTTCTTCTGCATGCTTCTCGATTCTCTCTGACGCCTCT
TTTCTCCCGACGCTGTTTCGTCAAACGCTTTTCGAAATGGCGATTTTGGA
TTCTGCTGGCGTTACTACGGTGACGGAGAACGGTGGCGGAGAGTTCGTCG
ATCTTGATAGGCTTCGTCGACGGAAATCGAGATCGGATTCTTCTAACGGA
CTTCTTCTCTCTGGTTCCGATAATAATTCTCCTTCGGATGATGTTGGAGC
TCCCGCCGACGTTAGGGATCGGATTGATTCCGTTGTTAACGATGACGCTC
AGGGAACAGCCAATTTGGCCGGAGATAATAACGGTGGTGGCGATAATAAC
GGTGGTGGAAGAGGCGGCGGAGAAGGAAGAGGAAACGCCGATGCTACGTT
TACGTATCGACCGTCGGTTCCAGCTCATCGGAGGGCGAGAGAGAGTCCAC
TTAGCTCCGACGCAATCTTCAAACAGAGCCATGCCGGATTATTCAACCTC
TGTGTAGTAGTTCTTATTGCTGTAAACAGTAGACTCATCATCGAAAATCT
TATGAAGTATGGTTGGTTGATCAGAACGGATTTCTGGTTTAGTTCAAGAT
CGCTGCGAGATTGGCCGCTTTTCATGTGTTGTATATCCCTTTCGATCTTT
CCTTTGGCTGCCTTTACGGTTGAGAAATTGGTACTTCAGAAATACATATC
AGAACCTGTTGTCATCTTTCTTCATATTATTATCACCATGACAGAGGTTT
TGTATCCAGTTTACGTCACCCTAAGGTGTGATTCTGCTTTTTTATCAGGT
GTCACTTTGATGCTCCTCACTTGCATTGTGTGGCTAAAGTTGGTTTCTTA
TGCTCATACTAGCTATGACATAAGATCCCTAGCCAATGCAGCTGATAAGG
CCAATCCTGAAGTCTCCTACTACGTTAGCTTGAAGAGCTTGGCATATTTC
ATGGTCGCTCCCACATTGTGTTATCAGCCAAGTTATCCACGTTCTGCATG
TATACGGAAGGGTTGGGTGGCTCGTCAATTTGCAAAACTGGTCATATTCA
CCCGGATTCATGGGATTTATAATAGAACAATATATAAATCCTATTGTCAGG
AACTCAAAGCATCCTTTGAAAGGCGATCTTCTATATGCTATTGAAAGAGT
GTTGAAGCTTTCAGTTCCAAATTTATATGTGTGGCTCTGCATGTTCTACT
GCTTCTTCCACCTTTGGTTAAACATATTGGCAGAGCTTCTCTGCTTCGGG
GATCGTGAATTCTACAAAGATTGGTGGAATGCAAAAAGTGTGGGAGATTA
CTGGAGAATGTGGAATATGCCTGTTCATAAATGGATGGTTCGACATATAT
ACTTCCCGTGCTTGCGCAGCAAGATACCAAAGACACTCGCCATTATCATT
GCTTTCCTAGTCTCTGCAGTCTTTCATGAGCTATGCATCGCAGTTCCTTG
TCGTCTCTTCAAGCTATGGGCTTTTCTTGGGATTATGTTTCAGGTGCCTT
TGGTCTTCATCACAAACTATCTACAGGAAAGGTTTGGCTCAACGGTGGGG
AACATGATCTTCTGGTTCATCTTCTGCATTTTCGGACAACCGATGTGTGT
GCTTCTTTATTACCACGACCTGATGAACCGAAAAGGATCGATGTCATGAA

ACAACTGTTCAAAAAATGACTTTCTTCAAACATCTATGGCCTCGTTGGAT
CTCCGTTGATGTTGTGGTGGTTCTGATGCTAAAACGACAAATAGTGTTAT
AACCATTGAAGAAGAAAAGACAATTAGAGTTGTTGTATCGCA.

The amino acid sequence deduced from the foregoing DNA sequence is:

(SEQ ID NO: 11)
MAILDSAGVTTVTENGGGEFVDLDRLRRRKSRSDSSNGLLLSGSDNNSPS
DDVGAPADVRDRIDSVVNDDAQGTANLAGDNNGGGDNNGGGRGGGEGRGN
ADATFTYRPSVPAHRRARESPLSSDAIFKQSHAGLFNLCVVVLIAVNSRL
IIENLMKYGWLIRTDFWFSSRSLRDWPLFMCCISLSIFPLAAFTVEKLVL
QKYISEPVVIFLHIIITMTEVLYPVYVTLRCDSAFLSGVTLMLLTCIVWL
KLVSYAHTSYDIRSLANAADKANPEVSYYVSLKSLAYFMVAPTLCYQPSY
PRSACIRKGWVARQFAKLVIFTGFMGFIIEQYINPIVRNSKHPLKGDLLY
AIERVLKLSVPNLYVWLCMFYCFFHLWLNILAELLCFGDREFYKDWWNAK
SVGDYWRMWNMPVHKWMVRHIYFPCLRSKIPKTLAIIIAFLVSAVFHELC
IAVPCRLFKLWAFLGIMIFQVPLVFITNYLQERFGSTVGNMIFWFIFCIF
GQPMCVLLYYHDLMNRKGSMS.

The Caenorhabditis elegans ACAT 5' cDNA EST is:

(SEQ ID NO: 12)
TGCAAATGCGTCAACAAACGGGACGACGGCGGCGTCAGCCTTCGGNAAAC
ATCTAATGGTTCTTTGGCTTCCAGTAGACGCTCCTCATTTGCACAAAATG
GTAATTCGTCAAGGGAAAAGTTCAGAAATGAGAGGACCTTGCGAGAAAGT
GGTACATACTGCTCAAGATTCATTGTTTTCGACGAGTTCTGGATGGACAA
ATTTCCGTGGATTCTTCAATTTGTCTATTTTACTTTTGGTACTTTCAAAT
GGACGCGTGGCACTTGAAAATGTGATCAAATATGGTATTTTGATAACACC
CCTTCAGTGGATCTCAACGTTTGTTGAGCATCACTACTCAATTTGGAGCT
GGCCAAATCTTGCTCTCATCCTATGCTCAAA.

The Caenorhabditis elegans ACAT 3' cDNA EST is:

(SEQ ID NO: 13)
TTTGATATGTACGGTAAATGGAAAAAAGGTATTCATGTATGGCAAGGTGG
TAATAAATGGCACTAAATATGTTTCAAAAGTGTGAGCAAACGTATGTGAG
AGACGAGAAAAATAAGAAAACGACCTGTAATACATGAAAAATATCAATAG
GAATTTTGAGATAATTTGGCAACATGCAATATAATGATTATAATAAAAAA
CTTGTCTTAAGACTAGAGAACTGCTAATTCAAAAAAAACAAATTGAGATA
AATCAAATACCAACGGTTTGGTTTTGAACTGCTGAAACACCAAAGTTCA
A.

The Caenorhabditis elegans ACAT protein sequence is:

(SEQ ID NO: 14)
MRQQTGRRRRQPSETSNGSLASSRRSSFAQNGNSSRKSSEMRGPCEKVVH
TAQDSLFSTSSGWTNFRGFFNLSILLLVLSNGRVALENVIKYGILITPLQ
WLSTFVEHHYSIWSWPNLALILCSNIQILSVFGMEKILERGWLGNGFAAV

-continued

FYTSLVIAHLTIPVVVTLTHKWKNPLWSVVMMGVYVIEALKFISYGHVNY

WARDARRKITELKTQVTDLAKKTCDPKQFWDLKDELSMHQMAAQYPANLT

LSNIYYFMAAPTLCYEFKFPRLLRIRKHFLIKRTVELIFLSFLIAALVQQ

WVVPTVRNSMKPLSEMEYSRCLERLLKLAIPNHLIWLLFFYTFFHSFLNL

IAELLRFADREFYRDFWNAETIGYFWKSWNIPVHRFAVRHIYSPMMRNNF

SKMSAFFVVFFVSAFFHEYLVSVPLKIFRLWSYYGMMGQIPLSIITDKVV

RGGRTGNIIVWLSLIVGQPLAILMYGHDWYILNFGVSAVQNQTVGI.

The *Glycine max* ACAT EST DNA sequence I is:

```
                                        (SEQ ID NO: 15)
AACGGAATTGAGACTCCAGAGAATATGCCAAAATGTATTAATAATTGTCA

CAACTTGGAAGGCTTTTGGAAAAACTGGCATGCTTCCTTCAACAAGTGGC

TTGTGAGGTATATATACATTCCTCTTGGGGATCTAAGAAAAAGCTACTA

AATGTGTGGGTTGTTTTCACATTTGTTGCAATCTGGCATGATTTAGAGTG

GAAGCTTCTTTCATGGGCATGGTTGACGTGTTTATTCTTCATCCCTGAGT

TGGTTTT.
```

The *Glycine max* ACAT EST DNA sequence II is:

```
                                        (SEQ ID NO: 16)
GTAAGCTTCAAGAGCTTAGCATANTTCCTGGTTGCCCCTANCATTATGTT

ACCAGCCAANCTATCCTCGCACACCTTATATTCGAAAGGGTTGGCTGTTT

CGCCAACTTGTCAACTGATAATATTTACAGGAGTTATGGGATTTATAATA

GAACAATACATTAATCCCATTGTACAAAATTCACAGCATCCTCTCAAGGG

AAACCTTCTTTACGCCATCGAGAGAGTTCTGAAG.
```

The *Glycine max* ACAT EST DNA sequence III is:

```
                                        (SEQ ID NO: 17)
GTGGAATGCCAAAACTGTTGAAGATTATTGGAGGATGTGAATATGCCTG

TTCACAAATGGATGATCCGCCACCTATATTTTCCATGTTTAAGGCACGGT

ATACCAAAGGCCGTTGCTCTTTTAATTGCCTTCCTGGTTCTGCTTTATTC

CATGAGCTGTGCATCGCTGTTCCTTGCCCACATATTCAAGTNGTGGGTTT

CNGNGGAATTNAGTTTCAGGTNCCTTGGGTTTCNACCNNAATTNNTNGGC

NAAAAAATTCCNNGAACCCCGGGGG.
```

The *Glycine max* ACAT EST DNA sequence IV is:

```
                                        (SEQ ID NO: 18)
CTGCTTTTGTATCTGGTGTCACGTTGATGCTATTAACTTGCATTGTGTGG

TTAAAATTGGTGTCATATGCACATACAAACTATGATATGAGAGCACTTAC

TGTTTCGAATGAAAAGGGAGAAACATTACCCAATACTTTGATATGGAGTA

TCCGTACACTGTGACCTTCAGGAGTTTGGCATACTTCATGGTTGCTCCTA

CATTATGCTATCAGACAAGCTATCCTCGCACACCTTCAGTTCGAAAGGGT

TGGGTGTTTCGTCAACT.
```

The full length human ACAT DNA sequence is:

```
                                        (SEQ ID NO: 19)
GTCTGGTGTGATGGGGACAGGGAGGGACTTCCCCTTACCCAGCACTGGTG

TTGGCTGAGGTGGGTGCTGAGTCTCAGAGCTTGGCATGGAGACCAGACAG

GGCTGGGTCTGCAAGCCTGAGGCTGCCGCCCTGAGCTCGGGCTGGGACGT

GCCCAGAGGTGTTGGGAGGATCTGGGGTGAGTACCCTGTGGCCAGGACTA

AAGGGGCTNCACCCTCCTGTCCATCCCTCGCAGATCTTGAGCAATGCCCG

GTTATTTCTGGAGAACCTCATCAAGTATGGCATCCTGGTGGACCCCATCC

AGGTGGTTTCTCTGTTCCTGAAGGATCCCTATAGCTGGCCCGCCCCATGC

CTGGTTATTGCGGCCAATGTCTTTGCTGTGGCTGCATTCCAGGTTGAGAA

GCGCCTGGCGGTGGGTGCCCTGACGGAGCAGGCGGGACTGCTGCTGCACG

TGGCCAACCTGGCCACCATTCTGTGTTTCCCAGCGGCTGTGGTCTTACTG

GTTGAGTCTATCACTCCAGTGGGCTCCCTGCTGGCGCTGATGGCGCACAC

CATCCTCTTCCTCAAGCTCTTCTCCTACCGCGACGTCAACTCATGGTGCC

GCAGGGCCAGGGCCAAGGCTGCCTCTGCAGGGAAGAAGGCCAGCAGTGCT

GCTGCCCCGCACACCGTGAGCTACCCGGACAATCTGACCTACCGCGATCT

CTACTACTTCCTCTTCGCCCCCACCTTGTGCTACGAGCTCAACTTTCCCC

GCTCTCCCCGCATCCGGAAGCGCTTTCTGCTGCGACGGATCCTTGAGATG

CTGTTCTTCACCCAGCTCCAGGTGGGGCTGATCCAGCAGTGGATGGTCCC

CACCATCCAGAACTCCATGAAGCCCTTCAAGGACATGGACTACTCACGCA

TCATCGAGCGCCTCCTGAAGCTGGCGGTCCCCAATCACCTCATCTGGCTC

ATCTTCTTCTACTGGCTCTTCCACTCCTGCCTGAATGCCGTGGCTGAGCT

CATGCAGTTTGGAGACCGGGAGTTCTACCGGGACTGGTGGAACTCCGAGT

CTGTCACCTACTTCTGGCAGAACTGGAACATCCCTGTGCACAAGTGGTGC

ATCAGACACTTCTACAAGCCCATGCTTCGACGGGGCAGCAGCAAGTGGAT

GGCCAGGACAGGGGTGTTCCTGGCCTCGCCCTTCTTCCACGAGTACCTGG

TGAGCGTCCCTCTGCGAATGTTCCGCCTCTGGGCGTTCACGGGCATGATG

GCTCAGATCCCACTGGCCTGGTTCGTGGGCCGCTTTTTCCAGGGCAACTA

TGGCAACGCAGCTGTGTGGCTGTCGCTCATCATCGGACAGCCAATAGCCG

TCCTCATGTACGTCCACGACTACTACGTGCTCAACTATGAGGCCCCAGCG

GCAGAGGCCTGAGCTGCACCTGAGGGCCTGGCTTCTCACTGCCACCTCAC

ACCCGCTGCCAGAGCCCACCTCTCCTCCTAGGCCTCGAGTGCTGGGGATG

GGCCTGGCTGCACAGCATCCTCCTCTGGTCCCAGGGAGGCCTCTCTGCCC

CTATGGGGCTCTGTCCTGCACCCCTCAGGGATGGCGACAGCAGGCCAGAC

ACAGTCTGATGCCAGCTGGGAGTCTTGCTGACCCTGCCCCGGGTCCGAGG

GTGTCAATAAAGTGCTGTCCAGTGACCTCTTCAGCCTGCCAGGGGCCTGG

GGCCTGGTGGGGGTATGGCCACACCCACAAGGGCGAGTGCCAGAGCTGT

GTGGACAGCTGTCCCAGGACCTGCCGGGGAGCAGCAGCTCCACTGCAGCA

GGGCGGGCATGGCCGGTAGGGGAGTGCAAGGCCAGGCAGACGCCCCCAT

TCCCCACACTCCCCTACCTAGAAAAGCTCAGCTCAGGCGTCCTCT.
```

The *Mortierella alpina* ACAT EST DNA sequence is:

(SEQ ID NO: 20)
GAGNNNNGNAACGTTTAGCCTNCCGTAGCCGCCAAAATCCAAGGGNCNAC
CNACCCTNCGTTANACTNAATTNGAAAATNCNNNCCCAACTTNAGGNACT
TNNAGNCCCCCCNACTTGACAACGGAGCACTATATTTACCCCGTGGTNGT
TCAACCCAGCCATCTCACCCTTGCGAGCATTGGTGCTGCTCTTGATACCC
TTCATGCTTAACTATCTCATGATCTTTTACATCATTTTCGAGTGCATCTG
CAACGCCTTTGCGGAACTAAGTTGCTTTGCGGATCGCAACTTTTACGAGG
ATTGGTGGAACTGCGTCAGCTTTGATGAGTGGGCACGCAAATGGAACAAG
CCTGTGCAACACTTCTTGCTCCGCCACGTGTACGACTCGAGCATCCGAGT
CCTTCCACTTGTCCGAAATCCAATGCCGCNAATTGCAAACGTTCCTTCCC
GGTCGTCAATGCGTTCAACGAACCTGGGTGAAGAATGGGTGGTGACAACG
TTAAAGTGCGCCCGGTATC.

The mouse ACAT EST DNA Sequence I is:

(SEQ ID NO: 21)
TGGAGGACAACGCGGGGTCTGATACGACTCACTATAGGGAATTTGGCCCT
CGAGCAGTAGATTCGGCACGATGGGCACGAGGACTCCATCATGTTCCTCA
AGCTTTATTCCTACCGGGATGTCAACCTGTGGTGCCGCCAGCGAAGGGTC
AAGGCCAAAGCTGTCTCTACAGGGAAGAAGGTCAGTGGGCTGCTGCGAG
CAAGCTGTGAGCTATCCAGACAACCTGACCTACCGAGATCTCGATTACTT
CATCTTTGCTCCTACTTTGTGTTATGAACTCAACTTTCCTCGGTCCCCCC
GAATACGAGAGCGCTTTCTGCTACGACGAGTTCTTGAGATGCTCTTTTTT
ACCCAGCTTCAAGTGGGGCTGATCCAACAGTGGATGGTCCCTACTATCCA
GAACTCCATGGAAGCCCTTTCAAGAGCTTCTGCAGTTTTGGAGACCGCGA
GTTCTACAGAGATTGGTGGAATGCTGAGTCTGTCACCGACTTTTGGCAGA
ACTGGAATATCCCCGTGG.

The mouse ACAT EST DNA sequence II is:

(SEQ ID NO: 22)
CCATGATGGCTCAGGTCCCACTGGCCTGGATTGTGGGCCGATTCTTCCAA
GGGAACTATGGCAATGCAGCTGTGTGGGTGACACTCATCATTGGGCAACC
GGTGGCTGTCTCATGTATGTCCACGACTACTACGTGCTCAACTACGATGC
CCCAGTGGGTCATGAGCTACTGCCAAAGGCAGCCCTCCCTAACCTGGGCC
TGGAGTTCTGGAGGGGTTCCTGGCTGCCTGCACACTCCTCCTAGTCTGGG
AGGCCTCTCTGCCCCTATGCGCTACTCCTGCTCTTGGGGATGGCATTTG

The full length rat ACAT DNA sequence is:

(SEQ ID NO: 23)
CACGACTGGGCCGCGACGTGGTGCGGGCCGAAGCCATGGGCGACCGCGGA
GGCGCGGGAAGCTCTCGGCGTCGGAGGACCGGCTCGCGGGTTCCATCCA
GGGTGGTAGTGGGCCCATGGTAGACGAAGAGGAGGTGCGAGACGCCGCTG
TGGGCCCCGACTTGGGCGCCGGGGGTGACGCTCCGGCTCCGGCTCCGGTT
CCGGCTCCAGCCCACACCCGGGACAAAGACCGGCAGACCAGCGTGGGCGA
CGGCCACTGGGAGCTGAGGTGCCATCGTCTGCAAGACTCTTTGTTCAGCT
CAGACAGCGGTTTCAGCAATTACCGTGGTATCCTGAATTGGTGCGTGGTG
ATGCTGATCCTGAGTAATGCAAGGTTATTTTTAGAGAATCTTATCAAGTA
TGGCATCCTGGTGGATCCCATCCAGGTGGTGTCTCTGTTTCTGAAGGACC
CCTACAGCTGGCCTGCCCCATGCTTGATCATTGCATCCAATATCTTTATT
GTGGCTACATTTCAGATTGAGAAGCGCCTGTCAGTGGGTGCCCTGACAGA
GCAGATGGGGCTGCTGCTACATGTGGTTAACCTGGCCACAATTATCTGCT
TCCCAGCAGCTGTGGCCTTACTGGTTGAGTCTATCACTCCAGTGGGTTCC
CTGTTTGCTCTGGCATCATACTCCATCATCTTCCTCAAGCTTTTCTCCTA
CCGGGATGTCAATCTGTGGTGCCGCCAGCGAAGGGTCAAGGCCAAAGCTG
TGTCTGCAGCGAAGAAGGTCAGTGGGGCTGCTGCCCAGAACACTGTAAGC
TATCCGGACAACCTGACCTACCGAGATCTCTATTACTTCATCTTTGCTCC
TACTTTGTGTTATGAACTCAACTTTCCTCGATCCCCCCGAATACGAAAGC
GCTTTCTGCTACGGCGGGTTCTTGAGATGCTCTTTTTCACCCAGCTTCAA
GTGGGGCTGATCCAGCAGTGGATGGTCCCTACTATCCAGAACTCCATGAA
GCCCTTCAAGGACATGGACTATTCACGAATCATTGAGCGTCTCTTAAAGC
TGGCGGTCCCCAACCATCTGATATGGCTCATCTTCTTCTATTGGCTTTTC
CACTCATGTCTCAATGCTGTGGCAGAGCTCCTGCAGTTTGGAGACCGCGA
GTTCTACAGGGACTGGTGGAATGCTGAGTCTGTCACCTACTTTTGGCAGA
ACTGGAATATCCCCGTGCACAAGTGGTGCATCAGACACTTCTACAAGCCT
ATGCTCAGACTGGGCAGCAACAAATGGATGGCCAGGACTGGGGTCTTTTT
GGCGTCAGCCTTCTTCCATGAGTACCTAGTGAGCATTCCCCTGAGGATGT
TCCGCCTCTGGGCATTCACAGCCATGATGGCTCAGGTCCCACTGGCCTGG
ATTGTGAACCGCTTCTTCCAAGGGAACTATGGCAATGCAGCTGTGTGGGT
GACACTCATCATTGGGCAACCGGTGGCTGTGCTCATGTATGTCCACGACT
ACTACGTGCTCAACTATGATGCCCCAGTGGGGGCCTGAGCTACTGCCAAA
GGCCAGCCCTCCCTAACCTGGGCCTGGAGTTCTGCAGGGCTTCCTGGCTG
CCTGCACACTCCTCCTAGTCTGGGAGGCCTCTCTGCCCCTATGGGGCCTA
CTCCTGCTCTTGGGGATGGCACCTGAGTCCAGCTGGTATGAGCCAGTGCT
GGGAGTCTGTGCTGACCAGGGGCTGAGGATATCAATAAAGAGCTATCTAA
AAAAAAAAAAAAAAA.

The rat ACAT protein sequence is:

(SEQ ID NO: 24)
MGDRGGAGSSRRRRTGSRVSIQGGSGPMVDEEEVRDAAVGPDLGAGGDAP
APAPVPAPAHTRDKDRQTSVGDGHWELRCHRLQDSLFSSDSGFSNYRGIL
NWCVVMLILSNARLFLENLIKYGILVDPIQVVSLFLKDPYSWPAPCLIIA
SNIFIVATFQIEKRLSVGALTEQMGLLLHVVNLATIICFPAAVALLVESI
TPVGSLFALASYSIIFLKLFSYRDVNLWCRQRRVKAKAVSAGKKVSGAAA
QNTVSYPDNLTYRDLYYFIFAPTLCYELNFPRSPRIRKRFLLRRVLEMLF

-continued

FTQLQVGLIQQWMVPTIQNSMKPFKDMDYSRIIERLLKLAVPNHLIWLIF

FYWLFHSCLNAVAELLQFGDREFYRDWWNAESVTYFWQNWNIPVHKWCIR

HFYKPMLRLGSNKWMARTGVFLASAFEHEYLVSIPLRMFRLWAFTAMMAQ

VPLAWIVNRFFQGNYGNAAVWVTLIIGQPVAVLMYVHDYYVLNYDAPVG

A.

The *Zea mays* ACAT EST DNA Sequence I is:

(SEQ ID NO: 25)
TAATCNAACCTCGNTNCNGCTTCAGCTGTATNCCATGAGATATGTAATGC

GGTGCCGTGCCACATANTCANATCTNGGCATNNCNGGGATCATNGTTCAG

ATACCGNTGGNATTCTTGACAAGATATCTCCATGCTACGTTCAAGCATGT

AATGGTGGGCAACATGATANTTTGGNTCTNCAGTATAGTCGGACAGCCGA

TGTNNNNNNNATCTATACTACCATGACGTCATGAACAGGCAGGCCCAGGCA

AGTAGATAGTNCGGCAGAGACATGTACTTCAACATCGANCATCAGNAGCA

NACNGAGCGAGCGGCANGAANCAGC.

The *Zea mays* ACAT EST DNA Sequence II is:

(SEQ ID NO: 26)
GAAGTATGGCTTATTAATAAGATCTGGCTTTTGGTTTAATGCTACATCAT

TGCGAGACTGGCCACTGCTAATGTGTTGGCTTAGTCTACCCATATTTCCC

CTTGGTGCATTTGCAGTCGAAAAGTTGGCATTCAACAATCTCATTAGTGA

TCCTGCTACTACCTGTTTTCACATCCTTTTTACAACATTTGAAATTGTAT

ATCCAGTGCTCGTGATTCTTAAGTGTGATTCTGCAGTTTTACAGGCTTTG

TGTTGATGTTTA.

The *Zea mays* ACAT EST DNA Sequence III is:

(SEQ ID NO: 27)
AGAAAATGGAACATGCCTGTGCATAAATGGATTGTTCGTCATATATATTT

TCCTTGCATGCGAAATGGTATATCAAAGGAAGTTGCTGTTTTTATATCGT

TCTTGTTTCTGCTGTACTTCATGAGTTATGTGTTGCTGTTCCCTGCCACA

TACTCAAGTTCTGGGCTTTTTTTAGGAATCATGCTTCAGATTCCCCTCAT

CATATTGACATCATACCTCAAAAATAAATTCAGTGACACAATGGTTGGCA

ATA.

The *Zea mays* ACAT EST DNA Sequence IV is:

(SEQ ID NO: 28)
TGAAGTATGGCTTATTAATAAGATCTGGCTTTTGGTTTAATGCTACATCA

TTGCGAGACTGGCCACTGCTAATGTGTTGCCTTAGTCTACCCATATTTCC

CCTTGGTGCATTTGCAGTCGAAAAGTTGGCATTCAACAATCTCATTAGTG

ATCCTGCTACTACCTGTTTTCACATCCTTTTTACAACATTTGAAATTGTA

TATCCAGTGCTCGTGATTCTTAAGTGTGATTCTGCAGTTTTATCAGGCTT

TGTG.

In addition to the foregoing, nucleotides 11,702-15,557 of Genbank accession number z68131 encode the ACAT protein corresponding to GenBank accession number 3873754. Nucleotides 937-10,600 of GenBank accession number z75526 encode the ACAT protein corresponding to GenBank accession number 3874043.

S-Adenosyl-L-Methionine-Sterol-C24-Methyltransferase

A nucleic acid sequence encoding an *Arabidopsis thaliana* S-adenosyl-L-methionine-sterol-C24-methyltransferase has been published by Husselstein et al. (1996) *FEBS Letters* 381: 87-92.

Tocopherol Biosynthesis in Plants

The plant tocopherol biosynthetic pathway can be divided into four parts:

1. Formation of homogentisic acid, which contributes to the aromatic ring of tocopherol, from shikimate pathway derived p-hydroxyphenylpyruvate;

2. Synthesis of phytylpyrophosphate, which contributes to the side chain of tocopherol, from the isoprenoid pathway, and prenyltransfer of the phytyl moiety to the aromatic ring;

3. Cyclization, which plays a key role in chirality and chromanol substructure of the vitamin E family; and 4. S-adenosyl methionine-dependent methylation of the aromatic ring, which determines the compositional quality of the vitamin E family produced ($\alpha$-, $\beta$-, $\gamma$-, or $\delta$-tocols).

The enzymes variously involved in these biochemical steps are as follows.

1) Synthesis of Homogentisic Acid

Homogentisate is well known as the aromatic precursor in the biosynthesis of tocopherols in the chloroplast, and is formed from the aromatic shikimate metabolite p-hydroxyphenylpyruvate. The aromatic amino acids phenylalanine, tyrosine, and tryptophan are formed by a reaction sequence leading from the two carbohydrate precursors, D-erythrose 4-phosphate and phosphoenolpyruvate, via shikimate, to further prearomatic and aromatic compounds (Bentley 1990, *Critical Rev. Biochem. Mol. Biol.* 25: 307-384). Approximately 20% of the total carbon fixed by green plants is routed through the shikimate pathway, with end products being aromatic amino acids and other aromatic secondary metabolites such as flavonoids, vitamins, lignins, alkaloids, and phenolics (Herrmann 1995, *Plant Physiol.* 107: 7-12, Kishore and Shah 1988, *Ann. Rev. Biochem.*, 57: 67-663). Various aspects of the shikimate pathway have been reviewed (Bentley 1990, *Critical Rev. Biochem. Mol. Biol.* 25: 307-384, Herrmann 1995, *Plant Physiol.* 107: 7-12, Kishore and Shah 1988, *Ann. Rev. Biochem.*, 57:67-663).

The first committed reaction in the shikimate pathway is catalyzed by the enzyme 3-deoxy-D-arabino-heptulosonate-7-phosphate synthase (DAHP synthase, EC. 4.1.2.15), which controls carbon flow into the shikimate pathway. The plastid-localized DAHP synthase catalyzes the formation of 3-deoxy-D-arabino-heptulosonate-7-phosphate by condensing D-erythrose-4-phosphate with phosphoenolpyruvate. This enzyme has been isolated and well characterized from plant sources including carrot and potato, has highest substrate specificity for D-erythrose-4-phosphate and phosphoenolpyruvate, is a dimer of subunits of Mr=53,000, and is activated by $Mn^{2+}$ (Herrmann 1995, *Plant Physiol.* 107: 7-12, 770). The aromatic amino acids are not feed back regulators: the purified enzyme is activated by tryptophan and to a lesser extent by tyrosine in a hysteric fashion (Suzich et al., 1985, *Plant Physiol.* 79: 765-770).

The next enzyme in the shikimate pathway, 3-dehydroquinate synthase (EC. 4.6.1.3), catalyzes the formation of dehydroquinate, the first carbocyclic metabolite in the biosynthesis of aromatic amino acids, from D-erythrose-4-phosphate with phosphoenolpyruvate. The enzyme reaction involves NAD cofactor-dependent oxidation-reduction, β-elimination, and intramolecular aldol condensation. 3-Dehydroquinate synthase has been purified from *Phaseolus mungo* seedlings and pea seedlings, and has a native Mr of 66,000 with a dimer subunit (Yamamoto, 1980, *Phytochem.*, 19: 779, Pompliano et al., 1989, *J. Am. Chem. Soc.*, 111: 1866).

3-Dehydroquinate dehydratase (EC 4.2.1.10) catalyzes the stereospecific syn-dehydration of dehydroquinate to dehydroshikimate, and is responsible for initiating the process of aromatization by introducing the first of three double bonds of the aromatic ring system. 3-Dehydroquinate dehydratase has not been well studied in plant sources, but has been cloned from *E. coli* (Duncan, et al., 1986, *Biochem. J.*, 238: 485).

Shikimate dehydrogenase (EC 1.1.1.25) catalyzes the NADPH-dependent conversion of dehydroshikimate to shikimate. Bifunctional dehydroquinate dehydratase (EC 4.2.1.10)-shikimate dehydrogenase has been well studied in spinach, pea seedlings, and corn (Bentley 1990, *Critical Rev. Biochem. Mol. Biol.* 25: 307-384, Kishore and Shah 1988, *Ann. Rev. Biochem.*, 57:67-663). The *E. coli* enzyme is a monomeric, monofunctional protein of Mr 32,000 (Chaudhuri and Coggins, 1985, *Biochem. J.*, 226: 217-223).

Shikimate kinase (EC 2.7.1.71) catalyzes the phosphorylation of shikimate to shikimate-3-phosphate. Shikimate kinase exists in isoforms in *E. coli* and *S. typhimurium*, and plant shikimate kinase has been only partially purified from mung bean and sorghum (Bentley 1990, *Critical Rev. Biochem. Mol. Biol.* 25: 307-384, Kishore and Shah 1988, *Ann. Rev. Biochem.*, 57: 67-663).

5-Enolpyruvyl-shikimate-3-phosphate synthase catalyzes the reversible transfer of the carboxyvinyl moiety of phosphoenolpyruvate to shikimate-3-phosphate, yielding 5-enolpyruvyl-shikimate-3-phosphate, and is one of the most characterized enzymes of the aromatic pathway. 5-Enolpyruvyl-shikimate-3-phosphate synthase has assumed considerable importance as this enzyme is the major target for inhibition by the broad spectrum, nonselective, postemergence herbicide, glyphosate. Chemical modification studies indicate that Lys, Arg, and His residues are essential for activity of the enzyme (Kishore and Shah 1988, *Ann. Rev. Biochem.*, 57: 67-663).

5-Enolpyruvyl-shikimate-3-phosphate synthase has been isolated and chemically and kinetically well characterized from microbial and plant sources, including tomato, petunia, *Arabidopsis*, and *Brassica* (Kishore and Shah 1988, *Ann. Rev. Biochem.*, 57: 67-663).

Chorismate synthase (EC 4.6.1.4) catalyzes the conversion of 5-enolpyruvyl-shikimate-3-phosphate to chorismic acid, and introduces the second double bond of the aromatic ring in a trans-1,4-elimination of inorganic phosphorous. Chorismate is the last common intermediate in the biosynthesis of aromatic compounds via the shikimate pathway. Very little is known about plant chorismate synthase. Although the enzyme reaction involves no change in the oxidation state of the substrate, chorismate synthase from various sources is unusual in requiring a reduced flavin cofactor, $FMNH_2$ or $FADH_2$, for catalytic activity ((Bentley 1990, *Critical Rev. Biochem. Mol. Biol.* 25: 307-384, Kishore and Shah 1988, *Ann. Rev. Biochem.*, 57: 67-663).

The next enzyme in the tocopherol biosynthetic pathway is chorismate mutase (EC 5.4.99.5), which catalyzes the conversion of chorismic acid to prephenic acid, Chorismic acid is a substrate for a number of enzymes involved in the biosynthesis of aromatic compounds. Plant chorismate mutase exists in two isoforms, chorismate mutase-1 and chorismate mutase-2, that differ in feed back regulation by aromatic amino acids (Singh et al., 1985, *Arch. Biochem. Biophys.*, 243: 374-384, Goers et al., 1984, *Planta,* 162: 109-116, and 117-124). It has been suggested that chloroplastic chorismate mutase-1 may play a central role in the biosynthesis of aromatic amino acids as this enzyme is activated by Tyr and Phe. The cytosolic isozyme chorismate mutase-2 is not regulated by aromatic amino acids, and may play a role in providing the aromatic nucleus for synthesis of aromatic secondary metabolites including tocopherol (d'Amato et al., 1984, *Planta,* 162: 104-108).

The branching from prephenic acid is extensive, and leads not only to Phe and Tyr, but also to a number of secondary metabolites. Tyrosine is synthesized from prephenate via either 4-hydroxyphenylpyruvate or arogenate. Both routes have been identified in plants, but the enzymes involved in tyrosine biosynthesis via arogenate have not been cloned or purified to homogeneity (Bentley 1990, *Critical Rev. Biochem. Mol. Biol.* 25: 307-384).

The formation of 4-hydroxyphenylpyruvate from prephenate is catalyzed by prephenate dehydrogenase (EC 1.3.1.12 (NAD-specific) and EC 1.3.1.13 (NADP specific)).

4-Hydroxyphenylpyruvate for tocopherol biosynthesis may also come from tyrosine pool by the action of tyrosine transaminase (EC 2.6.1.5) or L-amino acid oxidase (EC 1.4.3.2). Tyrosine transaminase catalyzes the pyridoxal-phosphate-dependent conversion of L-tyrosine to 4-hydroxyphenylpyruvate. This reversible enzyme reaction transfers the amino group of tyrosine to 2-oxoglutarate to form 4-hydroxyphenylpyruvate and glutamate. L-Amino acid oxidase catalyzes the conversion of tyrosine to 4-hydroxyphenylpyruvate by acting on the amino group of tyrosine, with oxygen as acceptor. This enzyme is not specific to tyrosine. In *E. coli*, aromatic amino acid amino transferase (EC 2.6.1.57), which converts 4-hydroxyphenylpyruvate to tyrosine, plays a major role in Phe and Tyr biosynthesis. An Asp aminotransferase or transaminase A (EC 2.6.1.1) has broad specificity, and will utilize phenylpyruvate of p-hydroxyphenylpyruvate to form Phe and Tyr, respectively.

The precursor molecule homogentisic acid is produced from the shikimate pathway intermediate p-hydroxyphenylpyruvate. p-Hydroxyphenylpyruvate dioxygenase (EC 1.13.11.27) catalyzes the formation of homogentisate from hydroxyphenylpyruvate through an oxidative decarboxylation of the 2-oxoacid side chain of the substrate, accompanied by hydroxylation of the aromatic ring and a 1,2 migration of the carboxymethyl group. Norris et al. reported functional identification of the pdsI gene as encoding p-hydroxyphenylpyruvate dioxygenase (Norris et al., 1995, *Plant Cell* 7: 2139-2149). p-hydroxyphenyl-pyruvate dioxygenase has been cloned from *Arabidopsis* and carrot (GenBank accession #U89267, AF000228, U87257). Fiedler et al. reported the localization and presence of this enzyme in both isolated spinach chloroplasts and peroxisomes (Fiedler et al., 1982, *Planta,* 155: 511-515). Garcia et al. purified and cloned a cytosolic form of hydroxyphenylpyruvate dioxygenase from cultured carrot protoplasts (Garcia et al., 1997 *Biochem. J.* 325: 761-769). These reports suggest that there exists two forms of hydroxyphenylpyruvate dioxygenase in chloroplasts and peroxisomes: the chloroplastic isoform would be involved in the biosynthesis of prenylquinones, and the peroxisomal and cytosolic isoform would be involved in the degradation of tyrosine.

2) Synthesis of Phytylpyrophosphate and Phytyl/Prenyl Transfer to Homogentisate

Carbon flow to phytol occurs via plastidic, non-mevalonate (Rohmer) and cytosolic, mevalonate pathways. Geranylgeranylpyrophosphate synthase (EC 2.5.1.29) catalyzes the formation of geranylgeranylpyrophosphate by condensation of isoprene moieties. The gene encoding geranylgeranylpyrophosphate synthase has been cloned from *Arabidopsis* and *Cantharanthus roseus* (Zhu et al., 1997, *Plant Cell Physiol.* 38: 357-361; Bantignies et al., 1995, *Plant Physiol.* 110: 336-336). This enzyme-synthesized geranylgeranylpyrophosphate pool splits for use in carotenoid and tocopherol biosynthesis, as well as for other isoprenoid compounds.

The NADPH-dependent hydrogenation of geranylgeranylpyrophosphate is catalyzed by geranylgeranylpyrophosphate hydrogenase (no EC number available, also called geranylgeranylpyrophosphate reductase) to form phytylpyrophosphate (Soll et al., 1983, *Plant Physiol.* 71: 849-854). This enzyme appears to be localized in two sites: one in the chloroplast envelope for the hydrogenation of geranylgeranylpyrophosphate to the phytyl moiety, and the other in the thylakoids for the stepwise reduction of chlorophyll esterified with geranylgeraniol to chlorophyll esterified with phytol. The chloroplast envelope-located geranylgeranylpyrophosphate hydrogenase has been implicated to play a role in tocopherol and phylloquinone synthesis. The ChlP gene cloned from *Synechocystis* has been functionally assigned, by complementation in *Rhodobactor sphaeroides*, to catalyze the stepwise hydrogenation of geranylgeraniol moieties to phytol moieties (Addlesse et al., 1996, *FEBS Lett.* 389: 126-130).

Homogentisate:phytyl transferase (no EC number available) catalyzes the decarboxylation, followed by condensation, of homogentisic acid with the phytol moiety of phytylpyrophosphate to form 2-methyl-6-phytyl-benzoquinol. The existence of this prenyltrnsferase activity has been demonstrated in spinach chloroplasts, and the activity is believed to be located in chloroplast envelope membranes (Fiedler et al., 1982, *Planta*, 155: 511-515). A possible prenyltransferase gene, termed the pdsII mutant, specific to tocopherol biosynthesis, has been identified by Norris et al. from a T-DNA-tagged population of *Arabidopsis* (Norris et al., 1995, *Plant Cell* 7: 2139-2149).

3) Cyclization

Tocopherol cyclase catalyzes the cyclization of 2,3-dimethyl-5-phytyl-benzoquinol to form γ-tocopherol, and plays a key role in the biosynthesis of the enantioselective chromanol substructure of the vitamin E subfamily (Stocker et al., 1996, *Bioorg. Medic. Chem.* 4: 1129-1134). Regarding its substrate specificity, it is not clear whether the enzyme prefers 2,3-dimethyl-5-phytylbenzoquinol or 2-methyl-6-phytylbenzoquinol. If the enzyme is specific to the former substrate, then 2-methyl-6 phytylbenzoquinol formed from prenyl-transferase requires methylation by an S-adenosylmethionine-dependent methyltransferase prior to cyclization. Tocopherol cyclase has been purified from the green algae *Chlorella protothecoides* and *Dunaliella salina*, and from wheat leaves (U.S. Pat. No. 5,432,069).

4) Methylation

Synthesis of γ-tocopherol from 2-methyl-6-phytylbenzoquinol occurs by two pathways, with either δ-tocopherol or 2,3-dimethyl-5-phytylbenzoquinol as an intermediate. α-tocopherol is then synthesized from γ-tocopherol in the final methylation step with S-adenosylmethionine. All the steps of α-tocopherol biosynthesis are located in the chloroplast membrane in higher plants. Formation of α-tocopherol from other tocopherols occurs due to S-adenosylmethionine (SAM)-dependent γ-tocopherol methyltransferase (EC 2.1.1.95). This enzyme has been partially purified from *Capsicum* and *Euglena gracilis* (Shigeoka et al., 1992, *Biochim. Biophys. Acta*, 1128: 220-226, d'Harlingue and Camara, 1985, *J. Biol. Chem.* 260: 15200-15203).

Biosynthesis of Tocotrienols

The tocotrienols are similar to the tocopherols in molecular structure, except that there are three double bonds in the isoprenoid side chain. Although tocotrienols are not detected in soybean, they are widely distributed in plant kingdom. The tocotrienol biosynthetic pathway is similar to that of tocopherol up to the formation of homogentisic acid; the subsequent biosynthetic pathway leading to tocotrienols is not known. One of two possibilities is that the phytyl/prenyltransferase is able to transfer GGPP (geranylgeranylpyrophosphate) to homogentisic acid, and the other possibility is that the side chain is desaturated after the addition of phytylpyrophosphate to homogentisate. However, evidence from a study by Stocker indicates that reduction of the side chain's double bond occurs at an earlier stage of the biosynthesis, that is, either phytylpyrophosphate or GGPP (geranylgeranyl-pyrophosphate) is condensed with HGA (homogentisic acid) to yield different hydroquinone precursors that are cyclized by the same enzyme (Stocker, A., Fretz, H., Frick, H., Ruttimann., and Woggon, W.-D. *Bioorg. Medicinal Chem.*, 1996, 4: 1129-1134).

Tocopherol Catabolism

The catabolism of tocopherol in plants is not well studied, and no enzyme in the catabolic pathway has been characterized. In humans, ingested tocopherols are metabolized in the liver. The primary oxidation product of tocopherol is tocopheryl quinone, which can be conjugated to yield the glucuronate after prior reduction to the hydroquinone. The glucuronate can be excreted into bile, or further catabolized to tocopheronic acid in the kidney and processed for urinary excretion (Traber, and Sies, *Ann. Rev. Nutr.* 1996, 16: 321-347).

In *Aspergillus nidulans*, aromatic amino acid catabolism involves the formation of homogentisic acid followed by aromatic ring cleavage by homogentisic acid dioxygenase (EC 1.13.11.5) to yield, after an isomerization step, fumarylacetoacetate, which is split by fumarylacetoacetate (Fernandez-Canon and Penalva, 1995, *J. Biol. Chem.*, 270: 21199-21205). Homogentisic acid dioxygenase uses the important tocopherol biosynthetic metabolite homogentisic acid for hydrolysis. Thus, use of this gene in an antisense mode could be employed to increase the pool of homogentisic acid.

Regulation of Tocopherol Biosynthesis

Tocopherol levels vary in different plants, tissues, and developmental stages, indicating a highly regulated biosynthetic pathway. The production of homogentisic acid by p-hydroxyphenylpyruvate dioxygenase is likely to be a key regulatory point for bulk flow through the pathway because of irreversible enzyme action and because homogentisic acid production is the first committed step in tocopherol biosynthesis (Norris et al., 1995, *Plant Cell* 7: 2139-2149). The other key regulatory step in tocopherol biosynthesis is the availability of the phytylpyrophosphate pool. Feeding studies (Fury et al., 1987, *Phytochem.*, 26: 2741-2747) in safflower callus culture demonstrated 1.8-fold and 18-fold increases in tocopherol synthesis by feeding homogentisate and phytol, respectively. In meadow rescue leaf, vitamin E increases in the initial phase of foliar senescence when phytol is cleaved off from the chlorophylls and when free phytol is available (Peskier et al., 1989, *J. Plant Physiol.* 135: 428-432). These reports suggest tight coupling of tocopherol biosynthesis to the availability of homogentisic acid and phytol.

A summary of the enzymes involved in tocopherol biosynthesis is provided in Table 2.

TABLE 2

Enzymes of the Tocopherol Biosynthetic Pathway

| Enzyme | EC Number |
| --- | --- |
| 3-Deoxy-D-arabino-heptulosonate-7-P-synthase (DAHP synthase) | 4.1.2.15 |
| 3-Dehydroquinate synthase | 4.6.1.3 |
| 3-dehydroquinate dehydratase | 4.2.1.10 |
| Shikimate dehydrogenase | 1.1.1.25 |
| Shikimate kinase | 2.7.1.71 |
| 5-enoylpyruvyl-shikimate-3-P-synthase (EPSPS) | 2.5.1.19 |
| Chorismate synthase | 4.6.1.4 |
| Chorismate mutase | 5.4.99.5 |
| Prephenate dehydrogenase | 1.3.1.12 |
| Prephenate dehydrogenase | 1.3.1.13 |
| Tyrosine transaminase | 2.6.1.5 |
| Aromatic amino acid transaminase | 2.6.1.57 |
| Transaminase A | 2.6.1.1 |
| L-Amino-acid oxidase | 1.4.3.2 |
| 4-Hydroxyphenylpyruvate dioxygenase (HPD or OHPP) | 1.13.11.27 |
| Homogentisic acid dioxygenase | 1.13.11.5 |
| Geranylgeranylpyrophosphate synthase (GGPP Synthase) | 2.5.1.29 |
| Geranylgeranylpyrophosphate hydrogenase (GGH) | no EC # |
| Homogentisate:phytyl transferase (Phytyl/Prenyltransferase) | no EC # |
| 2-methyl-6-phytylbenzoquinol methylase | no EC # |
| Tocopherol cyclase | no EC # |
| S-adenosyl methionine (SAM)-dependent γ-tocopherol methyltransferase (GTMT or tocopherol O-methyltransferase) | 2.1.1.95 |

Nucleic acids (genomic DNA, plasmid DNA, cDNA, synthetic DNA, mRNA, etc.) encoding enzymes listed in Table 2 above, or amino acid sequences of the purified enzymes, which permit design of nucleic acid probes facilitating the isolation of DNA coding sequences therefor, are known in the art and are available for use in the methods of the present invention as variously indicated by the GenBank accessions listed in Table 3.

TABLE 3

1. DAHP synthase (EC 4.1.2.15)

*A. thaliana* 3-deoxy-D-arabino-heptulosonate-7-phosphate synthase (DHS1) mRNA, complete cds
gi|166687|gb|M74819
*E. coli* aroF gene for DAHP synthase (Tyr), complete coding sequence
gi|145361|gb|K01989
*S. cerevisiae* aro4 gene for DAHP-Synthase (EC 4.1.2.15)
gi|416186|emb|X61107

2. 3-Dehydroquinate synthase (EC 4.6.1.3)

*Pseudomonas aeruginosa* dehydroquinate synthase (aroB) gene, partial cds
gi|309861|gb|L13866
*E. coli* aroB gene for 3-dehydroquinate synthase (EC 4.6.1.3)
gi|40967|emb|X03867

3. 3-Dehyroquinate dehydratase (4.2.1.10)

*Nicotiana tabacum* (clone: SP-3) dehydroquinate dehydratase/shikimate dehydrogenase (aroD-E) mRNA, 3' end gi|535770|gb|L32794
*Neisseria gonorrhoeae* dehydroquinate dehydratase (aroD) gene and recA gene, partial cds
gi|1143313|gb|U39803

4. Shikimate dehydrogenase (EC 1.1.1.25)

*E. coli* aroE gene for shikimate dehydrogenase (EC 1.1.1.25)
gi|40977|emb|Y00710
*Neisseria meningitidis* shikimate dehydrogenase (aroE) gene, complete cds
gi|1785881|gb|U82835

TABLE 3-continued

5. Shikimate kinase (EC 2.7.1.71)

*E. coli* shikimic acid kinase I (aroK) gene, complete cds
gi|662834|gb|L39822
*E. coli* aroL gene for shikimate kinase II (EC 2.7.1.71)
*L. esculentum* mRNA for shikimate kinase precursor
gi|19348|emb|X63560

6. EPSP Synthase (EC 2.5.1.19)

Petunia 5-enolpyruvylshikimate-3-phosphate synthase (EPSP synthase) gene, 5' end
gi|169212|gb|M37029
*E. coli* gene aroA for 5-enolpyruvylshikimate 3-phosphate synthase (EPSP synthase, EC 2.5.1.19, alternative name 3-phosphoshikimate 1-carboxyvinyltransferase)
gi|40965|emb|X00557
*Brassica napus* 5-enolpyruvylshikimate-3-phosphate synthase gene
gi|17814|emb|X51475
*Z. mays* mRNA for EPSP-synthase
gi|1524382|emb|X63374

7. Chorismate synthase (EC 4.6.1.4)

*L. esculentum* chorismate synthase 2 precursor
gi|410483|emb|Z21791|
*L. esculentum* chorismate synthase 1 precursor
gi|410481|emb|Z21796
*E. coli* aroC gene for chorismate synthase (EC 4.6.1.4)
gi|40969|emb|Y00720

8. Chorismate mutase (5.4.99.5)

*A. thaliana* mRNA for chorismate mutase
gi|429152|emb|Z26519
*E. coli* chorismate mutase/prephenate dehydratase (pheA) gene, 5' end of cds, and leader peptide, complete cds gi|147178|gb|M58024

9. Prephenate dehydrogenase (1.3.1.12 and 1.3.1.13)

*Erwinia herbicola* prephenate dehydrogenase (tyrA) gene, partial cds
gi|415009|gb|M74135

10. Tyrosine transaminase (2.6.1.5)

*E. coli* K12 tyrB gene encoding aminotransferase, complete cds
gi|148084|gb|M12047
*H. sapiens* mRNA for tyrosine aminotransferase
gi|37501|emb|X55675

11. 4-Hydroxyphenylpyruvate dioxygenase (1.13.11.27)

*Hordeum vulgare* mRNA for 4-hydroxyphenylpyruvate dioxygenase
gi|2695709|emb|AJ000693
*H. sapiens* mRNA for 4-hydroxyphenylpyruvate dioxygenase
gi|288104|emb|X72389
*Daucus carota* 4-hydroxyphenylpyruvate dioxygenase mRNA, complete cds
gi|2231614|gb|U87257
*Mycosphaerella graminicola* 4-hydroxyphenylpyruvate dioxygenase (HPPD) gene, complete cds
gi|2708689|gb|AF038152

12. Geranylgeranyl dehydrogenase

*Synechocystis* sp. PCC6803 chlP gene
gi|1332618|emb|X97972

13. Geranylgeranyl pyrophosphate synthase (2.5.1.29)

*Arabidopsis thaliana* mRNA for geranylgeranyl pyrophosphate synthase, partial cds
gi|1944370|dbj|D85029
*E. herbicola* phytoene synthase (crtE) gene, complete cds
gi|148399|gb|M38424

In addition to the foregoing, the following GenBank accessions should also be noted: P20049, P20692, P43901, 415010, 683582, S52579, 1653053, and 2634679 (prephenate dehydrogenase protein sequences); M74135, X78413, X60420, D90888, D90910, D89213, Z99115, and AE000638 (prephenate dehydrogenase nucleotide coding sequences); S10887, XNECY, XNRTY, and S33857 (tyrosine transaminase protein sequences); Q00667, Q93099, and 2708690 (4-hydroxyphenylpyruvate dioxygenase protein sequences);

U63008, AJ001836, U30797, Z75048, U58988, and AF000573 (4-hydroxyphenylpyruvate dioxygenase nucleotide coding sequences); JC5197 and XNECY (aromatic amino acid transaminase protein sequences); A05068, XNECD, XNRTDM, and XNHUDM (transaminase A protein sequences); 684996, S62687, S62692, and 2370457 (amino acid oxidase protein sequences); Z48565, AF027868, Z99114, and U78797 (amino acid oxidase nucleotide coding sequences). PCT International Publication WO 97/27285 discloses cDNA encoding *Arabidopsis* 4-hydroxyphenylpyruvate dioxygenase (HPD or OHPP). Further sources include Fuqua et al. (1991) *Gene* 109: 131-136, and Ruzafa et al. (1994) *FEMS Microbiology Letters* 124:179-184. U.S. Pat. No. 5,432,069 discloses purified, homogeneous tocopherol cyclase isolated from *Chlorella protothecoides*, *Dunaliella salina*, and wheat leaves.

The DNA sequence encoding geranylgeranylpyrophosphate hydrogenase in maize (SEQ ID: 29) is as follows:

```
GAATTCGGCT  CGAGGGCGGC  GGCTGCGGGT  GCCGGTGGTG  GGAGGCGGCC
CCGCCGGTGG  CGCCGCGGCG  GAGGCGCTGG  CCAAGGGCGG  CGTGGAGACG
GTGCTGATCG  AGCGGAAGAT  GGACAACTGC  AAGCCCTGCG  GCGGCGCTAT
CCCGCTGTGC  ATGGTGTCGG  AGTTCGACCT  GCCGCTCGAC  CTCGTGGACC
GCAAGGTGAG  GAAGATGAAG  ATGATTTCGC  CGTCCAACGT  CGCCGTCGAC
ATCGGCCGCA  CGCTCGCGCC  CCACGAGTAC  ATCGGGATGG  TCAGGCGCGA
GGTGCTCGAC  GCCTACCTCC  GCTCACGGGC  ACAGTCCGTC  GGCGCGGAGG
TCGTCAACGG  CCTCTTCCTA  AGGTACGAGG  CGCCCAAAGA  GCCGAACGGC
TCGTACGTGG  TGCACTACAA  CCACTACGAC  GGCAGCAACG  GCAAGGTCGG
CGGCGAGAAG  CGGTGGTTCG  AGGTGGACGC  GATCGTGGGC  GCGGACGGCG
CCAACTCTCG  CGTGCCCAAC  GACATGGGCG  CGGGCGACTA  CGAGTACGCC
ATCGCGTTCC  AGGAGCGCGT  CAAGATCCCC  GACGACAAGA  TGGTGTACTA
CGAGGAGCGC  GCGGAGATGT  ACGTCGGCGA  CGACGTCTCT  CCCGACTTCT
ACGGCTGGGT  GTTCCCCAAG  TGCGACCACG  TCGCCGTCGG  CACCGGCACC
GTCACGCACA  AGGCCGACAT  CAAGAAGTTT  CAGGCCGCCA  CGCGCCTCCG
CGCCAAGGAC  AAGATTGAGG  GCGGCAAGAT  CATCCGCGTC  GAGGCGCACC
CCATCCCCGA  GCACCCCAGG  CCTAAGAGGG  TGTCCGGGCG  GGTGACGCTT
GTGGGCGATG  CCGCGCCGTA  CGTGACCAAG  TGCTCTGCCG  AGGGCATCTA
CTTCGCGGCG  AAGAGCGGGC  GGATGTGCGC  CGAGCCCATC  GTGGCGGGCT
CCGCCAACGG  GACGCGGATG  GTGGAGGAGA  GCGACCTGCG  CAAGTACCTG
GCCGAGTTCG  ACCGCCTCTA  CTGGCCCACT  TACAAGGTGC  TGGACATCCT
GCAGAAGGTG  TTCTACCGCT  CCAACGCGGC  GCGCGAGGCC  TTCGTGGAGA
TGTGCGCCGA  CGACTACGTG  CAGAAGATGA  CCTTCGACAG  CTACCTCTAC
AAGCGCGTCG  TGCCGGGCAA  CCCGCTCGAC  GACATCAAGC  TCGCCGTCAA
CACCATCGGC  AGCCTCGTCA  GGGCCACCGC  ACTGCGCCGG  GAGATGGAGA
AGGTCACCTT  GTGAGCCGCC  GCCCGCCACC  TCATTGCCGT  CGAAATGGTG
TCGCAGCTGA  TCGGCCGGTG  TATTAGTAGA  GATTTGCGGC  TGATCGGGTT
AATTTAGGCCAACATGCGTG    GGCAGTGGGC  GCGGAGAGGA  AGAGAAACAA
GTTGTGCAAG  TGCAGCAAGT  AGATCAAAAG  TGCTGCCTGT  TTGTATCGAT
GGATCCTGCA  ACATATAGCA  TCTGGTGATG  TTGAGAATTC  GGAGCAGTTC
ATCGACTGGA  TTCTGACGCC  GGCAAGCATC  GACGTCAATG  AATGTCTAAT
ACTTAGTACA  TCAAGACATG  TAATAAAACT  GAAACTCCCC  CGTTCTGGTT
CAAAAAAAAAAAAAAAAAAAAAAAAAAAAAAAAGGGCGGCCGC
```

The amino acid sequence deduced from SEQ ID NO: 29 is:

```
LRVAVVGGGP  AGGAAAEALA  KGGVETVLIE  RKMDNCKPCG  GAIPLCMVSE  (SEQ ID NO: 30)

FDLPLDLVDR  KVRKMKMISP  SNVAVDIGRT  LAPHEYIGMV  RREVLDAYLR

SRAQSVGAEV  VNGLFLRYEA  PKEPNGSYVV  HYNHYDGSNG  KVGGEKRSFE

VDAIVGADGA  NSRVANDMGA  GDYEYAIAFQ  ERVKIPDDKM  VYYEERAEMY

VGDDVSPDFY  GWVFPKCDHV  AVGTGTVTHK  ADIKKFQAAT  RLRAKDKIEG

GKIIRVEAHP  IPEHPRPKRV  SGRVTLVGDA  AGYVTKCSGE  GIYFAAKSGR

MCAEAIVAGS  ANGTRMVEES  DLRKYLAEFD  RLYWPTYKVL  DILQKVFYRS

NAAREAFVEM  CADDYVQKMT  FDSYLYKRVV  PGNPLDDIKL  AVNTIGSLVR

ATALRREMEK  VTL*AAARDV  IAVEMVSQLI  GRCISRDLRL  IGLI*ANMRG

QWARRGRETS  CASAASRSKV  LPVCIDGSCN  I*HLVMLRIR  SSSSTGF*RR

QASTSMNV*Y  LVHQDM**N*  NSPVLVQKKK  KKKKKKKGG  R
```

The DNA sequence of SEQ ID NO: 29 can be used in any of the plants described in the present invention and in particular is useful for the alteration of tocopherol levels. In addition to the foregoing sterol compound and tocopherol biosynthetic enzyme DNA coding sequences, DNA coding sequences useful in the present invention can be derived from algae, fungi, bacteria, mammalian sources, plants, etc. Homology searches in existing databases using signature sequences corresponding to the active sites of enzymes can be employed to isolate equivalent, related genes from other noted sources, for example plants and microorganisms. Searches in EST databases can also be employed. Furthermore, the use of DNA sequences encoding the enzymes disclosed herein, or DNA encoding enzymes functionally enzymatically equivalent to the presently disclosed enzymes, for example DNA sequences that are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as Synechocystis, Shewanella, yeast, Pseudomonas, Rhodobacteria, etc., that lack specific biochemical reactions, or that have been mutated. The sequences of the DNA coding regions can be optimized by gene resynthesis, based on codon usage, for maximum expression in particular hosts.

Also encompassed by the present invention are nucleotide sequences biologically functionally equivalent to those disclosed herein, that encode conservative amino acid changes within the amino acid sequences of the presently disclosed enzymes, producing "silent" changes therein. Such nucleotide sequences contain corresponding base substitutions based upon the genetic code compared to the nucleotide sequences encoding the presently disclosed enzymes. Substitutes for an amino acid within the enzyme sequences disclosed herein can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Transformation of plants with structural DNA coding sequences that permit overexpression of enzymes that enhance the pools of substrates which contribute to the tocol and the phytol moieties of tocopherols and tocotrienols can be used to increase the biosynthetic activity of the tocopherol pathway, and can lead to increased production of particular tocopherol isomers, such as, for example, α-tocopherol, etc. One objective, for example, is to express coding sequences that enhance carbon flux for the formation of homogentisate and phytol, as well as those that encode methyl transferase(s) in oil accumulating tissues of plants. Formation of α-tocopherol from other tocopherols occurs due to S-adenosylmethionine (SAM)-dependent methylases such as γ-tocopherol methyl transferases. Overexpression of methyl transferases in combination with the other approaches described herein is also contemplated in the present methods. Thus, any of the DNAs encoding enzymes of the tocopherol biosynthetic pathway, discussed above, are useful in the present invention. Transformation of plants with an early tocopherol biosynthesis gene is sufficient to produce seeds having an elevated level of tocopherols. By "early tocopherol biosynthesis gene" is meant DNA encoding geranylgeranylpyrophosphate synthase, geranylgeranylpyrophosphate hydrogenase, 4-hydroxyphenylpyruvate dioxygenase, and phytyl/prenyl transferase. DNA encoding enzymes active in later steps of tocopherol biosynthesis ("secondary tocopherol biosynthesis genes") can be expressed to enhance carbon flux through the tocopherol pathway even further, and to produce specific tocopherol isomers. In this way, the tocopherol biosynthetic pathway can be modified to enhance production of any tocopherol compound of interest, such as α-tocopherol. As noted above, a variety of sources are available for the early tocopherol biosynthesis genes (and other tocopherol biosynthesis genes), and a gene from any of these sources can be utilized. If co-suppression occurs when a plant gene native to the target host plant is used to increase expression of a particular enzyme, a coding sequence from another source can be used as an alternative.

Oil comprising the tocopherols produced by the methods disclosed herein can be extracted from seeds to provide a valuable source of tocopherols. Alternatively, seeds with increased levels of tocopherols, or fruits and vegetables with increased levels of tocopherols, can be used directly. Preferred genes for introduction into plants to alter tocopherol quantity/quality include 3-deoxy-D-arabino-heptulosonate-7-P synthase (DAHP synthase), shikimate kinase, either or both of the prephenate dehydrogenases, 4-hydroxy-phenylpyruvate dioxygenase (OHPP or HPD), γ-tocopherol methyltransferase (GTMT), geranylgeranylpyrophosphate synthase (GGPP synthase), geranylgeranylpyrophosphate hydrogenase (GGH), phytyl/prenyltransferase, 2-methyl-6-phytylbenzoquinol methyl transferase, and tocopherol cyclase. 4-hydroxy-phenylpyruvate diooxygenase and geranylgeranylpyrophosphate hydrogenase will increase the homogentisate and phytol pools, respectively. Enzymes that control fluxes through pathways are well known to be regulated in higher organisms such as plants. Therefore, 4-hydroxyphenylpyruvate diooxygenase and geranylgeranylpyrophosphate hydrogenase genes of microbial origin which are not subject to regulation in plants, or those from higher organisms (plants, algae, fungi, etc.) that are deregulated, are especially attractive in this regard. Overexpression of enzymes such as 3-deoxy-arabino-heptulosonate 7-P (DAHP) synthase, prephenate dehydrogenase, and shikimate kinase would lead to increases in the levels of homogentisate. DNA encoding any of the tocopherol biosynthetic enzymes discussed herein can be introduced alone or in various combinations to enhance tocopherol quantity and/or alter tocopherol quality. When introduction of multiple enzymes is desirable, preferred combinations include, but are not limited to, 4-hydroxyphenylpyruvate dioxygenase (OHPP or HPD) plus geranylgeranylpyro-phosphate hydrogenase (GGH), and geranylgeranylpyrophosphate synthase (GGPP synthase) plus geranylgeranylpyrophosphate hydrogenase (GGH).

To increase tocotrienol levels, antisensing geranylgeranylpyrophosphate hydrogenase can lead to increased pools of geranylgeranyl-pyrophosphate. Such elevated pools of geranylgeranylpyrophosphate can be used by a phytyl/prenyl transferase to lead to increased production of tocotrienols.

Production of Transgenic Plants Producing Modified Levels of Sterol and Tocopherol Compounds Sitostanol, sitostanol ester, and tocopherol biosynthesis and accumulation in plants can be modified in accordance with the present invention by variously expressing the nucleic acid coding sequences discussed above, alone or in combination, as described herein. The expression of sequences encoding sterol methyltransferases facilitates the production of plants in which the biosynthesis and accumulation of campesterol, campestanol, and their esters can be reduced as these enzymes shunt sterol intermediates away from campesterol, and toward sitosterol and sitostanol. Note Scheme 1, step 18 in plants. Methods therefor are discussed below.

Plant Vectors

In plants, transformation vectors capable of introducing encoding DNAs involved in sterol compound and tocopherol biosynthesis are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally, a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding the protein. Plant transformation vectors also generally contain a selectable marker. Typical 5'-3' regulatory sequences include a transcription initiation start site, a ribosome binding site, an RNA processing signal, a transcription termination site, and/or a polyadenylation signal. Vectors for plant transformation have been reviewed in Rodriguez et al. (1988) *Vectors: A Survey of Molecular Cloning Vectors and Their Uses*, Butterworths, Boston; Glick et al. (1993) *Methods in Plant Molecular Biology and Biotechnology* CRC Press, Boca Raton, Fla.; and Croy (1993) *In Plant Molecular Biology Labfax*, Hames and Rickwood, Eds., BIOS Scientific Publishers Limited, Oxford, UK. Non-limiting examples of plant transformation vectors useful in the present invention include pMON30423, pMON29141, pMON43007, pCGN5139, and pMON43011, shown in FIGS. 1-5, respectively.

Target Tissues

Appropriate target tissues of plants for enhanced production of sterol compounds such as sitosterol, sitosterol esters, sitostanol, sitostanol esters, and tocopherols, and reduced production of campesterol, campestanol, and esters thereof, include, but are not limited to, fruits, flowers, seeds, roots, tubers, leaves, stems, buds, and other vegetable parts of plants. Within seeds, appropriate organ compartments include the embryo, the endosperm, and the aleurone layer. Within any of the noted target tissues, appropriate cellular compartments include, but are not limited to, the cell cytoplasm and plastids (e.g., proplastids, chloroplasts, chromoplasts, leucoplasts, amyloplasts, etc.).

Promoters

Promoters useful in the present invention include those that confer appropriate cellular and temporal specificity of expression. Such promoters include those that are constitutive or inducible, environmentally- or developmentally-regulated, or organelle-, cell-, or tissue-specific.

Often-used constitutive promoters include the CaMV 35S promoter (Odell et al. (1985) *Nature* 313: 810), the enhanced CaMV 35S promoter, the Figwort Mosaic Virus (FMV) promoter (Richins et al. (1987) *NAR* 20: 8451), the mannopine synthase (mas) promoter, the nopaline synthase (nos) promoter, and the octopine synthase (ocs) promoter.

Useful inducible promoters include heat-shock promoters (Ou-Lee et al. (1986) *Proc. Natl. Acad. Sci. USA* 83: 6815; Ainley et al. (1990) *Plant Mol. Biol.* 14: 949), a nitrate-inducible promoter derived from the spinach nitrite reductase gene (Back et al. (1991) *Plant Mol. Biol.* 17: 9), hormone-inducible promoters (Yamaguchi-Shinozaki et al. (1990) *Plant Mol. Biol.* 15: 905; Kares et al. (1990) *Plant Mol. Biol.* 15: 905), and light-inducible promoters associated with the small subunit of RuBP carboxylase and LHCP gene families (Kuhlemeier et al. (1989) *Plant Cell* 1: 471; Feinbaum et al. (1991) *Mol. Gen. Genet.* 226: 449; Weisshaar et al. (1991) *EMBO J.* 10: 1777; Lam and Chua (1990) *Science* 248: 471; Castresana et al. (1988) *EMBO J.* 7: 1929; Schulze-Lefert et al. (1989) *EMBO J.* 8: 651).

Examples of useful tissue-specific, developmentally-regulated promoters include fruit-specific promoters such as the E4 promoter (Cordes et al. (1989) *Plant Cell* 1: 1025), the E8 promoter (Deikman et al. (1988) *EMBO J.* 7: 3315), the kiwifruit actinidin promoter (Lin et al. (1993) *PNAS* 90: 5939), the 2A11 promoter (Houck et al., U.S. Pat. No. 4,943, 674), and the tomato pZ130 promoter (U.S. Pat. Nos. 5,175, 095 and 5,530,185); the β-conglycinin 7S promoter (Doyle et al. (1986) *J. Biol. Chem.* 261: 9228; Slighton and Beachy (1987) *Planta* 172: 356), and seed-specific promoters (Knutzon et al. (1992) *Proc. Natl. Acad. Sci. USA* 89: 2624; Bustos et al. (1991) *EMBO J.* 10: 1469; Lam and Chua (1991) *J. Biol. Chem.* 266: 17131; Stayton et al. (1991) *Aust. J. Plant.*

*Physiol.* 18: 507). Fruit-specific gene regulation is discussed in U.S. Pat. No. 5,753,475. Other useful seed-specific promoters include, but are not limited to, the napin, phaseolin, zein, soybean trypsin inhibitor, 7S, ADR12, ACP, stearoyl-ACP desaturase, oleosin, *Lasquerella* hydroxylase, and barley aldose reductase promoters (Bartels (1995) *Plant J.* 7: 809-822), the EA9 promoter (U.S. Pat. No. 5,420,034), and the Bce4 promoter (U.S. Pat. No. 5,530,194). Useful embryo-specific promoters include the corn globulin 1 and oleosin promoters. Useful endosperm-specific promoters include the rice glutelin-1 promoter, the promoters for the low-pI α-amylase gene (Amy32b) (Rogers et al. (1984) *J. Biol. Chem.* 259:12234), the high-pI α-amylase gene (Amy 64) (Khurseed et al. (1988) *J. Biol. Chem.* 263: 18953), and the promoter for a barley thiol protease gene ("Aleurain") (Whittier et al. (1987) *Nucleic Acids Res.* 15: 2515). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al. (1991) *Seed Sci. Res.* 1: 209), phaseolin, zein, soybean trypsin inhibitor, ACP, stearoyl-ACP desaturase, and oleosin. Seed-specific gene regulation is discussed in EP 0 255 378 B1 and U.S. Pat. Nos. 5,420,034 and 5,608,152. Promoter hybrids can also be constructed to enhance transcriptional activity (Hoffman, U.S. Pat. No. 5,106,739), or to combine desired transcriptional activity and tissue specificity.

Plant Transformation and Regeneration

A variety of different methods can be employed to introduce transformation/expression vectors into plant protoplasts, cells, callus tissue, leaf discs, meristems, etc., to generate transgenic plants. These methods include, for example, *Agrobacterium*-mediated transformation, particle gun delivery, microinjection, electroporation, polyethylene glycol-mediated protoplast transformation, liposome-mediated transformation, etc. (reviewed in Potrykus (1991) *Annu. Rev. Plant Physiol. Plant Mol. Biol.* 42: 205).

In general, transgenic plants comprising cells containing and expressing nucleic acids encoding enzymes facilitating the modifications in sterol compound and tocopherol biosynthesis and accumulation described herein can be produced by transforming plant cells with a DNA construct as described above via any of the foregoing methods; selecting plant cells that have been transformed on a selective medium; regenerating plant cells that have been transformed to produce differentiated plants; and selecting a transformed plant that expresses the enzyme-encoding nucleotide sequence(s) at a level such that the amount of sitosterol, sitosterol esters, sitostanol, sitostanol esters, tocopherol compound(s), and campesterol/campestanol and their esters is within the ranges described herein.

The encoding DNAs can be introduced either in a single transformation event (all necessary DNAs present on the same vector), a co-transformation event (all necessary DNAs present on separate vectors that are introduced into plants or plant cells simultaneously), or by independent transformation events (all necessary DNAs present on separate vectors that are introduced into plants or plant cells independently). Traditional breeding methods can subsequently be used to incorporate the desired combination of enzymes into a single plant, and to produce hybrid progeny of the invention plants.

Specific methods for transforming a wide variety of dicots and obtaining transgenic plants are well documented in the literature (Gasser and Fraley (1989) *Science* 244:1293; Fisk and Dandekar (1993) *Scientia Horticulturae* 55: 5; Christou (1994) *Agro Food Industry Hi Tech*, p. 17; and the references cited therein).

Successful transformation and plant regeneration have been achieved in the monocots as follows: asparagus (*Asparagus officinalis*; Bytebier et al. (1987) *Proc. Natl. Acad. Sci. USA* 84: 5345); barley (*Hordeum vulgarae*; Wan and Lemaux (1994) *Plant Physiol.* 104: 37); maize (*Zea mays*; Rhodes et al. (1988) *Science* 240: 204; Gordon-Kamm et al. (1990) *Plant Cell* 2: 603; Fromm et al. (1990) *Bio/Technology* 8: 833; Koziel et al. (1993) *Bio/Technology* 11: 194); oats (*Avena sativa*; Somers et al. (1992) *Bio/Technology* 10: 1589); orchardgrass (*Dactylis glomerata*; Horn et al. (1988) *Plant Cell Rep.* 7: 469); rice (*Oryza sativa*, including indica and japonica varieties; Toriyama et al. (1988) *Bio/Technology* 6: 10; Zhang et al. (1988) *Plant Cell Rep.* 7: 379; Luo and Wu (1988) *Plant Mol. Biol. Rep.* 6: 165; Zhang and Wu (1988) *Theor. Appl. Genet.* 76: 835; Christou et al. (1991) *Bio/Technology* 9: 957); rye (*Secale cereale*; De la Pena et al. (1987) *Nature* 325: 274); sorghum (*Sorghum bicolor*; Cassas et al. (1993) *Proc. Natl. Acad. Sci. USA* 90: 11212); sugar cane (*Saccharum* spp.; Bower and Birch (1992) *Plant J.* 2: 409); tall fescue (*Festuca arundinacea*; Wang et al. (1992) *Bio/Technology* 10: 691); turfgrass (*Agrostis palustris*; Zhong et al. (1993) *Plant Cell Rep.* 13: 1); and wheat (*Triticum aestivum*; Vasil et al. (1992) *Bio/Technology* 10: 667; Weeks et al. (1993) *Plant Physiol.* 102: 1077; Becker et al. (1994) *Plant J.* 5: 299).

Host Plants

Plants particularly attractive for the sterol and tocopherol modifications described herein include those that produce carbon substrates which can be employed for synthesis of these compounds. Non-limiting examples of such plants include various monocots and dicots, including high oil seed plants such as high oil seed *Brassica* (e.g., *Brassica nigra, Brassica napus, Brassica hirta, Brassica rapa, Brassica campestris, Brassica carinata*, and *Brassica juncea*), soybean (*Glycine max*), castor bean (*Ricinus communis*), cotton, safflower (*Carthamus tinctorius*), sunflower (*Helianthus annuus*), flax (*Linum usitatissimum*), corn (*Zea mays*), coconut (*Cocos nucifera*), palm (*Elaeis guineensis*), oilnut trees such as olive (*Olea europaea*), sesame, and peanut (*Arachis hypogaea*), as well as *Arabidopsis*, tobacco, wheat, barley, oats, amaranth, potato, rice, tomato, and legumes (e.g., peas, beans, lentils, alfalfa, etc.).

Enhancement of sitostanol compound production by the methods discussed herein is expected to result in yields of sitostanol, sitostanol esters, or mixtures thereof in an amount of at least about 57% by weight, preferably from about 57% to about 90% by weight, and more preferably from about 57% to about 65% by weight of the total sterol compounds present in seed oil. Expressed on a seed dry weight basis, sitostanol, sitostanol esters, or mixtures thereof are expected to be present in an amount of at least about 0.08%, preferably from about 0.08% to about 0.8%, and more preferably from about 0.08% to about 0.4% of seed dry weight.

Enhancement of tocopherol compound production by the methods discussed herein is expected to result in yields of tocopherols of at least about 0.02%, preferably from about 0.02% to about 0.2%, and more preferably from about 0.02% to about 0.025% of seed dry weight.

The magnitude of reduction in the amount of campesterol, campestanol, and/or their esters is expected to be in the range of from about 10% of that normally present to about 100% of that normally present.

Plastid Targeting of Expressed Enzymes for Sterol and Tocopherol Biosynthesis

The modifications in sterol compound and tocopherol biosynthesis and accumulation described herein can be produced in plants either by expression of the appropriate enzymes in the cytoplasm by the methods described herein, or in plastids. As there is a high carbon flux through acetyl-CoA in plastids, especially in seeds of oil-accumulating plants such as oilseed rape (*Brassica napus*), canola (*Brassica rapa, Brassica campestris, Brassica carinata*, and *Brassica juncea*), soybean (*Glycine max*), flax (*Linum usitatissimum*), and sunflower (*Helianthus annuus*) for example, targeting of the gene products of desired encoding DNAs to plastids, such as leucoplasts, of seeds, or transformation of seed plastids and expression therein of these encoding DNAs, are attractive strategies for producing high levels of sitosterol/sitostanol and/or their esters and tocopherol compounds in plants. These strategies can also be employed to reduce the biosynthesis and accumulation of campesterol/campestanol and/or their esters in plant plastids as well.

All of the enzymes discussed herein can be modified for plastid targeting by employing plant cell nuclear transformation constructs wherein DNA coding sequences of interest are fused to any of the available transit peptide sequences capable of facilitating transport of the encoded enzymes into plant plastids, and driving expression by employing an appropriate promoter such as any of those discussed above. Targeting of enzymes involved in altering sterol compound and tocopherol quantity and/or quality to plastids can be achieved by fusing DNA encoding plastid, e.g., chloroplast, leucoplast, amyloplast, etc., transit peptide sequences to the 5'-ATG of DNAs encoding enzymes affecting the biosynthesis and accumulation of these compounds. The sequences that encode a transit peptide region can be obtained, for example, from plant nuclear-encoded plastid proteins, such as the small subunit (SSU) of ribulose bisphosphate carboxylase, EPSP synthase, plant fatty acid biosynthesis related genes including fatty acyl-ACP thioesterases, acyl carrier protein (ACP), stearoyl-ACP desaturase, β-ketoacyl-ACP synthase and acyl-ACP thioesterase, or LHCPII genes, etc. Plastid transit peptide sequences can also be obtained from nucleic acid sequences encoding carotenoid biosynthetic enzymes, such as GGPP synthase, phytoene synthase, and phytoene desaturase. Other transit peptide sequences useful in the present invention are disclosed in Von Heijne et al. (1991) *Plant Mol. Biol. Rep.* 9: 104; Clark et al. (1989) *J. Biol. Chem.* 264: 17544; della-Cioppa et al. (1987) *Plant Physiol.* 84: 965; Romer et al. (1993) *Biochem. Biophys. Res. Commun.* 196: 1414; and Shah et al. (1986) *Science* 233: 478. Plant sterol compound/tocopherol biosynthetic enzyme-encoding sequences useful in the present invention can utilize native or heterologous transit peptides. The encoding sequence for a transit peptide effective in transport to plastids can include all or a portion of the encoding sequence for a particular transit peptide, and may also contain portions of the mature protein encoding sequence associated with a particular transit peptide. Numerous examples of transit peptides that can be used to deliver target proteins into plastids exist, and the particular transit peptide encoding sequences useful in the present invention are not critical as long as delivery into a plastid is obtained. Proteolytic processing within the plastid then produces the mature enzyme. This technique has proven successful not only with enzymes involved in polyhydroxyalkanoate biosynthesis (Nawrath et al. (1994) *Proc. Natl. Acad. Sci. USA* 91: 12760), but also with neomycin phosphotransferase II (NPT-II) and CP4 EPSPS (Padgette et al. (1995) *Crop Sci.* 35: 1451), for example.

Of particular interest are transit peptide sequences derived from enzymes known to be imported into the leucoplasts of seeds. Examples of enzymes containing useful transit peptides include those related to lipid biosynthesis (e.g., subunits of the plastid-targeted dicot acetyl-CoA carboxylase, biotin carboxylase, biotin carboxyl carrier protein, α-carboxytransferase, plastid-targeted monocot multifunctional acetyl-CoA carboxylase (Mr, 220,000); plastidic subunits of the fatty acid synthase complex (e.g., acyl carrier protein (ACP), malonyl-ACP synthase, KASI, KASII, KASIII, etc.); steroyl-ACP desaturase; thioesterases (specific for short, medium, and long chain acyl ACP); plastid-targeted acyl transferases (e.g., glycerol-3-phosphate: acyl transferase); enzymes involved in the biosynthesis of aspartate family amino acids; phytoene synthase; gibberellic acid biosynthesis (e.g., ent-kaurene synthases 1 and 2); and carotenoid biosynthesis (e.g., lycopene synthase).

Exact translational fusions to the transit peptide of interest may not be optimal for protein import into the plastid. By creating translational fusions of any of the enzymes discussed herein to the precursor form of a naturally imported protein or C-terminal deletions thereof, one would expect that such translational fusions would aid in the uptake of the engineered precursor protein into the plastid. For example, Nawrath et al. ((1994) *Proc. Natl. Acad. Sci. USA* 91: 12760) used a similar approach to create the vectors employed to introduce the polyhydroxybutyrate biosynthesis genes of *A. eutrophus* into *Arabidopsis*.

It is therefore fully expected that targeting of the enzymes discussed herein to fruit chloroplasts or chromoplasts, leaf chloroplasts, or seed plastids such as leucoplasts by fusing transit peptide gene sequences thereto will further enhance in vivo conditions for the modifications in sterol compound and tocopherol biosynthesis and accumulation in plant tissues described herein.

Plastid Transformation for Expression of Enzymes Involved in Sterol Compound and Tocopherol Biosynthesis and Accumulation Alternatively, enzymes facilitating the biosynthesis and accumulation of sterol compounds such as sitostanol and sitostanol esters, as well as tocopherols, and reducing the biosynthesis and accumulation of campesterol, campestanol, and/or their esters discussed herein can be expressed in situ in plastids by direct transformation of these organelles with appropriate recombinant expression constructs. Constructs and methods for stably transforming plastids of higher plants are well known in the art (Svab et al. (1990) *Proc. Natl Acad. Sci. USA* 87: 8526; Svab et al. (1993) *Proc. Natl. Acad. Sci. USA* 90: 913; Staub et al. (1993) *EMBO J.* 12: 601; Maliga et al., U.S. Pat. No. 5,451,513; Maliga et al., PCT International Publications WO 95/16783, WO 95/24492, and WO 95/24493; and Daniell et al., U.S. Pat. No. 5,693,507). These methods generally rely on particle gun delivery of DNA containing a selectable marker in addition to introduced DNA sequences for expression, and targeting of the DNA to the plastid genome through homologous recombination. Transformation of a wide variety of different monocots and dicots by particle gun bombardment is routine in the art (Hinchee et al. (1994) In: *Plant Cell and Tissue Culture*, I. Vasil and T. Thorpe (Eds.), Kluwer Academic Publishers, Netherlands, p. 231; Walden and Wingender (1995) *TIBS* 13: 324).

DNA constructs for plastid transformation generally comprise a targeting segment comprising flanking DNA sequences substantially homologous to a predetermined sequence of a plastid genome, which targeting segment enables insertion of DNA coding sequences of interest into the plastid genome by homologous recombination with the predetermined sequence; a selectable marker sequence, such as a sequence encoding a form of plastid 16S ribosomal RNA that is resistant to spectinomycin or streptomycin, or that encodes a protein which inactivates spectinomycin or streptomycin (such as the aadA gene), disposed within the targeting segment, wherein the selectable marker sequence confers a selectable phenotype upon plant cells, substantially all the plastids of which have been transformed with the DNA construct; and one or more DNA coding sequences of interest disposed within the targeting segment relative to the selectable marker sequence so as not to interfere with conferring of the selectable phenotype. In addition, plastid expression constructs also generally include a promoter region functional in a plant plastid and a transcription termination region capable of terminating transcription in a plant plastid, wherein these regions are operatively linked to the DNA coding sequences of interest.

A further refinement in chloroplast transformation/expression technology that facilitates control over the timing and tissue pattern of expression of introduced DNA coding sequences in plant plastid genomes has been described in PCT International Publication WO 95/16783 and U.S. Pat. No. 5,576,198. This method involves the introduction into plant cells of constructs for nuclear transformation that provide for the expression of a viral single subunit RNA polymerase and targeting of this polymerase into the plastids via fusion to a plastid transit peptide. Transformation of plastids with DNA constructs comprising a viral single subunit RNA polymerase-specific promoter specific to the RNA polymerase expressed from the nuclear expression constructs operably linked to DNA coding sequences of interest permits control of the plastid expression constructs in a tissue and/or developmental specific manner in plants comprising both the nuclear polymerase construct and the plastid expression constructs. Expression of the nuclear RNA polymerase coding sequence can be placed under the control of either a constitutive promoter, or a tissue- or developmental stage-specific promoter, thereby extending this control to the plastid expression construct responsive to the plastid-targeted, nuclear-encoded viral RNA polymerase. The introduced DNA coding sequence can be a single encoding region, or may contain a number of consecutive encoding sequences to be expressed as an engineered or synthetic operon. The latter is especially attractive where, as in the present invention, it is desired to introduce multigene biochemical pathways into plastids. This approach is not practical using standard nuclear transformation techniques since each gene introduced therein must be engineered as a monocistron, including an encoded transit peptide and appropriate promoter and terminator signals. Individual gene expression levels may vary widely among different cistrons, thereby possibly adversely affecting the overall biosynthetic process. This can be avoided by the chloroplast transformation approach.

Production of Transgenic Plants Comprising Introduced DNA Sequences for Modifying Sterol Compound and Tocopherol Biosynthesis Plant transformation vectors capable of delivering DNAs (genomic DNAs, plasmid DNAs, cDNAs, or synthetic DNAs) encoding plant-derived or other enzymes that affect the biosynthesis and accumulation of sterol compounds and tocopherols in plants for optimizing the pools of sitosterol, sitostanol, esters of either, and tocopherols, and for reducing the levels of campesterol, campestanol, and/or their esters, can be easily designed by art-recognized methods. Various strategies can be employed to introduce these encoding DNAs into plants to produce transgenic plants that biosynthesize and accumulate desirable levels of various sterol compounds and tocopherols, including:

1. Transforming individual plants with an encoding DNA of interest. Two or more transgenic plants, each containing one of these DNAs, can then be grown and cross-pollinated so as to produce hybrid plants containing the two DNAs. The hybrid can then be crossed with the remaining transgenic plants in order to obtain a hybrid plant containing all DNAs of interest within its genome.

2. Sequentially transforming plants with plasmids containing each of the encoding DNAs of interest, respectively.

3. Simultaneously cotransforming plants with plasmids containing each of the encoding DNAs, respectively.

4. Transforming plants with a single plasmid containing two or more encoding DNAs of interest.

5. Transforming plants by a combination of any of the foregoing techniques in order to obtain a plant that expresses a desired combination of encoding DNAs of interest.

Traditional breeding of transformed plants produced according to any one of the foregoing methods by successive rounds of crossing can then be carried out to incorporate all the desired encoding DNAs in a single homozygous plant line (Nawrath et al. (1994) *Proc. Natl. Acad. Sci. USA* 91: 12760; PCT International Publication WO 93/02187), or to produce hybrid offspring.

In methods 2 and 3, the use of vectors containing different selectable marker genes to facilitate selection of plants containing two or more different encoding DNAs is advantageous. Examples of useful selectable marker genes include those conferring resistance to kanamycin, hygromycin, sulphonamides, glyphosate, bialaphos, and phosphinothricin.

Stability of Transgene Expression

As several overexpressed enzymes may be required to produce optimal levels of substrates for the biosynthesis of sterol compounds and tocopherols, the phenomenon of co-suppression may influence transgene expression in transformed plants. Several strategies can be employed to avoid this potential problem (Finnegan and McElroy (1994) *Bio/Technology* 12: 883).

One commonly employed approach is to select and/or screen for transgenic plants that contain a single intact copy of the transgene or other encoding DNA (Assaad et al. (1993) *Plant Mol. Biol.* 22: 1067; Vaucheret (1993) *C.R. Acad. Sci. Paris, Science de la vie/Life Sciences* 316: 1471; McElroy and Brettell (1994) *TIBTECH* 12: 62). *Agrobacterium*-mediated transformation technologies are preferred in this regard.

Inclusion of nuclear scaffold or matrix attachment regions MAR) flanking a transgene has been shown to increase the level and reduce the variability associated with transgene expression in plants (Stief et al. (1989) *Nature* 341: 343; Breyne et al. (1992) *Plant Cell* 4: 463; Allen et al. (1993) *Plant Cell* 5: 603); Mlynarova et al. (1994) *Plant Cell* 6: 417; Spiker and Thompson (1996) *Plant Physiol.* 110: 15). Flanking a transgene or other encoding DNA with MAR elements may overcome problems associated with differential base composition between such transgenes or encoding DNAs and integrations sites, and/or the detrimental effects of sequences adjacent to transgene integration sites.

The use of enhancers from tissue-specific or developmentally-regulated genes may ensure that expression of a linked transgene or other encoding DNA occurs in the appropriately regulated manner.

The use of different combinations of promoters, plastid targeting sequences, and selectable markers for introduced transgenes or other encoding DNAs can avoid potential problems due to trans-inactivation in cases where pyramiding of different transgenes within a single plant is desired.

Finally, inactivation by co-suppression can be avoided by screening a number of independent transgenic plants to identify those that consistently overexpress particular introduced encoding DNAs (Register et al. (1994) *Plant Mol. Biol.* 25: 951). Site-specific recombination in which the endogenous copy of a gene is replaced by the same gene, but with altered expression characteristics, should obviate this problem (Yoder and Goldsbrough (1994) *Bio/Technology* 12: 263).

Any of the foregoing methods, alone or in combination, can be employed in order to insure the stability of transgene expression in transgenic plants of the present invention.

The following non-limiting examples illustrate various aspects of the present invention.

Example 1

Enhancement of Sitostanol Content in Seeds of Transgenic Plants by Seed-Specific Overexpression of a 3-Hydroxysteroid Oxidase To elevate the level of sitostanol in seeds of a plant of interest, the plant can be transformed with at least one expression cassette comprising a recombinant, double-stranded DNA molecule comprising, operatively linked in 5' to 3' sequence, a transcriptional and translational initiation region including a promoter which functions in plant cells to cause the production of an RNA sequence; a structural coding sequence encoding a 3-hydroxysteroid oxidase; and a 3' transcriptional and translational termination region functional in plant cells. Preferred plants include oil seeds such as canola, corn, cotton, sunflower, and soybean. The promoter can be a seed-specific or embryo-specific promoter such as the napin, soybean 7S, corn glob1, or *Lesquerella* hydroxylase promoters, or an endosperm-specific promoter such as the corn glutelin promoter or a zein promoter. The promoter can be homologous or heterologous with respect to the structural coding sequence. An example of a useful 3-hydroxysteroid oxidase structural coding sequence is the *Streptomyces* A19249 sequence disclosed in U.S. Pat. No. 5,518,908. Furthermore, the 3-hydroxysteroid oxidase structural coding sequence can be fused to a plastid transit peptide such as the pea or soybean RUBP carboxylase small subunit chloroplast transit peptide. The 3' termination region can be a non-translated region which functions in plant cells to cause the addition of polyadenylate nucleotides to the 3' end of the RNA sequence, for example the nos or E9 termination signal. The expression cassette can be contained within a vector effective in transforming plant cells, such as pCGN5139 (FIG. 4). The expression cassette or vector can contain a selectable marker such as an antibiotic resistance gene (e.g., conferring kanamycin or hygromycin resistance), or a herbicide resistance gene.

The expression cassette or vector can be introduced into a plant protoplast, plant cell, callus tissue, leaf disc, meristem, etc., by any method conventional in the art, including, for example, *Agrobacterium* Ti or Ri plasmid-mediated transformation, microprojectile bombardment, microinjection, electroporation, chemicals that induce free DNA uptake such as polyethylene glycol, liposome-mediated transformation, transformation via viruses or pollen, etc.

Following introduction of the expression cassette or vector, plant cells that have been transformed can be selected for on an appropriate selection medium. Transformed plant cells that survive selection can be regenerated to produce differentiated plants, and a transformed plant expressing 3-hydroxysteroid oxidase activity at the desired level can be selected by appropriate screening methods, for example by determining the sitosterol/sitostanol level by gas chromatography, or by Western blot analysis using antibody raised against the 3-hydroxysteroid oxidase. Preferred plants are those wherein the seeds produce sitostanol, at least one sitostanol ester, or mixtures thereof, in an amount of at least about 57% by weight, preferably from about 57% to about 90% by weight, and more preferably from about 57% to about 65% by weight, of the total sterol compounds in oil extracted from the seeds. Expressed on a percent seed dry weight basis, preferred plants are those that produce seed containing sitostanol, at least one sitostanol ester, or mixtures thereof, in an amount of at least about 0.08%, preferably from about 0.08% to about 0.8%, and more preferably from about 0.08% to about 0.4% of seed dry weight.

Example 2

Enhancement of Sitostanol Content in Seeds of Transgenic Plants by Coexpression of a 3-Hydroxysteroid Oxidase and a Steroid 5α-Reductase The same procedure as that described in Example 1 can be followed, additionally employing an expression cassette or vector comprising a steroid 5α-reductase-encoding DNA. Non-limiting examples of such DNAs are the *Arabidopsis* DET2 gene (Fujioka et al. (1997) *The Plant Cell* 9: 1951-1962), and the cDNAs from *Arabidopsis*, corn, and soybean, (SEQ ID NOS: 2, 4, 6 and 8), respectively. The sequence of a human steroid 5α-reductase is available as GenBank accession number G338476.

A transformed plant, seeds of which contain an elevated level of sitostanol, at least one sitostanol ester, or mixtures thereof, can be selected by appropriate screening methods, for example by gas chromatography. Preferred plants are those wherein the seeds produce sitostanol, at least one sitostanol ester, or mixtures thereof, in the amounts indicated in Example 1.

Example 3

Enhancement of Phytosterol Content in Seeds of Transgenic Plants by Seed-Specific Overexpression of HMG-CoA Reductase (HMGR)

In another embodiment of the present invention, the levels of sterol compounds, including sitosterol, sitostanol, campesterol, stigmasterol and at least one ester for each of the sterol compounds and mixtures thereof, can be elevated in plant seeds by overexpression of plant HMG-CoA reductases. Employing the same methods as those in Example 1, one can transform a plant of interest using expression cassette or vector comprising DNA encoding a polypeptide exhibiting 3-hydroxy-3-methylglutaryl-Coenzyme A reductase (HMG-CoA reductase or HMGR) activity. HMGR cDNAs from rubber and *Arabidopsis* have been successfully used to increase plant sterol levels in plant tissues (Schaller et al. (1995) *Plant Physiol.* 109: 761-770 and Gonzalez et al. (1997) *Third Terpnet Meeting of the European Network on Plant Isoprenoids Abstracts*, Abstract No. 33, page 33, respectively), but these have not be specifically targeted at increasing sterol levels in seeds.

Figure 6:
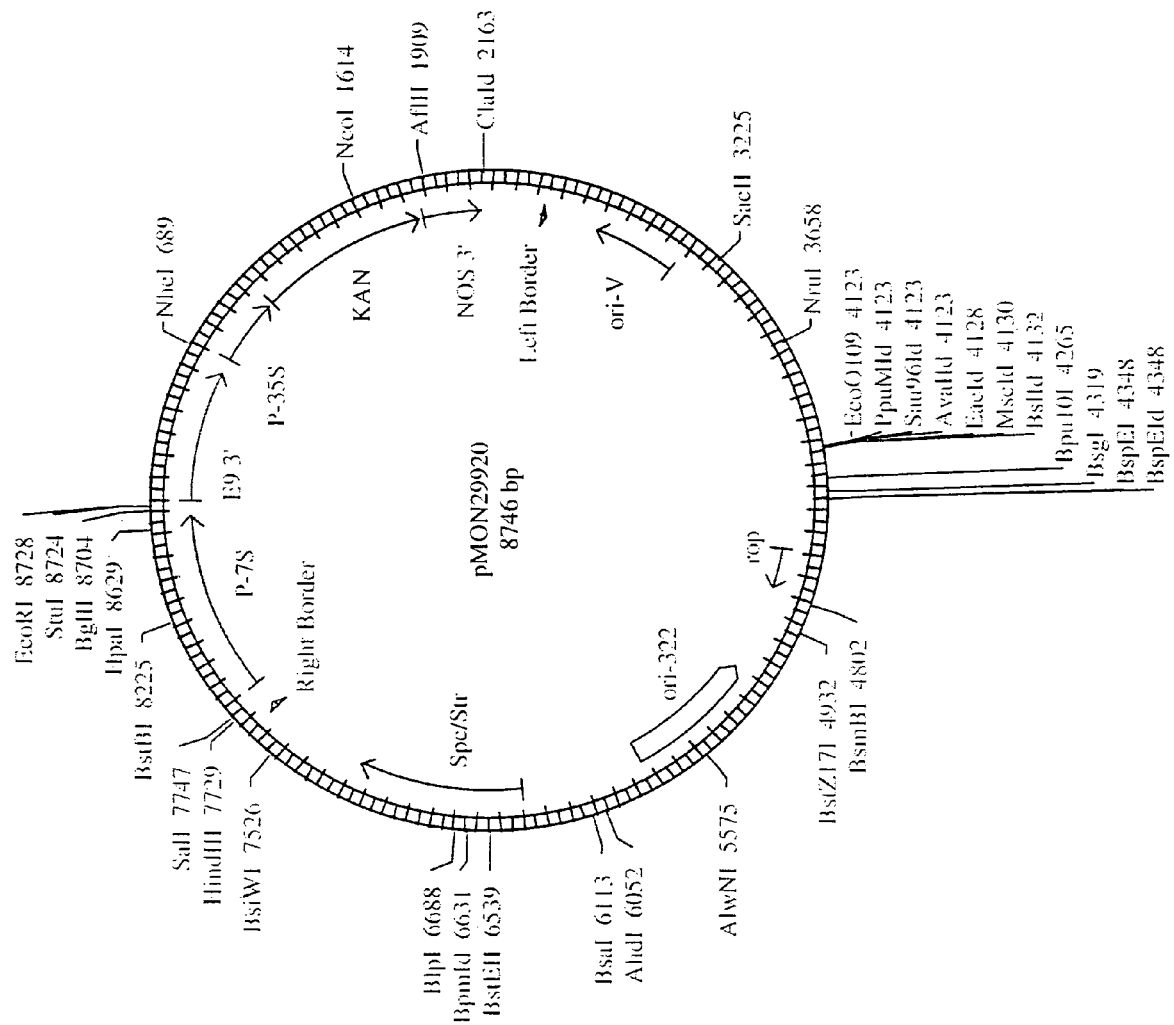
Figure 7:
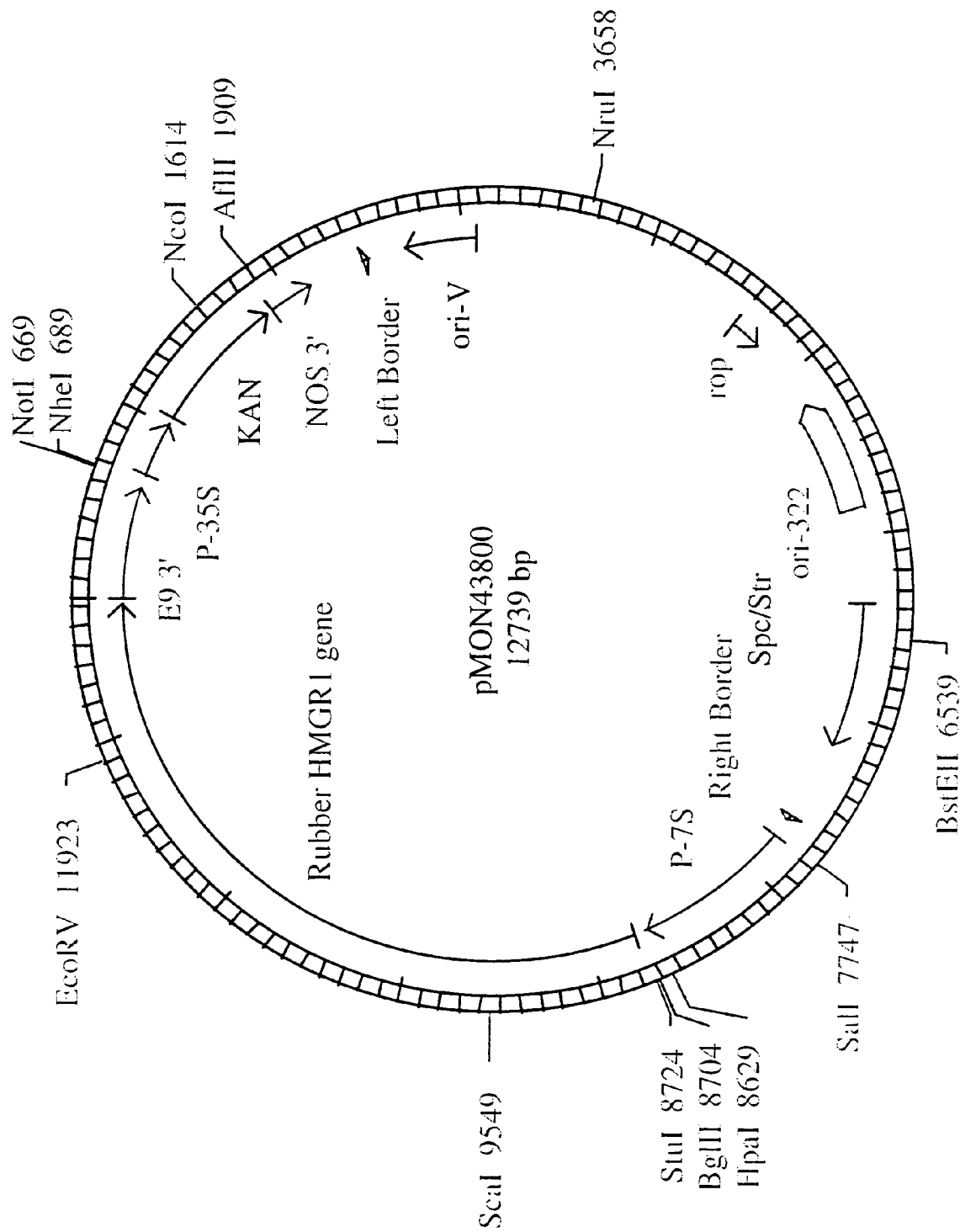
Figure 8:
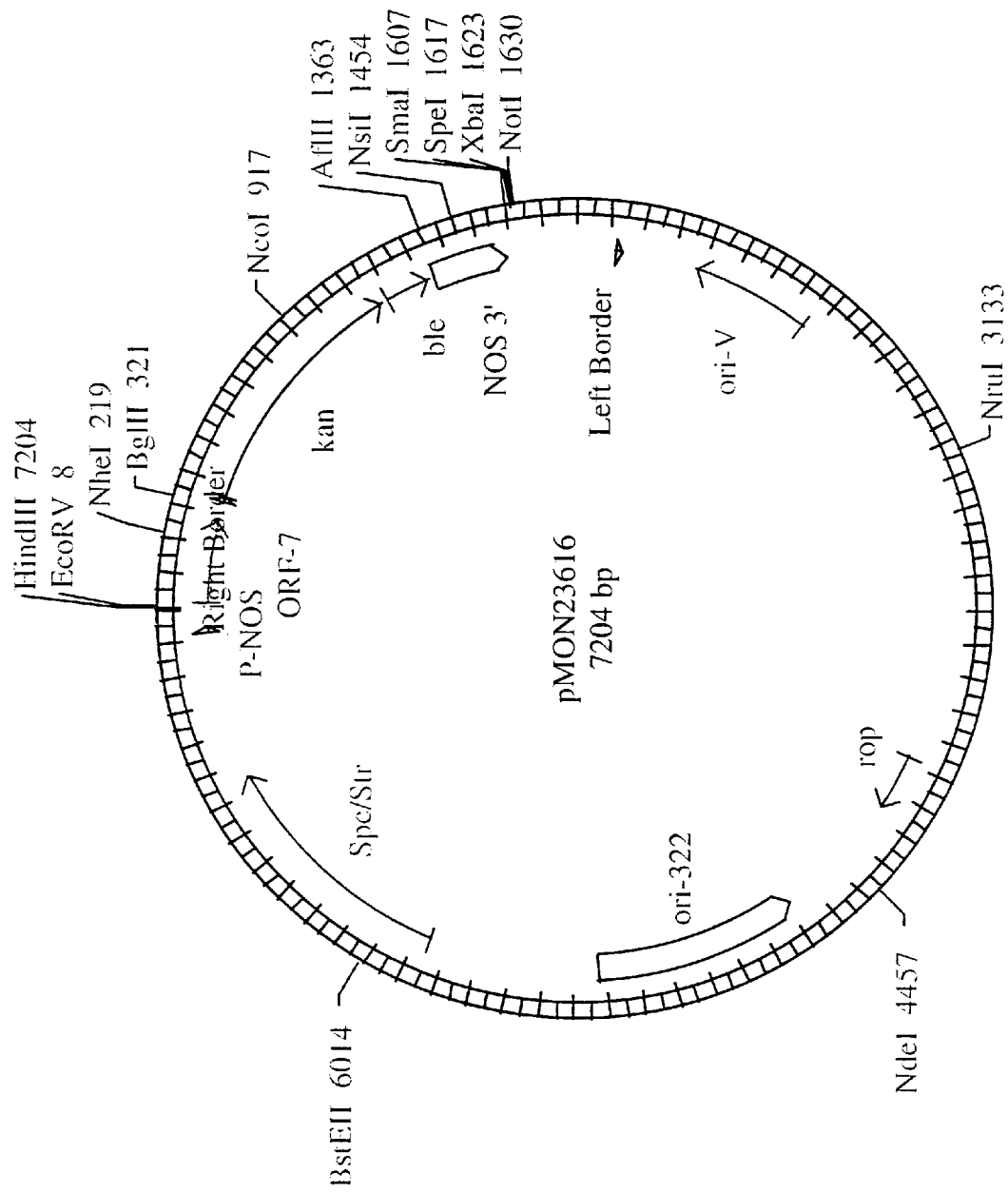
Figure 9:
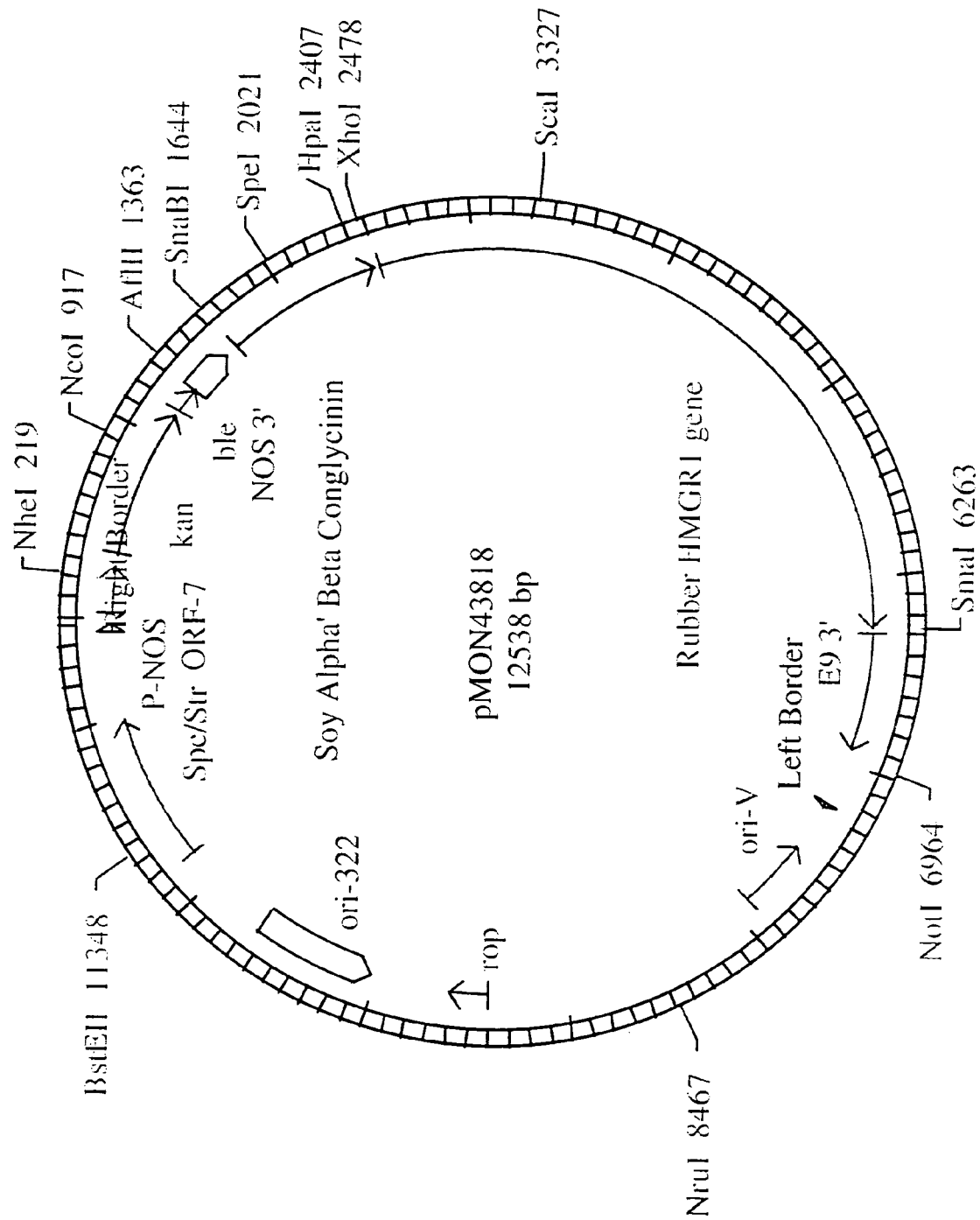

In order to examine the ability of HMGR overexpression for increasing sterol compound levels in seeds the following experiment was performed in *Glycine max*. A full-length HMGR gene from rubber genomic DNA was expressed in developing *Glycine max* seeds using the 7S promoter. This was achieved by excising the rubber HMGR gene from the plasmid pHEV 15 (Schaller et al., (1995) *Plant Physiol.*, 109: 761-770) using EcoRI. The 3.8 Kb fragment was inserted into the EcoRI site of pMON29920 (FIG. 6) such that the HMGR gene was flanked by the 7S promoter on the 5' end and the E9 3' terminator to create pMON43800 (FIG. 7). This was next digested with SalI and NotI to release a 7.7 Kb fragment that was then blunt-ended at the Sal I end before ligating to pMON23616 (FIG. 8) that was first cut with SmaI and NotI. This created a pMON43818 (FIG. 9) binary vector that contained the rubber HMGR gene driven by the 7S promoter and the NPTII gene for a selection marker driven by the NOS promoter and 3' NOS terminator. PMON43818 was used to transform *Agrobacterium tumefaciens* and transform *Glycine max* cotyledon explants.

Explants for transformation were prepared as follows: sterilized seeds were germinated on germination medium under light at 28° C. for 5-6 days. Germinated seeds were placed in the dark at 4° C. for 24 hours prior to excision. Seed coats were removed and hypocotyls of each seedling trimmed to a length of 0.5 cm to 1.0 cm in length. The cotyledons were then split open such that the hypocotyl was split down the middle. The primary leaves and apical region of each cotyledon was removed to expose the wounding region. Wounding was performed with 3-7 shallow, scalpel scores in line with the embryo axis, ensuring that the apical bud was damaged. Wounded explants were incubated in the culture of *Agrobacterium tumefaciens* containing pMON43008. Incubation was for 1 hour at room temperature. Inoculated explants were then transferred to a co-culture medium and placed under light at 23° C. for 3-4 days. At this time explants were transferred to a delay medium and placed in a 25° C. light growth room for 4 days.

After 4 days on delay, explants were transferred to a 186 ppm Kanamycin selection medium and placed in a 25° C. light growth room for 2 weeks. At the end of two weeks explants were transferred to 186 ppm WPM medium and placed again in a 25° C. light growth room for another 2 weeks. Cultures were transferred every 2 weeks to fresh medium for approximately 18-21 weeks. At the 6 week transfer, the cotyledons and any dead material was removed from the explants, and the petiole was cut. At each subsequent 2 week transfer the petiole was cut to expose fresh cells to the medium.

Transgenic shoots that were approximately ½' in length, with 2 nodes, 1 open trifoliate and an active growing point were selected, cut and transferred to rooting medium. Once a good root system was developed the plants were sent to the greenhouse to grow up in soils in pots.

Seeds from 15 transgenic plants and one nontransgenic control plant were harvested at maturity. Ten seeds from each plant were weighed and ground into a fine powder using an electric grinder. A known amount of cholestane (usually 100 µg in 100 µl ethanol) was added to each approximately 50 mg powder sample. Sterol compounds were hydrolyzed directly from the ground tissue by saponification with 2 ml of 10% KOH in methanol by refluxing the material at 60° C. for 30 minutes. The refluxed samples were cooled to room temperature and filtered through glass wool. An equal volume of water was added to each filtrate, and the nonsaponifiables were extracted by partitioning three times with equal volumes of hexane. The hexane phases were pooled and evaporated. The residues were resuspended in 1 ml of acetone, and quantitatively transferred to glass GC vials that were immediately capped. Sterols were analyzed by GC-FID using the following conditions: Inlet temperature of 220° C., detector temperature of 320° C., and column oven temperature programmed from 220° C. to 320° C. with initial temperature for 1 minute and final temperature for 16 minutes and ramp rate of 8°/min. The column used was a glass capillary DB-5 column of 50 m length, 320 µm diameter, and a film thickness of 0.25 µm. The carrier gas was helium at a flow rate of 1.0 ml/min. Results are presented in Table 4.

To fully characterize the sterol compounds present in the transgenic seeds, a representative sample was also analyzed by GC-MS for conformation of the sterol compounds present. The GC-MS conditions were as follows: inlet temp. 250° C., detector 320° C., oven programmed from 180° C. to 325° C. with initial equilibration time of 1.0 min, ramping to 310° C. at 4°/min at then at 20°/min to 325° C. The column was a DB-5 capillary glass column similar to the one used for GC-FID.

Total sterols increased by 3.2- and 3.9-fold in the best performing plants (transgenic events 3 and 4). These two events also showed the highest increases of individual sterols. Campesterol increased by 2.7-fold, sitosterol by 3.4-fold, sitostanol by 3.2-fold and other sterols by 6.5-fold in event 3 while stigmasterol increased by 2.3-fold in event 4. The other sterols, which account for the highest increase in total sterols, were pathway intermediates that included squalene, cycloartenol, 24-methylene cycloartenol, obtusifoliol, isofucosterol, and stigmasta-7-enol. These pathway intermediates normally form minor constituents in the sterol composition of seeds. However, in the transgenic seeds, probably due to increased carbon flux through the pathway, they accumulate in significant amounts. This suggests additional control points for sterol biosynthesis in plants such as squalene epoxidase, C-24 sterol methyltransferase, and C-14 obtusifoliol demethylase.

TABLE 4

| Event | Campe-sterol ug/g | Stigma-sterol ug/g | Sitosterol ug/g | Sitostanol ug/g | Others ug/g | Total ug/g |
|---|---|---|---|---|---|---|
| 1 | 161.9 | 148.2 | 551.3 | 36.8 | 264.8 | 1163 |
| 2 | 241.6 | 287.9 | 1128.8 | 96.6 | 1489.8 | 3244.5 |
| 3 | 442.4 | 320.1 | 1876.6 | 117.3 | 1728.4 | 4484.8 |
| 4 | 311.2 | 345.6 | 1645.6 | 113.8 | 1307.5 | 3723.6 |
| 5 | 395.5 | 323.0 | 1592.1 | 83.1 | 933.8 | 3327.5 |
| 6 | 370.5 | 301.6 | 1735.8 | 97.2 | 990.5 | 3495.6 |
| 7 | 351.0 | 307.0 | 1457.3 | 101.1 | 885.3 | 3101.7 |
| 8 | 248 | 172.4 | 1270.1 | 74.3 | 428.8 | 2193.6 |
| 9 | 221.1 | 140.7 | 1149 | 76.7 | 652.6 | 2240.1 |
| 10 | 234.2 | 184.8 | 1306.8 | 64.1 | 669.4 | 2459.3 |
| 11 | 156.5 | 125.4 | 679.2 | 38.8 | 142.3 | 1142.2 |
| 12 | 311.2 | 242.9 | 1457.3 | 67 | 418.6 | 2497 |
| 13 | 165.4 | 135.4 | 1320.1 | 59.7 | 1645.8 | 3326.4 |
| 14 | 190.8 | 152 | 1121.3 | 51.4 | 1040.7 | 2556.2 |
| 15 | 182.9 | 157.4 | 1118.5 | 55.2 | 376.6 | 1890.6 |
| 16 | 197.9 | 151.7 | 946.6 | 61.7 | 225.3 | 1583.2 |

Example 4

Enhancement of Sitosterol and Sitostanol Content in Seeds of Transgenic Plants by Coexpression of a HMG-CoA Reductase (HMGR and a 3-Hydroxysteroid Oxidase In another embodiment of the present invention, the level of sterol compounds, including sitosterol, at least one sitosterol ester, sitostanol, at least one sitostanol ester, and mixtures thereof, can be elevated in plant seeds by overexpression of an HMG-CoA reductase in combination with a 3-hydroxysteroid oxidase. Employing the same methods as those in Example 1, one can transform a plant of interest using an expression cassette or vector comprising DNA encoding a polypeptide exhibiting 3-hydroxy-3-methylglutaryl-Coenzyme A reductase (HMG-CoA reductase or HMGR) activity in addition to an expression cassette or vector comprising a 3-hydroxysteroid oxidase coding sequence. HMGR cDNAs from rubber and *Arabidopsis* have been successfully used to increase sitosterol levels in plant tissues (Schaller et al. (1995) *Plant Physiol.* 109: 761-770 and Gonzalez et al. (1997) *Third Terpnet Meeting of the European Network on Plant Isoprenoids Abstracts*, Abstract No. 33, page 33, respectively). Other HMGRs useful for increasing sitosterol levels include mutant forms of the genes selected from plant tissues known to overproduce sitosterol, and HMGR genes that have been altered via site-directed mutagenesis to deregulate their activity, resulting in variant enzymes that are not feed-back regulated.

Example 5

Enhancement of Sitosterol Content in Seeds of Transgenic Plants by Coexpression of a HMG-CoA Reductase and a Sterol Methyl Transferase In another embodiment of the present invention, the level of sitosterol, at least one sitosterol ester, sitostanol, at least one sitostanol ester, or mixtures thereof, can be elevated in plant seeds. Employing the same methods as those in Example 4, one can transform a plant of interest using an expression cassette or vector comprising DNA encoding a polypeptide exhibiting 3-hydroxy-3-methylglutaryl-Coenzyme A reductase activity in addition to an expression cassette or vector comprising DNA encoding a sterol methyltransferase (SMTII). An example of a useful SMTII coding sequence is that from *Arabidopsis thaliana* (Bouvier-Nave et al. (1997) *Eur. J. Biochem.* 246: 518-529). Plants into which both enzyme coding sequences have been introduced are expected to contain elevated levels of sitosterol, at least one sitosterol ester, sitostanol, at least one sitostanol ester, or mixtures thereof, as well as decreased levels of 24-methyl sterols such as campesterol, at least one campesterol ester, campestanol, at least one campestanol ester, and mixtures thereof Schaller et al. ((1997) *Third Terpnet Meeting of the European Network on Plant Isoprenoids Abstracts*, Abstract No. 44, page 44) have demonstrated a reduction in campesterol levels in transgenic tobacco constitutively overexpressing the *Arabidopsis* SMTII gene.

Figure 10:
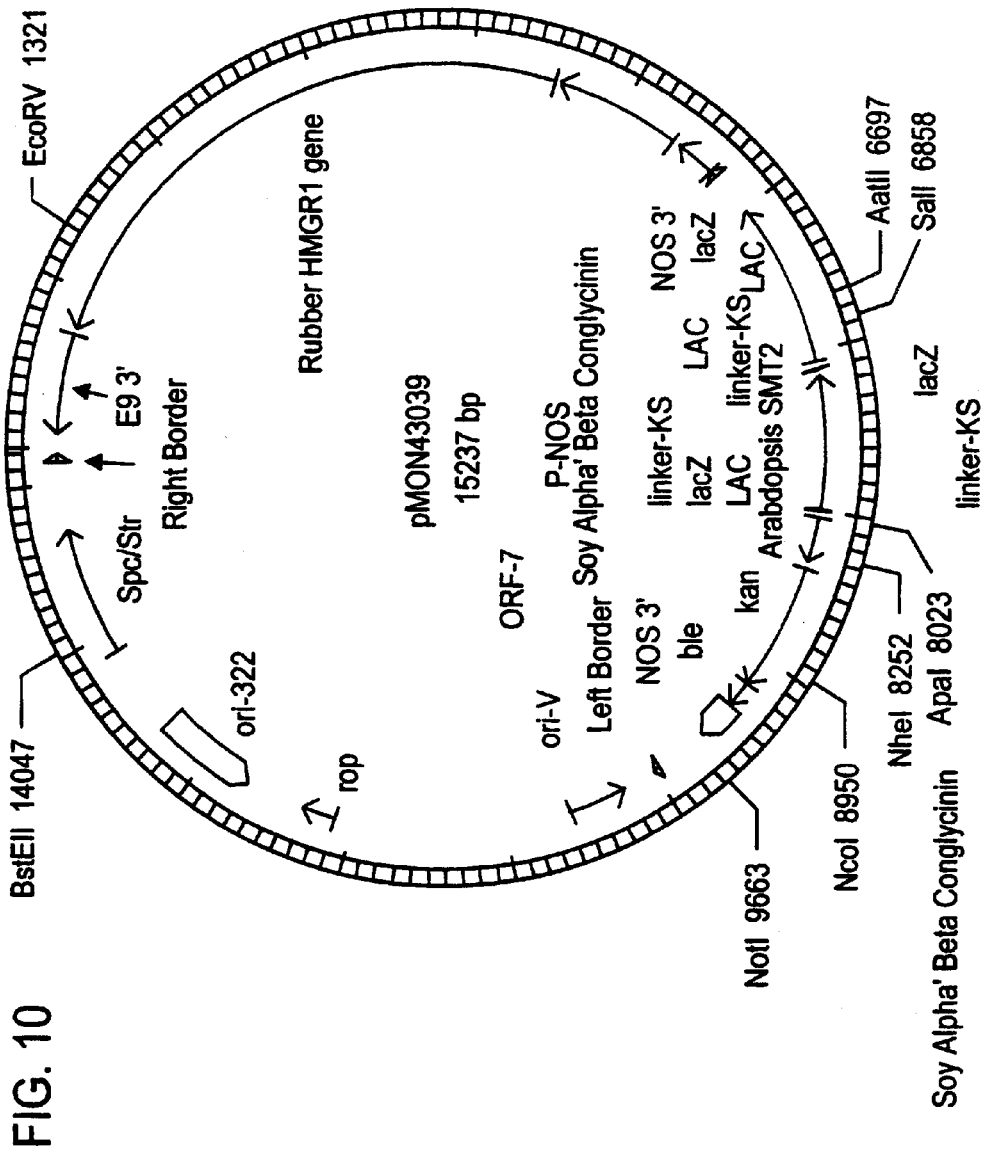

Experiments were performed with *Glycine max* to demonstrate this aspect. The strategy employed to obtain transgenic *Glycine max* plants expressing a rubber (*Hevea brasitiensis*) 3-hydroxy-3-methylglutaryl-Coenzyme A reductase (HMGR) gene and an *Arabidopsis thaliana* sterol methyltransferase (SMTII) gene in the developing embryos was as follows:

The binary vector pMON 43039 (FIG. 10) was constructed to contain the rubber HMGR and *Arabidopsis thaliana* SMTII with each driven by the seed-specific promoter 7S. The HMGR gene has the E9 3' terminator from pea rbcS E9 gene while the SMTII gene has the NOS 3' terminator from nopaline synthase gene. The selection marker gene is the NPTII gene for kanamycin resistance and is driven by the NOS promoter from *Agrobacterium tumefaciens* pTiT37 and the NOS 3' terminator sequence also from *Agrobacterium tumefaciens* pTiT37. *Agrobacterium tumefaciens* was transformed with pMON 43039.

Transformation of soybean explants was as described in Example 3. Seven transgenic events were generated. Ten seeds from each event were individually analyzed for phytosterols by methods described in Example 3. Data are presented in Table 5, where Plant 1 is a non-transgenic control and plants 2-8 are independent transgenic events. The data represent averages from results from ten seeds for each event. There is a 1.5- (events 5 and 7) to 2-fold (events 2, 3, and 4) increase in total sterols. Individually, there is a much greater increase in sitosterol (up to 2.6-fold in event 3) and sitostanol (up to 10-fold in event 6). At the same time there is a decrease in campesterol with up to 5.6-fold decrease in events 6 and 7. Additionally, phytosterol biosynthetic pathway intermediates accumulate to a greater extent in the transgenic events. These sterols are obtusifoliol, Stigmasta-7-enol, cycloartenol and 24-methylene cycloartanol.

The decrease in the amount of campesterol is consistent with the expected activity of the SMTII enzyme. This enzyme catalyzes the reaction 18 in Scheme 1. The substrate for this reaction, which is 24-methylene lophenol, can also undergo reaction 18b which is a C-4 demethylation. This latter route leads to the formation of 24-methyl sterols such as campesterol. It is presumed that increased activity of SMTII due to the higher expression of the introduced *Arabidopsis thaliana* SMTII gene allows for increased carbon flux through the pathway leading to sitosterol and thus reducing the availability of 24-methylene lophenol for reaction 18b which reduces the amount of campesterol formed.

Increase in total sterol content is due to the increased activity of the HMGR enzyme as described in Example 3.

TABLE 5

| Plant # | Campesterol ug/g | Stigmasterol ug/g | Obtusifoliol ug/g | Sitosterol ug/g | Sitostanol ug/g | Stigmasta-7-enol ug/g | Unknown 1 ug/g | Cycloartenol ug/g | 24-Methylene Cycloartanol ug/g | Total Sterols ug/g |
|---|---|---|---|---|---|---|---|---|---|---|
| 1 | 186.0 | 138.5 | 0.0 | 493.6 | 7.2 | 0.0 | 0.0 | 7.4 | 25.7 | 858.4 |
| 2 | 305.7 | 241.9 | 0.0 | 1278.6 | 52.0 | 26.0 | 26.8 | 35.7 | 37.2 | 2003.9 |
| 3 | 268.5 | 212.8 | 0.0 | 1293.7 | 50.3 | 41.2 | 16.7 | 35.2 | 45.8 | 1964.3 |
| 4 | 110.1 | 209.5 | 10.1 | 1275.0 | 67.4 | 47.6 | 38.8 | 49.0 | 49.9 | 1857.6 |
| 5 | 55.0 | 138.1 | 7.9 | 835.3 | 54.6 | 35.5 | 21.4 | 34.3 | 44.2 | 1226.4 |
| 6 | 33.4 | 166.6 | 31.7 | 1054.5 | 72.1 | 52.9 | 13.2 | 52.3 | 23.2 | 1499.8 |
| 7 | 33.7 | 135.1 | 13.2 | 841.9 | 48.2 | 46.1 | 8.7 | 36.3 | 31.3 | 1194.5 |
| 8 | 75.4 | 111.5 | 5.4 | 645.5 | 39.2 | 26.9 | 12.5 | 21.4 | 16.1 | 953.9 |

Example 6

Enhancement of Sitostanol and Tocopherol Content in Seeds of Transgenic Plants by Coexpression of a 3-Hydroxysteroid Oxidase and a Tocopherol Biosynthetic Enzyme In order to produce transgenic plants, seeds or other parts of which contain elevated levels of sitostanol, sitostanol esters, or mixtures thereof, as well as elevated levels of at least one tocopherol compound, the same procedure as that described in Example 1 can be followed, additionally employing an expression cassette or vector comprising at least one tocopherol biosynthesis enzyme encoding-DNA. Candidate tocopherol biosynthetic enzymes include those listed in Table 2. Preferred tocopherol biosynthesis enzyme encoding-DNAs include those encoding an enzyme selected from 3-deoxy-D-arabino-heptulosonate-7-P synthase, shikimate kinase, prephenate dehydrogenase, 4-hydroxyphenylpyruvate dioxygenase, geranylgeranylpyrophosphate synthase, geranylgeranylpyrophosphate hydrogenase, phytyl/prenyltransferase, 2-methyl-6-phytyl-benzoquinol methyl transferase, γ-tocopherol methyltransferase, and 1-deoxyxylulose-5-phosphate synthase.

A transformed plant, seeds or other vegetable or fruit parts of which contain an elevated level of sitostanol, at least one sitostanol ester, and mixtures thereof, as well as an elevated level of at least one tocopherol compound, can be selected by appropriate screening methods, for example by gas chromatography. Preferred plants are those wherein the seeds contain sitostanol, at least one sitostanol ester, or mixtures thereof, in an amount of at least about 57% by weight, preferably from about 57% to about 90% by weight, and more preferably from about 57% to about 65% by weight, of the total sterol compounds in oil extracted from the seeds. Expressed on a percent seed dry weight basis, preferred plants are those that produce seed containing sitostanol, at least one sitostanol ester, or mixtures thereof, in an amount of at least about 0.08%, preferably from about 0.08% to about 0.8%, and more preferably from about 0.08% to about 0.4% of seed dry weight.

The tocopherol compound, which can be α-, β-, γ-, δ-, or ε-tocopherol, or mixtures thereof, can be present in an amount of at least about 0.02%, preferably in the range of from about 0.02% to about 0.2%, more preferably in the range of from about 0.02% to about 0.025%, of the dry weight of the seed. A preferred tocopherol is α-tocopherol.

Example 7

Enhancement of the Content of Sterol Compounds and Tocopherols in Seeds of Transgenic Plants by Coexpression of a 3-Hydroxysteroid Oxidase, a Steroid 5α-Reductase, and a Tocopherol Biosynthetic Enzyme The same procedure as that described in Example 6 can be followed, additionally employing an expression cassette or vector comprising a steroid 5α-reductase-encoding DNA.

A transformed plant, seeds or other vegetable or fruit parts of which contain an elevated level of sitostanol, at least one sitostanol ester, and mixtures thereof, as well as an elevated level of at least one tocopherol compound, can be selected by appropriate screening methods, for example by gas chromatography. Preferred plants are those wherein the seeds contain sitostanol, at least one sitostanol ester, or mixtures thereof, in an amount of at least about 57% by weight, preferably from about 57% to about 90% by weight, and more preferably from about 57% to about 65% by weight, of the total sterol compounds in oil extracted from the seeds. Expressed on a percent seed dry weight basis, preferred plants are those that produce seed containing sitostanol, at least one sitostanol ester, or mixtures thereof, in an amount of at least about 0.08%, preferably from about 0.08% to about 0.8%, and more preferably from about 0.08% to about 0.4% of seed dry weight.

The tocopherol compound, which can be α-, β-, γ-, δ-, or ε-tocopherol, or mixtures thereof, can be present in an amount of at least about 0.02%, preferably in the range of from about 0.02% to about 0.2%, more preferably in the range of from about 0.02% to about 0.025%, of the dry weight of the seed. A preferred tocopherol is α-tocopherol.

Example 8

Coexpression of an S-Adenosylmethionine (SAM)-Dependent γ-Tocopherol Methyltransferase in Any of the Foregoing Examples to Convert γ-Tocopherol to α-Tocopherol An additional method of elevating the level of a tocopherol compound in a seed or other vegetable or fruit part of a plant comprises the same procedure as that described in any of the foregoing examples, and additionally employing an expression cassette or vector comprising an S-adenosylmethionine (SAM)-dependent γ-tocopherol methyltransferase-encoding DNA to convert γ-tocopherol to α-tocopherol. The amino acid sequences of the purified enzymes from *Capsicum* (Shigeoka et al. (1992) *Biochim. Biophys. Acta* 1128:220-226) and *Euglena gracilis* (d-Harlingue et al. (1985) *J. Biol. Chem.* 260:15200-15203) can be used to design nucleic acid probes for use in isolating DNA sequences encoding these enzymes. Identification of γ-tocopherol methyltransferase-encoding DNA sequences from *Synechocystis* PCC6803 and *Arabidopsis thaliana* has been reported by Shintani et al. ((1998) *Science* 282:2098-2100).

A transformed plant, seeds or other vegetable or fruit parts of which contain an elevated level of sitostanol, at least one sitostanol ester, and mixtures thereof, as well as an elevated level of at least one tocopherol compound, can be selected by appropriate screening methods, for example by gas chromatography. Preferred plants are those wherein the seeds contain sitostanol, at least one sitostanol ester, or mixtures thereof, in an amount of at least about 57% by weight, preferably from about 57% to about 90% by weight, and more preferably from about 57% to about 65% by weight, of the total sterol compounds in oil extracted from the seeds. Expressed on a percent seed dry weight basis, preferred plants are those that produce seed containing sitostanol, at least one sitostanol ester, or mixtures thereof, in an amount of at least about 0.08%, preferably from about 0.08% to about 0.8%, and more preferably from about 0.08% to about 0.4% of seed dry weight.

The tocopherol compound, which can be α-, β-, γ-, δ-, or ε-tocopherol, or mixtures thereof, can be present in an amount of at least about 0.02%, preferably in the range of from about 0.02% to about 0.2%, more preferably in the range of from about 0.02% to about 0.025%, of the dry weight of the seed. A preferred tocopherol is α-tocopherol.

Example 9

Plastid Expression of Enzymes Affecting the Biosynthesis and Accumulation of Sterol Compounds and Tocopherols Recombinant plants can be produced in which only the chloroplast DNA has been altered to incorporate the sterol compound and tocopherol enzyme-encoding sequences encompassed by the present invention. Promoters that function in chloroplasts are known in the art (Hanley-Bowden et al. (1987) *Trends in Biochemical Sciences* 12: 67-70). Methods and compositions for obtaining cells containing chloroplasts into which heterologous DNA has been inserted have been described, for example, by Maliga et al. (U.S. Pat. No. 5,451,513).and Daniell et al. (U.S. Pat. No. 5,693,507). A vector can be constructed which contains an expression cassette from which a peptide, polypeptide, or protein affecting the biosynthesis and accumulation of sterol and tocopherol compounds can be produced. An expression cassette can contain a chloroplast operable promoter sequence driving expression of, for example, a 3-hydroxysteroid oxidase gene, constructed in much the same manner as other recombinant constructs described herein, using PCR methodologies, restriction endonuclease digestion, ligation, etc. A chloroplast-expressible coding sequence can comprise a promoter and a 5' untranslated region from a heterologous gene or chloroplast gene such as psbA, which would provide for transcription and translation of a DNA sequence encoding a peptide, polypeptide, or protein affecting sterol compound and/or tocopherol biosynthesis in the chloroplast; a DNA sequence encoding the peptide, polypeptide, or protein; and a transcriptional and translational termination region such as a 3' inverted repeat region of a chloroplast gene that could stabilize an expressed mRNA coding for such peptide, etc. Expression from within the chloroplast would enhance accumulation of the expressed product. A host cell containing chloroplasts or other plastids can be transformed with the expression cassette, and the resulting cell containing the transformed plastids can be grown to express the encoded enzyme. A cassette can also include an antibiotic, herbicide tolerance, or other selectable marker gene in addition to the enzyme. The expression cassette can be flanked by DNA sequences obtained, for example, from a chloroplast DNA, which would facilitate stable integration of the expression cassette into the chloroplast genome, particularly by homologous recombination. Alternatively, the expression cassette may not integrate, but by including an origin of replication obtained from a chloroplast DNA, would be capable of providing for replication of, for example, an enzyme-encoding DNA gene within the chloroplast or other plastid.

Plants can be generated from cells containing transformed chloroplasts or other plastids, which can then be grown to produce seeds from which additional plants can be generated. Such transformation methods, particularly those in which chloroplast transformation is effected by integration into the chloroplast genome, possess the advantage that chloroplast genes are generally maternally inherited. This provides environmentally "safe" transgenic plants, virtually eliminating the possibility of escapes into the environment. Furthermore, chloroplasts and other plastids can be transformed multiple times to produce functional plastid genomes that express multiple desired recombinant proteins. Segregational events are thus avoided using chloroplast or plastid transformation. Furthermore, unlike plant nuclear genome expression, expression in chloroplasts or other plastids can be initiated from only one promoter and continue through a polycistronic region to produce multiple peptides from a single mRNA.

The expression cassette can be produced in much the same way that other plant transformation vectors are constructed. Plant plastid-operable DNA sequences can be inserted into a bacterial plasmid and linked to DNA sequences expressing desired enzyme products, such as a 3-hydroxysteroid oxidase, etc., so that the enzyme is produced within the chloroplast or other plastid, obviating the requirement for nuclear gene regulation, capping, splicing, or polyadenylation of nuclear regulated genes, or chloroplast or plastid targeting sequences. An expression cassette comprising a peptide, polypeptide, or protein that affects sterol compound and/or tocopherol biosynthesis and accumulation, which is either synthetically constructed or a native gene, can be inserted into a restriction site in a vector constructed for the purpose of transforming chloroplasts or other plastids. The cassette can be flanked upstream by a chloroplast- or plastid-functional promoter, and downstream by a chloroplast- or plastid-functional transcription and translation termination sequence. The resulting cassette can be incorporated into the chloroplast or plastid genome using well known homologous recombination methods.

Alternatively, transformation of chloroplasts or other plastids can be obtained by using an autonomously replicating plasmid or other vector capable of propagation within these organelles. One means of effectuating this method is to utilize a portion of the chloroplast or other plastid genome required for chloroplast or plastid replication initiation as a means for maintaining the plasmid or vector in the transformed chloroplast or other plastid. A sequence enabling stable replication of a chloroplast or plastid epigenetic element could easily be identified from random cloning of a chloroplast or other plastid genome into a standard bacterial vector which also contains a chloroplast or other plastid selectable marker gene, followed by transformation of chloroplasts or other plastids, and selection for transformed cells on an appropriate selection medium. Introduction of an expression cassette as described herein into a chloroplast- or other plastid-replicable epigenetic element would provide an effective means for localizing an enzyme-encoding DNA sequence to the chloroplast or other plastid.

A transformed plant, seeds or other vegetable or fruit parts of which contain an elevated level of sitostanol, at least one sitostanol ester, and mixtures thereof, as well as an elevated level of at least one tocopherol compound, can be selected by appropriate screening methods, for example by gas chromatography. Preferred plants are those wherein the seeds contain sitostanol, at least one sitostanol ester, or mixtures thereof, in an amount of at least about 57% by weight, preferably from about 57% to about 90% by weight, and more preferably from about 57% to about 65% by weight, of the total sterol compounds in oil extracted from the seeds. Expressed on a percent seed dry weight basis, preferred plants are those that produce seed containing sitostanol, at least one sitostanol ester, or mixtures thereof, in an amount of at least about 0.08%, preferably from about 0.08% to about 0.8%, and more preferably from about 0.08% to about 0.4% of seed dry weight.

The tocopherol compound, which can be α-, β-, γ-, δ-, or ε-tocopherol, or mixtures thereof, can be present in an amount of at least about 0.02%, preferably in the range of from about 0.02% to about 0.2%, more preferably in the range of from about 0.02% to about 0.025%, of the dry weight of the seed. A preferred tocopherol is α-tocopherol.

Example 10

Modification of Sterol Compound Composition of Oil in Transgenic *Brassica Napus* by Seed-Specific Expression of a 3-Hydroxysteroid Oxidase Gene Seeds of *Brassica napus* (rapeseed; canola) usually contain three major sterol compounds, viz., as percent of total sterol compounds, brassicasterol (~11%), campesterol (~34%), and sitosterol (~50%). Rapeseed oil is the major source of brassicasterol, which is not present in other vegetable seed oils such as those of soybean and cotton (Gunstone et al. (1994) *The Lipid Handbook*, Chapman & Hall, London, p. 125). The structures of brassicasterol, campesterol, and sitosterol, as well as those of the corresponding reduced phytostanols, are as follows:

Major sterol compounds of *Brassica napus*

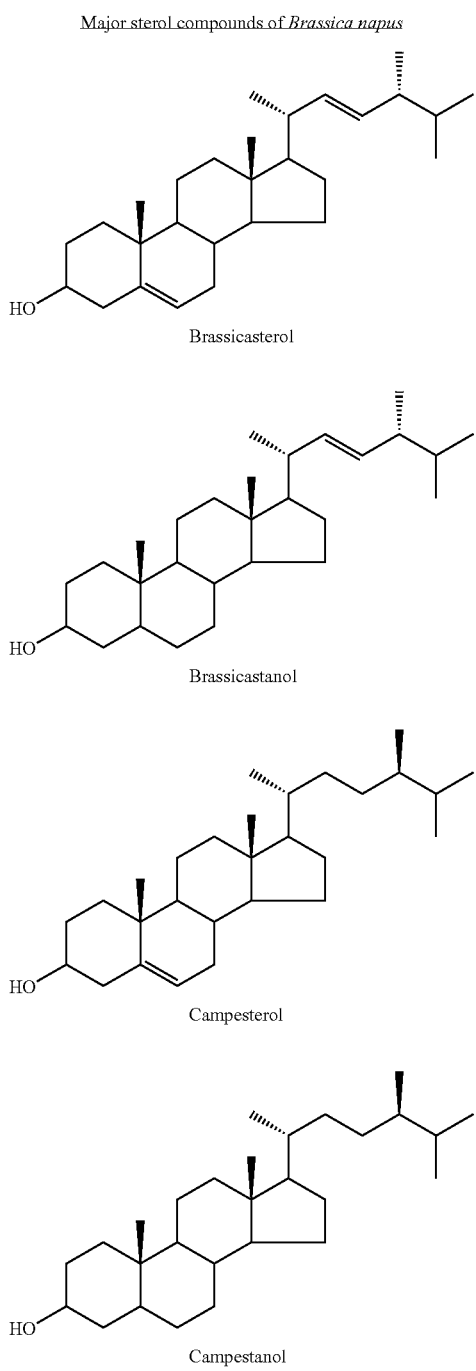

Brassicasterol

Brassicastanol

Campesterol

Campestanol

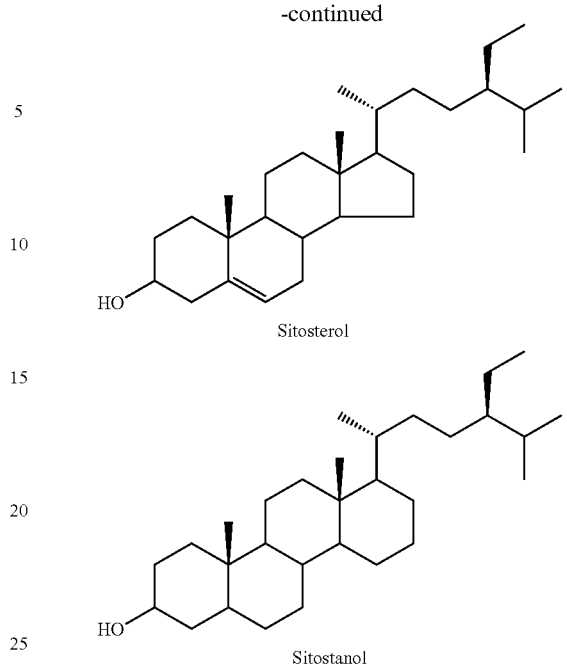

Sitosterol

Sitostanol

An experiment was performed wherein the *Streptomyces* A19249 3-hydroxysteroid oxidase disclosed in U.S. Pat. No. 5,518,908 was overexpressed in *Brassica napus* using the embryo-specific napin promoter to determine the effect on seed oil sterol compound composition. As shown below, this resulted in the production and accumulation of sitostanol, campestanol, and brassicastanol, in addition to the sitosterol, campesterol, and brassicasterol normally present. Brassicastanol is a novel phytostanol. The appearance of the reduced stanols was due to the reduction of the C-5 double bond in sitosterol, campesterol, and brassicasterol, presumably due to the activity of the 3-hydroxysteroid oxidase enzyme introduced into the transgenic plants.

The following strategy was employed to obtain transgenic *Brassica napus* plants expressing the *Streptomyces* 3-hydroxysteroid oxidase gene in developing embryos.

The *Streptomyces* 3-hydroxysteroid oxidase gene was excised from plasmid pMON30423 (FIG. 1) by digesting with the restriction enzymes AatII and NcoI. This released a fragment of approximately 4 Kb that contained the complete 3-hydroxysteroid oxidase gene (chox), the NOS 3' end, the bacterial ampicillin selection marker, and the pUC origin of replication. Plasmid pMON29141 (FIG. 2) was the source for the napin promoter and chloroplast targeting signal sequence. pMON29141 was digested with AatII and SpeI to release a 2.2 Kb fragment containing the M13-ori site, the napin promoter, and the fused pea RUBISCO small subunit chloroplast transit peptide/soy small subunit chloroplast transit peptide having the following amino acid sequence (SEQ ID NO: 31):

```
Met-Ala-Ser-Ser-Met-Ile-Ser-Ser-Pro-Ala-Val-Thr-Thr-Val-Asn-Arg-Ala-Gly-Ala-Gly-

[---------------------PEA SSU CTP-------------------------

Met-Val-Ala-Pro-Phe-Thr-Gly-Leu-Lys-Ser-Met-Ala-Gly-Phe-Pro-Phe-Thr-Gly-Leu-Lys-

----------------------PEA SSU CTP-------------------------

Ser-Met-Ala-Gly-Phe-Pro-Thr-Arg-Lys-Thr-Asn-Asn-Asp-Ile-Thr-Ser-Ile-Ala-Ser-Asn-

----------------------PEA SSU CTP-------------------------
```

```
                               -continued
Gly-Gly-Arg-Val-Gln-Cys-Met-Gln-Val-Trp-Pro-Pro-Ile-Gly-Lys-Lys-Lys-Phe-Glu-Thr
------------------][-----SOY SSU CTP------------------------]
```

Figure 1:
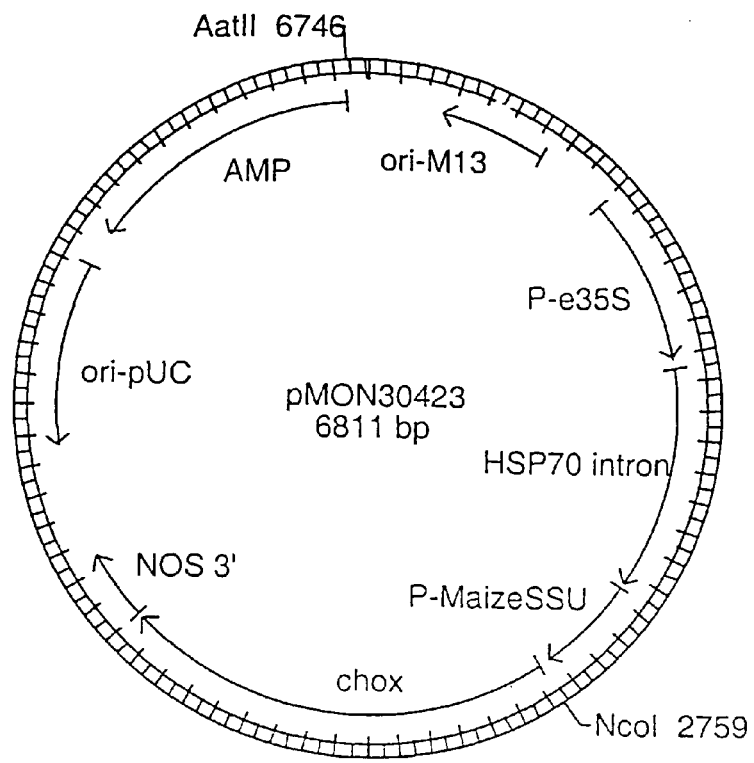
FIGS. 1-11 are maps showing the structures of plasmids pMON30423, pMON29141, pMON43007, pCGN5139, pMON43011, pMON29920, pMON43800, pMON23616, pMON43818, pMON43039 and pMON43008, respectively.
Figure 2:
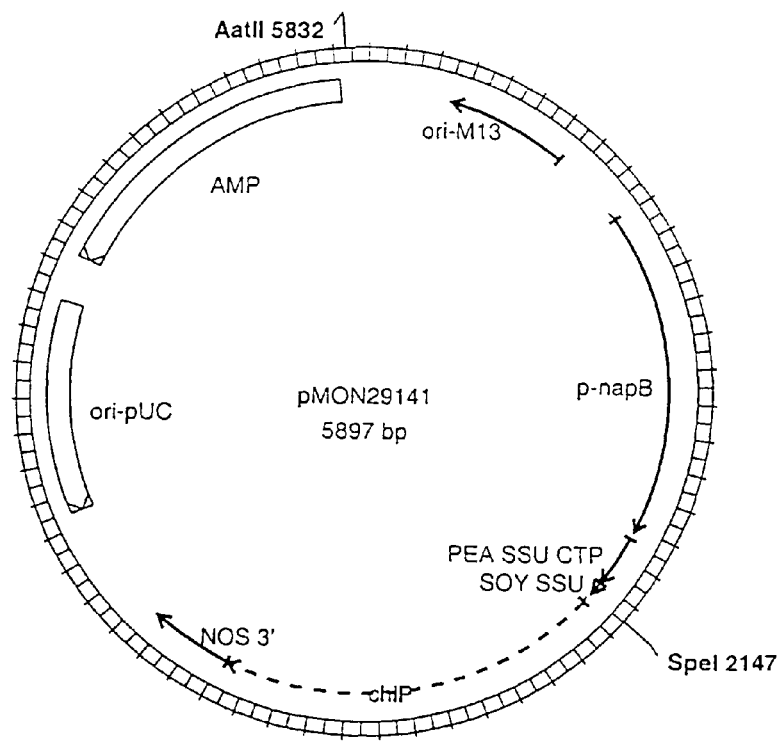
Figure 3:
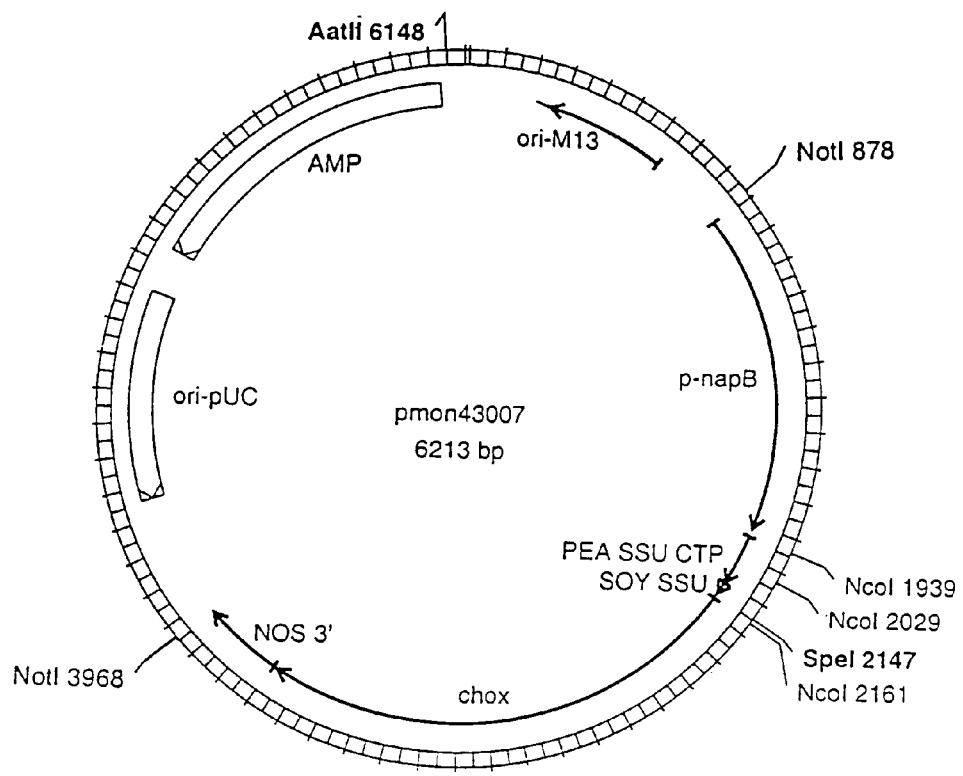

The 4 Kb fragment containing the 3-hydroxysteroid oxidase gene obtained from pMON30423, the 2.2 Kb napin fragment from pMON29141, and a SpeI-NcoI linker (Life Technologies, Inc., Gaithersburg, Md.) were ligated in a triple ligation mixture that resulted in the generation of the plasmid pMON43007 (FIG. 3). This plasmid was partially digested with NotI to release the cassette containing the napin promoter, the fused chloroplast transit peptide, the 3-hydroxysteroid oxidase gene, and the NOS 3' termination signal sequence. This cassette was cloned into the NotI site of the binary vector pCGN5139 (FIG. 4) to create pMON43011 (FIG. 5), which was used to transform *Agrobacterium tumefaciens*. *Brassica napus* hypocotyls were cocultivated with *Agrobacterium* cells carrying pMON43011 for transformation according to Radke et al. ((1992) *Plant Cell Reports* 11: 499-505); the MS-1, B5-1, and B5-BZ media contained 0.7% Phytagar. Transgenic plants were selected by resistance to kanamycin, and were grown in the greenhouse after appropriate selection and rooting was achieved.

Seed from 27 transgenic plants and one nontransgenic control plant were harvested at maturity. Seed were ground and extracted for sterol analysis as described in Example 3. The results are shown in Table 6 and FIG. 12. To fully characterize the sterol compounds present in the transgenic seeds, a representative sample, transgenic event number 9, was also analyzed by GC-MS for conformation of the sterol compounds present as described in Example 3. The mass spectrometry analysis identified brassicasterol, brassicastanol, campesterol, campestanol, sitosterol, and sitostanol as the major sterol compounds in the transgenic *Brassica napus* seeds.

As shown in Table 6, and graphically in FIG. 12, significant amounts of the phytostanols sitostanol, campestanol, and brassicastanol, in addition to the phytosterols sitosterol, campesterol, and brassicasterol normally present, accumulated in seeds of transgenic *Brassica napus* expressing the 3-hydroxysteroid oxidase gene under the control of the seed-specific napin promoter. Calculated as weight percent of total sterol compounds, in the highest stanol accumulating plants, from about 18% to about 22% of sitosterol was converted to sitostanol (transgenic event numbers 3, 9, 10, 20, 23, and 25), from about 17% to about 24% of campesterol was converted to campestanol (transgenic event numbers 3, 8, 9, 10, 15, 20, 23, 24, and 25), and from about 26% to about 43% of the brassicasterol was converted to brassicastanol (transgenic event numbers 3, 8, 9, 10, 15, 20, 23, 24, and 25). Thus, significant amounts of phytostanols not normally present in seed of *Brassica napus* were produced and accumulated in seed of the transgenic plants.

Brassicastanol has not been reported to occur in nature to date (Akihisa et al. (1992) In *Physiology and Biochemistry of Sterols*, Patterson et al., Eds., American Oil Chemists' Society, Champaign, Ill., pp. 172-228). The present results demonstrate the production of a novel phytostanol in a transgenic plant, in addition to the production of stanols from their corresponding, C-5 double bond-containing phytosterols, due to the activity of an introduced 3-hydroxysteroid oxidase. The other phytostanols observed in these transgenic seeds, i.e., sitostanol and campestanol, occur commonly, although they are minor constituents in most oil seeds. Phytostanols such as sitostanol and campestanol can be made commercially through hydrogenation of oils. However, by this process, brassicasterol will be hydrogenated to 22-dihydro-brassicastanol, in which both the C-5 and C-22 double bonds are reduced. It is therefore not commercially feasible to produce brassicastanol by hydrogenation of oils containing brassicasterol. Thus, the presence of brassicastanol in transgenic plants of the present invention is unexpected, and of unique commercial importance.

The occurrence of brassicastanol in transgenic rapeseed of the present invention expressing a 3-hydroxysteroid oxidase enzyme proves that this enzyme specifically reduces the C-5 double bond of phytosterols, and that its catalytic activity is not influenced by structural variations in the phytosterol side-chain. The three major phytosterols present in *Brassica* seeds, i.e., sitosterol, campesterol, and brassicasterol, vary in their side chains. Sitosterol has a C-24 ethyl side chain, campesterol has a C-24α methyl side chain, and brassicasterol has a C-24β methyl side chain and a C-22 double bond. Note the structures presented earlier in this example. In all three cases, the C-5 double bond in these phytosterols of transgenic seeds was reduced, while the C-22 double bond of brassicastanol remained intact. The following is a scheme for the enzymatic conversion of phytosterols (brassicasterol and β-sitosterol) to phytostanols (brassicastanol and β-sitostanol, respectively) catalyzed by 3-hydroxysteroid oxidases and sterol C-5 reductases (steroid 5α-reductases):

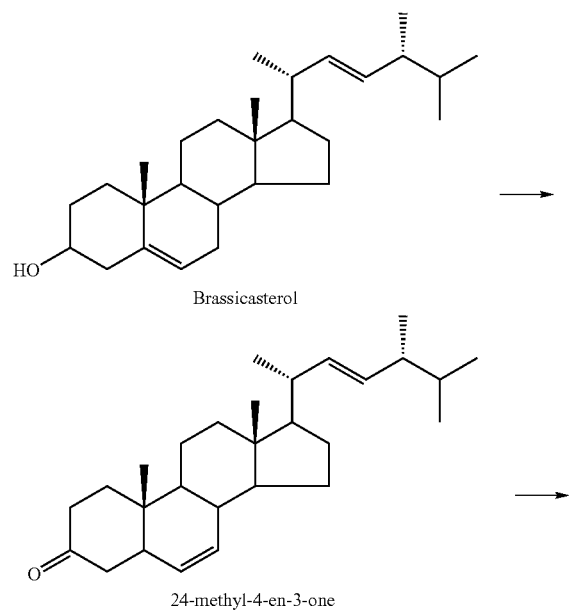

Scheme for the catalytic conversion of phytosterols to phytostanols by 3-hydroxysteroid oxidases and sterol C-5 reductases Brassicasterol 24-methyl-4-en-3-one -continued

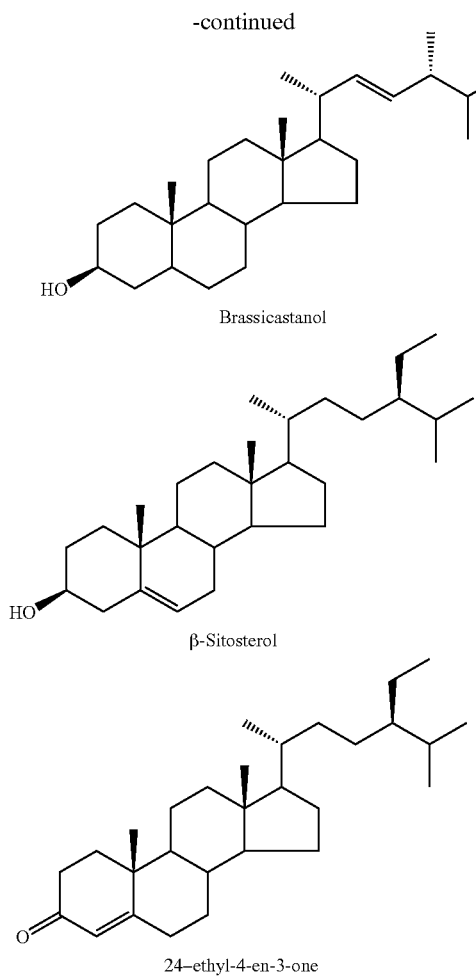

Brassicastanol

β-Sitosterol 24-ethyl-4-en-3-one

-continued

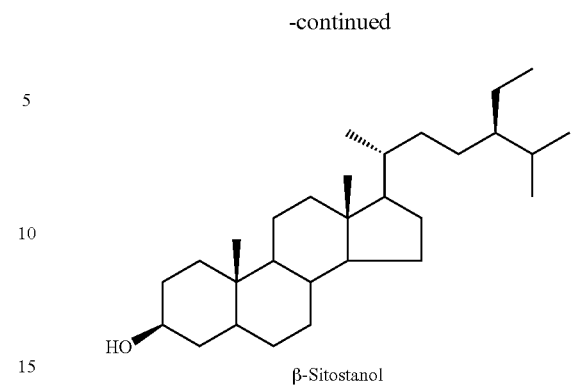

β-Sitostanol

Brassicastanol can be isolated from the sterol mixture using specific high performance liquid chromatographic (HPLC) methods known in the art. This will involve using reverse phase columns. Phytosterols and phytostanols can be separated from one another based on their structural properties, such as the number of double bonds in the rings and side chain, and also based on the number of methyl groups on the side chain, i.e., 24-methyl from 24-ethyl. 24-methyl epimers (24α from 24β) such as campestanol and brassicastanol can also be separated by using specific reverse-phase columns such as TSK-Gel ODS columns with a solvent system of methanol-isopropanol (4:1, v/v). These methods, and examples thereof, are extensively described in the monograph *Analysis of Sterols* by Goad L. J. and Akihisa T. (Chapter 4, pp 91-114, Chapman & Hall, London, UK, 1997).

TABLE 6

Phytosterol and Phytostanol Composition[1] of Transgenic *Brassica napus* Expressing a 3-Hydroxysteroid Oxidase Gene Under the Control of the Napin Promoter

| Plant[2] | Brassicasterol | Brassicastanol | % Brassicastanol[3] | Campesterol | Campestanol | % Campestanol[4] | Sitosterol | Sitostanol | % Sitostanol[5] |
|---|---|---|---|---|---|---|---|---|---|
| 1 | 10.9 | — | — | 34.1 | — | — | 50.0 | — | — |
| 2 | 8.3 | 2.1 | 20 | 32.0 | 2.1 | 6 | 46.9 | 3.7 | 7 |
| 3 | 5.6 | 3.3 | 37 | 25.9 | 6.4 | 20 | 43.5 | 9.6 | 18 |
| 4 | 8.4 | 2.5 | 23 | 30.3 | 5.2 | 15 | 43.8 | 2.9 | 6 |
| 5 | 8.0 | 2.4 | 23 | 28.7 | 5.0 | 15 | 45.5 | 3.7 | 8 |
| 6 | 9.7 | 1.4 | 13 | 30.2 | 0.8 | 3 | 51.5 | 1.7 | 3 |
| 7 | 9.4 | 1.6 | 15 | 33.3 | 1.0 | 3 | 48.3 | 1.7 | 3 |
| 8 | 6.1 | 3.5 | 36 | 25.4 | 7.2 | 22 | 42.1 | 7.9 | 16 |
| 9 | 7.6 | 4.4 | 37 | 26.6 | 7.4 | 22 | 39.3 | 8.8 | 18 |
| 10 | 5.5 | 4.1 | 43 | 25.5 | 8.1 | 24 | 40.9 | 11.8 | 22 |
| 11 | 9.0 | 2.4 | 21 | 28.6 | 1.8 | 6 | 49.5 | 2.7 | 5 |
| 12 | 8.4 | 2.6 | 24 | 30.1 | 2.1 | 7 | 46.2 | 3.4 | 7 |
| 13 | 12.1 | — | — | 36.0 | — | — | 46.6 | 0.4 | 1 |
| 14 | 12.5 | — | — | 30.8 | — | — | 50.3 | — | — |
| 15 | 7.4 | 3.5 | 32 | 23.1 | 5.4 | 19 | 46.4 | 8.8 | 16 |
| 16 | 9.1 | 2.0 | 18 | 31.7 | 1.2 | 4 | 48.5 | 1.0 | 2 |
| 17 | 9.8 | 2.4 | 20 | 31.3 | 1.8 | 3 | 47.9 | — | — |
| 18 | 14.6 | 0.3 | 2 | 30.6 | — | — | 48.5 | — | — |
| 19 | 9.9 | 2.4 | 20 | 28.2 | 1.3 | 4 | 49.3 | 2.0 | 4 |
| 20 | 7.3 | 3.1 | 30 | 25.9 | 6.1 | 19 | 41.8 | 9.3 | 18 |
| 21 | 11.2 | 0.4 | 3 | 29.8 | — | — | 53.1 | — | — |
| 22 | 9.2 | — | — | 34.1 | — | — | 51.7 | 0.7 | 1 |
| 23 | 7.0 | 4.4 | 39 | 24.9 | 6.9 | 22 | 39.4 | 10.5 | 21 |

TABLE 6-continued

Phytosterol and Phytostanol Composition[1] of Transgenic *Brassica napus* Expressing a 3-Hydroxysteroid Oxidase Gene Under the Control of the Napin Promoter

| Plant[2] | Brassicasterol | Brassicastanol | % Brassicastanol[3] | Campesterol | Campestanol | % Campestanol[4] | Sitosterol | Sitostanol | % Sitostanol[5] |
|---|---|---|---|---|---|---|---|---|---|
| 24 | 8.7 | 3.1 | 26 | 26.3 | 5.2 | 17 | 46.2 | 3.8 | 8 |
| 25 | 6.7 | 3.6 | 35 | 26.1 | 7.4 | 22 | 40.5 | 8.7 | 18 |
| 26 | 8.7 | 2.2 | 20 | 31.1 | 1.4 | 4 | 50.3 | 1.8 | 3 |
| 27 | 9.0 | 2.5 | 22 | 33.5 | 1.5 | 4 | 45.9 | 2.7 | 6 |

[1]Calculated as percent of total sterol compounds;
[2]1 is the non-transgenic control; 2-27 are independent transgenic events (plants) from which 10 R1 seeds per plant were analyzed for sterol compound composition;
[3]Expressed as brassicastanol/brassicasterol + brassicastanol × 100;
[4]Expressed as campestanol/campesterol + campestanol × 100;
[5]Expressed as sitostanol/sitosterol + sitostanol × 100

Example 11

Modification of Sterol Compound Composition of Oil in Transgenic *Glycine max* by Seed-Specific Expression of a 3-Hydroxysteroid Oxidase Gene Seeds of *Glycine max* (soybean) usually contain three major sterol compounds, viz., as percent of total sterol compounds, campesterol (~20%), stigmasterol (~18%) and Sitosterol (~57%). Structures of stigmasterol and stigmastanol are as follows:

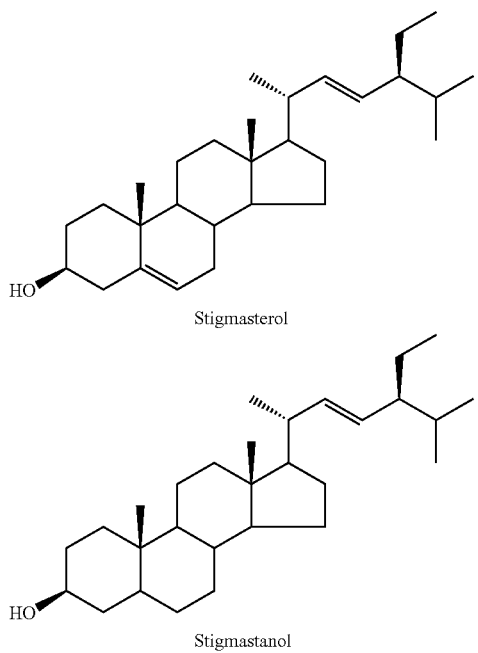

Stigmasterol

Stigmastanol

An experiment was performed wherein the *Streptomyces* A19249 3-hydroxysteroid oxidase disclosed in U.S. Pat. No. 5,518,908 was overexpressed in *Glycine max* using the embryo-specific 7S promoter to determine the effect on seed oil sterol compound composition. As shown below, this resulted in the production and accumulation of campestanol, stigmastanol and sitostanol, in addition to the campesterol, stigmasterol and sitosterol normally present. Stigmastanol is a novel phytostanol. The appearance of the reduced stanols was due to the reduction of the C-5 double bond in campesterol, stigmasterol and sitosterol, presumably due to the activity of the 3-hydroxysteroid oxidase enzyme introduced into the transgenic plants.

Figure 11:
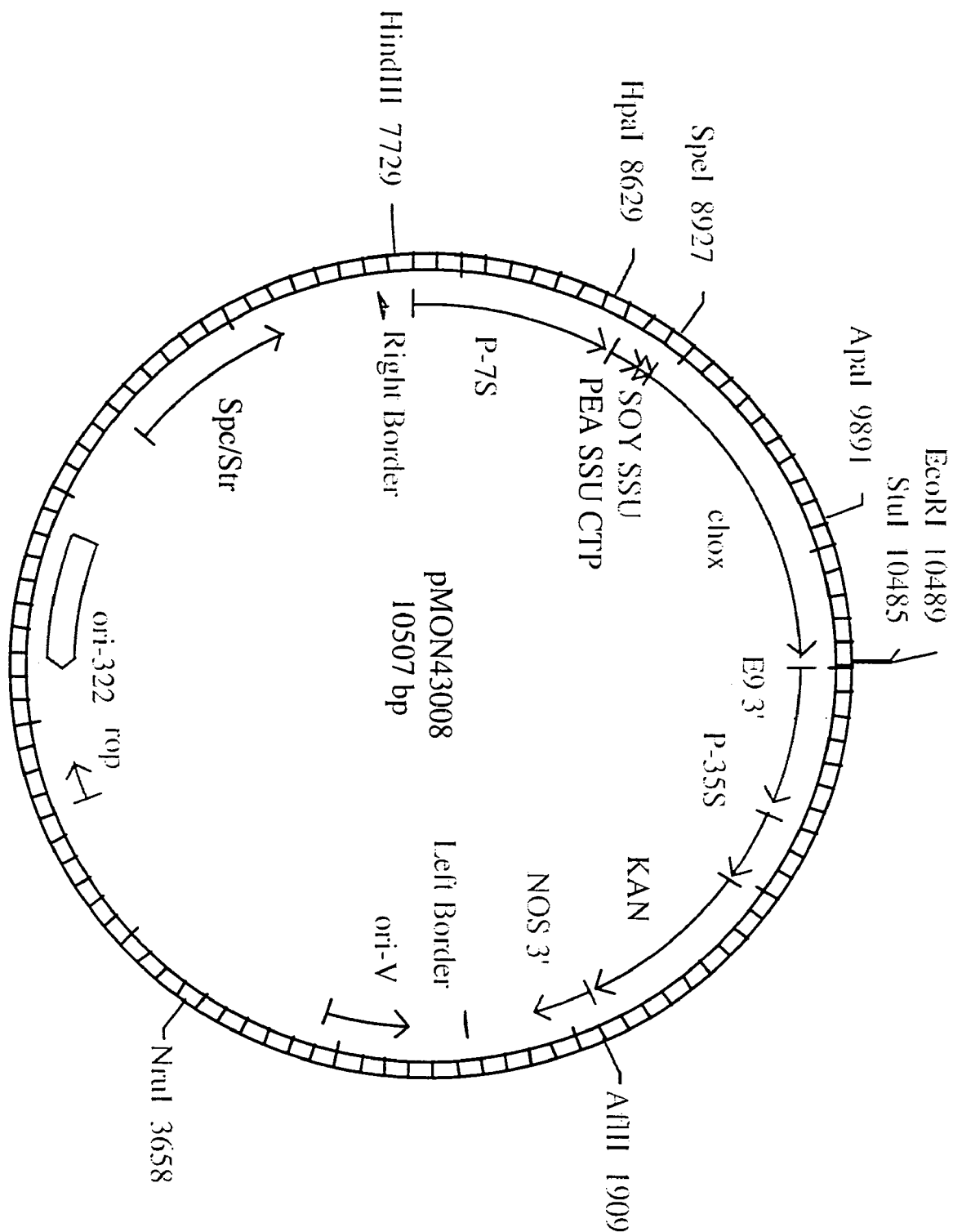

The following strategy was employed to obtain transgenic *Glycine max* plants expressing the *Streptomyces* 3-hydroxysteroid oxidase gene developing embryos. The plasmid pMON 43007 (FIG. 3) was generated as described in Example 10. This plasmid was digested with BglII and BamHI to release a 1.8 Kb fragment containing the fused chloroplast transit peptide and the 3-hydroxysteroid oxidase gene. This cassette was cloned into the BglII site of the binary vector pMON29920 (FIG. 6) to create pMON43008 (FIG. 11), which was used to transform *Agrobacterium tumefaciens*. Soybean explants were transformed as described in Example 3.

Seed from 30 transgenic plants and one nontransgenic control plant were harvested at maturity. Ten seeds from each plant were ground into a fine powder individually. A known amount of cholestane (usually 100 µg in 100 µl ethanol) was added to each approximately 50 mg powder sample. Sterol compounds were extracted and analyzed as described in Example 3. The results are shown in Table 7.

TABLE 7

| Plant | Campesterol | Campestanol | % Campestanol | Stigmasterol | Stigmastanol | % Stigmastanol | Sitosterol | Sitostanol | % Sitostanol |
|---|---|---|---|---|---|---|---|---|---|
| 1 | 19.5 | 0 | 0.0 | 18.2 | 0 | 0.0 | 58.1 | 4.2 | 6.7 |
| 2 | 4.4 | 11.2 | 71.8 | 6.9 | 7.8 | 53.1 | 26.2 | 43.4 | 62.4 |
| 3 | 6.2 | 9.4 | 60.3 | 7.8 | 7.5 | 49.0 | 32.4 | 36.7 | 53.1 |
| 4 | 18.7 | | 0.0 | 13.7 | | 0.0 | 62.8 | 4.7 | 7.0 |
| 5 | 3.2 | 13.8 | 81.2 | 6.3 | 11.7 | 65.0 | 16.6 | 48.4 | 74.5 |
| 6 | 23.4 | | 0.0 | 16.1 | | 0.0 | 55.9 | 4.6 | 7.6 |
| 7 | 21.1 | | 0.0 | 15 | | 0.0 | 59.6 | 4.3 | 6.7 |

TABLE 7-continued

| Plant | Campesterol | Campestanol | % Campestanol | Stigmasterol | Stigmastanol | % Stigmastanol | Sitosterol | Sitostanol | % Sitostanol |
|---|---|---|---|---|---|---|---|---|---|
| 8 | 20.9 | | 0.0 | 15.3 | | 0.0 | 60.4 | 3.4 | 5.3 |
| 9 | 7.2 | 13 | 64.4 | 7.5 | 8.4 | 52.8 | 25.5 | 38.5 | 60.2 |
| 10 | 2.8 | 14.8 | 84.1 | 4 | 11.6 | 74.4 | 13.3 | 53.5 | 80.1 |
| 11 | 8.3 | 10.6 | 56.1 | 8.1 | 5.7 | 41.3 | 30.9 | 36.4 | 54.1 |
| 12 | 19.2 | | 0.0 | 13.4 | | 0.0 | 64.8 | 2.6 | 3.9 |
| 13 | 19.5 | | 0.0 | 14.8 | | 0.0 | 63.1 | 2.6 | 4.0 |
| 14 | 20.4 | | 0.0 | 14.4 | | 0.0 | 62.8 | 2.4 | 3.7 |
| 15 | 11 | 7.7 | 41.2 | 9.1 | 5.5 | 37.7 | 38.7 | 28 | 42.0 |
| 16 | 6.8 | 11.1 | 62.0 | 6.9 | 7.8 | 53.1 | 26.5 | 40.9 | 60.7 |
| 17 | 10.7 | 7.9 | 42.5 | 10.3 | 6.4 | 38.3 | 34.1 | 30.4 | 47.1 |
| 18 | 16 | | 0.0 | 13.9 | | 0.0 | 64.7 | 5.4 | 7.7 |
| 19 | 6.1 | 8.9 | 59.3 | 6.9 | 6 | 46.5 | 31.6 | 40.4 | 56.1 |
| 20 | 7 | 8.1 | 53.6 | 6.9 | 5.6 | 44.8 | 38.1 | 34.2 | 47.3 |
| 21 | 15.4 | | 0.0 | 12.3 | | 0.0 | 66.5 | 5.8 | 8.0 |
| 22 | 5.6 | 9.3 | 62.4 | 5.8 | 6.2 | 51.7 | 31.7 | 41.3 | 56.6 |
| 23 | 6.6 | 9 | 57.7 | 7.3 | 5.5 | 43.0 | 33.4 | 38.1 | 53.3 |
| 24 | 7.3 | 7.9 | 52.0 | 7.6 | 4.9 | 39.2 | 37 | 35.3 | 48.8 |
| 25 | 6.8 | 9.4 | 58.0 | 6.7 | 6 | 47.2 | 31.4 | 39.6 | 55.8 |
| 26 | 5.4 | 9.6 | 64.0 | 6.4 | 6.9 | 51.9 | 30.3 | 41.2 | 57.6 |
| 27 | 8.2 | 7.2 | 46.8 | 8.4 | 5.1 | 37.8 | 39.8 | 31.3 | 44.0 |
| 28 | 9.5 | 6.1 | 39.1 | 8.8 | 3.7 | 29.6 | 44.1 | 27.9 | 38.8 |
| 29 | 5.3 | 8.8 | 62.4 | 5.8 | 5.6 | 49.1 | 31.2 | 43.4 | 58.2 |
| 30 | 15.5 | | 0.0 | 14.4 | | 0.0 | 65.3 | 4.8 | 6.8 |
| 31 | 4.3 | 9.2 | 68.1 | 6.6 | 8 | 54.8 | 25.4 | 46.4 | 64.6 |

Significant amounts of the phytostanols sitostanol, campestanol and stigmastanol, in addition to the phytosterols sitosterol, campesterol and stigmasterol normally present, accumulated in seeds of transgenic *Glycine max* expressing the 3-hydroxysteroid oxidase gene under the control of the seed-specific 7S promoter. Calculated as weight percent of total sterol compounds, in the highest phytostanol accumulating plants, from about 60% to about 80% of sitosterol was converted to sitostanol (transgenic event numbers 2, 5, 9, 10, 16, and 31), from about 51% to 74% of stigmasterol was converted to stigmastanol (transgenic event numbers 2, 5, 9, 10, 16, 22, 26, and 31) and from about 60% to 84% of campesterol was converted to campestanol (transgenic event numbers 2, 3, 5, 9, 10, 16, 22, 26, 29 and 31). Thus, significant amounts of phytostanols not normally present in seeds of *Glycine max* were produced and accumulated in seeds of transgenic plants.

Stigmastanol is a novel phytostanol produced in these transgenic plants. The other phytostanols observed in these transgenic seeds, i.e., sitostanol and campestanol, occur commonly, although they are minor constituents in most oil seeds. Phytostanols such as sitostanol and campestanol can be made commercially from sitosterol and campesterol through hydrogenation. However, by this process, stigmasterol will be hydrogenated to sitostanol, in which both the C-5 and C-22 double bonds are reduced. It is, therefore, not commercially feasible to produce stigmastanol by hydrogenation of oils containing stigmasterol. Thus, the presence of stigmastanol in transgenic plants of the present invention is unexpected, and of unique commercial importance.

The occurrence of stigmastanol in transgenic soybeans of the present invention expressing 3-hydroxysteroid oxidase enzyme proves that this enzyme specifically reduces the C-5 double bond of phytosterols. This observation along with that of the formation of brassicastanol in rapeseed, described in Example 9, proves that this enzyme's catalytic activity is not influenced by structural variations in the phytosterol side-chain. Brassicasterol has a C-24 methyl side chain and C-22 double bond while stigmasterol has C-24 ethyl side chain and C-22 double bond. The formation of brassicastanol and stigmastanol indicates that the enzyme 3-hydroxysteroid oxidase can reduce the C-5 double bond in both cases. The scheme of the enzymatic conversion of stigmasterol to stigmastanol catalyzed by 3-hydroxysteroid oxidases and sterol C-5 reductases (steroid 5α-reductases) is shown below:

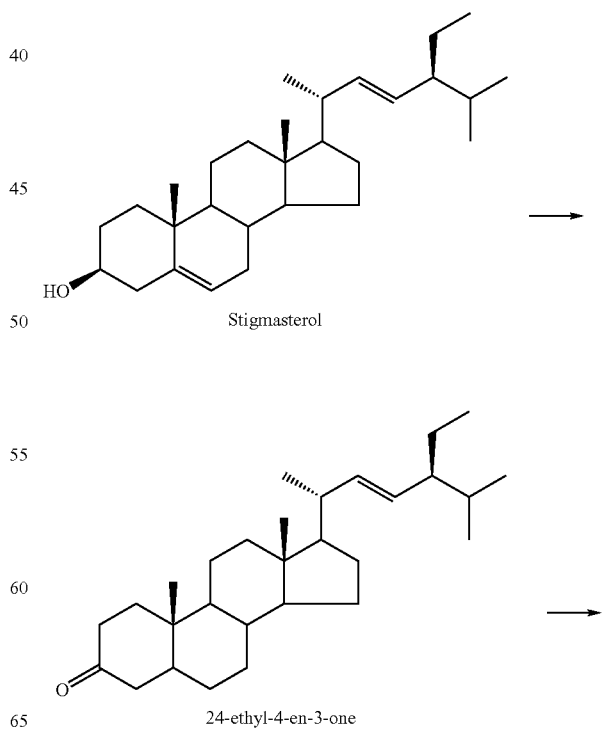

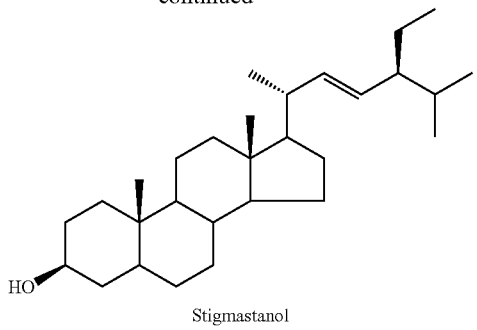
Stigmastanol

Seven of these 30 transgenic events (event numbers 2, 3, 5, 9, 10, 11, and 15) were carried forward to the next generation. For this 30 seeds from each event were planted in pots in the greenhouse and seeds collected at maturity. Leaf samples from each plant were also collected during the early stage of growth. Leaf samples were used to screen for the marker gene expression by performing NPTII ELISA assays using commercial kits. After seed harvest five seeds from each plant were ground to a fine powder and a portion weighed and subjected to sterol extraction and analysis as described in Example 9. Data from leaf ELISA and sterol analysis is presented in Table 8.

Several plants from each event did not survive in the greenhouse and so seeds from less than 30 plants per event were collected. Within each event there are both positive transgenic plants as well as negative, as can be seen from the NPTII ELISA data. The ratio between the positives and negatives will indicate the number of gene inserts per event. When only one copy of the transgene is inserted there should be a 3:1 segregation ratio. Thus, of the seven events, three have more than one insert copy. These are event numbers 3, 5 and 10. The rest have single insert copies. Further, in all events there is a good correlation between plants being NPTII positive and phytosterol to phytostanol conversion. This evidence further supports the fact that phytostanol formation is dependent on the presence of the 3-hydroxysteroid oxidase gene in the plant's genome. The trait is thus heritable.

TABLE 8

| Event # | Plant # | NPTII | Campe-sterol | Campe-stanol | % Campestanol | Stigmasterol | Stigmastanol | % Stigmastanol | Sitosterol | Sitostanol | % Sitostanol |
|---|---|---|---|---|---|---|---|---|---|---|---|
| 1 (Control) | 1 | − | 19.8 | 0 | 0.0 | 18.8 | 0 | 0.0 | 61.4 | 0 | 0.0 |
| 2 | 1 | − | 18.2 | 0 | 0.0 | 14.9 | 0 | 0.0 | 66.8 | 0 | 0.0 |
|  | 2 | + | 3.4 | 11.1 | 76.6 | 5.8 | 7.7 | 57.0 | 28.4 | 43.7 | 60.6 |
|  | 3 | + | 5.7 | 9.1 | 61.5 | 7 | 5.5 | 44.0 | 43.1 | 29.6 | 40.7 |
|  | 4 | + | 3.9 | 11.8 | 75.2 | 6 | 6.7 | 52.8 | 31.3 | 40.3 | 56.3 |
|  | 5 | + | 3.7 | 12 | 76.4 | 6.3 | 7.3 | 53.7 | 28.4 | 42.3 | 59.8 |
|  | 6 | − | 18.9 | 0 | 0.0 | 14.5 | 0 | 0.0 | 66.6 | 0 | 0.0 |
|  | 7 | + | 2.3 | 11.5 | 83.3 | 3.8 | 7.9 | 67.5 | 24.6 | 49.9 | 67.0 |
|  | 8 | − | 19.2 | 0 | 0.0 | 14.1 | 0 | 0.0 | 66.7 | 0 | 0.0 |
|  | 9 | − | 19 | 0 | 0.0 | 13.3 | 0 | 0.0 | 67.7 | 0 | 0.0 |
|  | 10 | + | 4 | 12.1 | 75.2 | 7.2 | 7.8 | 52.0 | 27.9 | 41 | 59.5 |
|  | 11 | + | 10.3 | 6.3 | 38.0 | 7.6 | 2.9 | 27.6 | 46 | 26.8 | 36.8 |
|  | 12 | + | 3.1 | 12.1 | 79.6 | 6 | 8.6 | 58.9 | 21.9 | 48.3 | 68.8 |
|  | 13 | − | 16.6 | 0 | 0.0 | 13.3 | 0 | 0.0 | 70.1 | 0 | 0.0 |
|  | 14 | + | 2.8 | 11 | 79.7 | 5 | 8 | 61.5 | 25.2 | 48 | 65.6 |
|  | 15 | + | 5.3 | 10.2 | 65.8 | 6.6 | 7.1 | 51.8 | 32.7 | 38 | 53.7 |
|  | 16 | + | 2.4 | 12.4 | 83.8 | 4.1 | 8.3 | 66.9 | 23.7 | 49 | 67.4 |
|  | 17 | + | 6.3 | 10.2 | 61.8 | 8.4 | 6.2 | 42.5 | 35.4 | 33.5 | 48.6 |
|  | 18 | + | 1.9 | 12.7 | 87.0 | 4.8 | 8.6 | 64.2 | 24.1 | 47.8 | 66.5 |
|  | 19 | − | 19.6 | 0 | 0.0 | 12.8 | 0 | 0.0 | 67.6 | 0 | 0.0 |
|  | 20 | − | 16.1 | 0 | 0.0 | 13.7 | 0 | 0.0 | 70.2 | 0 | 0.0 |
|  | 25 | + | 9.1 | 7 | 43.5 | 8.9 | 5 | 36.0 | 41.9 | 28.1 | 40.1 |
| 3 | 1 | + | 2.5 | 12.2 | 83.0 | 5.3 | 9.6 | 64.4 | 21.8 | 48.6 | 69.0 |
|  | 2 | + | 12.5 | 5.5 | 30.6 | 11.1 | 4.4 | 28.4 | 44 | 22.4 | 33.7 |
|  | 3 | + | 4.3 | 11.9 | 73.5 | 5.5 | 7.6 | 58.0 | 27.3 | 43.5 | 61.4 |
|  | 4 | − | 18.4 | 0 | 0.0 | 14 | 0 | 0.0 | 67.6 | 0 | 0.0 |
|  | 5 | + | 7.2 | 8.5 | 54.1 | 8.4 | 6.5 | 43.6 | 38.3 | 31 | 44.7 |
|  | 6 | − | 17 | 0 | 0.0 | 13.5 | 0 | 0.0 | 69.5 | 0 | 0.0 |
|  | 9 | + | 14.9 | 3.7 | 19.9 | 11.4 | 3.2 | 21.9 | 53.4 | 13.3 | 19.9 |
|  | 10 | + | 1.8 | 13.2 | 88.0 | 4.3 | 9.8 | 69.5 | 20.1 | 50.8 | 71.7 |
|  | 11 | + | 6.9 | 9.1 | 56.9 | 8.9 | 6.4 | 41.8 | 36.8 | 31.9 | 46.4 |
|  | 12 | + | 3.2 | 12.4 | 79.5 | 6 | 12.1 | 66.9 | 22.2 | 46.4 | 67.6 |
|  | 13 | + | 6.7 | 8 | 54.4 | 8.8 | 5.1 | 36.7 | 41 | 30.3 | 42.5 |
| 5 | 1 | + | 3.8 | 12 | 75.9 | 5.8 | 7.4 | 56.1 | 27.1 | 43.8 | 61.8 |
|  | 2 | + | 3.3 | 11.3 | 77.4 | 5.6 | 7.2 | 56.3 | 28.4 | 44.1 | 60.8 |
|  | 3 | + | 2.9 | 11.8 | 80.3 | 5.9 | 9 | 60.4 | 23.3 | 47.2 | 67.0 |
|  | 4 | − | 18.5 | 0 | 0.0 | 12.7 | 0 | 0.0 | 68.8 | 0 | 0.0 |
|  | 5 | + | 7.6 | 9.1 | 54.5 | 8.4 | 6.7 | 44.4 | 38.1 | 30.1 | 44.1 |
|  | 6 | + | 3 | 11.2 | 78.9 | 5.7 | 10.9 | 65.7 | 24.4 | 44.7 | 64.7 |
|  | 7 | + | 1.8 | 12.5 | 87.4 | 4.2 | 13.2 | 75.9 | 18.5 | 49.8 | 72.9 |
|  | 8 | + | 14 | 4.5 | 24.3 | 13.7 | 3.8 | 21.7 | 48.7 | 15.3 | 23.9 |
|  | 9 | + | 8.7 | 8.4 | 49.1 | 10 | 6.7 | 40.1 | 38.8 | 27.2 | 41.2 |
|  | 11 | + | 3.1 | 12.5 | 80.1 | 5.9 | 11.3 | 65.7 | 22.3 | 45 | 66.9 |
|  | 12 | + | 7.8 | 5.7 | 42.2 | 10.6 | 3.9 | 26.9 | 48.3 | 23.7 | 32.9 |
|  | 14 | + | 5.4 | 11.9 | 68.8 | 7.9 | 7.7 | 49.4 | 29.1 | 38.1 | 56.7 |
|  | 15 | − | 20.7 | 0 | 0.0 | 13.7 | 0 | 0.0 | 65.4 | 0 | 0.0 |
|  | 16 | + | 3.9 | 11 | 73.8 | 6.1 | 9.4 | 60.6 | 25.8 | 43.9 | 63.0 |

TABLE 8-continued

| Event # | Plant # | NPTII | Campesterol | Campestanol | % Campestanol | Stigmasterol | Stigmastanol | % Stigmastanol | Sitosterol | Sitostanol | % Sitostanol |
|---|---|---|---|---|---|---|---|---|---|---|---|
| 9 | 1 | + | 6.1 | 9.9 | 61.9 | 8.2 | 7.8 | 48.8 | 33 | 34.9 | 51.4 |
|  | 2 | + | 6.7 | 10 | 59.9 | 8.5 | 6.5 | 43.3 | 34.3 | 34 | 49.8 |
|  | 3 | + | 11.7 | 5.1 | 30.4 | 13.7 | 4.4 | 24.3 | 46.8 | 18.1 | 27.9 |
|  | 4 | + | 3.4 | 13.1 | 79.4 | 7.6 | 12 | 61.2 | 14.7 | 49.2 | 77.0 |
|  | 6 | + | 10.5 | 6.4 | 37.9 | 11.4 | 5 | 30.5 | 45.4 | 21.2 | 31.8 |
|  | 7 | + | 4.4 | 9.2 | 67.6 | 7.6 | 7.6 | 50.0 | 32.6 | 38.5 | 54.1 |
|  | 8 | − | 18.1 | 0 | 0.0 | 16.4 | 0 | 0.0 | 65.6 | 0 | 0.0 |
|  | 9 | + | 12.9 | 4.7 | 26.7 | 12.2 | 3.5 | 22.3 | 50.3 | 16.3 | 24.5 |
|  | 10 | + | 3 | 12.9 | 81.1 | 6.2 | 10.2 | 62.2 | 22.2 | 45.6 | 67.3 |
|  | 11 | − | 17.3 | 0 | 0.0 | 16.5 | 0 | 0.0 | 66.3 | 0 | 0.0 |
|  | 12 | + | 8.6 | 8.3 | 49.1 | 9.8 | 5.5 | 35.9 | 40.9 | 26.9 | 39.7 |
|  | 13 | − | 17.8 | 0 | 0.0 | 18.9 | 0 | 0.0 | 63.2 | 0 | 0.0 |
|  | 14 | − | 19 | 0 | 0.0 | 17 | 0 | 0.0 | 64 | 0 | 0.0 |
|  | 15 | + | 10.3 | 4.8 | 31.8 | 12.2 | 4.5 | 26.9 | 49.1 | 19 | 27.9 |
|  | 16 | + | 8.4 | 8.6 | 50.6 | 10.3 | 6.6 | 39.1 | 37.8 | 28.4 | 42.9 |
|  | 17 | + | 12 | 2.1 | 14.9 | 10.9 | 2.6 | 19.3 | 60.7 | 11.6 | 16.0 |
|  | 18 | − | 17.5 | 0 | 0.0 | 17.4 | 0 | 0.0 | 63.3 | 1.8 | 2.8 |
|  | 19 | + | 5.6 | 10.5 | 65.2 | 8.6 | 7.2 | 45.6 | 32.6 | 35.3 | 52.0 |
|  | 22 | + | 4.6 | 10.6 | 69.7 | 8.1 | 7.6 | 48.4 | 32 | 37.2 | 53.8 |
|  | 27 | + | 7 | 9 | 56.3 | 11.5 | 7.2 | 38.5 | 35.9 | 29.3 | 44.9 |
| 10 | 1 | + | 2.5 | 10.8 | 81.2 | 5.8 | 9.2 | 61.3 | 25.5 | 46.2 | 64.4 |
|  | 2 | + | 4.9 | 5 | 50.5 | 7.1 | 5.6 | 44.1 | 50.9 | 26.5 | 34.2 |
|  | 3 | + | 2.6 | 6.6 | 71.7 | 4.9 | 6.9 | 58.5 | 37.8 | 41.3 | 52.2 |
|  | 5 | + | 0 | 15.1 | 100.0 | 5.7 | 12 | 67.8 | 15.6 | 51.6 | 76.8 |
|  | 6 | + | 2.2 | 12.5 | 85.0 | 4.7 | 10.7 | 69.5 | 19.1 | 50.8 | 72.7 |
|  | 8 | + | 3.9 | 11.6 | 74.8 | 6.9 | 8.8 | 56.1 | 24.9 | 43.9 | 63.8 |
|  | 9 | + | 5.4 | 9.4 | 63.5 | 7.1 | 7.3 | 50.7 | 32.1 | 38.7 | 54.7 |
|  | 10 | + | 0 | 11.5 | 100.0 | 3.4 | 10.7 | 75.9 | 20.2 | 54.2 | 72.8 |
|  | 11 | − | 17.4 | 0 | 0.0 | 15.6 | 0 | 0.0 | 67 | 0 | 0.0 |
|  | 12 | + | 8.6 | 7.3 | 45.9 | 9 | 6.9 | 43.4 | 38.7 | 29.4 | 43.2 |
|  | 14 | + | 2.6 | 11.6 | 81.7 | 5.3 | 9.9 | 65.1 | 25.5 | 44.9 | 63.8 |
|  | 16 | + | 6.7 | 7.2 | 51.8 | 9.8 | 6.3 | 39.1 | 39 | 31 | 44.3 |
|  | 17 | + | 3.1 | 10.9 | 77.9 | 6.3 | 9.1 | 59.1 | 26.2 | 44.3 | 62.8 |
|  | 18 | + | 8 | 7.5 | 48.4 | 10.9 | 6.1 | 35.9 | 39.3 | 28.2 | 41.8 |
|  | 19 | + | 2.7 | 11.4 | 80.9 | 5.8 | 10.1 | 63.5 | 22.8 | 47.2 | 67.4 |
|  | 20 | + | 3.6 | 11.2 | 75.7 | 7.8 | 9.9 | 55.9 | 27.1 | 40.4 | 59.9 |
|  | 21 | + | 1.8 | 10.6 | 85.5 | 4.8 | 10.8 | 69.2 | 25 | 47 | 65.3 |
|  | 23 | + | 2.6 | 12.2 | 82.4 | 4.9 | 9.4 | 65.7 | 23.2 | 47.6 | 67.2 |
|  | 25 | + | 7.5 | 8.4 | 52.8 | 8.8 | 6.7 | 43.2 | 37.1 | 31.5 | 45.9 |
|  | 30 | + | 2 | 12.5 | 86.2 | 4.7 | 10.9 | 69.9 | 19 | 50.8 | 72.8 |
| 11 | 1 | − | 19.6 | 0 | 0.0 | 17.2 | 0 | 0.0 | 63.2 | 0 | 0.0 |
|  | 2 | + | 6.8 | 9.7 | 58.8 | 8.1 | 7.6 | 48.4 | 33.2 | 34.6 | 51.0 |
|  | 3 | + | 10.6 | 7.6 | 41.8 | 10.1 | 5.9 | 36.9 | 38.1 | 27.6 | 42.0 |
|  | 4 | − | 16.6 | 0 | 0.0 | 18.7 | 0 | 0.0 | 61.8 | 0 | 0.0 |
|  | 5 | + | 3.5 | 12.2 | 77.7 | 6.2 | 8.7 | 58.4 | 25.3 | 44.1 | 63.5 |
|  | 6 | + | 3.7 | 6.4 | 63.4 | 6.4 | 5.5 | 46.2 | 44.5 | 33.5 | 42.9 |
|  | 7 | + | 11.8 | 4.4 | 27.2 | 12.9 | 3.7 | 22.3 | 50.5 | 16.7 | 24.9 |
|  | 8 | + | 5.8 | 8.8 | 60.3 | 9.6 | 6.5 | 40.4 | 38.1 | 31.3 | 45.1 |
|  | 9 | + | 3.2 | 11.8 | 78.7 | 6 | 8.7 | 59.2 | 26.8 | 43.4 | 61.8 |
|  | 10 | + | 13.2 | 5.3 | 28.6 | 11.5 | 4.1 | 26.3 | 45.8 | 20.1 | 30.5 |
|  | 11 | − | 20.6 | 0 | 0.0 | 15.5 | 0 | 0.0 | 63.8 | 0 | 0.0 |
|  | 14 | + | 2.6 | 11.7 | 81.8 | 5.5 | 9.8 | 64.1 | 22.8 | 47.6 | 67.6 |
|  | 15 | − | 14 | 0 | 0.0 | 14 | 0 | 0.0 | 71.9 | 0 | 0.0 |
|  | 16 | + | 0 | 12.7 | 100.0 | 4.2 | 8.5 | 66.9 | 21.2 | 53.4 | 71.6 |
|  | 17 | + | 0 | 11.1 | 100.0 | 5.2 | 7.4 | 58.7 | 28.9 | 47.4 | 62.1 |
|  | 19 | + | 12.5 | 6.7 | 34.9 | 11.2 | 0 | 0.0 | 47.8 | 22.3 | 31.8 |
|  | 20 | + | 6.9 | 10.1 | 59.4 | 7.3 | 5.5 | 43.0 | 35.3 | 34.9 | 49.7 |
|  | 21 | + | 7.4 | 9.3 | 55.7 | 8.8 | 5.8 | 39.7 | 36.8 | 32.4 | 46.8 |
|  | 22 | + | 6.2 | 10.8 | 63.5 | 7.7 | 6.2 | 44.6 | 30.9 | 38.1 | 55.2 |
|  | 23 | + | 12 | 6.5 | 35.1 | 10.2 | 3.6 | 26.1 | 45.4 | 22.4 | 33.0 |
|  | 24 | − | 17.6 | 0 | 0.0 | 15.9 | 0 | 0.0 | 66.5 | 0 | 0.0 |
|  | 25 | + | 0 | 10.8 | 100.0 | 8.1 | 6.8 | 45.6 | 33.8 | 40.5 | 54.5 |
|  | 26 | + | 0 | 9.7 | 100.0 | 6.9 | 6.9 | 50.0 | 31.9 | 44.4 | 58.2 |
| 15 | 1 | + | 6.3 | 11 | 63.6 | 5.5 | 5.9 | 51.8 | 32.9 | 38.4 | 53.9 |
|  | 2 | − | 18.8 | 0 | 0.0 | 13.2 | 0 | 0.0 | 68.3 | 0 | 0.0 |
|  | 3 | + | 8.3 | 9.6 | 53.6 | 7.4 | 5.2 | 41.3 | 36.5 | 33 | 47.5 |
|  | 4 | − | 20 | 0 | 0.0 | 15.2 | 0 | 0.0 | 65.2 | 0 | 0.0 |
|  | 5 | + | 3.8 | 13.5 | 78.0 | 5.4 | 6.9 | 56.1 | 27.3 | 43.1 | 61.2 |
|  | 6 | − | 19.5 | 0 | 0.0 | 13.7 | 0 | 0.0 | 67.1 | 0 | 0.0 |
|  | 7 | + | 10.8 | 7.1 | 39.7 | 9.5 | 3.4 | 26.4 | 46.4 | 22.7 | 32.9 |
|  | 8 | + | 10.5 | 7.5 | 41.7 | 9.1 | 3.5 | 27.8 | 42.2 | 27.3 | 39.3 |
|  | 9 | + | 0 | 11 | 100.0 | 5.3 | 6.3 | 54.3 | 31.6 | 45.8 | 59.2 |
|  | 10 | + | 7 | 11.5 | 62.2 | 6.2 | 7.8 | 55.7 | 26.7 | 40.3 | 60.1 |
|  | 11 | + | 0 | 14.3 | 100.0 | 0 | 9.9 | 100.0 | 18.7 | 57.7 | 75.5 |
|  | 12 | + | 15.6 | 6 | 27.8 | 10.5 | 0 | 0.0 | 48.2 | 20.1 | 29.4 |
|  | 13 | − | 20.7 | 0 | 0.0 | 15.2 | 0 | 0.0 | 64.1 | 0 | 0.0 |

TABLE 8-continued

| Event # | Plant # | NPTII | Campe-sterol | Campe-stanol | % Campestanol | Stigmasterol | Stigmastanol | % Stigmastanol | Sitosterol | Sitostanol | % Sitostanol |
|---|---|---|---|---|---|---|---|---|---|---|---|
| | 14 | + | 6.9 | 10.8 | 61.0 | 5.9 | 11.5 | 66.1 | 30 | 34.6 | 53.6 |
| | 17 | + | 6.1 | 11.1 | 64.5 | 6.1 | 7.3 | 54.5 | 32.7 | 36.1 | 52.5 |
| | 18 | + | 9.3 | 8.9 | 48.9 | 8.3 | 5.2 | 38.5 | 38.4 | 29.9 | 43.8 |
| | 19 | + | 7.1 | 10.5 | 59.7 | 6.5 | 5.8 | 47.2 | 34.7 | 35.4 | 50.5 |
| | 20 | + | 12.3 | 5.8 | 32.0 | 9 | 3.3 | 26.8 | 47.3 | 22.2 | 31.9 |
| | 21 | + | 4.9 | 12.3 | 71.5 | 5.3 | 6.7 | 55.8 | 27.1 | 43.7 | 61.7 |
| | 22 | + | 8 | 10.4 | 56.5 | 7.7 | 4.3 | 35.8 | 37.1 | 32.1 | 46.4 |
| | 23 | + | 6.6 | 8.8 | 57.1 | 5.7 | 25.7 | 81.8 | 25.7 | 27.4 | 51.6 |
| | 25 | + | 0 | 16.1 | 100.0 | 0 | 6.7 | 100.0 | 19.5 | 57.7 | 74.7 |
| | 26 | + | 6.6 | 10.4 | 61.2 | 6.3 | 4.8 | 43.2 | 37.1 | 34.8 | 48.4 |
| | 28 | − | 20 | 0 | 0.0 | 14.4 | 0 | 0.0 | 65.5 | 0 | 0.0 |

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. An oil comprising a compound selected from the group consisting of brassicastanol, at least one brassicastanol ester, stigmastanol, or at least one stigmastanol ester, and a mixture thereof, wherein said brassicastanol has the structure

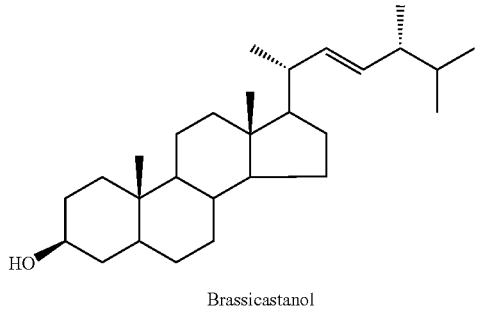

Brassicastanol and said stigmastanol has the structure

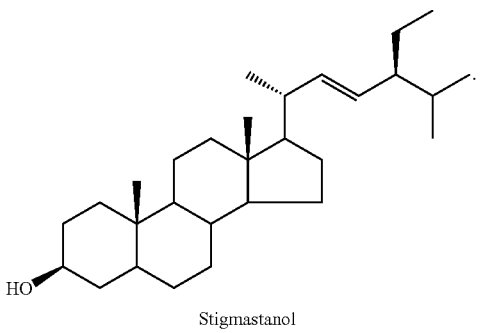

Stigmastanol

2. The oil of claim 1, wherein said oil is in a transgenic seed having a reduced level of a compound selected from the group consisting of campesterol, a campesterol ester, campestanol, a campestanol ester, and mixtures thereof, compared to a second oil produced in a corresponding or non-transgenic seed.

3. The oil according to claim 1, further comprising a compound selected from the group consisting of at least one sterol, at least one phytosterol, at least one phytosterol ester, at least one phytostanol, at least one phytostanol ester, and a mixture thereof.

4. The oil according to claim 3, further comprising a compound selected from the group consisting of a sitostanol, at least one sitostanol ester, and a mixture thereof, wherein said sitostanol, at least one sitostanol ester, or a mixture thereof comprises at least about 57% by weight of the total sterol compounds of said oil.

5. The oil according to claim 1, further comprising a campesterol ester, campestanol, at least one campestanol ester, and a mixture thereof, wherein said campesterol ester, campestanol, at least one campestanol ester, and a mixture thereof, comprises about 5% to about 9% by weight of the total sterol compounds of the oil.

6. The oil according to claim 1, wherein said oil is in a transgenic seed.

* * * * *